US012131807B2

(12) United States Patent
Eden et al.

(10) Patent No.: US 12,131,807 B2
(45) Date of Patent: *Oct. 29, 2024

(54) COMPUTATIONAL ANALYSIS OF BIOLOGICAL DATA USING MANIFOLD AND A HYPERPLANE

(71) Applicant: MeMed Diagnostics Ltd., Tirat HaCarmel (IL)

(72) Inventors: Eran Eden, Haifa (IL); Kfir Oved, Hof HaCarmel (IL); Roy Navon, Tel-Aviv (IL); Assaf Cohen-Dotan, Natania (IL); Olga Boico, Atlit (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,718

(22) Filed: Aug. 7, 2023

(65) Prior Publication Data

US 2024/0029818 A1 Jan. 25, 2024

Related U.S. Application Data

(60) Continuation of application No. 17/875,467, filed on Jul. 28, 2022, now Pat. No. 11,776,658, which is a
(Continued)

(51) Int. Cl.
*G16B 5/20* (2019.01)
*G06F 17/18* (2006.01)
(Continued)

(52) U.S. Cl.
CPC .............. *G16B 5/20* (2019.02); *G06F 17/18* (2013.01); *G16B 5/00* (2019.02); *G16B 20/00* (2019.02);
(Continued)

(58) Field of Classification Search
CPC ................... G06N 33/56983; G01N 33/56911
See application file for complete search history.

(56) References Cited

U.S. PATENT DOCUMENTS 5,639,617 A 6/1997 Bohuon
5,910,421 A 6/1999 Small, Jr. et al.
(Continued)

FOREIGN PATENT DOCUMENTS

AU 2012244350 11/2012
CN 1656378 8/2005
(Continued)

OTHER PUBLICATIONS

Hastie et al. "The Elements of Statistical Learning: Data Mining, Inference, and Prediction", Springer Series in Statistics, 2nd Ed., p. 1-745, 2001. (Part 1).
(Continued)

*Primary Examiner* — Nicholas J Tobergte

(57) ABSTRACT

A method of analyzing biological data containing expression values of a plurality of polypeptides in the blood of a subject. The method comprises: calculating a distance between a segment of a curved line and an axis defined by a direction, the distance being calculated at a point over the curved line defined by a coordinate along the direction. The method further comprises correlating the distance to the presence of, absence of, or likelihood that the subject has, a bacterial infection. The coordinate is defined by a combination of the expression values, wherein at least 90% of the segment is between a lower bound line and an upper bound line.

22 Claims, 66 Drawing Sheets

Specification includes a Sequence Listing.

Related U.S. Application Data continuation of application No. 16/998,006, filed on Aug. 20, 2020, now Pat. No. 11,450,406, which is a division of application No. 16/355,984, filed on Mar. 18, 2019, now Pat. No. 11,081,206, which is a continuation of application No. 15/503,439, filed as application No. PCT/IL2015/050823 on Aug. 12, 2015, now Pat. No. 10,303,846.

(60) Provisional application No. 62/105,938, filed on Jan. 21, 2015, provisional application No. 62/037,180, filed on Aug. 14, 2014.

(51) Int. Cl.
| | |
|---|---|
| G16B 5/00 | (2019.01) |
| G16B 20/00 | (2019.01) |
| G16B 20/20 | (2019.01) |
| G16B 25/10 | (2019.01) |
| G16B 40/00 | (2019.01) |
| G16B 40/20 | (2019.01) |
| G16B 40/30 | (2019.01) |
| G16H 50/50 | (2018.01) |
| G01N 33/569 | (2006.01) |
| G16B 25/00 | (2019.01) |

(52) U.S. Cl.
CPC ............ G16B 20/20 (2019.02); G16B 25/10 (2019.02); G16B 40/00 (2019.02); G16B 40/20 (2019.02); G16B 40/30 (2019.02); G16H 50/50 (2018.01); *G01N 33/56911* (2013.01); *G01N 33/56983* (2013.01); *G16B 25/00* (2019.02); *Y02A 90/10* (2018.01)

(56) References Cited

U.S. PATENT DOCUMENTS

| | | | |
|---|---|---|---|
| 6,077,665 | A | 6/2000 | Welrich et al. |
| 6,136,526 | A | 10/2000 | Venge |
| 6,210,661 | B1 | 4/2001 | Enssle et al. |
| 6,709,855 | B1 | 3/2004 | Stanton et al. |
| 6,756,483 | B1 | 6/2004 | Bergmann et al. |
| 6,953,435 | B2 | 10/2005 | Kondo et al. |
| 7,115,717 | B2 | 10/2006 | Mori et al. |
| 7,132,246 | B2 | 11/2006 | Bergmann et al. |
| 7,153,662 | B2 | 12/2006 | Bergmann et al. |
| 7,157,081 | B2 | 1/2007 | Bergmann et al. |
| 7,598,031 | B2 | 10/2009 | Liew |
| 7,629,116 | B2 | 12/2009 | Ott |
| 7,892,539 | B2 | 2/2011 | Winoto et al. |
| 8,021,836 | B2 | 9/2011 | Kolopp-Sarda et al. |
| 8,155,993 | B2 | 4/2012 | de Nijs et al. |
| 8,465,951 | B2 | 6/2013 | Rao et al. |
| 8,507,210 | B2 | 8/2013 | Bergmann et al. |
| 8,563,476 | B2 | 10/2013 | Lillard, Jr. |
| 8,697,370 | B2 | 4/2014 | Kas et al. |
| 8,821,876 | B2 | 9/2014 | Ginsburg et al. |
| 9,034,328 | B2 | 5/2015 | Takahashi |
| 9,709,565 | B2 | 7/2017 | Eden et al. |
| 9,726,668 | B2 | 8/2017 | Oved et al. |
| 9,850,539 | B2 | 12/2017 | Tsalik et al. |
| 10,010,252 | B2 | 7/2018 | Ide et al. |
| 10,209,260 | B2 | 2/2019 | Oved et al. |
| 10,303,846 | B2 | 5/2019 | Eden et al. |
| 10,502,739 | B2 | 12/2019 | Oved et al. |
| 10,859,574 | B2 | 12/2020 | Oved et al. |
| 11,385,241 | B2 | 7/2022 | Eden et al. |
| 11,466,331 | B2 | 10/2022 | Oved et al. |
| 2002/0001402 | A1 | 1/2002 | Berliner |
| 2002/0055176 | A1* | 5/2002 | Ray .................. A61B 5/150786 435/8 |
| 2002/0059030 | A1* | 5/2002 | Otworth ................. G16H 10/40 702/19 |
| 2004/0038201 | A1 | 2/2004 | Nau et al. |
| 2004/0043379 | A1 | 3/2004 | Hashimoto et al. |
| 2004/0171013 | A1 | 9/2004 | Lilius et al. |
| 2004/0197769 | A1* | 10/2004 | Wong ............... G01N 33/56983 435/5 |
| 2004/0209307 | A1 | 10/2004 | Valkirs et al. |
| 2005/0164238 | A1 | 7/2005 | Valkiris et al. |
| 2005/0227223 | A1 | 10/2005 | Miyawaki |
| 2005/0233395 | A1 | 10/2005 | Weiser et al. |
| 2006/0040301 | A1* | 2/2006 | Deirmengian ....... C12Q 1/6883 435/6.16 |
| 2006/0052278 | A1 | 3/2006 | Powell |
| 2006/0078998 | A1 | 4/2006 | Puskas et al. |
| 2006/0099628 | A1 | 5/2006 | Ching et al. |
| 2006/0246495 | A1 | 11/2006 | Garrett et al. |
| 2007/0015172 | A1 | 1/2007 | Zhang et al. |
| 2007/0184460 | A1 | 8/2007 | Ching et al. |
| 2007/0231816 | A1 | 10/2007 | Chaussabel et al. |
| 2007/0281319 | A1 | 12/2007 | Kolopp-Sarda et al. |
| 2008/0020379 | A1 | 1/2008 | Agan et al. |
| 2008/0064113 | A1 | 3/2008 | Goix et al. |
| 2008/0171323 | A1 | 7/2008 | Banchereau et al. |
| 2008/0261258 | A1 | 10/2008 | Smith et al. |
| 2009/0155180 | A1 | 6/2009 | Jump et al. |
| 2009/0203534 | A1 | 8/2009 | Hossain et al. |
| 2009/0246790 | A1 | 10/2009 | Cote et al. |
| 2010/0028874 | A1 | 2/2010 | Ramachandran et al. |
| 2010/0068147 | A1 | 3/2010 | Hibberd et al. |
| 2010/0143372 | A1 | 6/2010 | Yao et al. |
| 2010/0267569 | A1 | 10/2010 | Salmon et al. |
| 2010/0297611 | A1 | 11/2010 | Sambursky et al. |
| 2011/0059858 | A1 | 3/2011 | Kas et al. |
| 2011/0117563 | A1 | 5/2011 | Filipowicz et al. |
| 2011/0144914 | A1 | 6/2011 | Harrington |
| 2011/0166166 | A1 | 7/2011 | Henkin |
| 2011/0183856 | A1 | 7/2011 | Agan et al. |
| 2011/0225114 | A1* | 9/2011 | Gotthardt ............... G16H 10/20 706/50 |
| 2011/0275542 | A1 | 11/2011 | Eden et al. |
| 2011/0312534 | A1 | 12/2011 | Kayser et al. |
| 2012/0114661 | A1 | 5/2012 | Ginsburg |
| 2013/0166219 | A1 | 6/2013 | Shaw |
| 2013/0309168 | A1 | 11/2013 | Ho |
| 2014/0127827 | A1 | 5/2014 | Kim et al. |
| 2014/0206016 | A1 | 7/2014 | Lozano Sanchez et al. |
| 2014/0227324 | A1 | 8/2014 | Robinson et al. |
| 2014/0277284 | A1 | 9/2014 | Chen et al. |
| 2014/0349326 | A1* | 11/2014 | Ingber .................... G16H 20/10 436/98 |
| 2015/0017630 | A1 | 1/2015 | Oved et al. |
| 2016/0041153 | A1* | 2/2016 | Brown ............... G01N 33/5308 436/501 |
| 2016/0153993 | A1 | 6/2016 | Eden et al. |
| 2017/0030909 | A1 | 2/2017 | Oved et al. |
| 2017/0234873 | A1 | 8/2017 | Oved et al. |
| 2017/0235871 | A1 | 8/2017 | Eden et al. |
| 2017/0269081 | A1 | 9/2017 | Oved et al. |
| 2018/0074057 | A1 | 3/2018 | Eden et al. |
| 2018/0310854 | A1 | 11/2018 | Geva et al. |
| 2019/0011456 | A1 | 1/2019 | Oved et al. |
| 2019/0041388 | A1 | 2/2019 | Oved et al. |
| 2019/0085378 | A1 | 3/2019 | Eden et al. |
| 2019/0120837 | A1 | 4/2019 | Eden et al. |
| 2019/0161813 | A1 | 5/2019 | Oved et al. |
| 2019/0237156 | A1 | 8/2019 | Eden et al. |
| 2019/0242894 | A1 | 8/2019 | Oved et al. |
| 2019/0242895 | A1 | 8/2019 | Eden et al. |
| 2019/0271709 | A1 | 9/2019 | Eden et al. |
| 2019/0339189 | A1 | 11/2019 | Takeda et al. |
| 2020/0088728 | A1 | 3/2020 | Oved et al. |
| 2020/0124593 | A1 | 4/2020 | Oved et al. |
| 2020/0388347 | A1 | 12/2020 | Eden et al. |
| 2020/0393463 | A1 | 12/2020 | Oved et al. |
| 2020/0400668 | A1 | 12/2020 | Eden et al. |
| 2022/0011320 | A1 | 1/2022 | Eden et al. |
| 2022/0042994 | A1 | 2/2022 | Oved et al. |
| 2022/0236269 | A1 | 7/2022 | Eden et al. |
| 2022/0326256 | A1 | 10/2022 | Eden et al. |
| 2022/0329345 | A1 | 10/2022 | Kaplan |

(56) References Cited

U.S. PATENT DOCUMENTS

| | | |
|---|---|---|
| 2022/0399074 A1 | 12/2022 | Eden et al. |
| 2023/0045305 A1 | 2/2023 | Oved et al. |
| 2023/0184760 A1 | 6/2023 | Oved et al. |

FOREIGN PATENT DOCUMENTS

| | | |
|---|---|---|
| CN | 1751128 | 3/2006 |
| CN | 101208602 | 6/2008 |
| CN | 101479389 | 7/2009 |
| CN | 101523217 | 9/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 101932940 | 12/2010 |
| CN | 102081101 | 6/2011 |
| CN | 102257386 | 11/2011 |
| CN | 102301002 | 12/2011 |
| CN | 102858991 | 1/2013 |
| CN | 103097891 | 5/2013 |
| CN | 103119444 | 5/2013 |
| CN | 104126125 | 10/2014 |
| CN | 104159616 | 11/2014 |
| CN | 104204803 | 12/2014 |
| CN | 104204808 | 12/2014 |
| CN | 104969071 | 10/2015 |
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| RU | 2007122617 | 12/2008 |
| RU | 2011111875 | 10/2012 |
| UA | 78641 | 3/2013 |
| UA | 92843 | 9/2014 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |
| WO | WO 2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2008/028489 | 3/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/100907 | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/040062 | 3/2013 |
| WO | WO 2013/117746 | 8/2013 |
| WO | WO 2014/006408 | 1/2014 |
| WO | WO 2014/008545 | 1/2014 |
| WO | WO 2014/049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Hastie et al. "The Elements of Statistical Learning: Data Mining, Inference, and Prediction", Springer Series in Statistics, 2nd Ed., p. 1-745, 2001. (Part 2).
Hastie et al. "The Elements of Statistical Learning: Data Mining, Inference, and Prediction", Springer Series in Statistics, 2nd Ed., p. 1-745, 2001. (Part 3).
Hastie et al. "The Elements of Statistical Learning: Data Mining, Inference, and Prediction", Springer Series in Statistics, 2nd Ed., p. 1-745, 2001. (Part 4).
Mount "Bioinformatics: Sequence and Genome Analysis", Chaps. 1-10: 1-564, 2001. (Part 1).
Mount "Bioinformatics: Sequence and Genome Analysis", Chaps. 1-10: 1-564, 2001. (Part 2).
Mount "Bioinformatics: Sequence and Genome Analysis", Chaps. 1-10: 1-564, 2001. (Part 3).
Vapnik "Statistical Learning Theory", Adaptive and Learning Systems for Signal Processing, Communications, and Control, p. 1-732, 1998. (Part 1).
Vapnik "Statistical Learning Theory", Adaptive and Learning Systems for Signal Processing, Communications, and Control, p. 1-732, 1998. (Part 2).
Vapnik "Statistical Learning Theory", Adaptive and Learning Systems for Signal Processing, Communications, and Control, p. 1-732, 1998. (Part 3).
Vapnik "Statistical Learning Theory", Adaptive and Learning Systems for Signal Processing, Communications, and Control, p. 1-732, 1998. (Part 4).
Restriction Official Action Dated Nov. 27, 2023 from the US Patent and Trademark Office Re. U.S. Appl. No. 17/010,912. (8 pages).
Requisition Dated Oct. 10, 2023 From the Innovation, Science and Economic Development Canada, Canadian Intellectual Property Office Re. Application No. 3,027,341. (5 Pages).
Advisory Action Before the Filing of An Appeal Brief Dated Dec. 23, 2019 From the US Patent and Trademark Office Re. U.S. Appl. No. 16/157,193. (3 pages).
Advisory Action Dated Mar. 9, 2022 from US Patent and Trademark Office Re. U.S. Appl. No. 16/081,906. (3 pages).
Advisory Action Dated Dec. 20, 2021 from US Patent and Trademark Office Re. U.S. Appl. No. 16/081,069. (7 pages).
Applicant-Initiated Interview Summary Dated Jul. 6, 2016 From the US Patent and Trademark Office Re. U.S. Appl. No. 14/377,887.
Applicant-Initiated Interview Summary Dated Feb. 10, 2020 From the US Patent and Trademark Office Re. U.S. Appl. No. 16/157,193. (3 pages).
Applicant-Initiated Interview Summary Dated Jul. 17, 2015 From the US Patent and Trademark Office Re. U.S. Appl. No. 13/090,893.
Applicant-Initiated Interview Summary Dated Feb. 22, 2017 From the US Patent and Trademark Office Re. U.S. Appl. No. 14/377,887. (3 Pages).
Applicant-Initiated Interview Summary Dated Oct. 26, 2017 From the US Patent and Trademark Office Re. U.S. Appl. No. 15/237,728. (3 pages).
Applicant-Initiated Interview Summary Dated Jul. 30, 2018 From the US Patent and Trademark Office Re. U.S. Appl. No. 15/641,400. (3 pages).
Communication of Notices of Opposition (R79(1) EPC) Dated May 4, 2022 From the European Patent Office Re. Application No. 17759388.6. (1 Page).
Communication Pursuant to Article 94(3) EPC Dated Jun. 2, 2021 From the European Patent Office Re. Application No. 17827121.9. (5 Pages).
Communication Pursuant to Article 94(3) EPC Dated Jun. 4, 2020 From the European Patent Office Re. Application No. 17759388.6. (3 Pages).

(56) References Cited

OTHER PUBLICATIONS

Communication Pursuant to Article 94(3) EPC Dated May 7, 2019 From the European Patent Office Re. Application No. 15831781.8. (3 Pages).
Communication Pursuant to Article 94(3) EPC Dated Dec. 9, 2016 From the European Patent Office Re. Application No. 13703112.6. (4 Pages).
Communication Pursuant to Article 94(3) EPC Dated Oct. 9, 2018 From the European Patent Office Re. Application No. 11748712.4. (8 Pages).
Communication Pursuant to Article 94(3) EPC Dated Nov. 12, 2020 From the European Patent Office Re. Application No. 17759389.4. (6 Page).
Communication Pursuant to Article 94(3) EPC Dated Jun. 17, 2016 From the European Patent Office Re. Application No. 11748712.4.
Communication Pursuant to Article 94(3) EPC Dated Mar. 17, 2021 From the European Patent Office Re. Application No. 15868614.7. (5 Pages).
Communication Pursuant to Article 94(3) EPC Dated Aug. 18, 2020 From the European Patent Office Re. Application No. 11748712.4. (3 Pages).
Communication Pursuant to Article 94(3) EPC Dated Jul. 21, 2023 From the European Patent Office Re. Application No. 21178885.6 (6 Pages).
Communication Pursuant to Article 94(3) EPC Dated Sep. 23, 2022 From the European Patent Office Re. Application No. 17855163.6. (7 Pages).
Communication Pursuant to Article 94(3) EPC Dated Mar. 25, 2020 From the European Patent Office Re. Application No. 18162713.4. (5 Pages).
Communication Pursuant to Article 94(3) EPC Dated May 25, 2020 From the European Patent Office Re. Application No. 11748712.4. (7 Pages).
Communication Pursuant to Article 94(3) EPC Dated Sep. 25, 2020 From the European Patent Office Re. Application No. 17827122.7. (5 Pages).
Communication Pursuant to Article 94(3) EPC Dated Mar. 27, 2020 From the European Patent Office Re. Application No. 15868614.7. (6 Pages).
Communication Pursuant to Article 94(3) EPC Dated Jul. 31, 2019 From the European Patent Office Re. Application No. 18162713.4. (4 Pages).
Decision on Rejection Dated Aug. 30, 2022 From the National Intellectual Property Administration of the People's Republic of China Re. Application No. 201780073531.5 and Its Translation Into English. (13 Pages).
Decision to Refuse a European Patent Application Dated Mar. 15, 2023 From the European Patent Office Re. Application No. 17759389. 4. (4 Pages).
English Summary Dated Dec. 29, 2022 of Notification of Office Action Dated Dec. 2, 2022 From the State Intellectual Property Office of the People's Republic of China Re. Application No. 202010370187.X. (1 Page).
English Translation Dated May 10, 2022 of Examination Report Dated Apr. 14, 2022 From the Servico Publico Federal, Ministerio da Economia, Instituto Nacional da Propriedade Industrial do Brasil RE Application No. BR11 2017 002884 0. (3 Pages).
English Translation Dated Feb. 16, 2022 of Grounds of Reason of Rejection Dated Jan. 27, 2022 From the Korean Intellectual Property Office Re. Application No. 10-2017-7007002. (6 Pages).
European Search Report and the European Search Opinion Dated Oct. 6, 2021 From the European Patent Office Re. Application No. 21178885.6. (10 Pages).
European Search Report and the European Search Opinion Dated Jul. 14, 2021 From the European Patent Office Re. Application No. 21170448.1. (6 Pages).
European Search Report and the European Search Opinion Dated May 16, 2018 From the European Patent Office Re. Application No. 18162713.4. (7 Pages).
European Search Report and the European Search Opinion Dated Sep. 28, 2020 From the European Patent Office Re. Application No. 20164056.2. (10 Pages).
Examination Report Dated Oct. 6, 2017 From the Australian Government, IP Australia Re. Application No. 2013217935. (2 Pages).
Examination Report Dated Apr. 14, 2022 From the Servico Publico Federal, Ministerio da Economia, Instituto Nacional da Propriedade Industrial do Brasil RE Application No. BR11 2017 002884 0 together with an English Summary and Pending Claims. (8 Pages).
Examination Report Dated Feb. 19, 2022 From the Servico Publico Federal, Ministerio da Economia, Instituto Nacional da Propriedade Industrial do Brasil RE Application No. BR112014 019733.4. (4 Pages).
Examination Report Dated May 29, 2019 From the Australian Government, IP Australia Re. Application No. 2018202302. (5 Pages).
Examination Report Under Sections 12 & 13 of the Patents Act, 1970 and the Patents Rules, 2003 Dated Oct. 21, 2019 From the Government of India, Intellectual Property India, Patents, Designs, Trade Marks, Geographical Indications Re. Application No. 9122/DELNP/2012 (5 Pages).
Examination Report Under Sections 12 & 13 of the Patents Act, 1970 and the Patents Rules, 2003 Dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 Dated Nov. 30, 2018 From the Government of India, Intellectual Property India, Patents, Designs, Trade Marks, Geographical Indications Re. Application No. 1780/MUMNP/2014. (7 Pages).
Examination Report Under Sections 12 & 13 of the Patents Act, 1970 and the Patents Rules, 2003 Dated Mar. 31, 2021 From the Government of India, Intellectual Property India, Patents, Designs, Trade Marks, Geographical Indications, The Patent Office Re. Application No. 201727005513. (7 Pages).
Examiner-Initiated Interview Summary Dated Nov. 27, 2017 From the US Patent and Trademark Office Re. U.S. Appl. No. 15/518,491. (2 pages).
Final Official Action Dated Sep. 3, 2021 From the US Patent and Trademark Office Re. U.S. Appl. No. 16/316,631. (37 Pages).
Final Official Action Dated Sep. 10, 2021 from the US Patent and Trademark Office Re. U.S. Appl. No. 16/081,069. (61 pages).
Final Official Action Dated Jun. 15, 2021 From the US Patent and Trademark Office Re. U.S. Appl. No. 16/334,033. (36 Pages).
Final Official Action Dated Nov. 29 together with Interview Summary Dated Nov. 14, 2021 from US Patent and Trademark Office Re. U.S. Appl. No. 16/081,906. (45 pages).
Final Official Action Dated Sep. 8, 2020 from the US Patent and Trademark Office Re. U.S. Appl. No. 16/687,726. (28 pages).
Grounds of Reason of Rejection Dated Jan. 27, 2022 From the Korean Intellectual Property Office Re. Application No. 10-2017-7007002. (6 Pages).
Hearing Notice Dated Jul. 16, 2019 From the Government of India, Patent Office, Intellectual Property Building Re. Application No. 1780/MUMNP/2014. (3 Pages).
International Preliminary Report on Patentability Dated Apr. 11, 2019 From the International Bureau of WIPO Re. Application No. PCT/IL2017/051088. (6 Pages).
International Preliminary Report on Patentability Dated Apr. 11, 2019 From the International Bureau of WIPO Re. Application No. PCT/IL2017/051089. (7 Pages).
International Preliminary Report on Patentability Dated Sep. 13, 2018 From the International Bureau of WIPO Re. Application No. PCT/IL2017/050270. (7 Pages).
International Preliminary Report on Patentability Dated Sep. 13, 2018 From the International Bureau of WIPO Re. Application No. PCT/IL2017/050271. (9 Pages).
International Preliminary Report on Patentability Dated Jun. 22, 2017 From the International Bureau of WIPO Re. Application No. PCT/IL2015/051201. (7 Pages).

(56) References Cited

OTHER PUBLICATIONS

International Preliminary Report on Patentability Dated Feb. 23, 2017 From the International Bureau of WIPO Re. Application No. PCT/IL2015/050823. (7 Pages).
International Preliminary Report on Patentability Dated Jan. 24, 2019 From the International Bureau of WIPO Re. Application No. PCT/IL2017/050780. (9 Pages).
International Preliminary Report on Patentability Dated Jan. 24, 2019 From the International Bureau of WIPO Re. Application No. PCT/IL2017/050781. (7 Pages).
International Preliminary Report on Patentability Dated Apr. 27, 2017 From the International Bureau of WIPO Re. Application No. PCT/IL2015/051024. (7 Pages).
International Search Report and the Written Opinion Dated Mar. 12, 2012 From the International Searching Authority Re. Application No. PCT/IB2011/001299.
International Search Report and the Written Opinion Dated Sep. 14, 2017 From the International Searching Authority Re. Application No. PCT/IL2017/050781. (12 Pages).
International Search Report and the Written Opinion Dated Jun. 15, 2017 From the International Searching Authority Re. Application No. PCT/IL2017/050270. (13 Pages).
International Search Report and the Written Opinion Dated Jun. 15, 2017 From the International Searching Authority Re. Application No. PCT/IL2017/050271. (16 Pages).
International Search Report and the Written Opinion Dated Sep. 18, 2017 From the International Searching Authority Re. Application No. PCT/IL2017/050780. (15 Pages).
International Search Report and the Written Opinion Dated Jan. 20, 2016 From the International Searching Authority Re. Application No. PCT/IL2015/051024.
International Search Report and the Written Opinion Dated Feb. 22, 2016 From the International Searching Authority Re. Application No. PCT/IL2015/051201.
International Search Report and the Written Opinion Dated Dec. 25, 2017 From the International Searching Authority Re. Application No. PCT/IL2017/051088. (9 Pages).
International Search Report and the Written Opinion Dated Dec. 28, 2017 From the International Searching Authority Re. Application No. PCT/IL2017/051089. (10 Pages).
International Search Report and the Written Opinion Dated Nov. 29, 2015 From the International Searching Authority Re. Application No. PCT/IL2015/050823.
International Search Report Dated Apr. 5, 2013 From the International Searching Authority Re. Application No. PCT/EP2013/052619.
Interview Summary Dated Feb. 1, 2021 From the US Patent and Trademark Office Re. U.S. Appl. No. 16/687,726. (2 Pages).
Interview Summary Dated Dec. 3, 2021 from US Patent and Trademark Office Re. U.S. Appl. No. 16/081,069. (3 pages).
Interview Summary Dated Oct. 14, 2020 from the US Patent and Trademark Office Re. U.S. Appl. No. 16/081,906. (3 pages).
Interview Summary Dated Feb. 22, 2022 from US Patent and Trademark Office Re. U.S. Appl. No. 16/081,906. (2 pages).
Interview Summary Dated Apr. 29, 2022 from US Patent and Trademark Office Re. U.S. Appl. No. 16/081,906. (2 pages).
Notice of Allowance Dated Feb. 7, 2022 from US Patent and Trademark Office Re. U.S. Appl. No. 16/336,528. (46 pages).
Notice of Allowance Dated Mar. 2, 2022 from US Patent and Trademark Office Re. U.S. Appl. No. 16/081,069. (10 pages).
Notice Of Allowance Dated Feb. 4, 2019 From the US Patent and Trademark Office Re. U.S. Appl. No. 15/503,439. (6 pages).
Notice of Allowance Dated Jan. 5, 2022 from US Patent and Trademark Office Re. U.S. Appl. No. 16/316,631. (9 pages).
Notice of Allowance Dated May 10, 2023 from the US Patent and Trademark Office Re. U.S. Appl. No. 17/875,467. (122 pages).
Notice of Allowance Dated Sep. 10, 2020 from the US Patent and Trademark Office Re. U.S. Appl. No. 16/157,193. (13 pages).
Notice of Allowance Dated Mar. 16, 2022 from US Patent and Trademark Office Re. U.S. Appl. No. 16/998,006. (28 pages).
Notice of Allowance Dated Mar. 17, 2022 from US Patent and Trademark Office Re. U.S. Appl. No. 16/334,033. (29 pages).
Notice of Allowance Dated May 17, 2022 From the US Patent and Trademark Office Re. U.S. Appl. No. 16/081,906. (14 Pages).
Notice of Allowance Dated Apr. 19, 2021 from the US Patent and Trademark Office Re. U.S. Appl. No. 16/238,582. (22 pages).
Notice of Allowance Dated May 22, 2020 from the US Patent and Trademark Office Re. U.S. Appl. No. 16/355,984. (18 pages).
Notice Of Allowance Dated Jul. 29, 2019 From the US Patent and Trademark Office Re. U.S. Appl. No. 15/237,728. (21 pages).
Notice of Allowance Dated and Interview Summary Jul. 19, 2021 from the US Patent and Trademark Office Re. U.S. Appl. No. 16/687,726. (24 pages).
Notice of Non-Compliant Amendment Dated Aug. 4, 2015 From the US Patent and Trademark Office Re. U.S. Appl. No. 13/090,893.
Notice of Reason for Rejection Dated Nov. 12, 2019 From the Japan Patent Office Re. Application No. 2017-126712 and an English Summary. (3 Pages).
Notice of Reason for Rejection Dated Aug. 20, 2019 From the Japan Patent Office Re. Application No. 2017-507867 and Its Translation Into English. (5 Pages).
Notice of Reason(s) for Rejection Dated Dec. 7, 2021 From the Japan Patent Office Re. Application No. 2020-021606 and Its Translation Into English. (11 Pages).
Notice of Reason(s) for Rejection Dated Dec. 14, 2021 From the Japan Patent Office Re. Application No. 2020-109710 and Its Translation Into English. (7 Pages).
Notice of Reason(s) for Rejection Dated Jun. 15, 2021 From the Japan Patent Office Re. Application No. 2020-109710 and Its Translation Into English. (12 Pages).
Notice of Reasons for Rejection Dated Nov. 1, 2016 From the Japan Patent Office Re. Application No. 2014-556086 and Its Translation Into English. (12 Pages).
Notice of Reasons for Rejection Dated Apr. 2, 2019 From the Japan Patent Office Re. Application No. 2017-126712 and Its Translation Into English. (8 Pages).
Notice of Reasons for Rejection Dated Jun. 19, 2018 From the Japan Patent Office Re. Application No. 2017-126712 and Its Translation Into English. (9 Pages).
Notice of Reasons for Rejection Dated Apr. 20, 2021 From the Japan Patent Office Re. Application No. 2020-021606 and Its Translation Into English. (9 Pages).
Notice on Office Action and the Search Report Dated Feb. 25, 2015 From The State Intellectual Property Office of the People's Republic of China Re. Application No. 201180030792.1 and Its Translation Into English.
Notification of Lack of Unity and Search Report Dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Notification of Office Action and Search Report Dated Dec. 2, 2022 From the State Intellectual Property Office of the People's Republic of China Re. Application No. 202010370187.X. (12 Pages).
Notification of Office Action and Search Report Dated Jul. 2, 2021 From the State Intellectual Property Office of the People's Republic of China Re. Application No. 201780055014.5. (23 Pages).
Notification of Office Action and Search Report Dated Aug. 3, 2021 From the State Intellectual Property Office of the People's Republic of China Re. Application No. 201780055347.8 and Its Translation of Office Action Into English. (26 Pages).
Notification of Office Action and Search Report Dated Jun. 3, 2021 From the State Intellectual Property Office of the People's Republic of China Re. Application No. 20180014541.1 and Its Translation Into English. (17 Pages).
Notification of Office Action and Search Report Dated Mar. 4, 2016 From the State Intellectual Property Office of the People's Republic of China Re. Application No. 201380019055.0.
Notification of Office Action and Search Report Dated Dec. 9, 2022 From the State Intellectual Property Office of the People's Republic of China Re. Application No. 202010215941.2. (11 Pages).

(56) References Cited

OTHER PUBLICATIONS

Notification of Office Action and Search Report Dated Jan. 11, 2019 From the State Intellectual Property Office of the People's Republic of China Re. Application No. 201580055946.0. (5 Pages).
Notification of Office Action and Search Report Dated Feb. 13, 2017 From the State Intellectual Property Office of the People's Republic of China Re. Application No. 201380019055.0 and Its Translation of Office Action Into English. (10 Pages).
Notification of Office Action and Search Report Dated Jul. 13, 2021 From the State Intellectual Property Office of the People's Republic of China Re. Application No. 20180781584.9 and an English Summary. (4 Pages).
Notification of Office Action and Search Report Dated Mar. 15, 2022 From the State Intellectual Property Office of the People's Republic of China Re. Application No. 201780055347.8 and Its Translation of Office Action Into English. (28 Pages).
Notification of Office Action and Search Report Dated Feb. 19, 2019 From the State Intellectual Property Office of the People's Republic of China Re. Application No. 201580075265.0 and a Summary of the Notification of Office Action Into English.(7 Pages).
Notification of Office Action and Search Report Dated Jun. 19, 2018 From the State Intellectual Property Office of the People's Republic of China Re. Application No. 201580075265.0 and its English Summary. (14 Pages).
Notification of Office Action and Search Report Dated Apr. 20, 2022 From the National Intellectual Property Administration of the People's Republic of China Re. Application No. 201780073531.5 and Its Translation Into English Including Claims. (31 Pages).
Notification of Office Action and Search Report Dated Feb. 20, 2021 From the State Intellectual Property Office of the People's Republic of China Re. Application No. 201780014568.0 and Its Translation Into English. (22 Pages).
Notification of Office Action and Search Report Dated Dec. 23, 2021 From the State Intellectual Property Office of the People's Republic of China Re. Application No. 201780014541.1 and Its Translation of Office Action Into English. (14 Pages).
Notification of Office Action and Search Report Dated Jul. 28, 2020 From the State Intellectual Property Office of the People's Republic of China Re. Application No. 201810781584.9 and Its Translation of Office Action Into English. (17 Pages).
Notification of Office Action and Search Report Dated Oct. 30, 2017 From the State Intellectual Property Office of the People's Republic of China Re. Application No. 201610817276.8. (10 Pages).
Notification of Office Action and Search Report Dated Sep. 30, 2021 From the State Intellectual Property Office of the People's Republic of China Re. Application No. 201780073531.5 and Its Translation of Office Action Into English. (14 Pages).
Notification of Office Action Dated Sep. 1, 2021 From the State Intellectual Property Office of the People's Republic of China Re. Application No. 201780014568.0 and Its Translation Into English. (7 Pages).
Notification of Office Action Dated Jul. 2, 2019 From the State Intellectual Property Office of the People's Republic of China Re. Application No. 201580075265.0. (3 Pages).
Notification of Office Action Dated Dec. 3, 2021 From the State Intellectual Property Office of the People's Republic of China Re. Application No. 201780055014.5 and Its Translation Into English. (5 Pages).
Notification of Office Action Dated Jul. 3, 2015 From the State Intellectual Property Office of the People's Republic of China Re. Application No. 201380019055.0.
Notification of Office Action Dated Jun. 3, 2019 From the China National Intellectual Property Administration Re. Application No. 201610817276.8 and Its Translation Into English. (10 Pages).
Notification of Office Action Dated Aug. 4, 2016 From the State Intellectual Property Office of the People's Republic of China Re. Application No. 201380019055.0 and Its Translation Into English.
Notification of Office Action Dated Mar. 5, 2021 From the State Intellectual Property Office of the People's Republic of China Re. Application No. 201810781584.9 and Its Translation of Office Action Into English. (13 Pages).
Notification of Office Action Dated May 6, 2014 From the State Intellectual Property Office of the People's Republic of China Re. Application No. 201180030792.1 and Its Translation Into English.
Notification of Office Action Dated May 11, 2022 From the State Intellectual Property Office of the People's Republic of China Re. Application No. 201780014541.1 and Its Translation Into English. (11 Pages).
Notification of Office Action Dated Jun. 20, 2018 From the State Intellectual Property Office of the People's Republic of China Re. Application No. 201580055946.0 and Its Summary in English. (5 Pages).
Notification of Office Action Dated Jan. 21, 2016 From the State Intellectual Property Office of the People's Republic of China Re. Application No. 201180030792.1 and Its Translation Into English.
Notification of Office Action Dated Aug. 22, 2019 From the State Intellectual Property Office of the People's Republic of China Re. Application No. 201580055946.0. (3 Pages).
Notification of Office Action Dated Jan. 24, 2022 From the State Intellectual Property Office of the People's Republic of China Re. Application No. 201780014568.0 and its Translation into English. (9 Pages).
Notification of Office Action Dated Aug. 25, 2017 From the State Intellectual Property Office of the People's Republic of China Re. Application No. 201380019055.0. (6 Pages).
Notification of Office Action Dated Aug. 28, 2015 From the State Intellectual Property Office of the People's Republic of China Re. Application No. 201180030792.1 and Its Translation Into English.
Notification of Office Action Dated Aug. 30, 2018 From the State Intellectual Property Office of the People's Republic of China Re. Application No. 201610817276.8 and Its Translation Into English. (22 Pages).
Notification of Reexamination Dated Jan. 12, 2018 From the State Intellectual Property Office of the People's Republic of China Re. Application No. 2013800190 and Its Machine Translation into English.
Office Action Dated Feb. 18, 2019 From the Israel Patent Office Re. Application No. 250585 and Its Translation Into English. (6 Pages).
Office Action Dated Nov. 28, 2019 From the Israel Patent Office Re. Application No. 254095 and Its Translation Into English. (7 Pages).
Office Action Dated Feb. 29, 2016 From the Israel Patent Office Re. Application No. 233998 and Its Translation Into English.
Office Action Dated Jul. 30, 2020 From the Israel Patent Office Re. Application No. 261529 and Its Translation Into English. (5 Pages).
Office Action Dated Jul. 30, 2020 From the Israel Patent Office Re. Application No. 261530 and Its Translation Into English. (5 Pages).
Official Action Dated Sep. 1, 2015 From the US Patent and Trademark Office Re. U.S. Appl. No. 13/090,893.
Official Action Dated Aug. 2, 2023 from the US Patent and Trademark Office Re. U.S. Appl. No. 16/081,069. (36 pages).
Official Action Dated Feb. 3, 2020 From the US Patent and Trademark Office Re. U.S. Appl. No. 16/355,984. (24 pages).
Official Action Dated Apr. 4, 2016 From the US Patent and Trademark Office Re. U.S. Appl. No. 13/090,893.
Official Action Dated Jan. 4, 2019 From the US Patent and Trademark Office Re. Application No. 151713,722. (72 pages).
Official Action Dated Nov. 4, 2020 From the US Patent and Trademark Office Re. U.S. Appl. No. 16/238,582. (37 Pages).
Official Action Dated Mar. 5, 2020 From the US Patent and Trademark Office Re. U.S. Appl. No. 15/713,722. (24 pages).
Official Action Dated May 5, 2021 From the US Patent and Trademark Office Re. U.S. Appl. No. 16/336,528. (108 Pages).
Official Action Dated Feb. 6, 2018 From the US Patent and Trademark Office Re. U.S. Appl. No. 15/503,439. (63 pages).
Official Action Dated Nov. 7, 2016 From the US Patent and Trademark Office Re. U.S. Appl. No. 13/090,893. (26 pages).
Official Action Dated Jun. 9, 2022 from US Patent and Trademark Office Re. U.S. Appl. No. 17/007,095. (118 pages).
Official Action Dated Mar. 9, 2021 From the US Patent and Trademark Office Re. U.S. Appl. No. 16/316,631. (121 Pages).

(56) References Cited

OTHER PUBLICATIONS

Official Action Dated Jun. 10, 2013 From the US Patent and Trademark Office Re. U.S. Appl. No. 13/090,893.
Official Action Dated Mar. 10, 2021 From the US Patent and Trademark Office Re. U.S. Appl. No. 16/081,906. (127 Pages).
Official Action Dated Apr. 12, 2018 From the US Patent and Trademark Office Re. U.S. Appl. No. 15/518,491. (59 pages).
Official Action Dated Aug. 12, 2015 From the US Patent and Trademark Office Re. U.S. Appl. No. 14/377,887.
Official Action Dated May 12, 2017 From the US Patent and Trademark Office Re. U.S. Appl. No. 15/237,728. (27 pages).
Official Action Dated Apr. 13, 2016 From the US Patent and Trademark Office Re. U.S. Appl. No. 14/377,887.
Official Action Dated Mar. 13, 2014 From the US Patent and Trademark Office Re. U.S. Appl. No. 13/090,893.
Official Action Dated Apr. 15, 2019 From the US Patent and Trademark Office Re. U.S. Appl. No. 15/237,728. (16 Pages).
Official Action Dated Dec. 15, 2016 From the US Patent and Trademark Office Re. U.S. Appl. No. 14/377,887. (22 pages).
Official Action Dated May 15, 2018 From the US Patent and Trademark Office Re. U.S. Appl. No. 15/237,728. (55 pages).
Official Action Dated May 15, 2020 From the US Patent and Trademark Office Re. U.S. Appl. No. 16/238,582. (92 Pages).
Official Action Dated Oct. 15, 2019 From the US Patent and Trademark Office Re. U.S. Appl. No. 15/1713,722. (57 Pages).
Official Action Dated Nov. 16, 2018 From the US Patent and Trademark Office Re. U.S. Appl. No. 15/503,439. (41 pages).
Official Action Dated Sep. 16, 2019 From the US Patent and Trademark Office Re. U.S. Appl. No. 16/355,984. (44 pages).
Official Action Dated Dec. 17, 2018 From the US Patent and Trademark Office Re. U.S. Appl. No. 15/237,728. (39 pages).
Official Action Dated Jul. 17, 2023 from US Patent and Trademark Office Re. U.S. Appl. No. 17/717,200. (133 pages).
Official Action Dated Nov. 18, 2016 From the US Patent and Trademark Office Re. U.S. Appl. No. 15/237,728. (33 pages).
Official Action Dated Sep. 18, 2019 From the US Patent and Trademark Office Re. U.S. Appl. No. 16/157,193. (30 pages).
Official Action Dated Apr. 19, 2023 from the US Patent and Trademark Office Re. U.S. Appl. No. 17/507,994. (189 pages).
Official Action Dated Oct. 20, 2020 From the US Patent and Trademark Office Re. U.S. Appl. No. 16/081,069. (112 Pages).
Official Action Dated Nov. 22, 2021 from the US Patent and Trademark Office Re. U.S. Appl. No. 16/998,006. (116 pages).
Official Action Dated Apr. 23, 2019 From the US Patent and Trademark Office Re. U.S. Appl. No. 16/157,193. (47 pages).
Official Action Dated Nov. 23, 2020 From the US Patent and Trademark Office Re. U.S. Appl. No. 16/355,984. (9 pages).
Official Action Dated Oct. 24, 2019 From the US Patent and Trademark Office Re. U.S. Appl. No. 15/531,747. (37 Pages).
Official Action Dated Jan. 26, 2017 From the US Patent and Trademark Office Re. U.S. Appl. No. 15/015,309. (45 pages).
Official Action Dated Mar. 26, 2015 From the US Patent and Trademark Office Re. U.S. Appl. No. 13/090,893.
Official Action Dated Mar. 26, 2020 from the US Patent and Trademark Office Re. U.S. Appl. No. 16/687,726. (47 pages).
Official Action Dated Apr. 30, 2018 From the US Patent and Trademark Office Re. U.S. Appl. No. 15/641,400. (62 pages).
Official Action Dated Dec. 30, 2020 from the US Patent and Trademark Office Re. U.S. Appl. No. 16/334,033. (112 pages).
Official Action Dated Mar. 30, 2018 From the US Patent and Trademark Office Re. U.S. Appl. No. 15/531,747. (67 pages).
Official Action Dated Mar. 31, 2020 from the US Patent and Trademark Office Re. U.S. Appl. No. 15/531,747. (21 pages).
Official Action Dated Dec. 6, 2022 from the US Patent and Trademark Office Re. U.S. Appl. No. 16/081,069. (20 pages).
Official Action Dated May 7, 2020 from the US Patent and Trademark Office Re. U.S. Appl. No. 16/157,193. (23 pages).
Opposition to European Patent No. 3423589 Memed Diagnostics Ltd. on Behalf of J.A. Kemp LLP Dated Apr. 21, 2022 From the European Patent Office Re. Application No. 17759388.6. (31 Pages).

Partial European Search Report and Provisional Opinion Dated Jun. 25, 2020 From the European Search Report Re. Application No. 20164056.2. (11 Pages).
Partial European Search Report and the European Search Opinion Dated Jan. 31, 2023 From the European Patent Office Re. Application No. 22169859.0. (13 Pages).
Patent Examination Report Dated Feb. 8, 2021 From the Australian Government, IP Australia Re. Application No. 2015302870. (4 Pages).
Request for Examination Dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).
Requisition Dated Mar. 2, 2023 From the Innovation, Science and Economic Development Canada, Canadian Intellectual Property Office Re. Application No. 3,015,043. (5 Pages).
Requisition Dated Oct. 4, 2019 From the Innovation, Science and Economic Development Canada, Canadian Intellectual Property Office Re. Application No. 2,863,819. (3 Pages).
Requisition Dated Nov. 5, 2021 From the Innovation, Science and Economic Development Canada, Canadian Intellectual Property Office Re. Application No. 2,968,650. (7 Pages).
Requisition Dated Dec. 7, 2020 From the Innovation, Science and Economic Development Canada, Canadian Intellectual Property Office Re. Application No. 2,863,819. (4 Pages).
Requisition Dated Jun. 7, 2022 From the Innovation, Science and Economic Development Canada, Canadian Intellectual Property Office Re. Application No. 2,968,650. (3 Pages).
Requisition Dated Feb. 9, 2022 From the Innovation, Science and Economic Development Canada, Canadian Intellectual Property Office Re. Application No. 2,954,601. (3 Pages).
Requisition Dated Nov. 9, 2018 From the Innovation, Science and Economic Development Canada, Canadian Intellectual Property Office Re. Application No. 2,796,666. (3 Pages).
Requisition Dated Jul. 15, 2022 From the Innovation, Science and Economic Development Canada, Canadian Intellectual Property Office Re. Application No. 3,133,249. (4 Pages).
Requisition Dated Jan. 18, 2018 From the Innovation, Science and Economic Development Canada, Canadian Intellectual Property Office Re. Application No. 2,796,666. (5 Pages).
Requisition Dated Feb. 21, 2019 From the Innovation, Science and Economic Development Canada, Canadian Intellectual Property Office Re. Application No. 2,863,819. (8 Pages).
Requisition Dated Mar. 21, 2023 From the Innovation, Science and Economic Development Canada, Canadian Intellectual Property Office Re. Application No. 3,015,046. (6 pages).
Requisition Dated Jul. 30, 2021 From the Innovation, Science and Economic Development Canada, Canadian Intellectual Property Office Re. Application No. 2,954,601. (16 Pages).
Restriction Official Action Dated Apr. 2, 2020 From the US Patent and Trademark Office Re. U.S. Appl. No. 16/081,069. (7 Pages).
Restriction Official Action Dated Nov. 2, 2017 From the US Patent and Trademark Office Re. U.S. Appl. No. 15/531,747. (9 pages).
Restriction Official Action Dated Feb. 4, 2022 from US Patent and Trademark Office Re. U.S. Appl. No. 17/007,095. (6 pages).
Restriction Official Action Dated Dec. 5, 2019 From the US Patent and Trademark Office Re. U.S. Appl. No. 16/081,906. (9 pages).
Restriction Official Action Dated Nov. 8, 2018 From the US Patent and Trademark Office Re. U.S. Appl. No. 16/157,193. (5 pages).
Restriction Official Action Dated May 10, 2018 From the US Patent and Trademark Office Re. U.S. Appl. No. 15/713,722. (6 Pages).
Restriction Official Action Dated Sep. 10, 2020 from the US Patent and Trademark Office Re. U.S. Appl. No. 16/316,631. (6 pages).
Restriction Official Action Dated Feb. 13, 2013 From the US Patent and Trademark Office Re. U.S. Appl. No. 13/090,893.
Restriction Official Action Dated May 15, 2015 From the US Patent and Trademark Office Re. U.S. Appl. No. 14/377,887.
Restriction Official Action Dated Mar. 29, 2021 From the US Patent and Trademark Office Re. U.S. Appl. No. 16/081,069. (8 Pages).
Restriction Official Action Dated Nov. 29, 2019 From the US Patent and Trademark Office Re. U.S. Appl. No. 16/238,582. (7 pages).

(56) References Cited

OTHER PUBLICATIONS

Restriction Official Action Dated Jul. 30, 2020 from the US Patent and Trademark Office Re. U.S. Appl. No. 16/081,906. (7 pages).
Restriction Official Action Dated Aug. 31, 2017 From the US Patent and Trademark Office Re. U.S. Appl. No. 15/518,491. (6 pages).
Restriction Official Action Dated Dec. 9, 2020 from the US Patent and Trademark Office Re. U.S. Appl. No. 16/336,528. (7 pages).
Search Report and Opinion Dated Dec. 10, 2019 From the Servico Publico Federal, Ministerio da Economia, Instituto Nacional da Propriedade Industrial do Brasil Re. Application No. BR112017002884-0 and Its Translation Into English. (7 Pages).
Search Report and Opinion Dated Aug. 20, 2019 From the Servico Publico Federal, Ministerio da Economia, Instituto Nacional da Propriedade Industrial do Brasil Re. Application No. BR112014 019733-4 and Its Summary in English. (4 Pages).
Search Report Dated May 6, 2014 From the State Intellectual Property Office of the People's Republic of China Re. Application No. 201180030792.1 and Its Translation Into English.
Second Notice of Allowance Dated Dec. 12, 2018 From the US Patent and Trademark Office Re. U.S. Appl. No. 15/641,400. (7 pages).
Second Notice of Allowance Dated May 12, 2021 From the US Patent and Trademark Office Re. U.S. Appl. No. 16/355,984. (32 Pages).
Summary Dated Dec. 22, 2022 of Notification of Office Action and Search Report Dated Dec. 9, 2022 From the State Intellectual Property Office of the People's Republic of China Re. Application No. 202010215941.2. (4 Pages).
Summons to attend Oral Proceedings Pursuant to Rule 115(1) EPC Dated Jun. 10, 2022 From the European Patent Office Re. Application No. 17759389.4, (5 Pages).
Supplementary European Search Report and the European Search Opinion Dated May 4, 2020 From the European Patent Office Re. Application No. 17855163.6. (9 Pages).
Supplementary European Search Report and the European Search Opinion Dated Mar. 15, 2018 From the European Patent Office Re. Application No. 15831781.8. (11 Pages).
Supplementary European Search Report and the European Search Opinion Dated Sep. 17, 2018 From the European Patent Office Re. Application No. 15868614.7. (18 Pages).
Supplementary European Search Report and the European Search Opinion Dated Feb. 18, 2020 From the European Patent Office Re. Application No. 17827121.9. (5 Pages).
Supplementary European Search Report and the European Search Opinion Dated May 18, 2020 From the European Patent Office Re. Application No. 17855164.4. (13 Pages).
Supplementary European Search Report and the European Search Opinion Dated Jan. 21, 2020 From the European Patent Office Re. Application No. 17827122.7. (9 Pages).
Supplementary European Search Report and the European Search Opinion Dated Jan. 28, 2020 From the European Patent Office Re. Application No. 17759389.4. (11 Pages).
Supplementary European Search Report and the European Search Opinion Dated Mar. 28, 2023 From the European Patent Office Re. Application No. 22204952.0. (12 Pages).
Supplementary European Search Report and the European Search Opinion Dated Sep. 30, 2019 From the European Patent Office Re. Application No. 17759388.6. (11 Pages).
Supplementary Partial European Search Report and the European Provisional Opinion Dated Jun. 1, 2018 From the European Patent Office Re. Application No. 15868614.7. (23 Pages).
Supplementary Partial European Search Report and the European Provisional Opinion Dated Oct. 24, 2019 From the European Patent Office Re. Application No. 17759389.4. (15 Pages).
Technical Examination Report Dated Aug. 11, 2022 from the National Institute of Industrial Property of Brazil Re. Application No. BR 11 2017 002884 0 with an English Translation. (8 pages).
Translation Dated Sep. 4, 2017 of Notification of Office Action Dated Aug. 25, 2017 From the State Intellectual Property Office of the People's Republic of China Re. Application No. 201380019055. 0.
Translation Dated Apr. 5, 2016 of Notification of Office Action Dated Mar. 4, 2016 From the State Intellectual Property Office of the People's Republic of China Re. Application No. 201380019055. 0.
Translation Dated Jul. 10, 2019 of Notification of Office Action Dated Jul. 2, 2019 From the State Intellectual Property Office of the People's Republic of China Re. Application No. 201580075265.0. (1 Page).
Translation Dated Sep. 11, 2019 of Notification of Office Action Dated Aug. 22, 2019 From the State Intellectual Property Office of the People's Republic of China Re. Application No. 201580055946. 0. (1 Page).
Translation Dated Mar. 20, 2019 of Notification of Office Action Dated Feb. 19, 2019 From the State Intellectual Property Office of the People's Republic of China Re. Application No. 201580075265. 0. (5 Pages).
Translation Dated Nov. 21, 2019 of Reason for Rejection From the Japanese Patent Office Re. Application No. 2017-126712. (2 Pages).
Translation Dated Sep. 21, 2015 of Office Action Dated Jul. 3, 2015 From the State Intellectual Property Office of the People's Republic of China Re. Application No. 201380019055.0.
Translation Dated Jul. 22, 2021 of Notification of Office Action Dated Jul. 13, 2021 From the State Intellectual Property Office of the People's Republic of China Re. Application No. 20180781584. 9. (2 Pages).
Translation Dated Sep. 22, 2019 of Search Report and Opinion Dated Aug. 20, 2019 From the Servi?o Publico Federal, Ministerio da Economia, Instituto Nacional da Propriedade Industrial do Brasil Re. Application No. BR112014 019733-4 and Its Summary in English. (4 Pages).
Translation Dated Jul. 27, 2021 of Notification of Office Action Dated Jul. 2, 2021 From the State Intellectual Property Office of the People's Republic of China Re. Application No. 201780055014.5. (12 Pages).
Translation Dated Jan. 30, 2019 of Notification of Office Action Dated Jan. 11, 2019 From the State Intellectual Property Office of the People's Republic of China Re. Application No. 201580055946. 0.(1 Page).
Translation of Notification of Office Action and Search Report Dated Oct. 30, 2017 From the State Intellectual Property Office of the People's Republic of China Re. Application No. 201610817276. 8. (16 Pages).
Abdel-Razik et al. "Diagnostic Utility of Interferon Gamma-induced Protein 10 kDa in Spontaneous Bacterial Peritonitis: Single-Center Study", European Journal of Gastroenterology & Hepatology, 27(9): 1087-1093, Sep. 2015.
Affymetrix "Whole-Transcript Expression Analysis", Affymetrix, 8 pages, 2007.
Alexander et al. "*Staphylococcus aureus* and *Salmonella enterica* Serovar Dublin Induce Tumor Necrosis Factor-Related Apoptosis-Inducing Ligand Expression by Normal Mouse and Hurnan Osteoblasts", Infection and Immunity, 69(3): 1581-1586, Mar. 2001.
Ali et al. "Reliability of Serum Procalcitonin Concentrations for the Diagnosis of Sepsis in Neonates", Egypt Journal of Immunology, 15(1): 75-84, 2008. Abstract only.
Altmann et al. "Elevated Cardiac Troponin I in Sepsis and Septic Shock: No Evidence for Thrombus Associated Myocardial Necrosis", PLOSE One, 5(2): 1-5, 2010.
Ammann et al. "Elevation of Troponin I in Sepsis and Septic Shock", Intensive Care Medicine, 27: 965-969, May 16, 2001.
Arshed et al. "Elevated Troponin I in the Absence of Coronary Artery Disease: A Case Report with Review of Literature", Journal of Clinical Medicine Research, 7(10): 820-824, Aug. 23, 2015.
Bai et al. "A New Early Diagnostic Marker for Inflammatory Diseases—sTREM-1", International Journal of Pathology and Clinical Medicine, 27(1): 73-76, Feb. 2007.

(56) References Cited

OTHER PUBLICATIONS

Barnhart et al. "Changes in Cellular mRNA Stability, Splicing, and Polyadenylation Through HuR Protein Sequestration by a Cytoplasmic RNA Virus", Cell Reports, XP055621573, 5(4): 909-917, Nov. 27, 2013.

Becker et al. "Procalcitonin in Sepsis and Systemic Inflammation: a Harmful Biomarker and a Therapeutic Target", British Journal of Pharmacology, 159: 253-264, 2010.

Bessiere et al. "Prognostic Value of Troponins in Sepsis: a Meta-Analysis", Intensive Care Medicine, 39: 1181-1189, Apr. 18, 2018.

Biezeveld et al. "Sustained Activation of Neutrophils in the Course of Kawasaki Disease: An Association with Matrix Metalloproteinases", Clinical & Experimental Immunology 141(1): 183-188, Jul. 2005.

Bloos et al. "Rapid Diagnosis of Sepsis"; Virulence, 5(1): 154-160, 2014.

Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.

Bone et al. "Definitions for Sepsis and Organ Failure and Guidelines for the Use of Innovative Therapies in Sepsis", Chest, 101(6): 1644-1655, 1992.

Borjesson et al. "Insights Into Pathogen Immune Evasion Mechanisms: Anaplasma Phagocytophilum Fails to Induce An Apoptosis Differentiation Program in Human Neutrophils", The Jurnal of Immunology, 174: 6364-6372, 2005.

Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.

Brost et al. "Differential Expression of the TRAIL/TRAIL-receptor System in Patients with Inflammatory Bowel Disease", Pathology—Research and Practice, 206(1):43-50, Jan. 15, 2010.

Cai et al. "The Study on the Relationship Between PCT and CRP in Infective Diseases", Journ al of Qiqihar University of Medicine, 32(5): 696-697, 2011.

Calvano et al. "A Network-Based Analysis of Systemic Inflammation in Humans", Nature, 437: 1032-1037, Oct. 13, 2005.

Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.

Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.

Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.

Chaussabel et al. "Assessing the Human Immune System Through Blood Transcriptomics", BMC Biology, 8: 84-1-84-14, Jul. 1, 2010.

Chen et al. "Discordant Protein and mRNA Expression in Lung Adenocarcinomas", Molecular & Cellular Proteomics: MCP, 1(4): 304-313, Apr. 2002.

Chieux et al. "MxA Protein in Capillary Blood of Children With Viral Infections", Journal of Medical Virology, 59: 547-551, 1999.

Chieux et al. "The MxA Protein Levels in Whole Blood Lysates of Patients With Various Viral Infections", Journal of Virological Methods, 70: 183-191, 1998.

CNKI "Clinical Study on the Level of Plasma Tumor Necrosis Factor-Related Apoptosis-Inducing Ligand (TRAIL) in Evaluating the Prognosis of Patients With Sepsis", CNKI Master's E-Journals, 5: 4-26, Apr. 16, 2014.

CNKI English Translation of "Clinical Study on the Level of Plasma Tumor Necrosis Factor-Related Apoptosis-Inducing Ligand (TRAIL) in Evaluating the Prognosis of Patients With Sepsis", CNKI Master's E-Journals, 5: 4-26, Apr. 16, 2014.

Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.

Corada et al. "Monoclonal Antibodies Directed to Different Regions of Vascular Endothelial Cadherin Extracellular Dornain Affect Adhesion and Clustering of the Protein and Modulate Endothelial Permeability", Blood, 97(6): 1679-1684, Mar. 15, 2001.

Cowland et al. "Molecular Characterization and Pattern of Tissue Expression of the Gene for Neutrophil Gelatinase-Associated Lipocalin from Humans", Genomics, 45:17-23,1997.

Cristianini et al. "An Introduction to Support Vector Machines and Other Kernel-Based Learning Methods: Contents", Cambridge University Press, 4 P., 2000.

Crowe et al. "Quantitative Immunocytofluorographic Analysis of CD4 Surface Antigen Expression and HIV Infection of Human Peripheral Blood Monocyte/Macrophages", Aids Research and Human Retroviruses, 3(2): 135-145, 1987.

Cummins et al. "The TRAIL to Viral Pathogenesis: The Good, the Bad and the Ugly", Current Molecular Medicine, XP055056835, 9(4): 495-505, May 1, 2009.

De la Grange et al. "A New Advance in Alternative Splicing Databases: From Catalogue to Detailed Analysis of Regulation of Expression and Function of Human Alternative Splicing Variants", BMC Bioinformatics, 8: 180-1-180-14, Jun. 4, 2007.

Dirke et al. "TRAIL and DcR1 Expressions Are Differentially Regulated in the Pancreatic Islets of STZ-Versus CY-AppHed NOD Mice", Experimental Diabetes Research, Article ID 625813, pp. 1-11, 2011.

Duda et al. "Contents", Pattern Classification, 2nd Ed., 11 P., 2001.

Eberl et al. "A Rapid Crosstalk of Human gamma delta T Cells and Monocytes Drives the Acute Inflammation in Bacterial Infections", PLOS Pathogens 5(2): 1-16, 2009.

Falschlehner et al. "Following TRAIL's Path in the Immune System", Immunology, XP055056763, 127(2): 145-154, Jun. 1, 2009. Chapter 'TRAIL in Viral and Bacterial Infections'.

Feezor et al. "Molecular Characterization of the Acute Inflammatory Response to Infections With Gram-Negaitve Versus Gram-Positive Bacteria", Infection and Immunity, 71(10): 5803-5813, Oct. 2003.

Forde et al. "The Beneficial Pleiotropic Effects of Tumour Necrosis Factor-Related Apoptosis—Inducing Ligand (TRAIL) Within the Vasculature: A Review of the Evidence", Atherosclerosis, XP029468976, 247: 87-96, Available Online Feb. 9, 2016.

Furey et al. "Support Vector Machine Classification and Validation of Cancer Tissue Samples Using Microarray Expression Data", Bioinformatics, 16(10): 906-914, Oct. 2000.

Gaedtke et al. "Elevated Troponin is Associated with Mortality in Severe Sepsis and Septic Shock Patients", American Journal of Respiratory and Critical Care Medicine, 189: 1-2, 2014.

Greenspan et al. "Defining Epitopes: It's Not as Easy as It Seems", Nature Biotechnology, 17: 936-937, Oct. 1999.

Halminen et al. "Expression of MxA Protein in Blood Lymphocytes Discriminates Between Viral and Bacterial Infections in Febrile Children", Pediatric Research, 41(5): 647-650, May 1997.

Hanley et al. "A Method of Comparing the Areas Under Receiver Operating Characteristics Curves Derived From the Same Cases", Radiology, 148(3): 839-843, Sep. 1983.

Henriquez-Camacho et al. "Biomarkers for Sepsis"; BioMed Research International, 547818: 6 pages, 2014.

Herzig et al. "The Role of CXCL10 in the Pathogenesis of Experimental Septic Shock", Critical Care, 18(3): R113-1-R113-18, Jun. 2, 2014.

Hinson et al. "Viperin Is Highly Induced in Neutrophils and Macrophages during Acute and Chronic Lymphocytic Choriomeningitis Virus Infection", The Journal of Immunology, 184:5723-5731, 2010.

Hoffmann et al. "TRAIL Limits Excessive Host Immune Responses in Bacterial Meningitis", JCI The Journal of Clinical Investigation, 117(7): 2004-2013, Jul. 2, 2007.

Holland et al. "STAT3 Mutations in the Hyper-IgE Syndrome", The New England Journal of Medicine, 357(16): 1608-1619, Oct. 18, 2007.

(56) References Cited

OTHER PUBLICATIONS

Hu et al. "Gene Expression Profiles in Febrile Children With Defined Viral and Bacterial Infection", Proc. Natl. Acad. Sci. USA, Pnas, 110(31): 12792-12797, Published Online Jul. 15, 2013.

Ioannidis et al. "Plasticity and Virus Specifity of the Airway Epithelial Cell Immune Response During Respiratory Virus Infection", Journal of Virology, 86(10): 5422-36, Mar. 7, 2012.

Ip et al. "Value of Serum Procalcitonin, Neopterin, and C-Reactive Protein in Differentiating Bacterial From Viral Etiologies in Patients Presenting With Lower Respiratory Tract Infections", Diagnostic Microbiology and Infectious Disease, 59(2): 131-136, Oct. 2007.

Janols et al. "Lymphocyte and Monocyte Flow Cytometry Immunophenotyping as a Diagnostic Tool in Uncharacteristic Inflammatory Disorders", BMC Infectious Diseases, XP002663504, 10(205): 1-9, 2010. Abstract.

Jenner et al. "Insights Into Host Responses Against Pathogens From Transcriptional Profiling", Nature Review Microbiology, 3: 281-294, Apr. 2005.

Ju et al. "Research Progress of Some Inflammatory Markers in Infectious Diseases", Chinese Journal of Practical Internal Medicine, 30(Suppl.1): 80-81, Jun. 2010. With an English Translation.

Kaizer et al. "Gene Expression in Peripheral Blood Mononuclear Cells From Children With Diabetes", The Journal of Clinical Endocrinology & Metabolism, 92(9): 3705-3711, 2007.

Kang et al. "Low serum TNF-Related Apoptosis—Inducing Ligand (TRAIL) Levels Are Associated with Acute Ischemic Stroke Severity", Atherosclerosis, 240: 228-233, 2015.

Kawada et al. "Analysis of Gene-Expression Profiles by Oligonucleotide Microarray in Children With Influenza", Journal of General Virology, 87: 1677-1683, 2006.

Kichev et al. "Tumor Necrosis Factor-Related Apoptosis-Inducing Ligand (TRAiL) Signaling and Cell Death in the Immature Central Nervous System after Hypoxia-Ischemia and Inflammation", Journal of Biological Chemistry 289(13): 9430-9439, 2014.

Kohavi et al. "Wrappers for Feature Subset Selection", Artifical Intelligence, 97: 273-324, 1997.

Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.

Kramer et al. "Development and Characerization of New Rat Monoclonal Antibodies for Procalcitonin", Analytical and Bionalytical Chemistry, 392: 727-736, Aug. 19, 2008.

Lampe et al. "Expression of the Interferon-Induced MxA Protein in Viral Encephalitis", Neuropathology and Applied Neurobiology, 29(3): 273-279, May 27, 2003.

Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl. 1): 28S-32S, 1998. Abstract.

Leibovici et al. "The Benefit of Appropriate Empirical Antibiotic Treatment in Patients with Bloodstream Infection", Journal of Internal Medicine, 244(5): 379-386, Nov. 1, 1998.

Liabeuf et al. "The Circulating Soluble TRAIL is A Negative Marker for Inflammation Inversely Associated With the Mortality Risk in Chronic Kidney Disease Patients", Nephrology Dialysis Transplantation, XP055497900, 25(8): 2596-2602, Advance Access Publication Feb. 26, 2010. Abstract, p. 2597, Right Col. 2nd Para, Figs.2, 3.

Lighter et al. "Chemokine IP-10: an Adjunct Marker for Latent Tuberculosis Infection in Children", The International Journal of Tuberculosis and Lung Disease, 13(6): 731-736, Jun. 2009.

Liu et al. "CXCL10/IP-10 in Infectious Diseases Pathogenesis and Potential Therapeutic Implications", Cytokine & Growth Factor Reviews, 22(3): 121-130, Jun. 2011.

Liu et al. "Early Days: Genomics and Human Responses to Infection", Current Opinion in Microbiology, 9: 312-319, Available Online May 6, 2006.

Lloyd et al. "Modelling The Human Immune Response: Performance of a 1011 Human Antibody Repertoire Against a Broad Panel of Therapeutically Relevant Antigens", Protein Engineering, Design & Selection 22(3): 159-168, Oct. 29, 2008.

Ludwig et al. "Tumor Necrosis Factor Related Apoptosis Inducing Ligand: A Novell Mechanism for Bacillus Calmette Guerin Induced Antitumor Activity" Cancer Research 64: 3386-3390,May 15, 2004.

Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.

Michowitz et al. "The Involvement of Tumor Necrosis Factor-Related Apoptosis-Inducing Ligand(TRAIL) in Atherosclerosis.", Journal of the American College of Cardiology, 45(7): 1018-1024, 2005.

Nakabayashi et al. "MxA-Based Recognition of Viral Illness in Febrile Children by a Whole Blood Assay", Pediatric Research, 60(6): 770-774, 2006.

Neu et al. "Expression of Tumor Necrosis Factor-Alpha-Related Apoptosis-Inducing Ligand and Its Proapoptotic Receptors is Down-Regulated during Gastric Infection with Virulent cagA+/vacAsl+ Helicobacter pylori Strains", The Journal of Infectious Diseases 191(4): 571-578, Feb. 15, 2005.

New England Biolabs "New England Biolabs Catalog", New England Biolabs, 1-4 pages, 1996.

Ng et al. "IP-10 is an Early Diagnostic Marker for Identification of Late-Onset Bacterial Infection in Preterm Infants", Pediatric Research, 61(1): 93-98, Jan. 2007.

Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.

Niessner et al. "Prognostic Value of Apoptosis Markers in Advanced Heart Failure Patients", European Heart Journal, XP055497907, 30(7): 789-796, Published Online Feb. 4, 2009. Abstract, Table 2, Fig.2.

Oda et al. "A Comprehensive Map of the Toll-Like Receptor Signaling Network", Molecular Systems Biology, 2(2006.0015): 1-20, Apr. 18, 2006.

Osmancik et al. "Prognostic Value of TNF-Related Apoptosis Inducing Ligand (TRAIL) in Acute Coronary Syndrome Patients", PLoS One, 8(2): e53860, 2013.

Oved et al. "A Novel Host-Proteome Signature for Distinguishing Between Acute Bacterial and Viral Infections", Plos One, XP055456891, 10(3): e0120012-1-e120012-18, Mar. 18, 2015.

Padlan "X-Ray Crystallography of Antibodies", Advances in Protein Chemistry, 49: 57-133; 1996.

Pauksen et al. "Serum Mesurements of Human Neutrophil Lipocalin (HNL) Discriminate Between Acute Bacterial and Viral Infections", Scandinavian Journal of Clinical and Laboratory Investigation, 55(2):125-131, 1995.

Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.

Pepe et al. "Combining Diagnostic Test Results to Increase Accuracy", Biostatistics, XP055033234, 1(2): 123-140, Jun. 2000.

Povoa et al. "C-Reactive Protein, An Early Marker of Community-Acquired Sepsis Resolution: A Multi-Center Prospective Observational Study", Critical Care, 15(4): R169-1-R169-10, Published Online Jul. 15, 2011.

Punyadeera et al. "A Biomarker Panel to Discriminate Between Systemic Inflammatory Response Syndrome and Sepsis and Sepsis Severity", Journal of Emergencies, Trauma and Shock, 3(1): 26-35, Jan.-Mar. 2010.

Qian et al. "Identification of Genes Critical for Resistance to Infection by West Nile Virus Using RNA-Seq Analysis", Viruses, 5(7): 1664-1681, Jul. 8, 2013.

Quint et al. "Serum IP-10 as a Biomarker of Human Rhinovirus Infection at Exacerbation of COPD", Science Direct, Chest, 137(4): 812-822, Apr. 2010.

Radom-Aizik et al. "Effects of 30 Min. of Aerobic Exercise on Gene Expression in Human Neutrophils", Journal of Applied Physiology, 104: 236-243, 2008.

(56) References Cited

OTHER PUBLICATIONS

Ramilo et al. "Gene Expression Patterns in Blood Leukocytes Discriminate Patients With Acute Infections", Blood, 109(5): 2066-2077, Mar. 1, 2007.
RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.
Rosseau et al. "Comparative Transcriptional Profiling of the Lung Reveals Shared and Distinct Features of *Streptococcus pneumoniae* and Influenza A Virus Infection", Immunology, 120: 380-391, 2006.
Rothstein et al. "Chronic Inhibition of Superoxide Dismutase Produces Apoptotic Death of Spinal Neurons", PNAS, (10): 4155-4159, May 1994.
Rudikoff et al. "Single Amino Acid Substitution Altering Antigen-Binding Specificity", PNAS, 79(6): 1979-1983, Mar. 1982.
Ruhwald et al. "IP-10 Can Be Measured in Dried Plasma Spots in Patients with Chronic Hepatitis C Infection", PLoS ONE 7(9): e45181, 1-4, Sep. 14, 2012.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig.1.
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Sheyin et al. "The Prognostic Significance of Troponin Elevation in Patients with Sepsis: A Meta-Analysis", Heart & Lung, 44(1): 75-81, Jan.-Feb. 2015.
Shimetani et al. "Levels of Three Inflammation Markers, C-Reactive Protein, Serum Amyloid a Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Shommu et al. "Metabolomic and Inflammatory Mediator Based Biomarker Profiling as a Potential Novel Method to Aid Pediatric Appendicitis Identification", Plos One, XP055692841, 13(3): e0193563-1-e0193563-13, Mar. 12, 2018.
Singer et al. "The Third International Consensus Definitions for Sepsis and Septic Shock (Sepsis-3)", Journal of the American Medical Association, JAMA, XP055456889, 315(8): 801-810, Feb. 23, 2016.
Smith et al. "Quantitative Assessment of Human Whole Blood RNA as a Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089-8099, Dec. 1, 2005.
Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically III Patients", Critical Care Medicine, 36(4): 1125-1128, 2008.
Tang et al. "Hypoxic Preconditioning Enhances the Benefit of Cardiac Progenitor Cell Therapy for Treatment of Myocardial Infarction by Inducing CXCR4 Expression", Circulation Research, XP055473182, 104(10): 1209-1216, May 22, 2009. Online Table 1.
Tang et al. "The Use of Gene-Expression Profiling to Identify Candidate Genes in Human Sepsis", American Journal of Respiratory and Critical Care Medicine, 176: 676-684, Originally Published Jun. 15, 2007.
ThermoFisher Scientific "Interferon Alpha Inducible Protein 27: IFI27", ThermoFisher Scientific, Product Details, 2 P., 2020.
ThermoFisher Scientific "Interferon Induced Protein 44 Like: IFI44L", ThermoFisher Scientific, Product Details, 2 P., 2020.

ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h Col. Para 3—p. 222, r-h Col., Para 1.
Tian et al. "Soluble Tumor Necrosis Factor Related Apoptosis Inducing Ligand Level as a Predictor of Severity of Sepsis and the Risk of Mortality in Septic Patients", PLOS One, XP055497898, 8(12): e82204-1-e82204-5, Dec. 12, 2013.
Tisato et al. "Low Circulating TRAIL Levels Are Associated With Increase of Resistin and Lipocalin-2/ngal Adipokines in Postmenopausal Women", Mediators of Inflammation, Article ID 5356020, 8 Pages, 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones, Carotenoids, Inflammatory Markers, and Proteomics as Examples", Cancer Epidemiol Biomarkers and Prevention, 15(9): 1578-1581, Sep. 2006.
UCSC "Human Gene IFI27 (ENST00000621160.5) From GENCODE V39", UCSC Browser, Retrieved From the Internet, 3 Pages, Last Updated Jan. 17, 2022.
UCSC "Human Gene IFIT1 (ENST00000371804.4) From GENCODE V39", Ucsc Browser, Retrieved From the Internet, 4 Pages, Last Updated Jan. 17, 2022.
UCSC "Ucsc Browser on Human Feb. 2009 (GRCh37/hg19) Assembly: Showing Location of Probes on the Affymetrix ExonChip Binding to Exons of ANKRD22", UCSC Genome Browser, Version 387, XP055621243, Retrieved From the Internet, 7 P., Jan. 2009.
UCSC "UCSC Genome Browser on Human (GRCh38/hg38)", UCSC Genome Browser, Version 429, Chr10: 91152344-91163592, Retrieved From the Internet, 1 Page, Apr. 14, 2022.
UCSC "UCSC Genome Browser on Human (GRCh38/hg38)", UCSC Genome Browser, Version 429, Chr14: 94577158-94582955, Retrieved From the Internet, 1 Page, Apr. 14, 2022.
UCSC "UCSC Genome Browser on Human (GRCh38/hg38)", UCSC Genome Browser, Version 440, Chr14: 94109241-94118186, Retrieved From the Internet, 7 Pages, Jan. 12, 2022.
UCSC "UCSC Genome Browser on Human (GRCh38/hg38)", UCSC Genome Browser, Version 440, Chr17: 41754609-41786711, Retrieved From the Internet, 4 Pages, Jan. 12, 2022.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Interent, 8 P., Jan. 2009.
Vermot-Desroches et al. "Characterization of Monoclonal Antibodies Directed Against Trail or Trail Receptors", Cellular Immunology, 236(1-2): 86-91, Jul.-Aug. 2005.
Vogel et al. "Sequence Signatures and mRNA Concentration Can Explain Two-Thirds of Protein Abundance Variation in a Human Cell Line", Molecular Systems Biology, 6(Art.400): 1-9, Published Online Aug. 24, 2010.
Volpato et al. "Association of Tumor Necrosis Factor-Related Apoptosis-Inducing Ligand with Total and Cardiovascular Mortality in Older Adults", Atherosclerosis, 215: 452-458, 2011.
Wang et al. "Rotavirus Infection Alters Peripheral T-Cell Homeostasis in Children With Acute Diarrhea", Journal of Virology, 81(8): 3904-3912, Apr. 2007.
Wang et al. The significance of MMP-8, MMP-9 and FFN levels in pregnant women with bacterial vaginosis, Maternal and Child Health Care of China, vol. 28, No. 28, 2013, pp. 4615-4617.
Whiteside et al. "Role of Human Natural Killer Cells in Health and Disease", Clinical and Diagnostic Laboratory Immunology, 1(2): 125-133, Mar. 31, 1994.

(56) References Cited

OTHER PUBLICATIONS

Wu "Increased Troponin in patients with Sepsis and Septic Shock: Myocardial Necrosis or Reversible Myocardial Depression", Intensive Care Medicine, 27: 959-961, 2001.
Xu et al. "Lipocalins as Biochemical Markers of Disease", Biochimica et Biophysica Acta, XP002376345, 1482(1): 298-307, Oct. 18, 2000.
Yamaji et al. "Significance of Eukaryotic Translation Elongation Factor 1A in Tobacco Mosaic Virus Infection", Archives of Virology, XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212, 1-h Col., p. 213, 1-h Col., Fig.4.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
Zhang "Research Progress of Interferon-Inducible Protein 10 and Its Effect in Newborn Infection Diagnosis", Chinese Journal of Neonatology, 4: 60-62, Jul. 15, 2013.
Zhang et al. "Expression of Tumor Necrosis Factor-Related Apoptosis-Inducing Ligand in Serum of Severe Hepatitis Patients with Nosocomial Infections and its Clinical Significance", Chinese Journal of Nosocomiology, 24, Abstract, 2012.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection", Clinical and Vaccine Immunology, 14(7): 918-923, Jul. 2007.
Notification of Office Action Dated Aug. 29, 2023 From the State Intellectual Property Office of the People's Republic of China Re. Application No. 202010370187.X. (3 Pages).
Official Action Dated Aug. 29, 2023 from the US Patent and Trademark Office Re. U.S. Appl. No. 17/372,575. (144 pages).
Fosgerau et al. "Interleukin-6 Autoantibodies are Involved in the Pathogenesis of a Subset of Type 2 Diabetes", Journal of Endocrinology, 204: 265-273, 2010.
Gupta et al. "Dinstict Functions of Autoantibodies Against Interferon in Systemic Lupus Erythematosus", Arthritis & Rheumatology, 68(7): 1677-1687, Jul. 2016.
Meyer "Anti-CRP antibodies in Systemic Lupus Erythematosus", Joint Bone Spine, 77"384-389, Jun. 2, 2010.
Thermo Scientific "ELISA Technical Guide and Protocols", Thermo Scientific, TR0065.0, 2010 (14 Pages).
Official Action Dated Oct. 26, 2023 from the US Patent and Trademark Office Re. U.S. Appl. No. 18/077,277. (252 pages).
Van Deursen et al. "Prognostic Value of Plasma Neutrophil Gelatinase-Associated Lipocalin for Mortality in Patients With Heart Failure", Circulation: Heart Failure, 7: 35-42, Jan. 2014.
English Summary Dated Jan. 25, 2024 of Decision on Rejection Dated Jan. 4, 2024 From the State Intellectual Property Office of the People's Republic of China Re. Application No. 202010370187.X (1 Page).
English Summary and Translation Dated Sep. 13, 2023 of Notification of Office Action Dated Aug. 29, 2023 From the State Intellectual Property Office of the People's Republic of China Re. Application No. 202010370187.X. (3 pages).
Hearing Notice Dated Sep. 9, 2023 From the Government of India, Intellectual Property India, The Patent Office Re. Application No. 201727005513. (3 Pages).
Examination Report Dated Nov. 1, 2023 From the Australian Government, IP Australia Re. Application No. 2022200802. (6 Pages).
Communication Pursuant to Article 94(3) EPC Dated Jan. 31, 2024 From the European Patent Office Re. Application No. 17855163.6 (4 Pages).
Restriction Official Action Dated Feb. 1, 2024 from the US Patent and Trademark Office Re. U.S. Appl. No. 17/841,704. (6 pages).
Decision on Rejection Dated Jan. 4, 2024 From the State Intellectual Property Office of the People's Republic of China Re. Application No. 202010370187.X and Its Machine Translation Into English. (9 Pages).
Communication Pursuant to Article 94(3) EPC Dated Oct. 30, 2023 From the European Patent Office Re. Application No. 17855164.4 (7 Pages).
"C-Reactive Protein", Australian Prescriber, 20(3): 74-76, Jun. 2007.
Official Action Dated Apr. 3, 2024 from the US Patent and Trademark Office Re. U.S. Appl. No. 17/507,994. (50 pages).
Official Action Dated Apr. 8, 2024 from the US Patent and Trademark Office Re. U.S. Appl. No. 17/010,912. (233 pages).
Requisition Dated Apr. 5, 2024 From the Innovation, Science and Economic Development Canada, Canadian Intellectual Property Office Re. Application No. 3,190,715. (3 Pages).
Haider et al. "C-Reactive Protein is Expressed and Secreted by Peripheral Blood Mononuclear Cells", Clinical and Experimental Immunology, 146: 533-539, 2006.
Stiver "The Treatment of Influenza With Antiviral Drugs", CMAJ, Canadian Medical Association, 168(1): 49-57, Jan. 7, 2003.
Suarez et al. "Superiority of Transcriptional Profiling Over Procalcitonin for Distinguishing Bacterial From Viral Lower respiratory Tract Infections in Hospitalized Adults", The Journal of Infectious Diseases, 212: 213-222, Jul. 15, 2015.
Notice of Allowance Dated Mar. 13, 2024 from the US Patent and Trademark Office Re. U.S. Appl. No. 17/372,575. (28 pages).
Notice of Allowance Dated Mar. 27, 2024 from the US Patent and Trademark Office Re. U.S. Appl. No. 17/717,200. (34 pages).
Askarieh et al. "Systemic and Intrahepatic Interferon-Gamma-Inducible Protein 10 kDa Predicts the First-Phase Decline in Hepatitis C Virus RNA and Overall Viral Response to Therapy in Chronic Hepatitis C", Hepatology, 51: 1523-1530, 2010.
Bartolome et al. "Interleukin-28B Polymorphisms and Interferon Gamma Inducible Protein-10 Serum Levels in Seronegative Occult Hepatitis C Virus Infection", Journal of Medical Virology, 88(2):268-274, Feb. 2016.
Feld et al. "Plasma Interferon-Gamma-Inducible Protein-10 Levels Are Associated with Early, but Not Sustained Virological Response during Treatment of Acute or Early Chronic HCV Infection", PLoS One 8(11): e80003, 1-11, Nov. 20, 2013.
Grebely et al. "Plasma Interferon-gamma-Inducible Protein-10 (IP-10) Levels During Acute Hepatitis C Virus Infection", Hepatology 57(6): 2124-2134, Jun. 2013.
Lagging et al. "IP-10 Predicts Viral Response and Therapeutic Outcome in Difficult-to-treat Patients with HCV Genotype 1 Infection", Hepatolgy 44(6): 1617-1625, Dec. 2006.
Sonneveld et al. "Pre-treatment Levels of IP-10 Predict Response to Peginterferon in HBeAg-positive Chronic Hepatitis B Patients 396", Hepatology 56(4): 386A-387A, Oct. 2012.
Communication Pursuant to Article 94(3) EPC Dated Apr. 8, 2024 From the European Patent Office Re. Application No. 22169859.0. (6 Pages).
Official Action Dated May 8, 2024 from the US Patent and Trademark Office Re. U.S. Appl. No. 18/077,277. (63 pages).
Official Action Dated May 9, 2024 from the US Patent and Trademark Office Re. U.S. Appl. No. 17/841,704. (166 pages).

(56) References Cited

OTHER PUBLICATIONS

Landro et al. "Decreased Serum Lipocalin-2 Levels in Human Immunodeficiency Virus-infected Patients: Increase During Highly Active Anti-retroviral Therapy", Clinical and Experimantal Immunology, 152: 57-63. 2008.

Nicholson et al. "Late-Breaking Abstract: Plasma Level of TRAIL is Associated with Severity of Sepsis and Predicts Survival After Critical Illness", European Respiratory Journal, 48:OA3021, pp. 1-5, Nov. 2016.

Official Action Dated Jun. 4, 2024 from the US Patent and Trademark Office Re. U.S. Appl. No. 16/081,069. (33 pages).

* cited by examiner

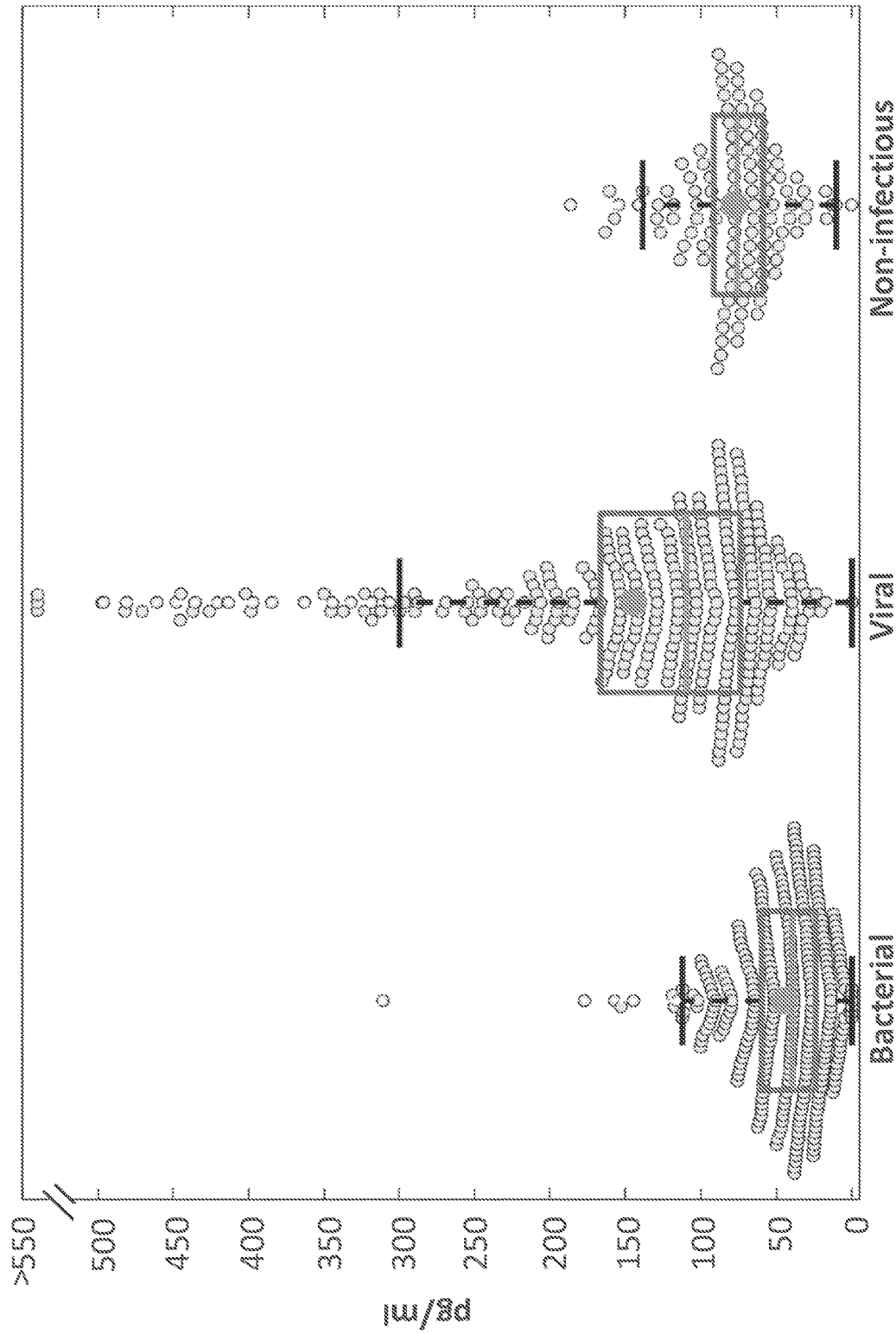

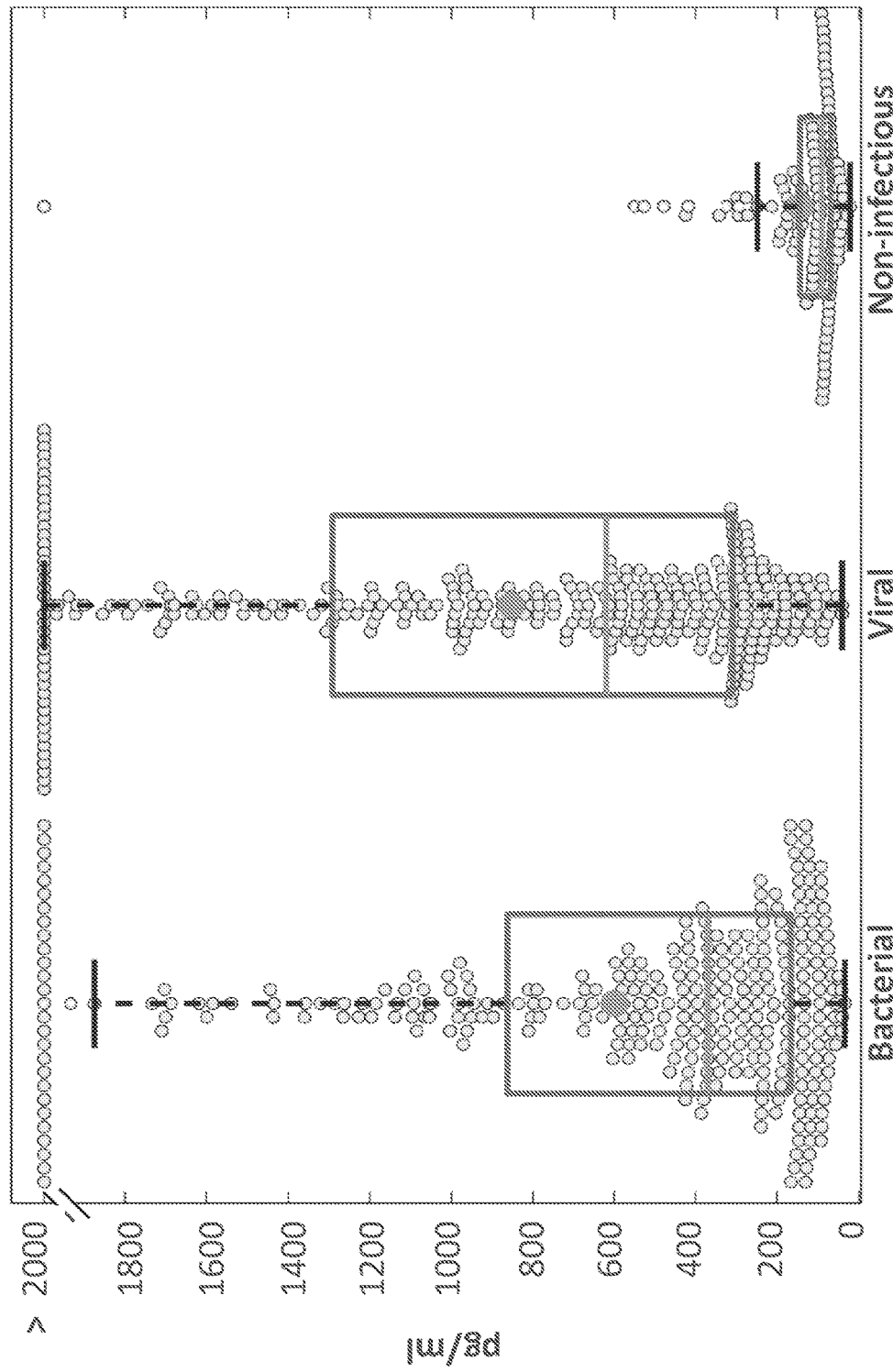

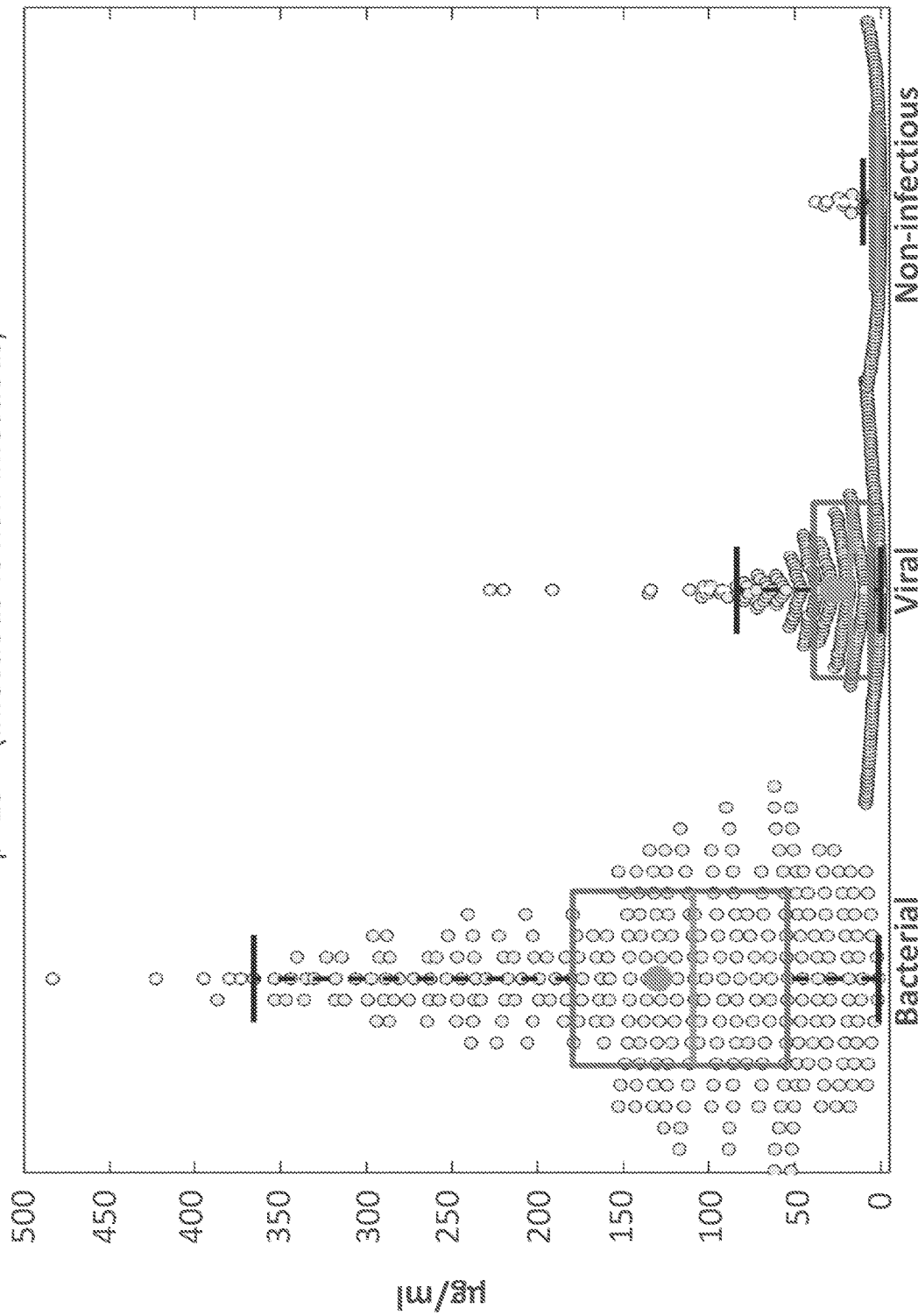

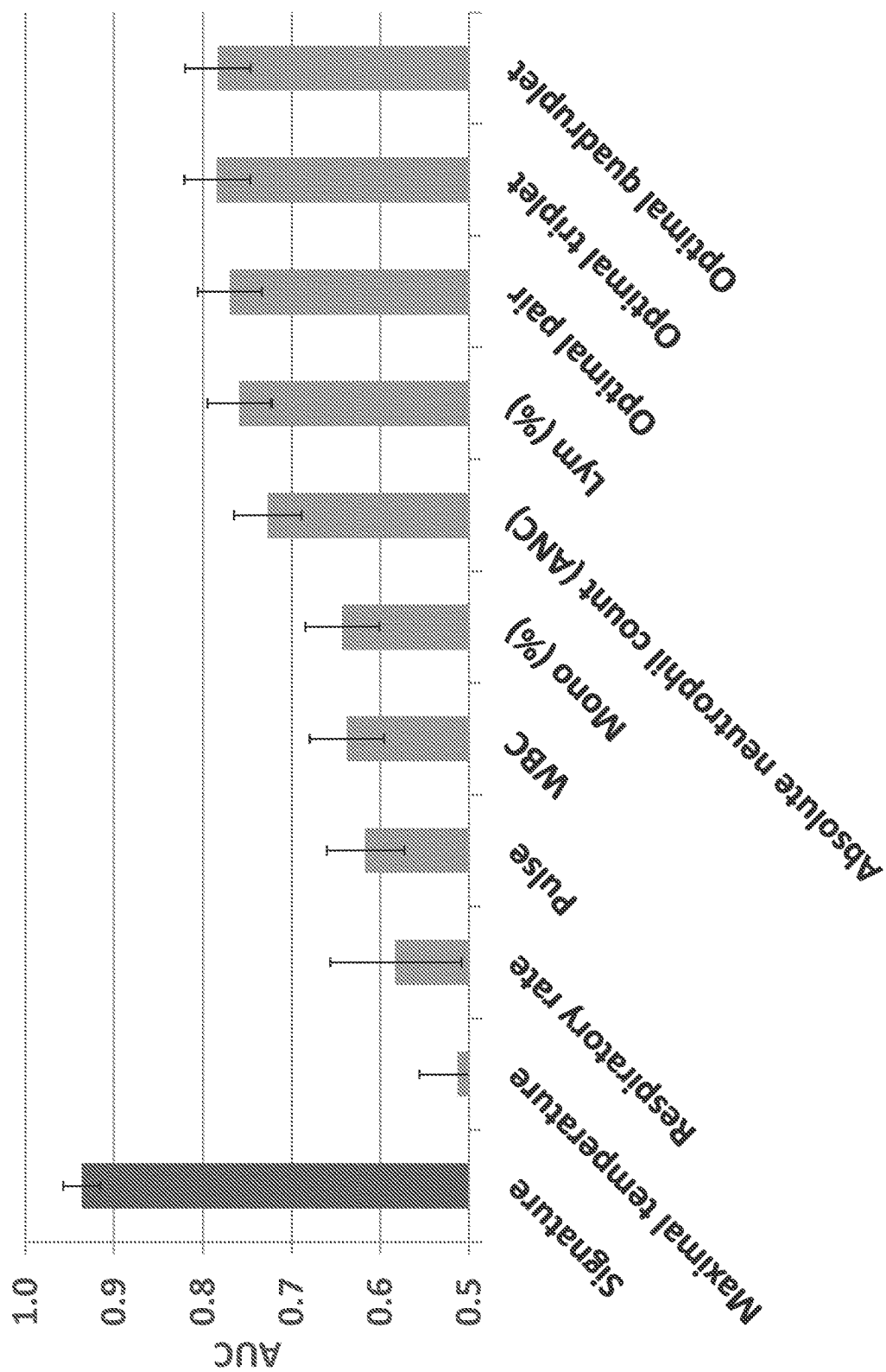

| Criteria | Subgroup | No. of patients (bacterial, viral) | AUC |
|---|---|---|---|
| Patients cohorts | Clear diagnosis | 210 (27, 173) | |
| | Unanimous | 527 (225, 271) | |
| | Majority | 653 (319, 334) | |
| Age | 0-18 | 402 (130, 272) | |
| | >18 | 251 (189, 62) | |
| Maximal Temp | <38.5 | 149 (78, 71) | |
| | 38.5-38.99 | 105 (47, 58) | |
| | 39-39.49 | 188 (96, 92) | |
| | >39.5 | 211 (98, 113) | |
| Time from symptoms onset | 0-2 | 264 (120, 144) | |
| | 2-4 | 191 (92, 99) | |
| | 4-6 | 115 (62, 53) | |
| | 6-12 | 83 (45, 38) | |
| Physiological system | Respiratory | 301 (148, 153) | |
| | GI | 88 (38, 50) | |
| | Systemic | 147 (40, 107) | |
| Clinical syndrome | Fever without source | 123 (17, 106) | |
| | LRTI | 153 (101, 52) | |
| | URTI | 127 (39, 88) | |
| Comorbidities | Hyperlipidemia | 72 (62, 10) | |
| | Renal / Urinary | 47 (36, 11) | |
| | Hypertension | 94 (79, 15) | |
| | Lung disease | 56 (37, 19) | |

FIG. 4- cont.
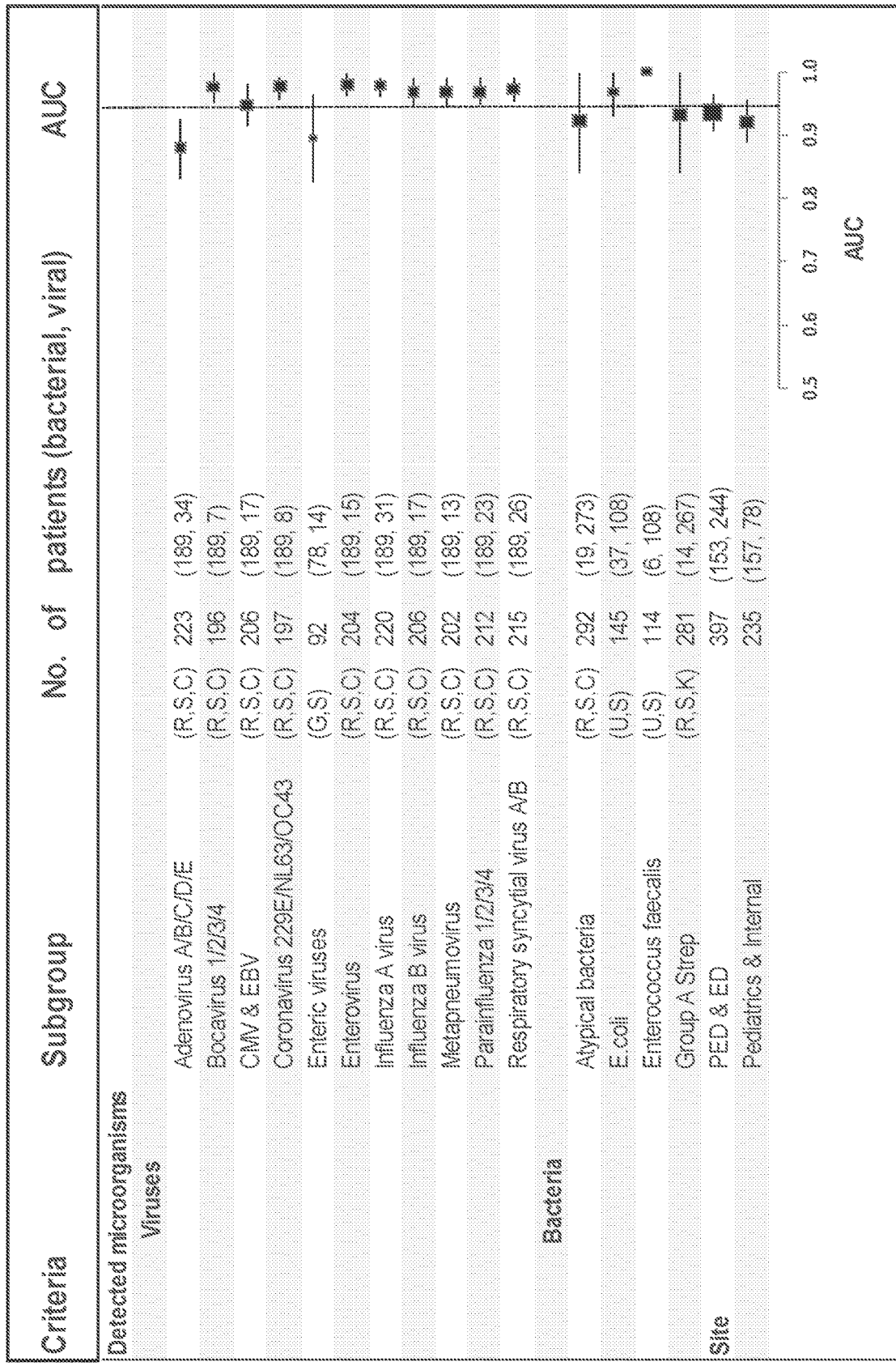

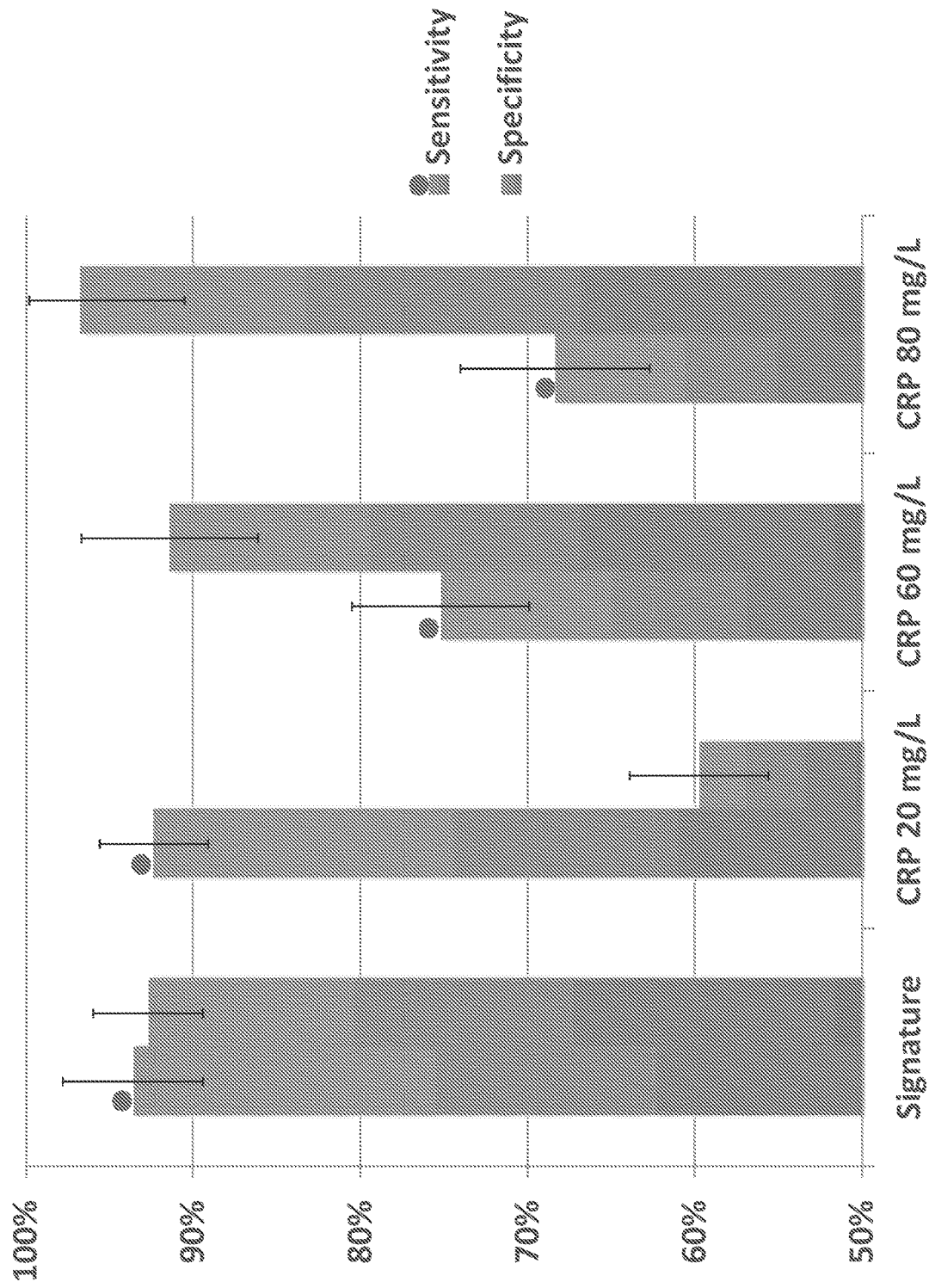

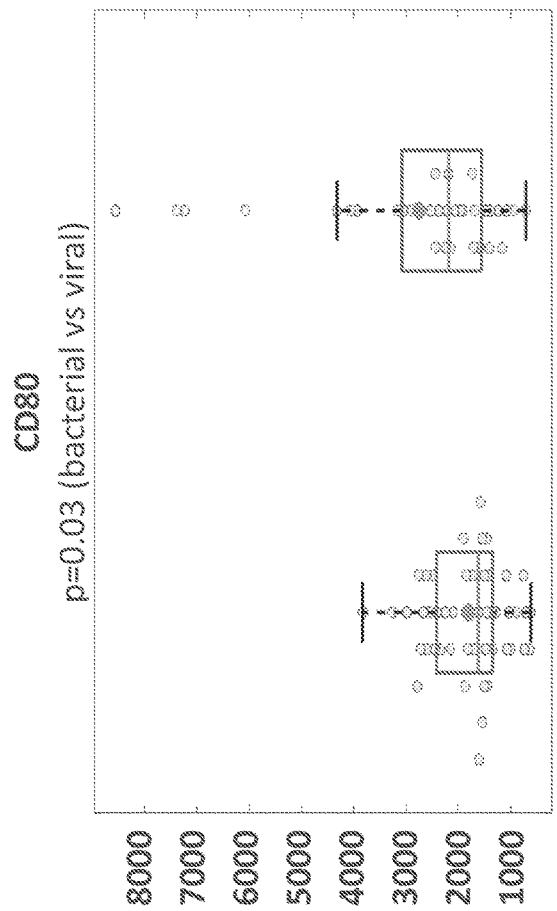
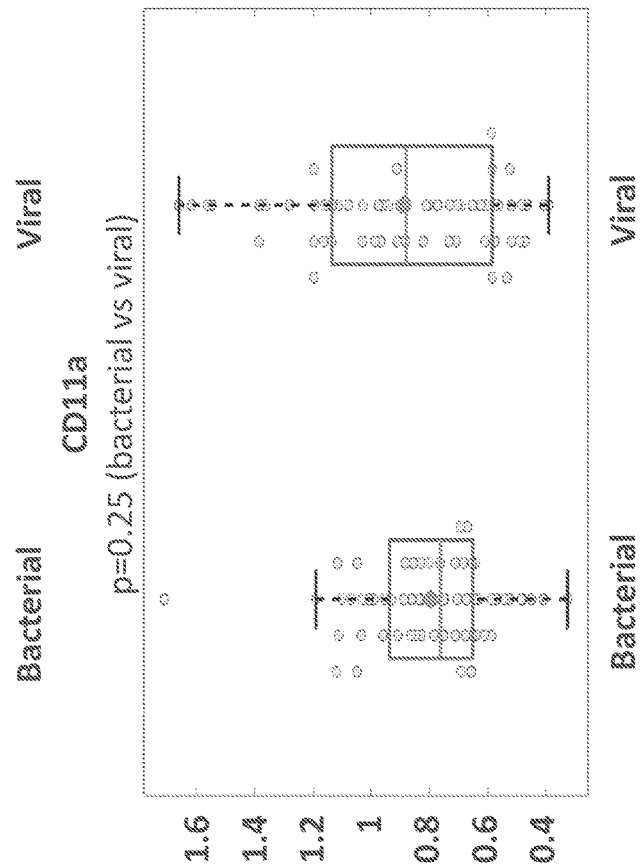
FIG. 18A
FIG. 18B

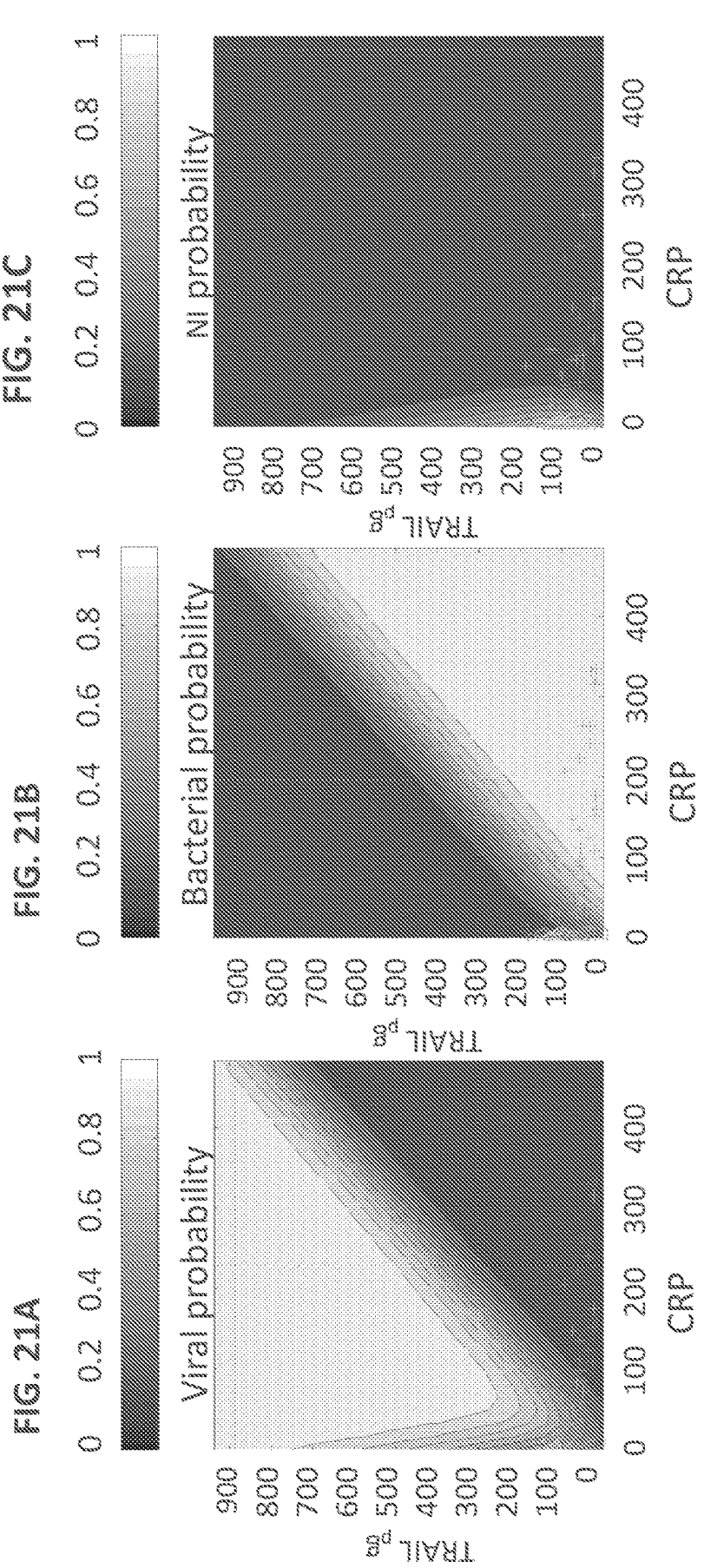

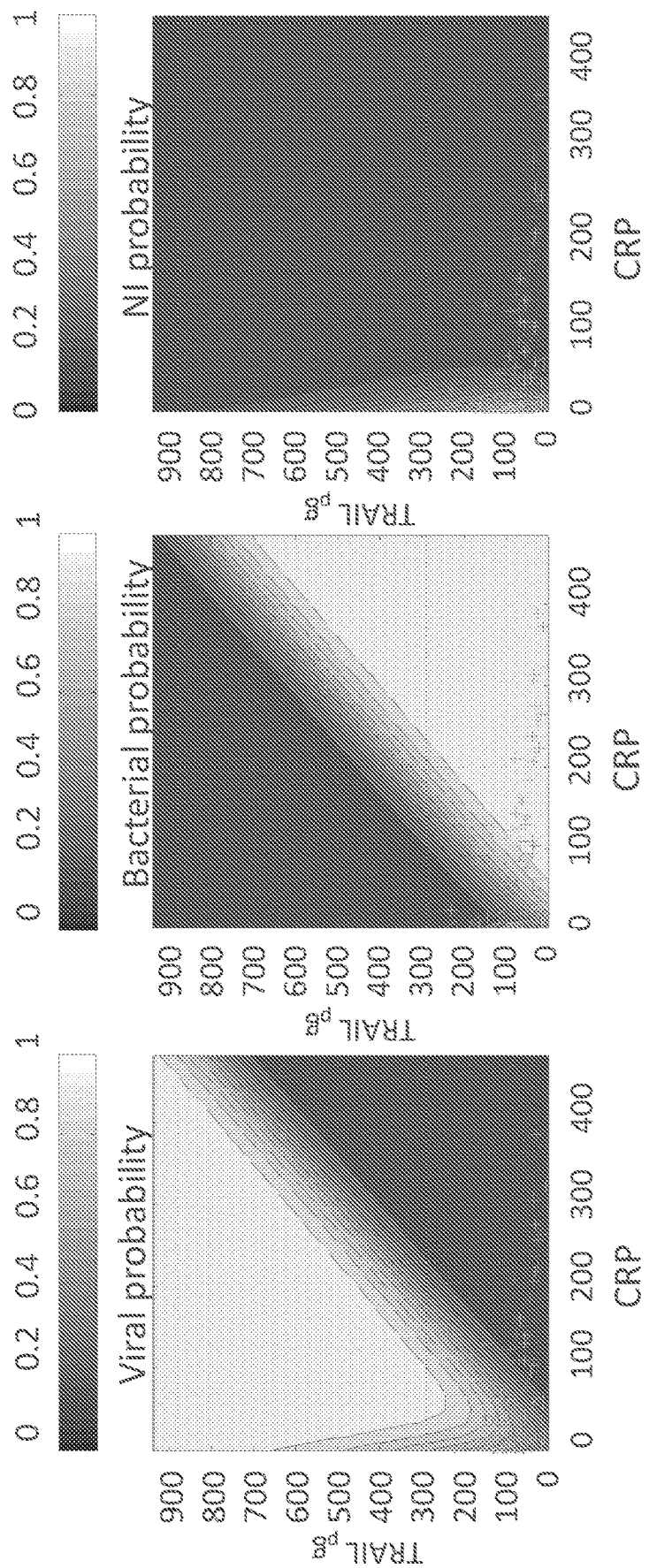

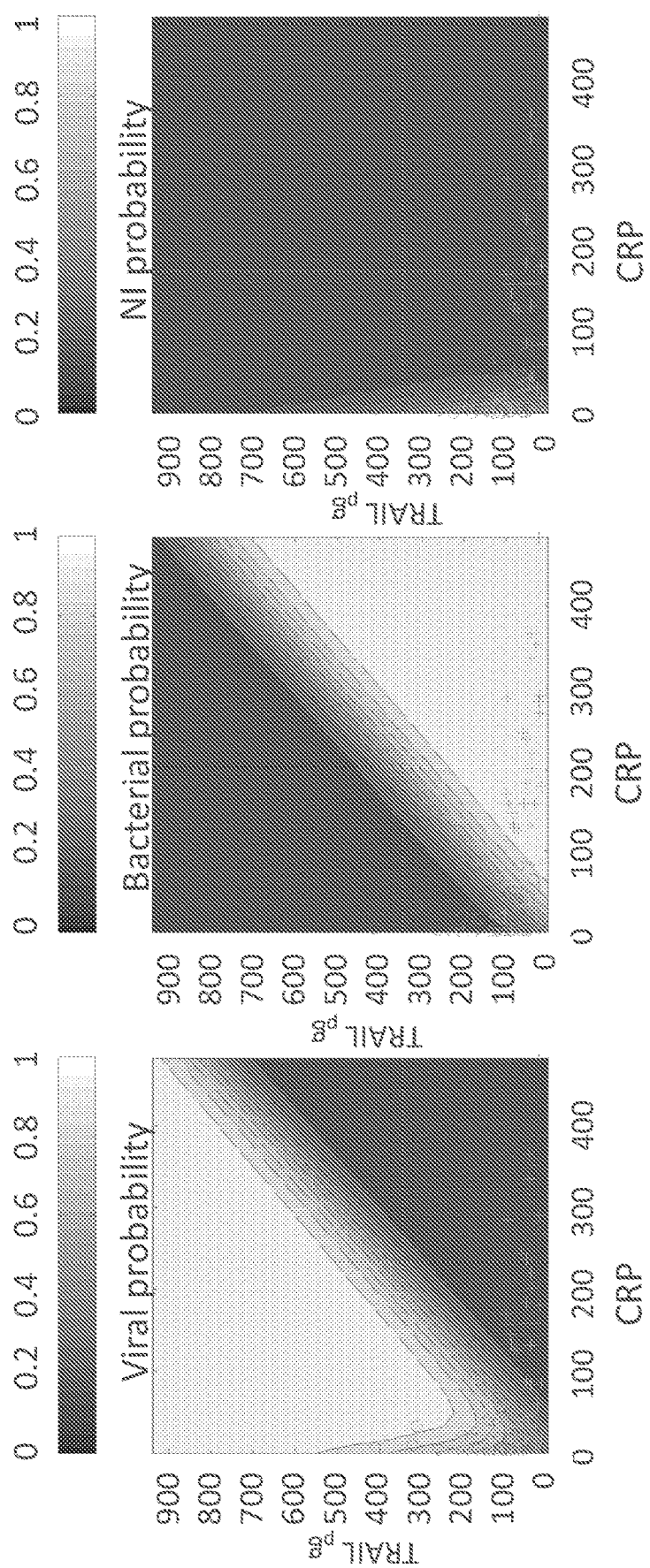

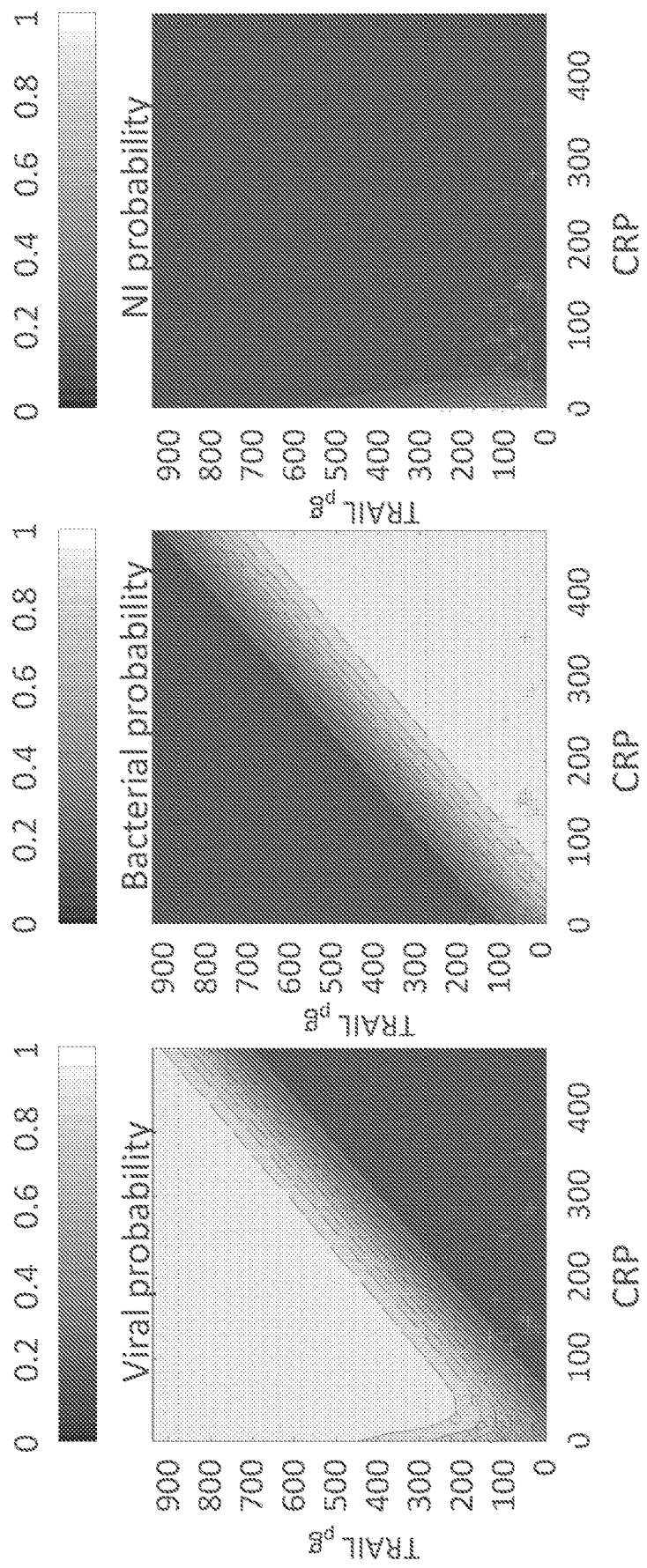

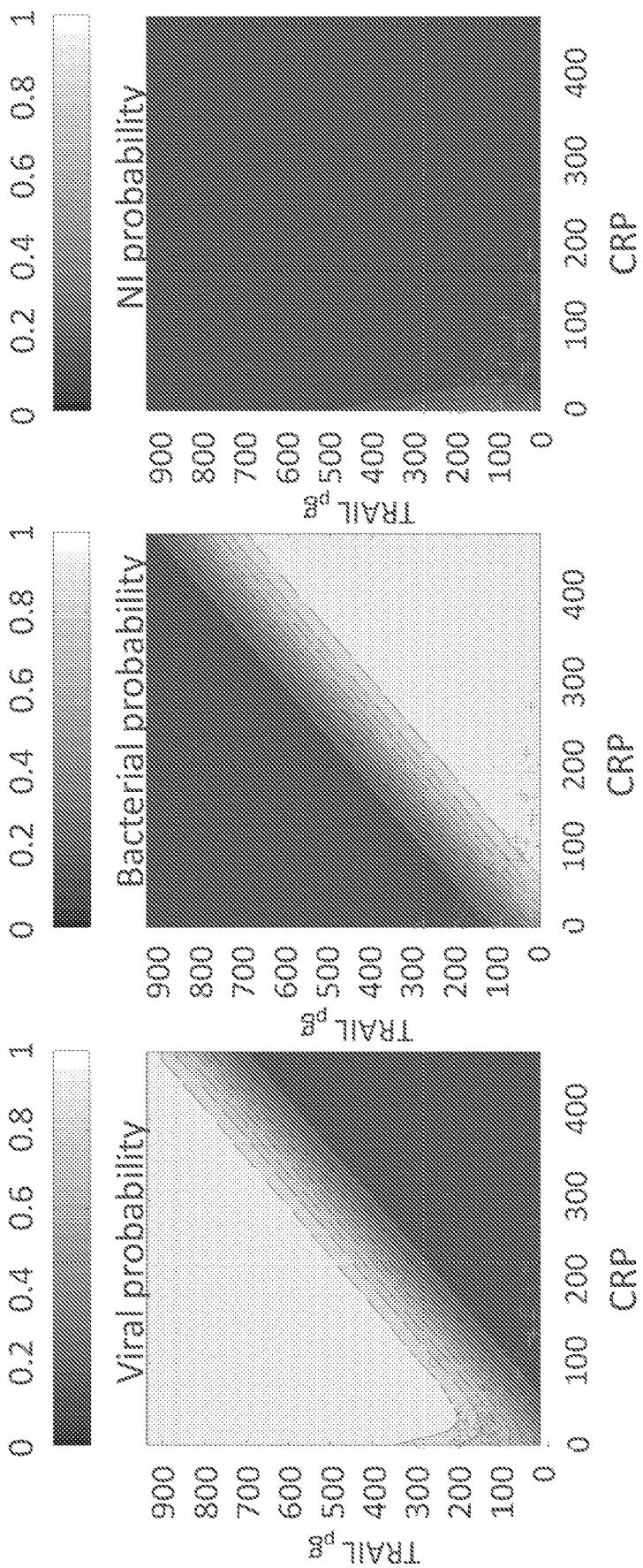

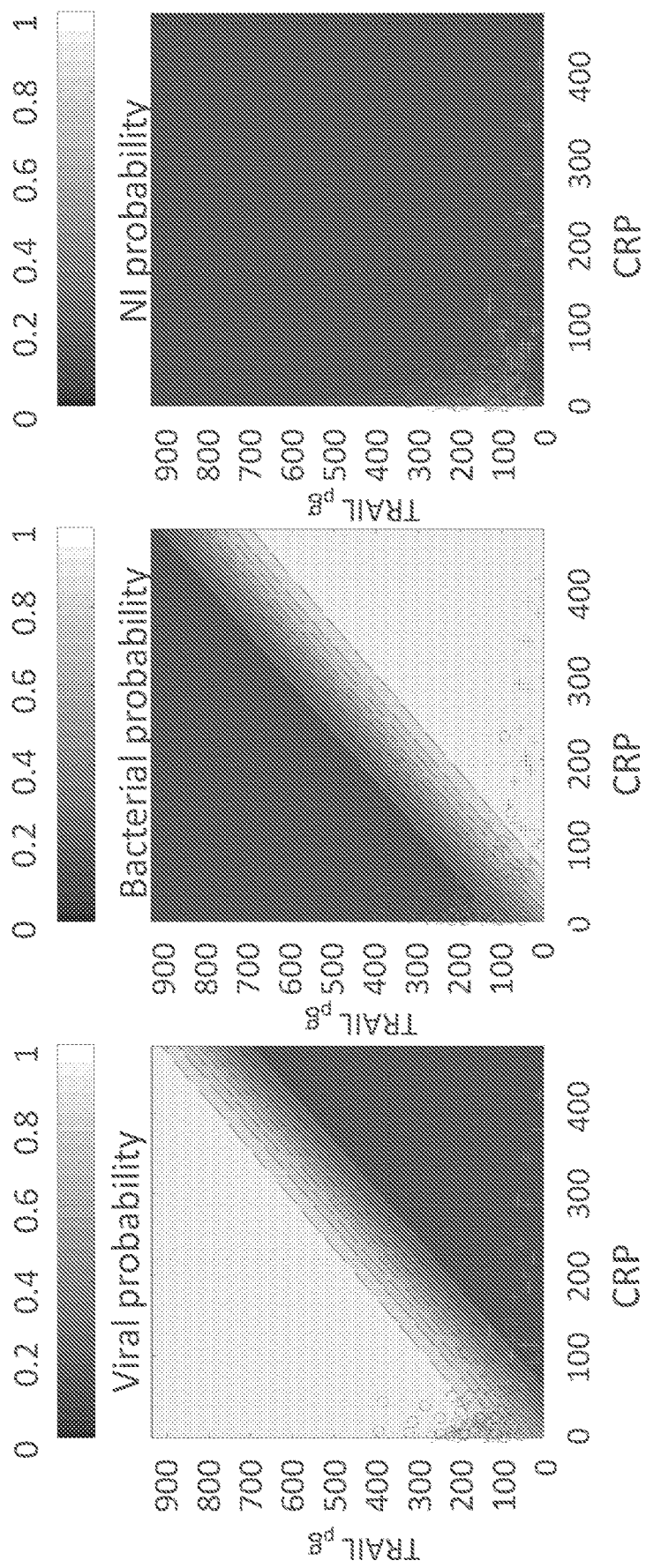

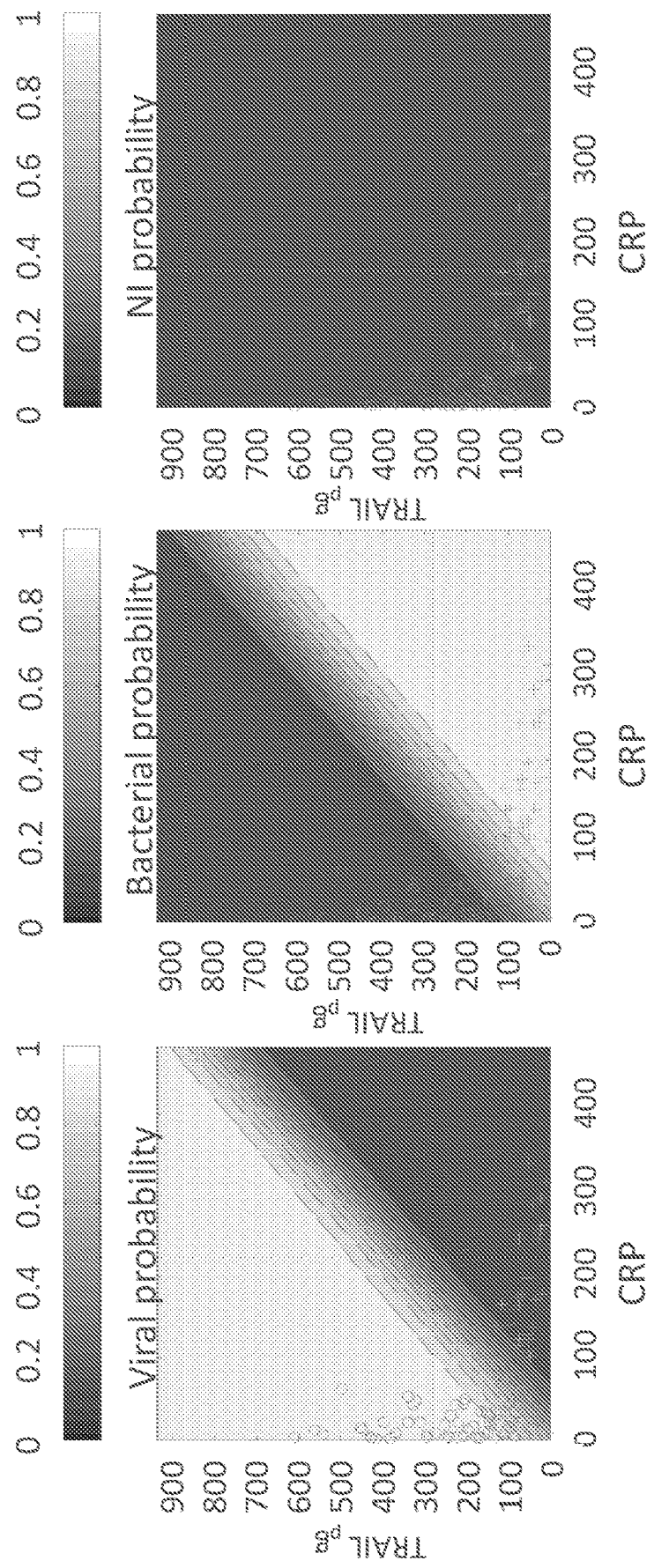

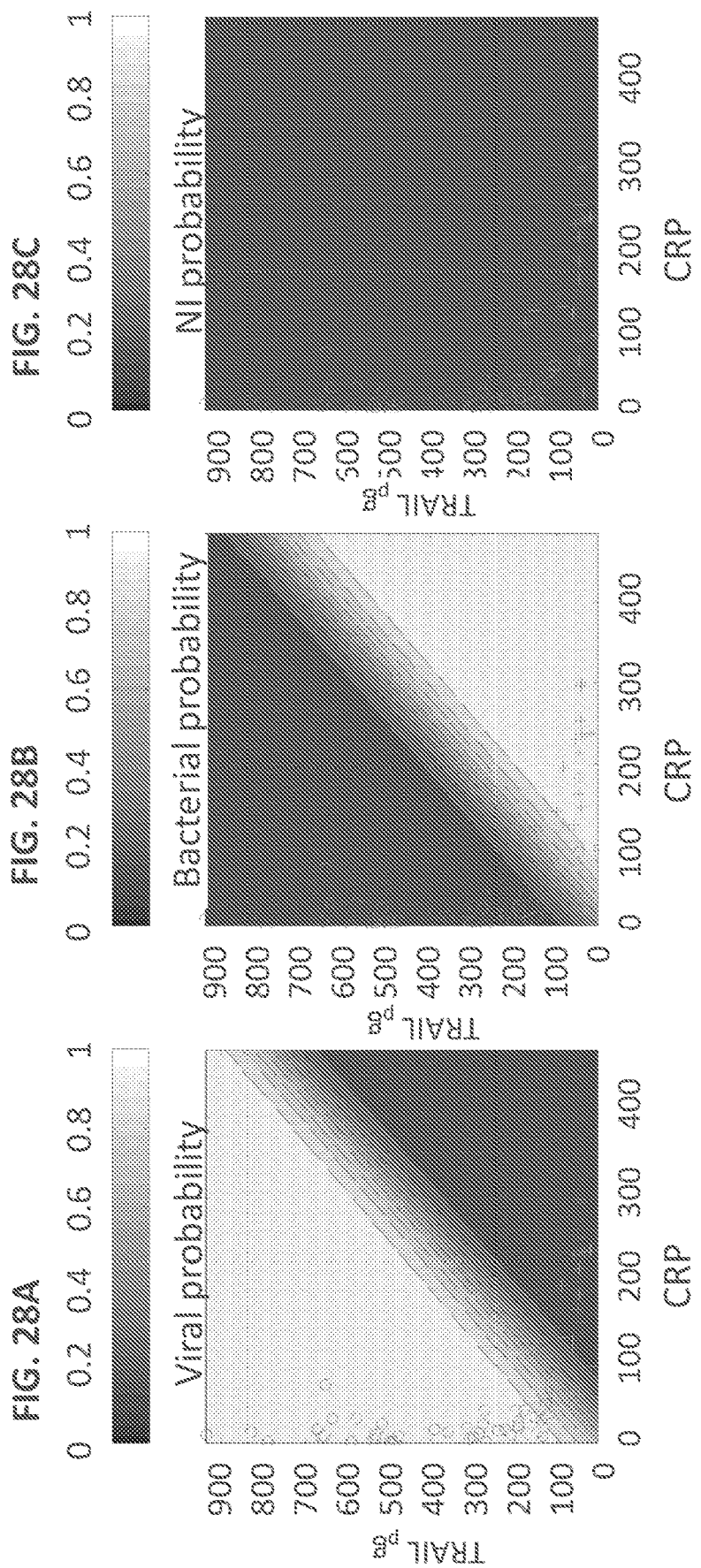

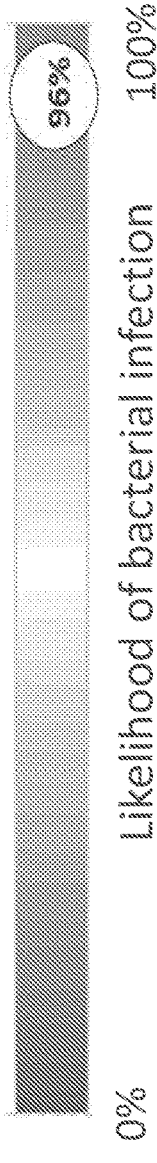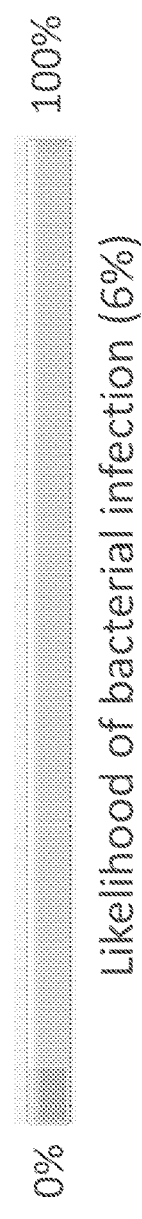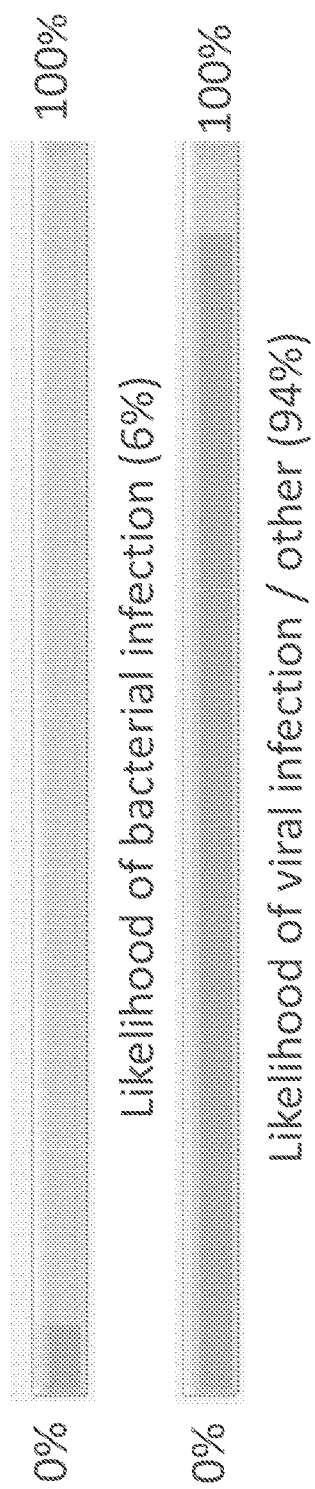
FIG. 29A
FIG. 29B
FIG. 29C

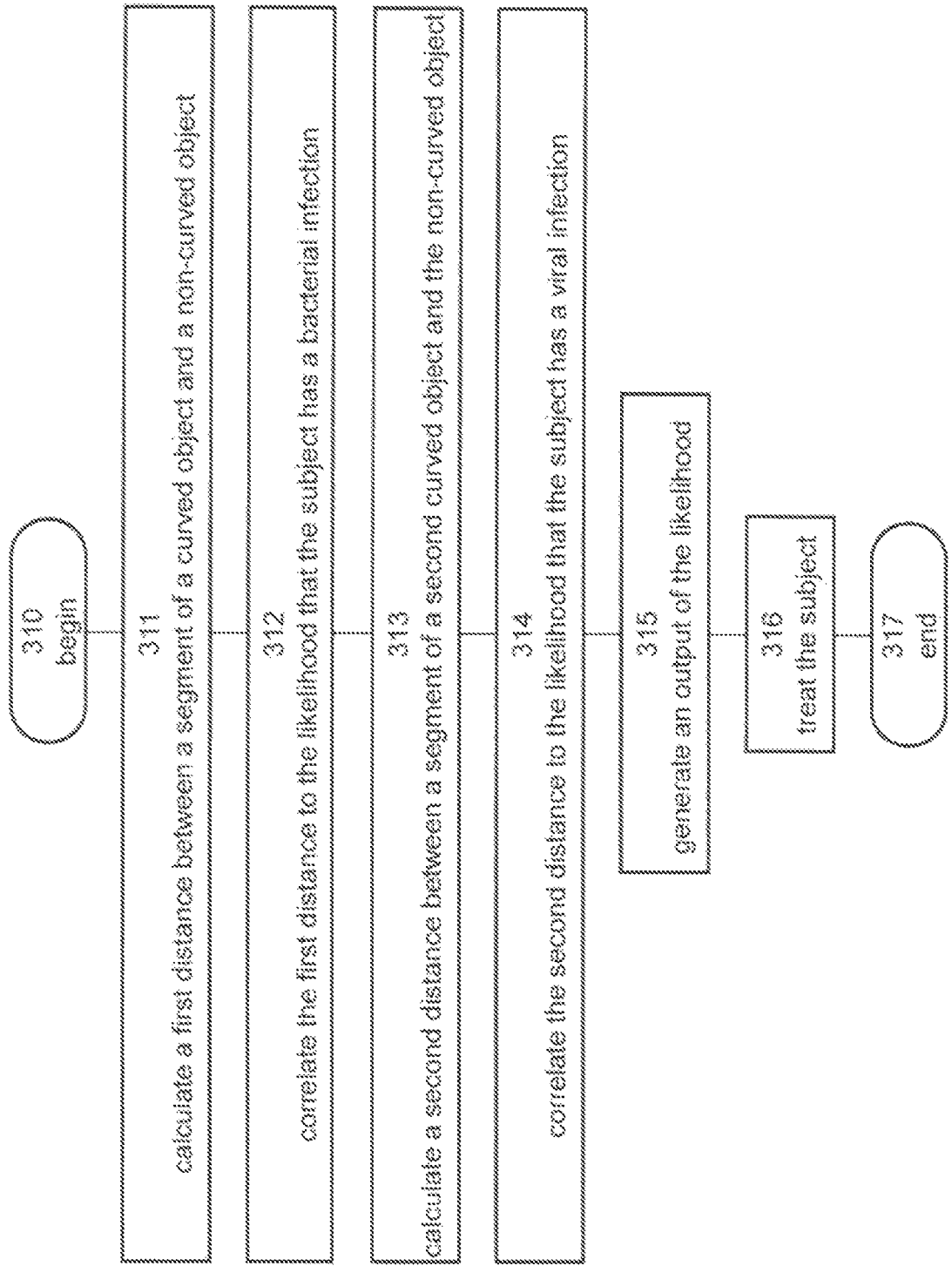

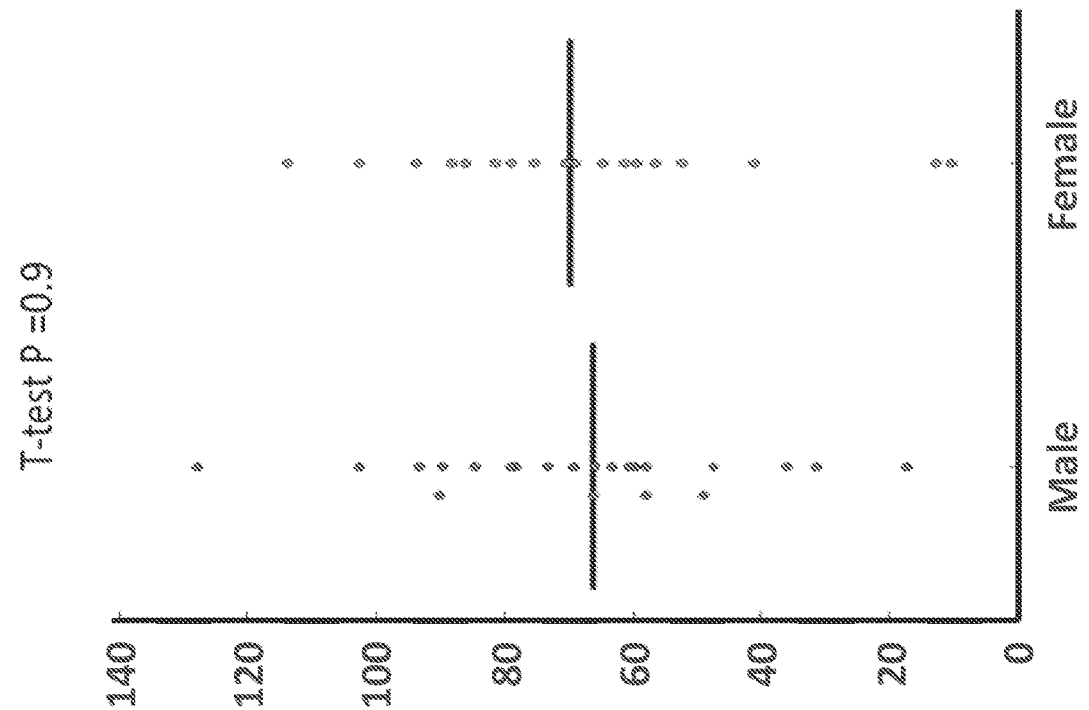
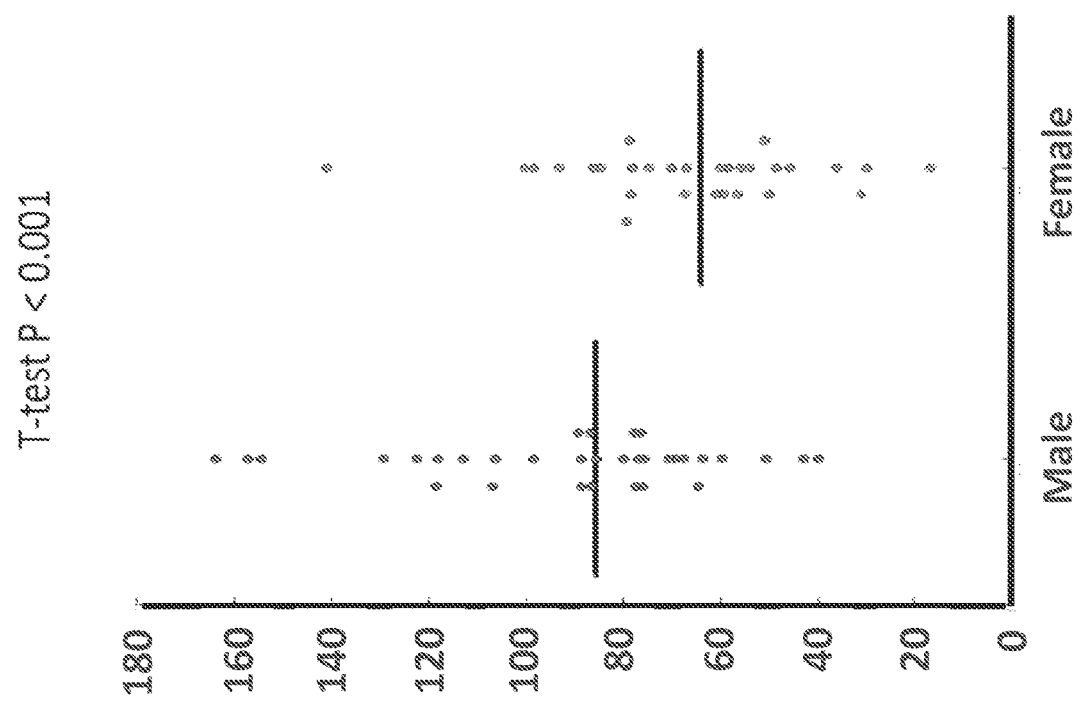
FIG. 37A
FIG. 37B

COMPUTATIONAL ANALYSIS OF BIOLOGICAL DATA USING MANIFOLD AND A HYPERPLANE

RELATED APPLICATIONS

This application is a continuation of U.S. patent application Ser. No. 17/875,467, filed on Jul. 28, 2022, which is a continuation of U.S. patent application Ser. No. 16/998,006, filed on Aug. 20, 2020, now U.S. Pat. No. 11,450,406, which is a division of U.S. patent application Ser. No. 16/355,984 filed on Mar. 18, 2019, now U.S. Pat. No. 11,081,206 which is a U.S. continuation of U.S. patent application Ser. No. 15/503,439 filed on Feb. 13, 2017, now U.S. Pat. No. 10,303,846, which is a National Phase of PCT Patent Application No. PCT/IL2015/050823 having International Filing Date of Aug. 12, 2015, which claims the benefit of priority under 35 USC § 119(e) of U.S. Provisional Patent Application Nos. 62/105,938 filed on Jan. 21, 2015 and 62/037,180 filed on Aug. 14, 2014. The contents of the above applications are all incorporated by reference as if fully set forth herein in their entirety.

SEQUENCE LISTING STATEMENT

The XML file, entitled 97189SequenceListing.xml, created on Jul. 18, 2023, comprising 163,109 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to computational analysis, and, more particularly, but not exclusively, to computational analysis of biological data, e.g., for the purpose of distinguishing between bacterial infection and non-bacterial disease, and/or between a bacterial infection and viral infection, and/or between an infectious and non-infectious disease.

Antibiotics (Abx) are the world's most prescribed class of drugs with a 25-30 billion $US global market. Abx are also the world's most misused drug with a significant fraction of all drugs (40-70%) being wrongly prescribed (Linder, J. A. and R. S. Stafford 2001; Scott, J. G. and D. Cohen, et al. 2001; Davey, P. and E. Brown, et al. 2006; Cadieux, G. and R. Tamblyn, et al. 2007; Pulcini, C. and E. Cua, et al. 2007), ("CDC—Get Smart: Fast Facts About Antibiotic Resistance" 2011).

One type of Abx misuse is when the drug is administered in case of a non-bacterial disease, such as a viral infection, for which Abx is ineffective. For example, according to the USA center for disease control and prevention CDC, over 60 Million wrong Abx prescriptions are given annually to treat flu in the US. The health-care and economic consequences of the Abx over-prescription include: (i) the cost of antibiotics that are unnecessarily prescribed globally, estimated at >$10 billion annually; (ii) side effects resulting from unnecessary Abx treatment are reducing quality of healthcare, causing complications and prolonged hospitalization (e.g. allergic reactions, Abx associated diarrhea, intestinal yeast etc.) and (iii) the emergence of resistant strains of bacteria as a result of the overuse (the CDC has declared the rise in antibiotic resistance of bacteria as "one of the world's most pressing health problems in the 21$^{st}$ century" (Arias, C. A. and B. E. Murray 2009; "CDC—About Antimicrobial Resistance" 2011).

Antibiotics under-prescription is not uncommon either. For example up to 15% of adult bacterial pneumonia hospitalized patients in the US receive delayed or no Abx treatment, even though in these instances early treatment can save lives and reduce complications (Houck, P. M. and D. W. Bratzler, et al. 2002).

Technologies for infectious disease diagnosis have the potential to reduce the associated health and financial burden associated with Abx misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Current solutions (such as culture, PCR and immunoassays) do not fulfill all these requirements: (i) Some of the assays yield poor diagnostic accuracy (e.g. low sensitivity or specificity) (Uyeki et al. 2009), and are restricted to a limited set of bacterial or viral strains; (ii) they often require hours to days; (iii) they do not distinguish between pathogenic and non-pathogenic bacteria (Del Mar, C 1992), thus leading to false positives; (iv) they often fail to distinguish between a mixed and a pure viral infections and (v) they require direct sampling of the infection site in which traces of the disease causing agent are searched for, thus prohibiting the diagnosis in cases where the pathogen resides in an inaccessible tissue, which is often the case.

Consequentially, there still a diagnostic gap, which in turn often leads physicians to either over-prescribe Abx (the "Just-in-case-approach"), or under-prescribe Abx (the "Wait-and-see-approach") (Little, P. S. and I. Williamson 1994; Little, P. 2005; Spiro, D. M. and K. Y. Tay, et al. 2006), both of which have far reaching health and financial consequences.

Accordingly, a need exists for a rapid method that accurately differentiates between bacterial (including mixed bacterial plus viral infection), viral and non-bacterial, non-viral disease patients that addresses these challenges.

WO 2013/117746 teaches signatures and determinants for distinguishing between a bacterial and viral infection.

SUMMARY OF THE INVENTION

According to an aspect of some embodiments of the present invention there is provided a method of analyzing biological data, the biological data containing expression values of a plurality of polypeptides in the blood of a subject. The method comprises: calculating a distance between a segment of a curved line and an axis defined by a direction, the distance being calculated at a point over the curved line defined by a coordinate $\delta_1$ along the direction. The method further comprises correlating the distance to the presence of, absence of, or likelihood that the subject has a bacterial infection. The coordinate $\delta_1$ is defined by a combination of the expression values, wherein at least 90% of the segment is between a lower bound line $f(\delta_1) - \varepsilon_0$ and an upper bound line $f(\delta_1) + \varepsilon_1$, wherein the $g(\delta_0)$ equals $1/(1+\exp(\delta_1))$, and wherein each of the go and the gi is less than 0.5.

According to some embodiments of the invention the method comprises obtaining the likelihood based on the distance, comparing the likelihood to a predetermined threshold, and, treating the subject for the bacterial infection when the likelihood is above the predetermined threshold.

According to an aspect of some embodiments of the present invention there is provided a method of analyzing biological data, the biological data containing expression values of a plurality of polypeptides in the blood of a subject. The method comprises: calculating a distance between a segment of a curved line and an axis defined by a direction, the distance being calculated at a point over the curved line defined by a coordinate $\delta_0$ along the direction. The method further comprises correlating the distance to the presence of, absence of, or likelihood that the subject has a viral infection. The coordinate $\delta_0$ is defined by a combination of the expression values, wherein at least 90% of the segment is between a lower bound line $g(\delta_0)-\epsilon_0$ and an upper bound line $g(\delta_0)+\epsilon_1$, wherein the $f(\delta_0)$ equals $1/(1+\exp(\delta_0))$, and wherein each of the $\epsilon_0$ and the $\epsilon_1$ is less than 0.5.

According to some embodiments of the invention the method comprises obtaining the likelihood based on the distance, comparing the likelihood to a predetermined threshold, and, treating the subject for the viral infection when the likelihood is above the predetermined threshold.

According to some embodiments of the invention the combination of the expression values comprises a linear combination of the expression values.

According to some embodiments of the invention the combination of the expression values includes at least one nonlinear term corresponding to at least one of the expression values.

According to an aspect of some embodiments of the present invention there is provided a method of analyzing biological data, the biological data containing expression values of a plurality of polypeptides in the blood of a subject. The method comprises: calculating a first distance between a segment of a curved surface and a plane defined by a first direction and a second direction. The first distance being calculated at a point over the surface defined by first coordinate $\delta_0$ along the first direction and a second coordinate Si along the second direction. The method further comprises correlating the first distance to the presence of, absence of, or likelihood that the subject has a bacterial infection. Each of the coordinates is defined by a different combination of the expression values, wherein at least 90% of the segment is between a lower bound surface $f(\delta_0,\delta_1)-\epsilon_0$ and an upper bound surface $f(\delta_0,\delta_1)+\epsilon_1$, wherein the $f(\delta_0,\delta_1)$ equals $\exp(\delta_1)/(1+\exp(\delta_0)+\exp(\delta_1))$, and wherein each of the go and the gi is less than 0.5.

According to some embodiments of the invention for at least one of the coordinates, the combination of the expression values comprises a linear combination of the expression values.

According to some embodiments of the invention for at least one of the coordinates, the combination of the expression values includes at least one nonlinear term corresponding to at least one of the expression values.

According to some embodiments of the invention the method comprises obtaining the likelihood based on the first distance, comparing the likelihood to a predetermined threshold, and, treating the subject for the bacterial infection when the likelihood is above the predetermined threshold.

According to some embodiments of the invention the method comprises calculating a second distance between a segment of second curved surface and the plane; and correlating the second distance to the presence of, absence of, or likelihood that the subject has a viral infection. According to some embodiments of the invention at least 90% of the segment of the second surface is between a second lower bound surface $g(\delta_0,\delta_1)-\epsilon_2$ and a second upper bound surface $g(\delta_0,\delta_1)+\epsilon_3$, wherein the $g(\delta_0,\delta_1)$ equals $\exp(\delta_0)/(1+\exp(\delta_0)+\exp(\delta_1))$, and wherein each of the $\epsilon_2$ and the $\epsilon_3$ is less than 0.5.

According to some embodiments of the invention the method comprises obtaining the likelihood based on the second distance, comparing the likelihood to a second predetermined threshold, and, treating the subject for the viral infection when the likelihood is above the second predetermined threshold.

According to some embodiments of the invention the method comprises obtaining the likelihood that the subject has a bacterial infection based on the distance, obtaining the likelihood that the subject has a viral infection based on the second distance, comparing each of the likelihoods to a respective predetermined threshold, and, when each of the likelihoods is below the respective predetermined threshold, then determining that the patient is likely to have a non-infectious disease.

According to an aspect of some embodiments of the present invention there is provided a method of analyzing biological data, the biological data containing expression values of a plurality of polypeptides in the blood of a subject. The method comprises: calculating a distance between a segment of a curved surface and a plane defined by a first direction and a second direction. The distance is calculated at a point over the surface defined by first coordinate $\delta_0$ along the first direction and a second coordinate $\delta_1$ along the second direction. The method comprises correlating the distance to the presence of, absence of, or likelihood that the subject has, a viral infection; wherein each of the coordinates is defined by a different combination of the expression values, wherein at least 90% of the segment is between a lower bound surface $g(\delta_0,\delta_1)-\epsilon_0$ and an upper bound surface $g(\delta_0,\delta_1)+\epsilon_1$, wherein the $g(\delta_0,\delta_1)$ equals $\exp(\delta_0)/(1+\exp(\delta_0)+\exp(\delta_1))$, and wherein each of the so and the si is less than 0.5.

According to some embodiments of the invention each of the plurality of polypeptides is selected from the group consisting of CRP, IP-10, TRAIL, IL1ra, PCT and SAA.

According to some embodiments of the invention the plurality of polypeptides comprises at least three polypeptides.

According to some embodiments of the invention the plurality of polypeptides comprises at least three polypeptides selected from the group consisting of CRP, IP-10, TRAIL, IL1ra, PCT and SAA.

According to some embodiments of the invention the plurality of polypeptides comprises at least CRP and TRAIL.

According to some embodiments of the invention the plurality of polypeptides comprises at least CRP, TRAIL and IP-10.

According to some embodiments of the invention the method comprises generating an output of the likelihood, the output is presented as text.

According to some embodiments of the invention the method comprises generating an output of the likelihood, the output is presented graphically.

According to some embodiments of the invention the method comprises generating an output of the likelihood, the output is presented using a color index.

According to some embodiments of the invention the blood sample is whole blood.

According to some embodiments of the invention the blood sample is a fraction of whole blood.

According to some embodiments of the invention the blood fraction comprises serum or plasma.

According to some embodiments of the invention the method comprises determining the expression values, and wherein at least one of the expression values is determined electrophoretically or immunochemically.

According to some embodiments of the invention the immunochemical determination is effected by flow cytometry, radioimmunoassay, immunofluorescence or by an enzyme-linked immunosorbent assay.

According to some embodiments of the invention the calculating and the correlating is executed by a computer remote from the subject.

According to some embodiments of the invention the calculating and the correlating is executed by a computer near the subject.

According to some embodiments of the invention the calculating and the correlating is executed by a cloud computing resource of a cloud computing facility.

According to some embodiments of the invention the expression values are measured by a measuring system performing at least one automated assay selected from the group consisting of an automated ELISA, an automated immunoassay, and an automated functional assay, and the method comprises receiving said the biological data from said measuring system.

According to some embodiments of the invention the receiving is over an internet network via a network interface.

According to an aspect of some embodiments of the present invention there is provided a computer-implemented method for analyzing biological data. The method comprises: displaying on a display device a graphical user interface (GUI) having a calculation activation control; receiving expression values of polypeptides in the blood of a subject; responsively to an activation of the control by a user, automatically calculating a score based on the expression values; generating on the GUI a graphical scale having a first end identified as corresponding to a viral infection of the subject, and a second end identified as corresponding to a bacterial infection the subject; and generating a mark on the scale at a location corresponding to the score.

According to some embodiments of the invention the expression values are received by communicating with an external machine that measures the expression values. According to some embodiments of the invention the GUI comprises a communication control, wherein the communication with the external machine is in response to an activation of the communication control by the user.

According to some embodiments of the invention the GUI comprises a plurality of an expression value input fields, wherein the expression values are received via the input fields.

According to some embodiments of the invention the score is a likelihood that the subject has bacterial infection. According to some embodiments of the invention the score is a likelihood that the subject has viral infection.

According to an aspect of some embodiments of the present invention there is provided a computer software product, comprising a computer-readable medium in which program instructions are stored, which instructions, when read by a hardware processor, cause the hardware processor to receive expression values of a plurality of polypeptides in the blood of a subject who has an unknown disease, and to execute the method as delineated above and optionally as further detailed below.

According to an aspect of some embodiments of the present invention there is provided a system for analyzing biological data. The system comprises: a user interface configured to receive expression values of a plurality of polypeptides in the blood of a subject who has an unknown disease; and a hardware processor having a computer-readable medium storing the computer software product.

According to an aspect of some embodiments of the present invention there is provided a system for analyzing biological data. The system comprises: a first compartment configured to measure expression values of a plurality of polypeptides in the blood of a subject who has an unknown disease; a second compartment comprising a hardware processor having a computer-readable storing the computer software product.

According to some embodiments of the invention the first compartment, the second compartment and the display are mounted on or integrated with a body of a hand-held device.

According to an aspect of some embodiments of the present invention there is provided a method of analyzing a dataset. The method comprises: (a) accessing a dataset comprising classification groups based on expression values of a plurality of polypeptides in the blood of a subject who has an unknown disease in blood samples of multiple subjects, wherein the classification groups comprise a bacterial infection, a viral infection and a non-viral, non bacterial disease; and (b) analyzing the classification groups to provide at least a first probabilistic classification function $f(\delta_0,\delta_1)$ representing the likelihood that a particular subject has a bacterial infection, the first classification function being a function of a first coordinate $\delta_0$ and a second coordinate $\delta_1$, and wherein each of the coordinates is defined by a different combination of the expression values.

According to some embodiments of the invention the method further comprising calculating a second classification function $g(\delta_0,\delta_1)$ representing the likelihood that a particular subject has a viral infection, the second classification function being also a function of the first and the second coordinates.

According to some embodiments of the invention the method comprises calculating a third classification function $h(\delta_0,\delta_1)$ representing the likelihood that a particular subject has a non-viral, non bacterial disease, the third classification function being also a function of the first and the second coordinates.

According to some embodiments of the invention, for at least one of the coordinates, the combination of the expression values comprises a linear combination of the expression values.

According to some embodiments of the invention for at least one of the coordinates, the combination of the expression values includes at least one nonlinear term corresponding to at least one of the expression values.

According to some embodiments of the invention the method comprises generating an output of the analyzing.

According to some embodiments of the invention the dataset comprises one or more multidimensional entries.

According to some embodiments of the invention the method wherein each entry in the dataset comprises at least one clinical parameter of the respective subject.

According to some embodiments of the invention the method wherein the clinical parameter is selected from the group consisting of a sex, an age, a temperature, a time from symptoms onset and a weight.

According to some embodiments of the invention the analysis comprises machine learning.

According to some embodiments of the invention the machine learning comprises a supervised machine learning.

According to some embodiments of the invention the machine learning comprises at least one procedure selected from the group consisting of clustering, support vector machine, linear modeling, k-nearest neighbors analysis, decision tree learning, ensemble learning procedure, neural networks, probabilistic model, graphical model, Bayesian network, logistic regression and association rule learning.

According to some embodiments of the invention the method wherein the machine learning is selected from the group consisting of support vector machine, neural networks and logistic regression.

According to some embodiments of the invention the blood sample is whole blood.

According to some embodiments of the invention the blood sample is a fraction of whole blood.

According to some embodiments of the invention the blood fraction comprises serum or plasma.

According to some embodiments of the invention the expression value is determined electrophoretically or immunochemically.

According to some embodiments of the invention the immunochemical determination is effected by flow cytometry, radioimmunoassay, immunofluorescence or by an enzyme-linked immunosorbent assay.

According to an aspect of some embodiments of the present invention there is provided a method of predicting a prognosis for a disease. The method comprises measuring the TRAIL protein serum level in subject having the disease, wherein when the TRAIL level is below a predetermined level, the prognosis is poorer than for a subject having a disease having a TRAIL protein serum level above the predetermined level.

According to some embodiments of the invention the method wherein the disease is an infectious disease.

According to some embodiments of the invention the method wherein the disease is not an infectious disease.

According to an aspect of some embodiments of the present invention there is provided a method of determining a treatment course for a disease in a subject. The method comprises measuring the TRAIL protein serum level in the subject, wherein when the TRAIL level is below a predetermined level, the subject is treated with a treatment of last resort.

According to some embodiments of the invention the predetermined level is below 20 pg/ml.

According to an aspect of some embodiments of the present invention there is provided a method of determining an infection type in a female subject of fertility age.

The method comprises comparing the TRAIL protein serum level in the subject to a predetermined threshold, the predetermined threshold corresponding to the TRAIL protein serum level of a healthy female subject of fertility age, or a group of healthy female subjects of fertility age, wherein a difference between the TRAIL protein serum level and the predetermined threshold is indicative of an infection type.

According to an aspect of some embodiments of the present invention there is provided a method of determining an infection type in a male subject of fertility age.

The method comprises comparing the TRAIL protein serum level in the subject to a predetermined threshold, the predetermined threshold corresponding to the TRAIL protein serum level of a healthy male subject of fertility age, or a group of healthy male subjects of fertility age, wherein a difference between the TRAIL protein serum level and the predetermined threshold is indicative of an infection type.

According to some embodiments of the invention when the TRAIL protein serum level is above the predetermined threshold, the infection type is viral.

According to some embodiments of the invention when the TRAIL protein serum level is above the predetermined threshold, the infection type is not bacterial.

According to some embodiments of the invention when the TRAIL protein serum level is below the predetermined threshold, the infection type is bacterial.

According to some embodiments of the invention when the TRAIL protein serum level is below the predetermined threshold, the infection type is not viral.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-2C. The proteins TRAIL, IP-10 and CRP are differentially expressed in bacterial, viral and non-infectious patients. Box plots for TRAIL (A), IP-10 (B), and CRP (C), measured over the Majority cohort (n=765) are presented. Boxed line and circle correspond to group median and average respectively; t-test p-values between bacterial and viral groups and between infectious (bacterial and viral) vs. non-infectious (including healthy subjects) are depicted.

FIGS. 3A-3B. Comparison of the signature to lab parameters and protein biomarkers for diagnosing bacterial vs. viral patients. (A) Performance of clinical and lab parameters as well as the best performing pair (ANC and Lym %), triplet (ANC, Lym % and Pulse), and quadruplets (ANC, Lym %, Pulse, Mono %) of parameters, the values of which were combined using a logistic regression. Comparison was done on the Majority cohort (bacterial and viral patients, n=653), apart from pulse (recorded in 292 bacterial and 326 viral patients), and respiratory rate (recorded in 292 bacterial and 326 viral patients). The signature performed significantly better ($P<10^{-15}$) than the optimal quadruplet. (B) The signature performed significantly better ($P<10^{-8}$) than biomarkers with a well-established role in the host response to infections. For each of the select biomarkers, analysis was performed in a subgroup of the Majority cohort ($43 \leq n \leq 154$ for each analysis, a convenience sample, n depended on the strength of the signal). Error bars represent 95% CI.

FIGS. 17A-17B. Comparison of the performance of the signature and CRP using different cutoffs. A. Performance measured in the Unanimous (bacterial, viral) cohort (n=527); B. Performance measured in the Majority (bacterial, viral) cohort (n=653). Error bars represent 95% CI. Signature sensitivity (left) and specificity (right) were calculated after filtering out 14% of the patients with a marginal immune response.

FIGS. 18A-18H. Scatter plots of levels of selected protein biomarkers (arbitrary units) in bacterial and viral patients. Boxed line and circle correspond to group median and average respectively. T-test p-values between bacterial and viral groups are depicted.

FIGS. 21A-21C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 0 to 100.

FIGS. 22A-22C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 100 to 200.

FIGS. 23A-23C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 200 to 300.

FIGS. 24A-24C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 300 to 400.

FIGS. 25A-25C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 400 to 500.

FIGS. 26A-26C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 500 to 1000.

FIGS. 27A-27C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 ranging from 1000 to 2000.

FIGS. 28A-28C. Probability of viral (A) bacterial or mixed (B) and non-infectious or healthy (C) as a function of TRAIL (y-axis), CRP (x-axis), and IP-10 concentrations, as obtained according to some embodiments of the present invention for IP-10 which is 2000 or more.

FIGS. 29A-29F illustrate exemplary outputs of the method for distinguishing between bacterial and non-bacterial infection according to an embodiment of the present invention.

FIG. 31 is a flowchart diagram of a method suitable for analyzing biological data obtained from a subject, according to various exemplary embodiments of the present invention.

FIGS. 37A-37B are graphs illustrating the difference in TRAIL concentrations in males and females of fertility age.

DESCRIPTION OF SPECIFIC EMBODIMENTS OF THE INVENTION

Figure 1A:
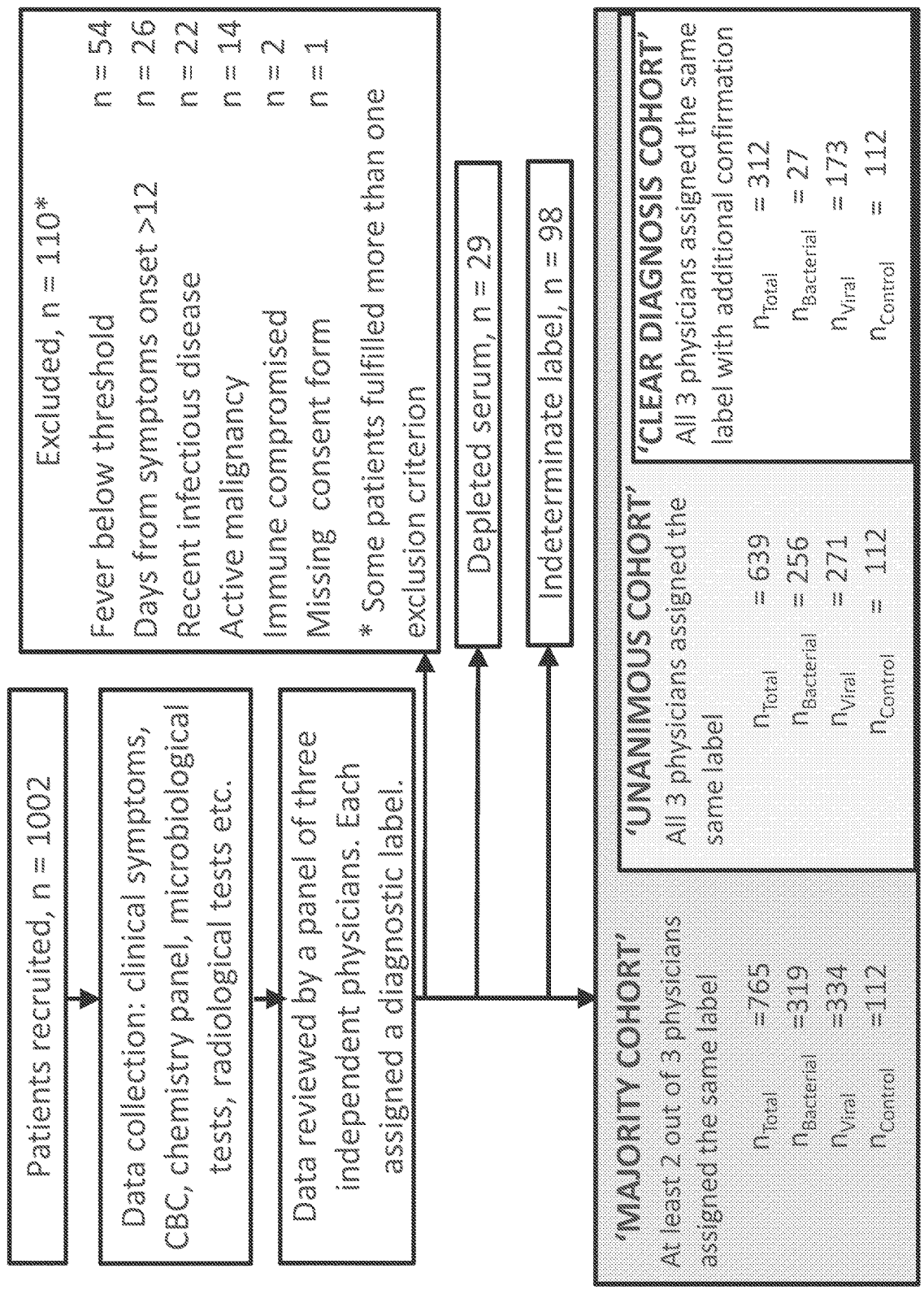
FIGS. 1A-1B. Study workflow. (A) An overview of the study workflow. $n_{Bacterial}$, $n_{Viral}$ and $n_{Control}$ represent the number of bacterial (including mixed bacterial plus viral co-infections), viral and control (with no apparent infectious disease) cases, respectively. (B) Proteins discovery and validation process.

The present invention, in some embodiments thereof, relates to computational analysis, and, more particularly, but not exclusively, to computational analysis of biological data, e.g., for the purpose of distinguishing between bacterial infection and non-bacterial disease, and/or between a bacterial infection and viral infection, and/or between an infectious and non-infectious disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Different infectious agents have unique molecular patterns that can be identified and targeted by the immune system. Pathogen-associated molecular patterns (PAMPs) are an example of such molecules that are associated with different groups of pathogens and may be recognized by cells of the innate immune system using Toll-like receptors (TLRs) and other pattern recognition receptors (e.g. NOD proteins).

These patterns may vary considerably between different classes of pathogens and thus elicit different immune responses. For example, TLR-4 can recognize lipopolysaccharide, a constituent of gram negative bacteria, as well as lipoteichoic acids, constituent of gram positive bacteria, hence promoting an anti-microbial response of the immune system. TLR-3 can recognize single stranded RNA (often indicative of a viral infection) and thus prompt the appropriate anti-viral response. By distinguishing between different classes of pathogens (e.g bacterial versus viral) the immune system can mount the appropriate defense.

In the past few decades, several host markers have been identified that can be used for differential diagnosis of infection source in various indications. By measuring markers derived from the host rather than the pathogen, it is possible to minimize "false-positive" diagnoses due to non-pathogenic strains of bacteria that are part of the body's natural flora. One example is Procalcitonin (PCT), a precursor of the hormone calcitonin produced by the C-cells of the thyroid gland. PCT levels in the blood stream of healthy individuals is hardly detectable (in the pg/ml range) but it might increase dramatically, as a result of a severe infection with levels rising up to 100 ng/ml. PCT is heavily used to diagnose patients with systemic infection, sepsis, with sensitivity of 76% and specificity of 70%. However, studies that tested the diagnostic value of PCT in other non-systemic infection such as pneumonia or upper respiratory tract infections found it to be limited, especially when used in isolation.

The present inventors previously identified novel sets of biomarkers whose pattern of expression significantly correlates with infection type—as documented in International Patent Application WO2011132086 and WO2013/117746, both of which are incorporated herein by reference.

The present invention, in some embodiments thereof, is based on the use of signature of polypeptides for the diagnosis of bacterial infections, viral infections and non-bacterial, non-viral diseases. The methods of the present embodiments employ pattern recognition algorithms for the identification of the type of infection a subject is suffering from, which in turn allows for the selection of an appropriate treatment regimen. Various embodiments of the invention address limitations of current diagnostic solutions by: (i) allowing accurate diagnostics on a broad range of pathogens; (ii) enabling rapid diagnosis (within minutes); (iii) insensitivity to the presence of non-pathogenic bacteria and viruses (thus reducing the problem of false-positive); and (iv) eliminating the need for direct sampling of the pathogen, thus enabling diagnosis of inaccessible infections. Thus, some methods of the invention allow for the selection of subjects for whom antibiotic treatment is desired and prevent unnecessary antibiotic treatment of subjects having only a viral infection or a non-infectious disease. Some methods of the invention also allow for the selection of subjects for whom anti-viral treatment is advantageous.

To corroborate the findings in International Patent Application WO2013/117746, the present inventors have now increased the number of patients taking part in a multi-center clinical trial, enrolling 1002 hospital patients with different types of established infections as well as controls (patients with established non-viral/non-bacterial disease and healthy individuals).

Seeking to improve the level of accuracy and sensitivity of the previously described methods, the present inventors have now used a trinary classifier, which classifies patients (those having an established disease type) into one of three classes: bacterial infection, viral infection and non-bacterial, non-viral disease. Comparing the levels of a combination of polypeptides of a test subject with the expression patterns obtained in the study yielded superior results in terms of sensitivity and specificity compared to a binary classifier as summarized in Example 3 and Tables 9-12.

In the context of the present invention, the following abbreviations may be used: ANC=Absolute neutrophil count; ANN=Artificial neural networks; AUC=Area under the receiver operating curve; BP=*Bordetella pertussis*; CHF=Congestive heart failure; CI=Confidence interval; CID=Congenital immune deficiency; CLL=Chronic lymphocytic leukemia; CMV=Cytomegalovirus; CNS=Central nervous system; COPD=Chronic obstructive pulmonary disease; CP=*Chlamydophila pneumonia*; CRP=C-reactive protein; CSF=Cerebrospinal fluid; CV=Coefficient of variation; DOR=Diagnostic odds ratio; EBV=Epstein bar virus; eCRF=Electronic case report form; ED=Emergency department, ELISA=Enzyme-linked immunosorbent assay; FDR=False discovery rate; FMF=Familial Mediterranean fever; G-CSF=Granulocyte colony-stimulating factor; GM-CSF=Granulocyte-macrophage colony-stimulating factor; HBV=Hepatitis B virus; HCV=Hepatitis C virus; HI=*Haemophilus influenza*; HIV=Human immunodeficiency virus; IDE=Infectious disease experts; IL=Interleukin; IRB=institutional review board; IVIG=Intravenous immunoglobulin; KNN=K-nearest neighbors; LP=*Legionella pneumophila*; LR+=Positive likelihood ratio; LR−=Negative likelihood ratio; LRTI=Lower respiratory tract infections; mAb=Monoclonal antibodies; MDD=Minimum detectable dose; MDS=Myelodysplastic syndrome; MP=*Mycoplasma pneumonia*; MPD=Myeloproliferative disease; NPV=Negative predictive value; PCT=Procalcitonin; PED=Pediatric emergency department; PPV=Positive predictive value; QA=Quality assurance; RSV=Respiratory syncytial virus; RV=Rhinovirus; SIRS=systemic inflammatory syndrome; SP=*Streptococcus pneumonia*; STARD=Standards for Reporting of Diagnostic Accuracy; SVM=Support vector machine; TNF=Tumor necrosis factor; URTI=Upper respiratory tract infection; UTI=Urinary tract infection; WBC=White blood cell; WS=Wilcoxon rank-sum.

In the context of the present invention, the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathews Correlation coefficient) is calculated as follows: MCC=(TP*TN−FP*FN)/{(TP+FN)*(TP+FP)*(TN+FP)*(TN+FN)}^0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Mathews correlation coefficient (MCC), or as a likelihood, odds ratio, Receiver Operating Characteristic (ROC) curve, Area Under the Curve (AUC) among other measures.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

Aspects of the invention will now be described in detail.

FIG. 31 is a flowchart diagram of a method suitable for analyzing biological data obtained from a subject, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

In some embodiments of the present invention the subject has been previously treated with an antibiotic, and in some embodiments of the present invention the subject has not been previously treated with an antibiotic.

Any of the methods described herein can be embodied in many forms. For example, it can be embodied in on a tangible medium such as a computer for performing the method operations. It can be embodied on a computer readable medium, comprising computer readable instructions for carrying out the method operations. It can also be embodied in electronic device having digital computer capabilities arranged to run the computer program on the tangible medium or execute the instruction on a computer readable medium.

Computer programs implementing the method of the present embodiments can commonly be distributed to users on a distribution medium such as, but not limited to, CD-ROMs or flash memory media. From the distribution medium, the computer programs can be copied to a hard disk or a similar intermediate storage medium. In some embodiments of the present invention, computer programs implementing the method of the present embodiments can be distributed to users by allowing the user to download the programs from a remote location, via a communication network, e.g., the internet. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The computational operations of the method of the present embodiments can be executed by a computer, either remote from the subject or near the subject. When the computer is remote from the subject, it can receive the data over a network, such as a telephone network or the Internet. To this end, a local computer can be used to transmit the data to the remote computer. This configuration allows performing the analysis while the subject is at a different location (e.g., at home), and also allows performing simultaneous analyses for multiple subjects in multiple different locations.

The computational operations of the method can also be executed by a cloud computing resource of a cloud computing facility. The cloud computing resource can include a computing server and optionally also a storage server, and can be operated by a cloud computing client as known in the art.

The method according to some embodiments may be used to "rule in" a bacterial infection. Alternatively, the method may be used to rule out a non-bacterial infection. The method according to some embodiments can be used to "rule out" a bacterial infection and "rule in" a non-bacterial disease.

The method according to some embodiments may be used to "rule in" a viral infection. Alternatively, the method may be used to rule out a non-viral infection.

The method according to some embodiments can be used to "rule out" a viral infection and "rule in" a non-viral disease.

The method according to some embodiments may be used to "rule in" an infectious disease. Alternatively, the method may be used to rule out a non-infectious disease. The method according to some embodiments can be used to "rule out" an infectious disease and "rule in" a non-infectious disease.

The biological data analyzed by the method contain expression values of a plurality of polypeptides in the blood of a subject. In some embodiments the biological data comprises expression values of only two polypeptides, in some embodiments the biological data comprises expression values of at least three polypeptides, in some embodiments biological data comprises expression values of only three polypeptides, in some embodiments biological data comprises expression values of at least four polypeptides, in some embodiments biological data comprises expression values of only four polypeptides, in some embodiments biological data comprises expression values of at least five polypeptides, and in some embodiments biological data comprises expression values of only five polypeptides.

The present Inventors contemplate many types of polypeptides. Representative examples include, without limitation, CRP, IP-10, TRAIL, IL1ra, PCT and SAA. In some embodiments the plurality of polypeptides comprises at least CRP and TRAIL, and in some embodiments the plurality of polypeptides comprises at least CRP, TRAIL and IP-10.

In some embodiments of the present invention, the biological data is provided in the form of a subject-specific dataset, as further detailed herein.

According to a particular embodiment, the levels of secreted (i.e. soluble) polypeptides (e.g., TRAIL, CRP and IP-10) are analyzed by the method.

The term "subject" as used herein is preferably a human. A subject can be male or female. The subject may be a newborn, baby, infant or adult. A subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more risk factors for having an infection. A subject may also have an infection but show no symptoms of infection.

The subject whose disease is being diagnosed according to some embodiments of the present invention is referred to below as the "test subject". The present Inventors have collected knowledge regarding the expression pattern of polypeptides, of a plurality of subjects whose disease has already been diagnosed, and have devised the analysis technique of the present embodiments based on the collected knowledge. This plurality of subjects is referred to below as "pre-diagnosed subjects" or "other subjects".

As used herein, the phrase "bacterial infection" refers to a condition in which a subject is infected with a bacterium. The infection may be symptomatic or asymptomatic. In the context of this invention, the bacterial infection may also comprise a viral component (i.e. be a mixed infection being the result of both a bacteria and a virus).

The bacterial infection may be acute or chronic.

An acute infection is characterized by rapid onset of disease, a relatively brief period of symptoms, and resolution within days. A chronic infection is an infection that develops slowly and lasts a long time. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scaring. Thus, acute and chronic infections may elicit different underlying immunological mechanisms.

The bacterial infection may be the result of gram-positive, gram-negative bacteria or atypical bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium complex*, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" as used herein refer to bacteria characterized by the presence of a double membrane surrounding each bacterial cell.

Representative Gram-negative bacteria include *Acinetobacter calcoaceticus*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica* and *Yersinia pestis*.

The term "Atypical bacteria" refers to bacteria that do not fall into one of the classical "Gram" groups. Typically they are intracellular bacterial pathogens. They include, without limitations, *Mycoplasmas* spp., *Legionella* spp. *Rickettsiae* spp., and *Chlamydiae* spp.

The term "non-bacterial disease" as used herein, refers to any disease or condition that is not caused by infectious bacteria.

Referring to FIG. 31, the method begins at 310 and continues to 311 at which a first distance d between a segment $S_{ROI}$ of a first curved object S and a non-curved object $\pi$ is calculated. Generally, the first curved object S is a manifold in n dimensions, where n is a positive integer, and the non-curved object $\pi$ is a hyperplane in an n+1 dimensional space.

The concept of n-dimensional manifolds and hyperplanes in n+1 dimensions are well known to those skilled in the art of geometry. For example, when n=1 the first curved object is a curved line, and the non-curved object $\pi$ is a hyperplane in 2 dimensions, namely a straight line defining an axis. When n=2, the first curved object is a curved surface, and the non-curved object $\pi$ is a hyperplane in 3 dimensions, namely a flat plane, referred to below as "a plane".

The hyperplane $\pi$ is defined by n directions. For example, when the non-curved object is an axis, it is defined by a single direction, and when the non-curved object is a plane it is defined by two directions, referred to as a first direction and a second direction.

The distance between the manifold S and hyperplane $\pi$ is calculated at a point P over the hyperplane. P is defined by n coordinates. For example, when the hyperplane is an axis, P is defined by a single coordinate $\delta_1$, along the single direction, and when the hyperplane is a plane, P is define by a pair of coordinates denoted $(\delta_0, \delta_1)$, where $\delta_0$ is referred to as "a first coordinate" and is defined along the first direction, and $\delta_1$ is referred to as "a second coordinate" and is defined along the second direction. Unless explicitly stated otherwise, a reference to coordinate $\delta_0$ describes an optional embodiment which is contemplated when S is a surface and $\pi$ is a plane.

The directions are denoted using the same Greek letters as the respective coordinates, except that the directions are denoted by underlined Greek letters to indicate that these are vectors. Thus, the first direction is denoted $\underline{\delta_0}$, and the second direction is denoted $\underline{\delta_1}$.

Figure 32A:
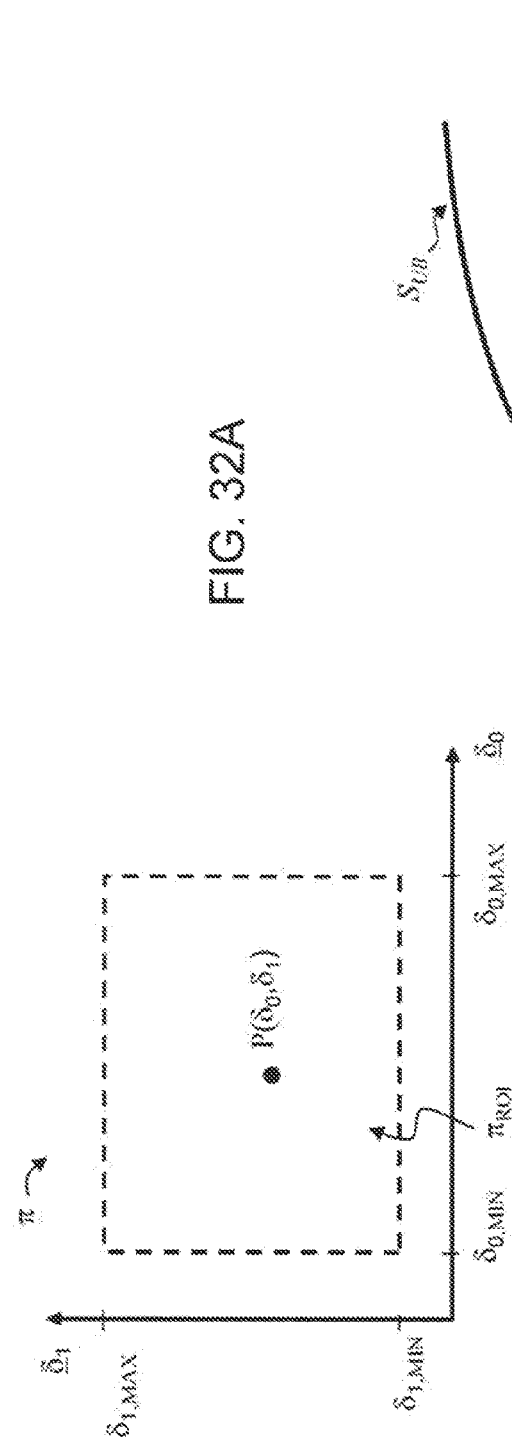
FIGS. 32A-32B are schematic illustrations describing a procedure for calculating a distance of a surface from a plane according to some embodiments of the present invention.

FIG. 32A illustrates the hyperplane $\pi$ for the case of n=2. In these embodiments, it is a plane defined by directions $\underline{\delta_0}$ and $\underline{\delta_1}$. Also shown is a point P at $(\delta_0, \delta_1)$.

Directions $\underline{\delta_0}$ and $\underline{\delta_1}$, are shown orthogonal to each other, but this need not necessarily be the case, since the angle between $\underline{\delta_0}$ and $\underline{\delta_1}$ can be different from 90°. Within the plane $\pi$, there is a planar region-of-interest $\pi_{ROI}$ spanning from a minimal first coordinate $\delta_{0,MIN}$ to a maximal first coordinate $\delta_{0,MAX}$ along direction $\underline{\delta}_0$, and from a minimal second coordinate $\delta_{1,MIN}$ to a maximal second coordinate $\delta_{1,MAX}$ along direction $\underline{\delta}_1$. The point P is within the region-of-interest $\pi_{ROI}$. When n=1 (not shown), $\pi$ is an axis and the region-of-interest $\pi_{ROI}$ is a linear segment of $\pi$ spanning from $\delta_{1,MIN}$ to $\delta_{1,MAX}$ along direction $\underline{\delta}_1$.

Figure 32B:
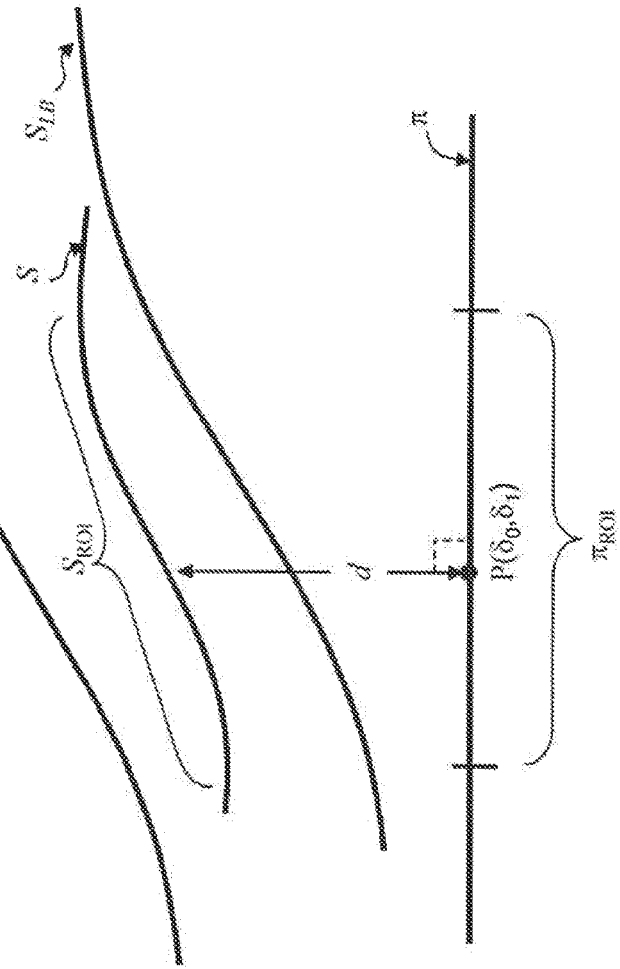

The calculation of the first distance $\bar{d}$ is illustrated in FIG. 32B which illustrates the hyperplane it and manifold S. The distance d is measured from S to the point P, perpendicularly to $\pi$. It is to be understood that while each of objects $\pi$ and S is illustrated as a one dimensional line, this need not necessarily be the case, since S and $\pi$ are generally n-dimensional mathematical objects. For example, when S is a surface and $\pi$ is a plane both $\pi$ and S are two dimensional mathematical objects. The segment $S_{ROI}$ of S is above a region-of-interest $\pi_{ROI}$. For example, when it is a plane $7t_{ROI}$ is a planar region-of-interest, and when $\pi$ is an axis, $\pi_{ROI}$ is a linear segment along the axis. Thus, $\pi_{ROI}$ is the projection of $S_{ROI}$ on it. For n=2, $S_{ROI}$ is preferably a non-planar segment of (the surface) S, and for n=1, $S_{ROI}$ is preferably a curved segment of (the curve) S.

Each of the n coordinates is defined by a combination of expression values of the polypeptides. For example, for n=1, the coordinate $\delta_1$ is defined by a combination of expression values of the polypeptides, and for n=2 each of the coordinates $\delta_0$ and $\delta_1$ is defined by a different combination of expression values of the polypeptides.

For example, $\delta_1$ and optionally also $\delta_0$ are combinations of the polypeptides, according to the following equation:

$$\delta_0 = a_0 + a_1 D_1 + a_2 D_2 + a_2 D_2 + \ldots + \phi_0$$

$$\delta_1 = b_0 + b_1 D_1 + b_2 D_2 + \ldots + \phi_1,$$

where $a_0, a_1, \ldots$ and $b_0, b_1, \ldots$ are constant and predetermined coefficients, and each of the variables $D_1, D_2, \ldots$ is an expression levels of one of the polypeptides, and $\phi_0$ and $\phi_1$ are functions that are nonlinear with respect to at least one of the expression levels.

Each of the functions $\phi_0$ and $\phi_1$ is optional and may, independently, be set to zero (or, equivalently, not included in the calculation of the respective coordinate). When $\phi_0=0$ the coordinate $\delta_0$ is a combination of the polypeptides, and when $\phi_1=0$ the coordinate $\delta_1$ is a combination of the polypeptides.

The nonlinear functions $\phi_0$ and $\phi_1$ can optionally and preferably be expressed as a sub of powers of expression levels, for example, according to the following equations:

$$\phi_0 = \Sigma_i q_i X_i^{\gamma i}$$

$$\phi_1 = \Sigma_i q_i X_i^{\lambda i},$$

where i is a summation index, $q_i$ and $r_i$ are sets of coefficients, $X_i \in \{D_1, D_2, \ldots\}$, and each of $\gamma i$ and $\lambda i$ is a numerical exponent. Note that the number of terms in each of the nonlinear functions $\phi_0$ and $\phi_1$ does not necessarily equals the number of the polypeptides, and that two or more terms in each sum may correspond to the same polypeptide, albeit with a different numerical exponent.

Representative examples of coefficients suitable for the present embodiments are provided in the Examples section that follows (see Tables 3, 13-17, 29 and 31-36).

When $\phi_0=0$, $\phi_1=0$ and the polypeptides include TRAIL, $\delta_0$ is optionally and preferably an increasing function of an expression value of TRAIL, and $\delta_1$ is a decreasing function of TRAIL. When $\phi_0=0$, $\phi_1=0$ and the polypeptides include CRP, $\delta_1$ and optionally also $\delta_0$ are optionally and preferably increasing functions of an expression value of CRP. When the polypeptides include IP-10, $\delta_1$ and optionally also $\delta_0$ are optionally and preferably are increasing functions of an expression value of IP-10.

In embodiments in which $\phi_0=0$, $\phi_1=0$ and the polypeptides include TRAIL, CRP and IP-10, each $\delta_0$ and $\delta_1$ can be a linear combination of TRAIL, CRP and IP-10, according to the following equation:

$$\delta_0 = a_0 + a_1 C + a_2 I + a_3 T$$

$$\delta_1 = b_0 + b_1 C + b_2 I + b_3 T,$$

where C, I and T are, respectively, the expression levels of CRP, IP-10 and TRAIL.

Preferably, both $a_1$ and $b_1$ are positive. Preferably both $a_2$ and $b_2$ are positive.

Preferably, $a_3$ is positive, and $b_3$ is negative. Representative examples of coefficients suitable for the embodiments in which the combination is linear combination and the polypeptides are CRP, IP-10 and TRAIL are provided in the Examples section that follows (see Tables 3, 13-17 and 33).

In embodiments in which $\phi_0 \neq 0$, $\phi_1 \neq 0$ and the polypeptides include TRAIL, CRP and IP-10, each $\delta_0$ and $\delta_1$ can be a combination of TRAIL, CRP and IP-10, according to the following equations:

$$\delta_0 = a_0 + a_1 C + a_2 I + a_3 T + \phi_0$$

$$\delta_1 = b_0 + b_1 C + b_2 I + b_3 T + \phi_1,$$

where each of $\phi_0$ and $\phi_1$ is a nonlinear function of at least one or at least two of C, I and T. As a representative example, $\phi_0$ and $\phi_1$ can be expressed as:

$$\phi_0 = q_1 C^{\gamma 1} + q_2 C^{\gamma 2} + q_3 T^{\gamma 3}$$

$$\phi_1 = r_1 C^{\gamma 1} + r_2 C^{\gamma 2} + r_3 T^{\gamma 3}.$$

Representative examples of coefficients suitable for the embodiments in which the polypeptides are CRP, IP-10 and TRAIL and the nonlinear functions are not taken to be zero are provided in the Examples section that follows (see Table 36).

The boundaries $\delta_{0,MIN}$, $\delta_{0,MAX}$, $\delta_{1,MIN}$ and $\delta_{1,MAX}$ of $\pi_{ROI}$ preferably correspond to the physiologically possible ranges of the expression values of the polypeptides.

When measured using the protocols described in Example 8, more preferably Example 9, below, the physiologically possible ranges are typically from 0 to about 400 ug/ml (CRP), from 0 to about 3000 µg/ml (IP-10), and from 0 to about 700 µg/ml (TRAIL). Some subjects may exhibit concentrations that lie outside these ranges. —In various exemplary embodiments of the invention, when the expression values of TRAIL, CRP and IP-10 are measured according to the protocol described in Example 8, more preferably Example 9, below, the values of the coefficients $a_0, \ldots, a_3$ and $b_0, \ldots, b_3$ are taken from Table 3, below, and the boundaries of $\pi_{ROI}$ are: $\delta_{0,MIN}=-1.3$ $\delta_{0,MAX}=45$ $\delta_{1,MIN}=-14.3$ and $\delta_{1,MAX}=49.6$.

When the expression values of TRAIL, CRP and IP-10 are measured by a protocol which is different from the protocol described in Example 8, more preferably Example 9, below, the values of the coefficients $a_0, \ldots, a_3$ and $b_0, \ldots, b_3$ are different from the values in Table 3 below, and therefore the boundaries of $\pi_{ROI}$ are also different from the above values. In such cases, the values of the coefficients and boundaries are correlative to the aforementioned values wherein the correlation for each coefficient and boundary is derived from the correlation between the expression value of the respective protein as measured according to the protocol described in Example 8, more preferably Example 9, and the expression value of the respective protein as actually measured.

At least a major part of the segment $S_{ROI}$ of curved object S is between two curved objects referred to below as a lower bound curved object $S_{LB}$ and an upper bound curved object SUB.

As used herein "major part of the segment $S_{ROI}$" refers to a part of a smoothed version $S_{ROI}$ whose length (when n=1), surface area (when n=2) or volume (when n≥3) is 60% or 70% or 80% or 90% or 95% or 99% of a smoothed version of the length, surface area or volume of $S_{ROI}$, respectively.

As used herein, "a smooth version of the segment $S_{ROI}$" refers to the segment $S_{ROI}$, excluding regions of $S_{ROI}$ at the vicinity of points at which the Gaussian curvature is above a curvature threshold, which is X times the median curvature of $S_{ROI}$, where X is 1.5 or 2 or 4 or 8.

The following procedure can be employed for the purpose of determining whether the major part of the segment $S_{ROI}$ is between $S_{LB}$ and $S_{UB}$. Firstly, a smoothed version of the segment $S_{ROI}$ is obtained. Secondly, the length (when n=1), surface area (when n=2) or volume (when n≥3) $A_1$ of the smoothed version of the segment $S_{ROI}$ is calculated. Thirdly, the length (when n=1) surface area (when n=2) or volume (when n≥3) $A_2$ of the part of the smoothed version of the segment $S_{ROI}$ that is between $S_{LB}$ and $S_{UB}$ is calculated. Fourthly, the percentage of $A_2$ relative to $A_1$ is calculated.

FIGS. 33A-33D illustrates a procedure for obtaining the smooth version of $S_{ROI}$.

Figure 33A:
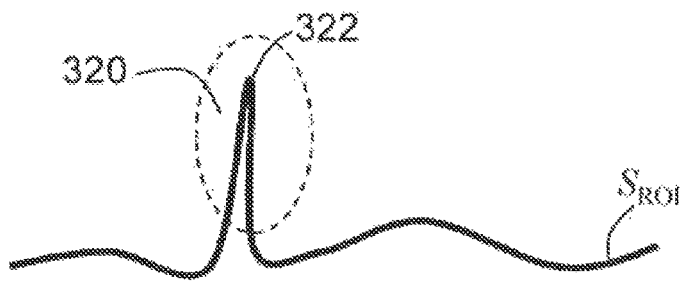
FIGS. 33A-33D are schematic illustrations describing a procedure for obtaining the smooth version of a segment of a surface, according to some embodiments of the present invention.
Figure 33B:
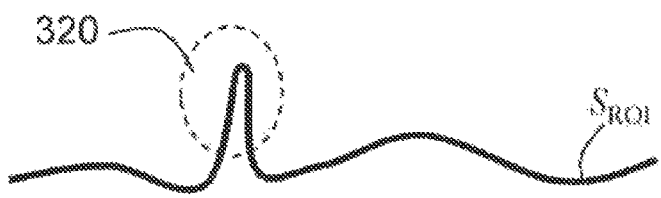
Figure 33C:
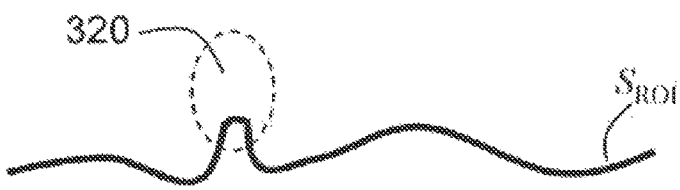
Figure 33D:

For clarity of presentation, $S_{ROI}$ is illustrated as a one dimensional segment, but the skilled person would understand that $S_{ROI}$ is generally an n-dimensional mathematical object. The Gaussian curvature is calculated for a sufficient number of sampled points on $S_{ROI}$. For example, when the manifold is represented as point cloud, the Gaussian curvature can be calculated for the points in the point cloud. The median of the Gaussian curvature is then obtained, and the curvature threshold is calculated by multiplying the obtained median by the factor X. FIG. 33A illustrates $S_{ROI}$ before the smoothing operation. Marked is a region 320 having one or more points 322 at which the Gaussian curvature is above the curvature threshold. The point or points at which with the Gaussian curvature is maximal within region 320 is removed and region 320 is smoothly interpolated, e.g., via polynomial interpolation, (FIG. 33B). The removal and interpolation is repeated iteratively (FIG. 33C) until the segment $S_{ROI}$ does not contain regions at which the Gaussian curvature is above the curvature threshold (FIG. 33D).

When n=1 (namely when S is a curved line), $S_{LB}$ is a lower bound curved line, and $S_{UB}$ an upper bound curved line. In these embodiments, $S_{LB}$ and $S_{UB}$ can be written in the form:

$$S_{LB}=f(\delta_1)-\varepsilon_0,$$

$$S_{UB}=f(\delta_1)+\varepsilon_1$$

where $f(\delta_1)$ is a probabilistic classification function of the coordinate $\delta_1$ (along the direction $\underline{\delta}_1$) which represents the likelihood that the test subject has a bacterial infection. In some embodiments of the invention $f(\delta_1)=1/(1+\exp(\delta_1))$. Both $S_{LB}$ and $S_{UB}$ are positive for any value of $\delta_1$ within $\pi_{ROI}$. Also contemplated, are embodiments in which $f(\delta_1)$ is a probabilistic classification function which represents the likelihood that the test subject has a viral infection. Further contemplated, are embodiments in which $f(\delta_1)$ is a probabilistic classification function which represents the likelihood that the test subject has an infection.

When n=2 (namely when S is a curved surface), $S_{LB}$ is a lower bound curved surface, and $S_{UB}$ an upper bound curved surface. In these embodiments, $S_{LB}$ and $S_{UB}$ can be written in the form:

$$S_{LB}=f(\delta_0,\delta_1)-\varepsilon_0,$$

$$S_{UB}=f(\delta_0,\delta_1)+\varepsilon_1$$

where $f(\delta_0,\delta_1)$ is a probabilistic classification function of the first and second coordinates (along the first and second directions) which represents the likelihood that the test subject has a bacterial infection. In some embodiments of the invention $f(\delta_0,\delta_1)=\exp(\delta_1)/(1+\exp(\delta_0)+\exp(\delta_1))$. Both $S_{LB}$ and $S_{UB}$ are positive for any value of $\delta_0$ and $\delta_1$ within $\gamma_{ROI}$.

In any of the above embodiments each of the parameters $\varepsilon_0$ and $\varepsilon_1$ is less than 0.5 or less than 0.4 or less than 0.3 or less than 0.2 or less than 0.1 or less than 0.05.

Referring again to FIG. 31, the method proceeds to 312 at which the calculated distance d is correlated to the presence of, absence of, or likelihood that the subject has, a disease or condition corresponding to the type of the probabilistic function f. For example, when the probabilistic function f represents the likelihood that the test subject has a bacterial infection, the calculated distance d is correlated to the presence of, absence of, or likelihood that the subject has, a bacterial infection.

In various exemplary embodiments of the invention the correlation includes determining that the distance d is the likelihood that the subject has a bacterial infection. The likelihood is optionally and preferably compared to a predetermined threshold $\omega_B$, wherein the method can determine that it is likely that the subject has a bacterial infection when the likelihood is above $\omega_B$, and that it is unlikely that the subject has a bacterial infection otherwise. Typical values for $\omega_B$ include, without limitation, about 0.2, about 0.3, about 0.4, about 0.5, about 0.6 and about 0.7. Other likelihood thresholds are also contemplated.

In some embodiments of the present invention, when the method determines that it is likely that the subject has a bacterial infection, the subject is treated (316) for the bacterial infection, as further detailed herein.

The present inventors found a probabilistic classification function $g(\delta_0,\delta_1)$ which represents the likelihood that the test subject has a viral infection. In various exemplary embodiments of the invention $g(\delta_0,\delta_1)$ equals $\exp(\delta_0)/(1+\exp(\delta_0)+\exp(\delta_1))$.

The function g can, according to some embodiments of the present invention, be utilized also for estimating the presence of, absence of, or likelihood that the subject has, a viral infection. Thus, in some embodiments, the method proceeds to 313 at which a second distance between a segment of a second curved surface and the plane π is calculated, and 314 at which the second distance is correlated to the presence of, absence of, or likelihood that the subject has, a viral infection. The procedure and definitions corresponding to 313 and 314 are similar to the procedure and definitions corresponding to 311 and 312 described above, mutatis mutandis. Thus, for example, a major part of the segment of the second surface is between a second lower bound surface $g(\delta_0,\delta_1)-\varepsilon_2$ and a second upper bound surface $g(\delta_0,\delta_1)+\varepsilon_3$, wherein each of $\varepsilon_2$ and $\varepsilon_3$ is less than 0.5 or less than 0.4 or less than 0.3 or less than 0.2 or less than less than 0.1 or less than 0.05.

In some embodiments of the present invention, when the method determines that it is likely that the subject has a viral infection, the subject is treated (316) for the viral infection, as further detailed herein.

In various exemplary embodiments of the invention the correlation includes determining that the second distance is the likelihood that the subject has a viral infection. The likelihood is optionally and preferably compared to a predetermined threshold $\omega_V$, wherein the method can determine that it is likely that the subject has a viral infection when the likelihood is above $\omega_V$, that it is unlikely that the subject has a viral infection otherwise. Typical values for $\omega_V$ include, without limitation, about 0.5, about 0.6 about 0.7 and about 0.8. Other likelihood thresholds are also contemplated.

In embodiments in which operations 313 and 314 are executed, operations 311 and 312 can be either executed or not executed. For example, the present embodiments contemplate a procedure in which operations 311 and 312 are not executed, and the method determines the likelihood that the subject has a viral infection, without calculating the first distance and without correlating the first distance to the presence of, absence of, or likelihood that the subject has, a bacterial infection.

Alternatively, all operations 311-314 can be executed, wherein 311 and 312 are executed irrespectively of the outcome of 314, and 313 and 314 are executed irrespectively of the outcome of 312. In these embodiments, the method optionally and preferably determines both the likelihood that the subject has a bacterial infection, and the likelihood that the subject has a viral infection. Each of these likelihoods can be compared to the respective predetermined threshold ($\omega_B$ or $\omega_V$). When each of the likelihoods is below the respective threshold, the method can determine that the patient is likely to have a non-bacterial and non-viral infectious disease. For example, the method can determine that it is likely that the subject has a non-infectious disease, a fungal disease or a parasitic disease.

Still alternatively, whether or not some operations are executed is dependent on the outcome of one or more other operations. For example, the method can execute 311 and 312, so as to determine the likelihood that the subject has a bacterial infection. Thereafter, the determined likelihood is compared to the threshold $\omega_B$. The method skips the execution of 313 and 314 if the determined likelihood is above $\omega_B$, and executes 313 and 314 otherwise. Another example of these embodiments is a procedure in which the method executes 313 and 314, so as to determine the likelihood that the subject has a viral infection. Thereafter, the determined likelihood is compared to the threshold $\omega_V$. The method skips the execution of 311 and 312 if the determined likelihood is above $\omega_V$, and executes 311 and 312 otherwise.

The method optionally and preferably continues to 315 at which an output of the likelihood(s) is generated. The output can be presented as text, and/or graphically and/or using a color index. The output can optionally include the results of the comparison to the threshold $\omega_B$. FIGS. 29A-29F and 38A-38E illustrate exemplary outputs suitable for distinguishing between bacterial and non-bacterial infection according to an embodiment of the present invention.

The method ends at 317.

FIGS. 38A-38E are screenshots of a graphical user interface (GUI) suitable for receiving user input in a computer-implemented method for analyzing biological data according to some embodiments of the present invention.

The GUI comprises a calculation activation control 390, that may be in the form of a button control. The GUI may also comprise a plurality of expression value input fields 380, wherein each expression value input field is configured for receiving from a user an expression value of a polypeptide in the blood of a subject. The user feeds into the input fields the expression values of the polypeptides. Alternatively, the expression values are can be received by establishing a communication between the computer and an external machine (not shown) that measures the expression values. In these embodiments, it is not necessary for the user to manually feed the expression values into the input fields. In some embodiments, the GUI comprises a communication control 392, e.g., in the form of a button control, wherein the communication with the external machine is in response to an activation of the communication control by the user.

Responsively to an activation of control 390 by the user, the computer calculates a score based on the expression values as received automatically or via fields 380. The core can be the likelihood that the subject has a bacterial infection and/or a viral infection. The score can be calculated for example, by calculating a distance between a curved surface and a plane defined by the two directions as further detailed hereinabove. A graphical scale 382 can be generated on the GUI. The graphical scale can include a first end, identified as corresponding to a viral infection, and a second end, identified as corresponding to a bacterial infection.

Figure 38A:
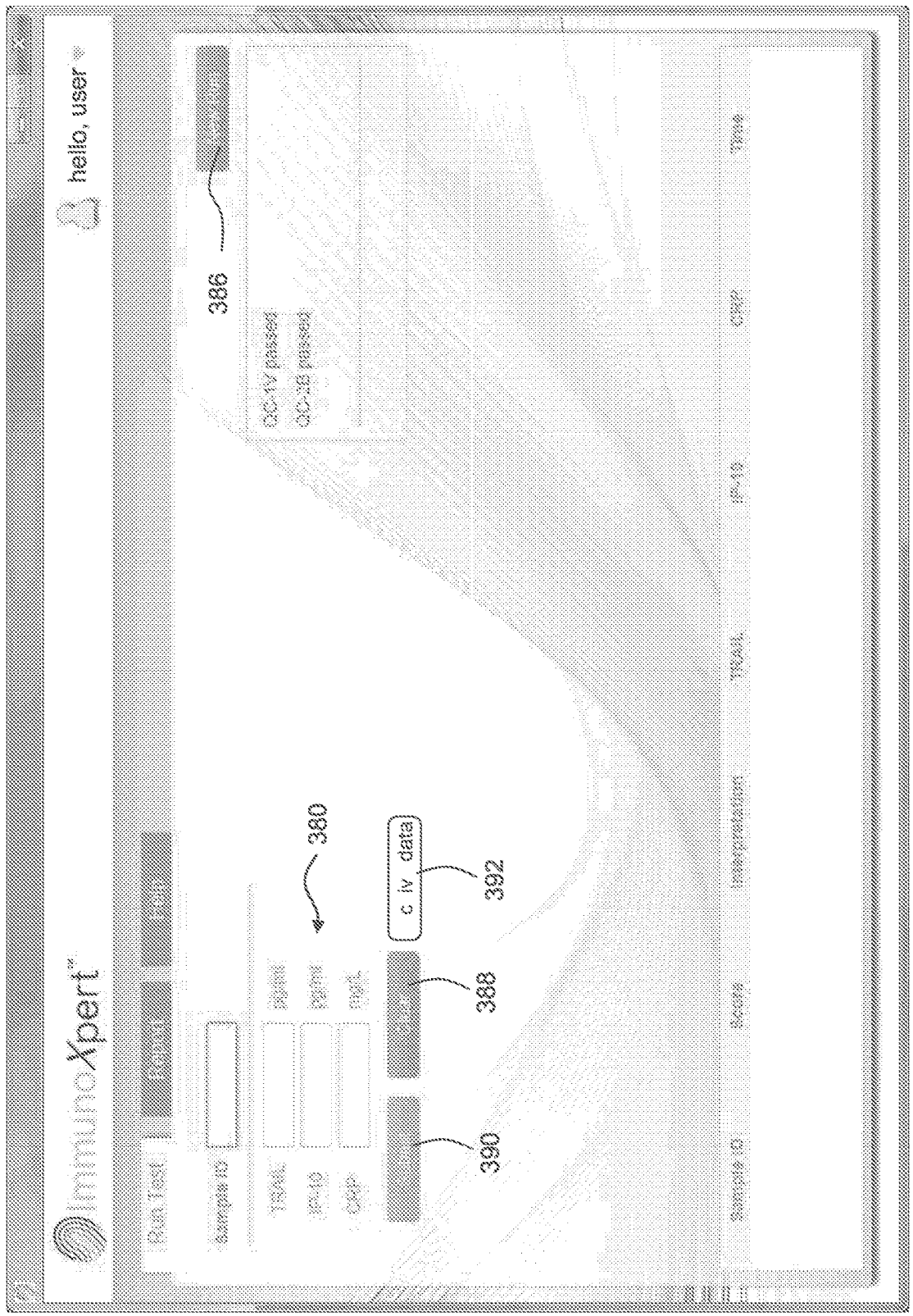
FIGS. 38A-38E are screenshots of a graphical user interface (GUI) suitable for receiving user input in a computer-implemented method for analyzing biological data according to some embodiments of the present invention.
Figure 38B:
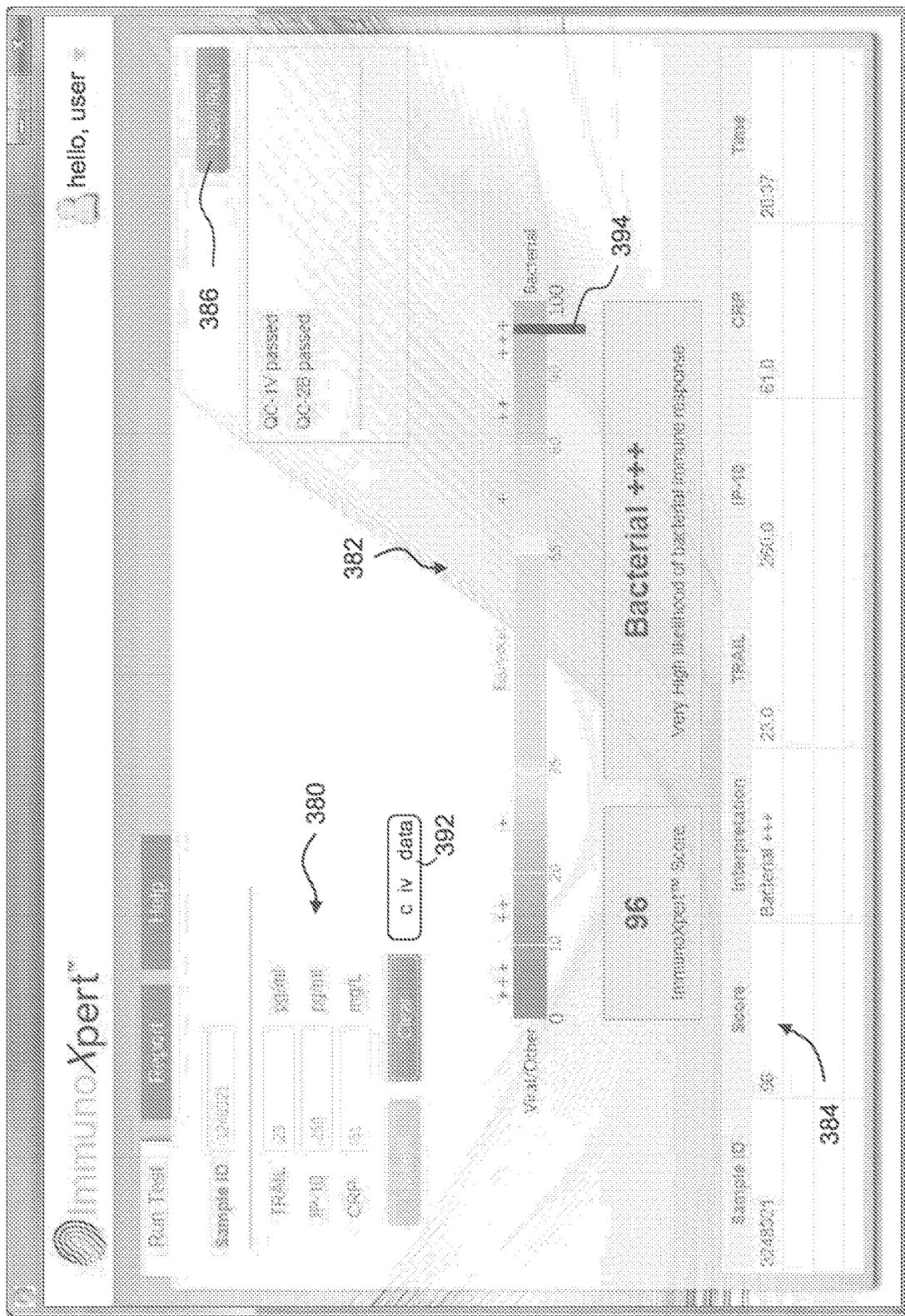
Figure 38C:
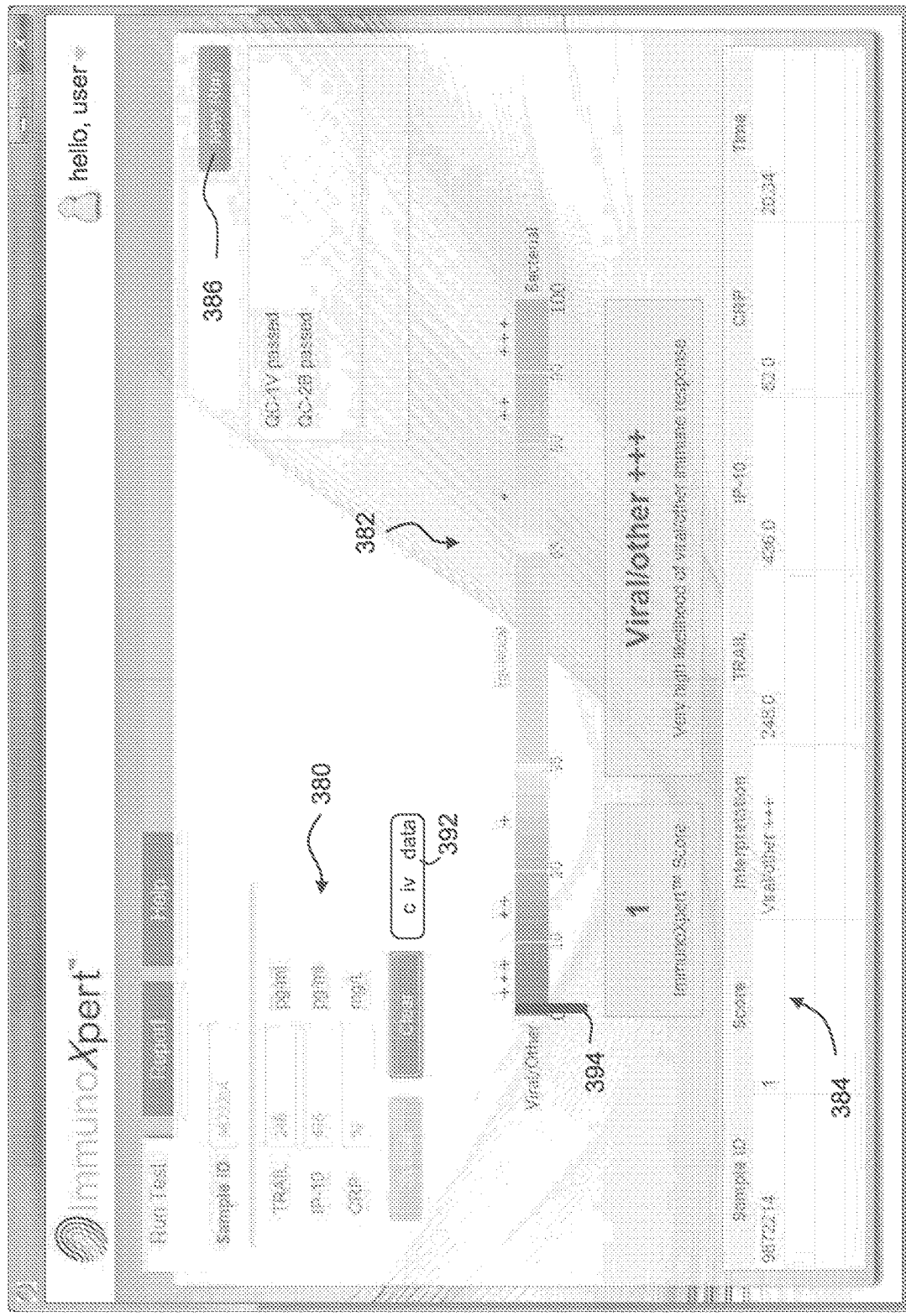
Figure 38D:
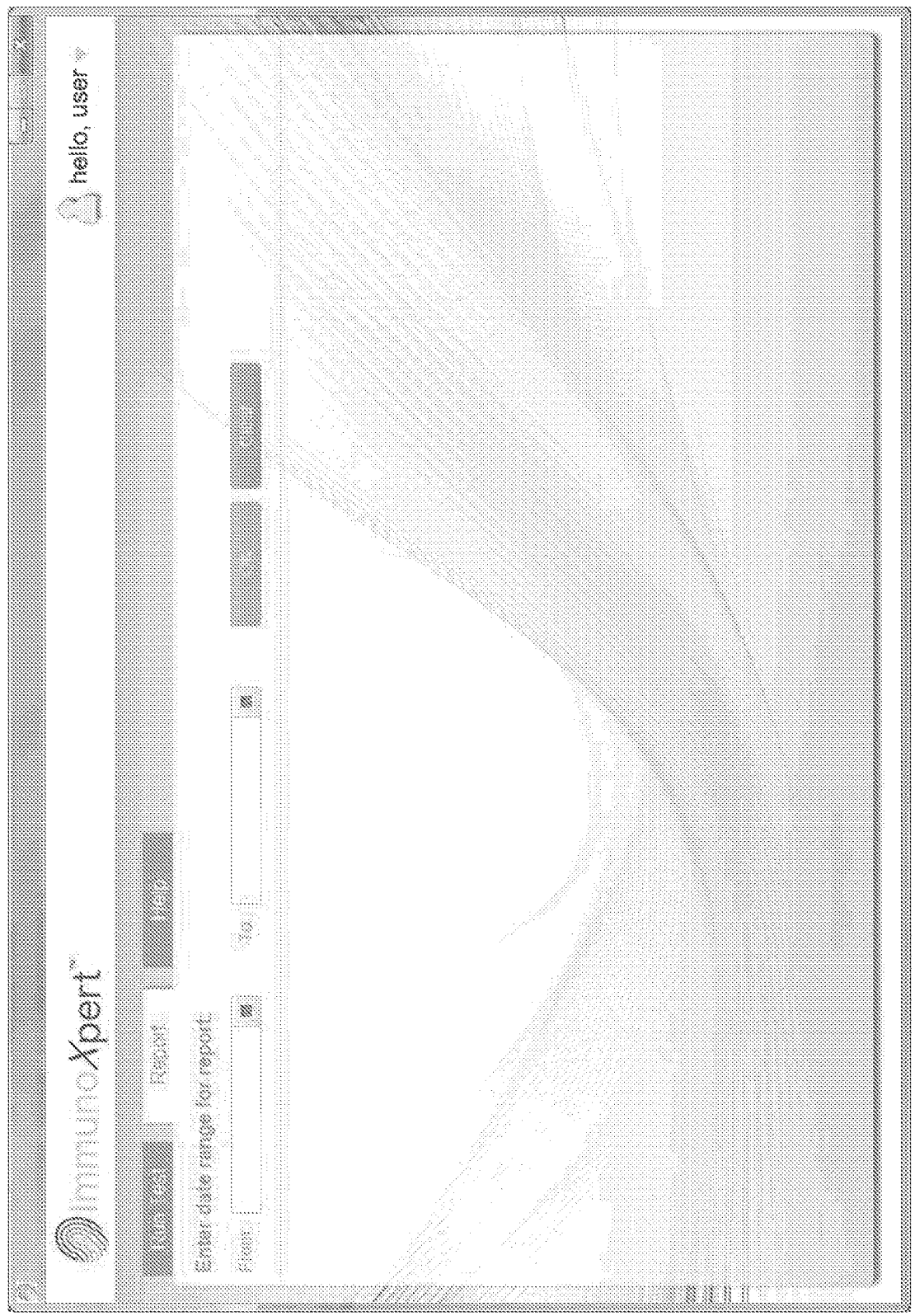
Figure 38E:
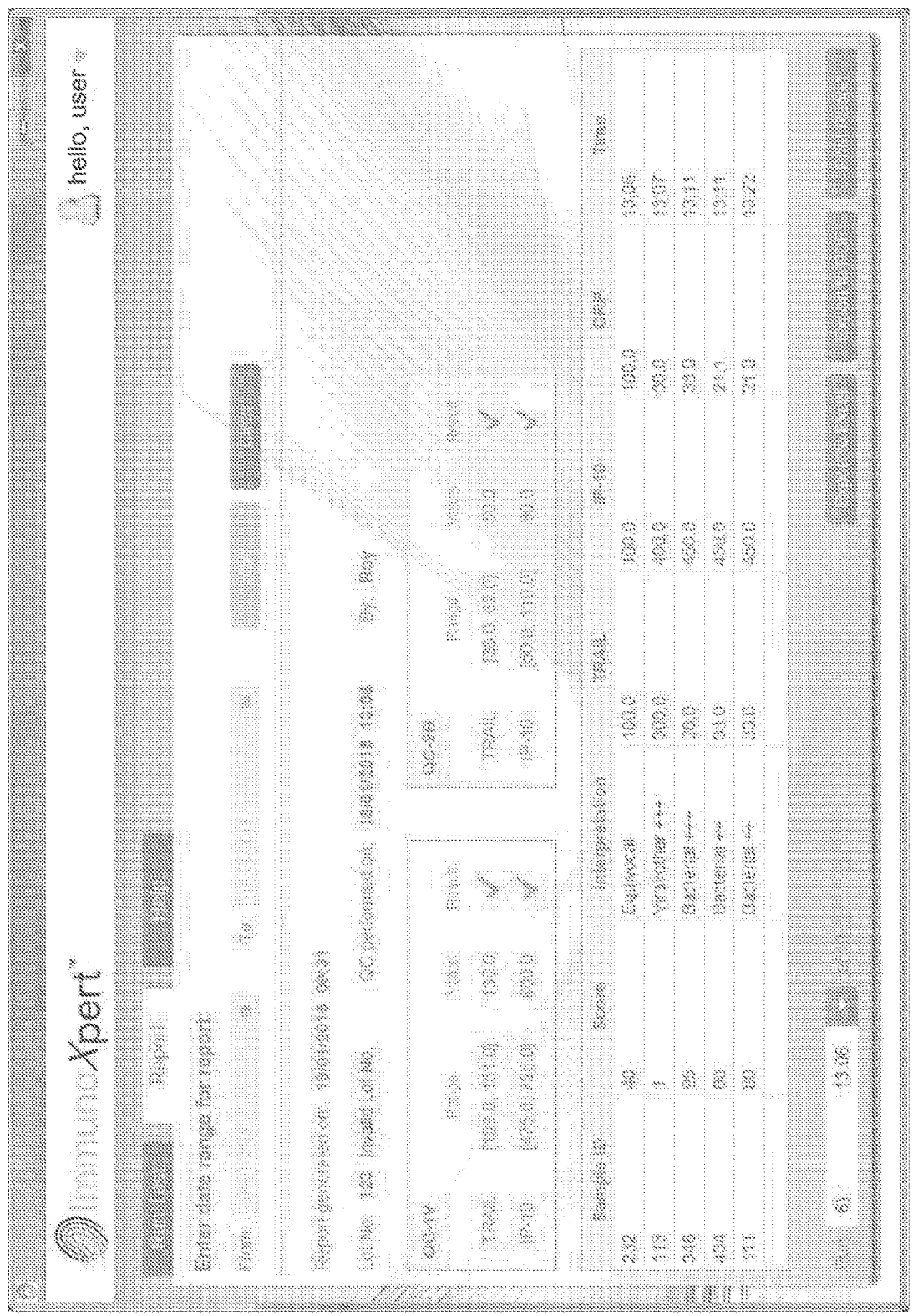

Once the score is calculated, a mark 394 can optionally and preferably be made on the graphical 382 at a location corresponding to the calculated likelihood. FIG. 38A shows the GUI before the values have been fed into the input fields, FIG. 38B shows mark 394 on scale 382 at a location that corresponds to a likelihood of 96% that the infection is bacterial, and FIG. 38C shows mark 394 on scale 382 at a location that corresponds to a likelihood of 1% that the infection is bacterial (or, equivalently, likelihood of 99% that the infection is viral). Optionally, the GUI also displays the calculated score numerically.

The GUI optionally and preferably includes one or more additional controls 386, 388 that may be in the form of button controls. For example, control 388 can instruct the computer to clear the input fields 380 when the user activates the control 388. This allows the user to feed values that correspond to a different sample. In some embodiments, the GUI also generates an output 384 that summarizes the results of the previous samples. Control 386 can instruct the computer to clear the input fields 380 as well as the output 384 when the user activates the control 386. This allows the user to begin a new run (optionally with multiple samples) without logging out of the GUI.

A representative example of a protocol suitable for the present embodiments is as follows.

The GUI presents an authenticated user with a dialog that allows the user to feed in quality control (QC) values of an experiment. The QC is validated, and the GUI in FIG. 38A is generated. The user feeds in the expression values in fields 380 and activate control 390 to receive the result (e.g., FIGS. 38B and 38C). To feed in expression values of another blood sample the user activates control 388. The result of each sample is added to output 384 which can be, for example, in the form of a table. To enter a new experiment without closing the software or logging out the user activates control 386 to clear output 384 and enter new QC values. Preferably, all the operations are logged in one or more log files.

In some embodiments of the present invention GUI also includes a report screen (FIGS. 38D and 38E) that displays the results of previous experiments, for example, in response to a date based request.

It will be appreciated that the polypeptide names presented herein are given by way of example. Many alternative names, aliases, modifications, isoforms and variations will be apparent to those skilled in the art. Accordingly, it is intended to embrace all the alternative protein names, aliases, modifications isoforms and variations.

Gene products, are identified based on the official letter abbreviation or gene symbol assigned by the international Human Genome Organization Naming Committee (HGNC) and listed at the date of this filing at the US National Center for Biotechnology Information (NCBI) web site also known as Entrez Gene.

TRAIL: The protein, TNF Related Apoptosis Inducing Ligand (TRAIL), encoded by this gene is a cytokine that belongs to the tumor necrosis factor (TNF) ligand family. Additional names of the gene include without limitations APO2L, TNF-related apoptosis-inducing ligand, TNFSF10 and CD253. TRAIL exists in a membrane bound form and a soluble form, both of which can induce apoptosis in different cells, such as transformed tumor cells. This protein binds to several members of the TNF receptor superfamily such as TNFRSF10A/TRAILR1, NFRSF10B/TRAILR2, NFRSF10C/TRAILR3, TNFRSF10D/TRAILR4, and possibly also to NFRSF11B/OPG.

The activity of this protein may be modulated by binding to the decoy receptors such as NFRSF10C/TRAILR3, TNFRSF10D/TRAILR4, and NFRSF11B/OPG that cannot induce apoptosis. The binding of this protein to its receptors has been shown to trigger the activation of MAPK8/JNK, caspase 8, and caspase 3. Alternatively spliced transcript variants encoding different isoforms have been found for this gene. TRAIL can be proteolytically cleaved from the cell surface to produce a soluble form that has a homotrimeric structure.

According to a particular embodiment, the level of the soluble (i.e. secreted) form of TRAIL is measured.

According to another embodiment, the membrane form of TRAIL is measured.

According to still another embodiment, both the membrane form of TRAIL and the secreted form of TRAIL are measured.

According to another aspect of the present invention there is provided a method of determining an infection type in a subject comprising measuring the concentration of soluble TRAIL and insoluble TRAIL, wherein the concentration is indicative of the infection type.

In one embodiment, when the concentration of the soluble TRAIL is higher than a pre-determined threshold value, a bacterial infection is ruled out for the subject.

In another embodiment, when the concentration of the soluble TRAIL is higher than a pre-determined threshold value, a viral infection is ruled in for the subject.

Exemplary protein sequences for soluble TRAIL are set forth in SEQ ID NO: 37 and SEQ ID NO: 38.

An exemplary mRNA sequence of membrane human TRAIL is set forth in SEQ ID NO: 1.

An exemplary amino acid sequences of membrane human TRAIL is set forth in SEQ ID NOs: 4.

Other exemplary cDNA and amino acid sequences for TRAIL are set forth in SEQ ID NOs: 2, 3 and 5-8.

IP10: This gene encodes a chemokine of the CXC subfamily and ligand for the receptor CXCR3. Binding of this protein to CXCR3 results in pleiotropic effects, including stimulation of monocytes, natural killer and T-cell migration, and modulation of adhesion molecule expression. Additional names of the gene include without limitations: IP-10, CXCL10, Gamma-IP10, INP10 and chemokine (C-X-C motif) ligand 10.

Exemplary cDNA sequence of human IP10 is set forth in SEQ ID NOs: 9-12. An exemplary amino acid sequence of human IP10 is set forth in SEQ ID NO: 13.

CRP: C-reactive protein; additional aliases of CRP include without limitation RP11-419N10.4 and PTX1. The protein encoded by this gene belongs to the pentaxin family. It is involved in several host defense related functions based on its ability to recognize foreign pathogens and damaged cells of the host and to initiate their elimination by interacting with humoral and cellular effector systems in the blood. Consequently, the level of this protein in plasma increases greatly during acute phase response to tissue injury, infection, or other inflammatory stimuli. CRP displays several functions associated with host defense: it promotes agglutination, bacterial capsular swelling, phagocytosis and complement fixation through its calcium-dependent binding to phosphorylcholine.

Exemplary cDNA sequence of human CRP is set forth in SEQ ID NOs: 14-16.

An exemplary amino acid sequence of human CRP is set forth in SEQ ID NO: 17.

IL1RA: The protein encoded by this gene is a cytokine receptor that belongs to the interleukin 1 receptor family. This protein is a receptor for interleukin alpha (IL1A), interleukin beta (IL1B), and interleukin 1 receptor, type I (IL1R1/IL1RA). It is an important mediator involved in many cytokine induced immune and inflammatory responses. Additional names of the gene include without limitations: CD121A, IL-1RT1, p80, CD121a antigen, CD121A, IL1R and IL1ra.

Exemplary cDNA sequences of human IL1RA are set forth in SEQ ID NOs: 18, 19 and 20.

Exemplary amino acid sequences of human IL1RA are set forth in SEQ ID NOs:21-24.

PCT: Procalcitonin (PCT) is a peptide precursor of the hormone calcitonin, the latter being involved with calcium homeostasis. Procalcitonin ("pCT") is a protein consisting of 116 amino acids and having a molecular weight of about 13,000 dalton. It is the prohormone of calcitonin which under normal metabolic conditions is produced and secreted by the C cells of the thyroid. pCT and calcitonin synthesis is initiated by translation of preprocalcitonin ("pre-pCT"), a precursor peptide comprising 141 amino acids. The amino acid sequence of human pre-pCT was described by Moullec et al. in FEBS Letters, 167:93-97 in 1984. pCT is formed after cleavage of the signal peptide (first 25 amino acids of pre-pCT).

Exemplary cDNA sequences of human PCT are set forth in SEQ ID NOs: 31-32.

Exemplary amino acid sequences of human PCT are set forth in SEQ ID NOs:33-36.

SAA: encodes a member of the serum amyloid A family of apolipoproteins. The encoded protein is a major acute phase protein that is highly expressed in response to inflammation and tissue injury. This protein also plays an important role in HDL metabolism and cholesterol homeostasis. High levels of this protein are associated with chronic inflammatory diseases including atherosclerosis, rheumatoid arthritis, Alzheimer's disease and Crohn's disease. This protein may also be a potential biomarker for certain tumors. Alternate splicing results in multiple transcript variants that encode the same protein.

Exemplary cDNA sequences of human SAA are set forth in SEQ ID NOs: 25-27.

Exemplary amino acid sequences of human SAA are set forth in SEQ ID NO:28-30.

It will be appreciated that since patient to patient DNA variations may give rise to SNPs which can cause differences in the amino acid sequence of the proteins, the present inventors also contemplate proteins having amino acid sequences at least 90%, 95% or 99% homologous to the sequences provided herein above.

Measuring the polypeptide (for example, TRAIL, IP-10 and CRP) levels is typically affected at the protein level as further described herein below.

Methods of Detecting Expression and/or Activity of Proteins

Expression and/or activity level of proteins expressed in the cells of the cultures of some embodiments of the invention can be determined using methods known in the arts and typically involve the use of antibodies. Such methods may be referred to as immunoassays. Immunoassays may be run in multiple steps with reagents being added and washed away or separated at different points in the assay. Multi-step assays are often called separation immunoassays or heterogeneous immunoassays. Some immunoassays can be carried out simply by mixing the reagents and sample and making a physical measurement. Such assays are called homogenous immunoassays or less frequently non-separation immunoassays. The use of a calibrator is often employed in immunoassays. Calibrators are solutions that are known to contain the analyte in question, and the concentration of that analyte is generally known. Comparison of an assay's response to a real sample against the assay's response produced by the calibrators makes it possible to interpret the signal strength in terms of the presence or concentration of analyte in the sample.

The antibody may be monoclonal, polyclonal, chimeric, or a fragment of the foregoing, and the step of detecting the reaction product may be carried out with any suitable immunoassay.

Suitable sources for antibodies for the detection of the polypeptides include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptides described herein.

Polyclonal antibodies for measuring polypeptides include without limitation antibodies that were produced from sera by active immunization of one or more of the following: Rabbit, Goat, Sheep, Chicken, Duck, Guinea Pig, Mouse, Donkey, Camel, Rat and Horse.

Examples of additional detection agents, include without limitation: scFv, dsFv, Fab, sVH, F(ab')$_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

Enzyme linked immunosorbent assay (ELISA): Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA).

After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are aspecifically bound. After the final wash step, the plate is developed by adding an enzymatic substrate to produce a visible signal, which indicates the quantity of antigen in the sample.

Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Automated Immunoassay: An automated analyzer applied to an immunoassay (often called "Automated Immunoassay") is a medical laboratory instrument designed to measure different chemicals and other characteristics in a number of biological samples quickly, with minimal human assistance. These measured properties of blood and other fluids may be useful in the diagnosis of disease. Many methods of introducing samples into the analyzer have been invented. This can involve placing test tubes of sample into racks, which can be moved along a track, or inserting tubes into circular carousels that rotate to make the sample available. Some analyzers require samples to be transferred to sample cups. However, the effort to protect the health and safety of laboratory staff has prompted many manufacturers to develop analyzers that feature closed tube sampling, preventing workers from direct exposure to samples. Samples can be processed singly, in batches, or continuously. Examples of automated immunoassay machines include, without limitation, ARCHITECT ci4100, ci8200 (2003), ci16200 (2007), ARCHITECT i1000SR, ARCHITECT i2000, i2000SR, i4000SR, AxSYM/AxSYM Plus, 1994 U.S., DS2, AIMS, AtheNA, DSX, ChemWell, UniCel DxI 860i Synchron Access Clinical System, UniCel DxC 680i Synchron Access Clinical System, Access/Access 2 Immunoassay System, UniCel DxI 600 Access Immunoassay System, UniCel DxC 600i Synchron Access Clinical System, UniCel DxI 800 Access Immunoassay System, UniCel DxC 880i Synchron Access Clinical System, UniCel DxI 660i Synchron Access Clinical System, SPA PLUS (Specialist Protein Analyzer), VIDAS Immunoassay Analyzer, BioPlex 2200, PhD System EVOLIS PR 3100TSC Photometer, MAGO 4S/2011 Mago Plus Automated EIA Processor, LIAISON XL/2010 LIAISON, ETI-MAX 3000 Agility, Triturus, HYTEC 288 PLUSDSX, VITROS ECi Immunodiagnostic System, VITROS 3600 Immunodiagnostic System, Phadia Laboratory System 100E, Phadia Laboratory System 250, Phadia Laboratory System 1000, Phadia Laboratory System 2500, Phadia Laboratory System 5000, cobas e 602/2010, cobas e411, cobas e601, MODULAR ANALYTICS E170, Elecsys 2010, Dimension EXL 200/2011, Dimension Xpand Plus Integrated Chemistry System, Dimension RxL Max/Max Suite Integrated Chemistry System; Dimension RxL Integrated Chemistry System, Dimension EXL with LM Integrated Chemistry System, Stratus CS Acute Care Diagnostic System, IMMULITE 2000 XPi Immunoassay System, ADVIA Centaur CP Immunoassay System, IMMULITE 2000, IMMULITE 1000, Dimension Vista 500 Intelligent Lab System, Dimension Vista 1500 Intelligent Lab System, ADVIA Centaur XP, AIA-900, AIA-360, AIA-2000, AIA-600 II, AIA-1800. Measurements of CRP, IP-10 and TRAIL can also be performed on a Luminex machine.

Lateral Flow Immunoassays (LFIA): This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Immunohistochemical analysis: Immunoassays carried out in accordance with some embodiments of the present invention may be homogeneous assays or heterogeneous assays. In a homogeneous assay the immunological reaction usually involves the specific antibody (e.g., anti-TRAIL, CRP and/or IP-10 antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase.

According to a particular embodiment, the antibody is immobilized to a porous strip to form a detection site. The measurement or detection region of the porous strip may include a plurality of sites, one for TRAIL, one for CRP and one for IP-10. A test strip may also contain sites for negative and/or positive controls.

Alternatively, control sites can be located on a separate strip from the test strip. Optionally, the different detection sites may contain different amounts of antibodies, e.g., a higher amount in the first detection site and lesser amounts in subsequent sites. Upon the addition of test sample, the number of sites displaying a detectable signal provides a quantitative indication of the amount of polypeptides present in the sample. The detection sites may be configured in any suitably detectable shape and are typically in the shape of a bar or dot spanning the width of a test strip.

The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No.

4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$) enzyme labels (e.g., horseradish peroxidase, alkaline phosphatase), and fluorescent labels (e.g., fluorescein, Alexa, green fluorescent protein, rhodamine) in accordance with known techniques.

Monoclonal antibodies for measuring TRAIL include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1, Human TRAIL/TNFSF10 MAb (Clone 75411), Mouse IgG1, Human TRAIL/TNFSF10 MAb (Clone 124723), Mouse IgG1, Human TRAIL/TNFSF10 MAb (Clone 75402), Mouse IgG1.

Antibodies for measuring TRAIL include monoclonal antibodies and polyclonal antibodies for measuring TRAIL. Antibodies for measuring TRAIL include antibodies that were developed to target epitopes from the list comprising of: Mouse myeloma cell line NS0-derived recombinant human TRAIL (Thr95-Gly281 Accession #P50591), Mouse myeloma cell line, NS0-derived recombinant human TRAIL (Thr95-Gly281, with an N-terminal Met and 6-His tag Accession #P50591), E. coli-derived, (Val114-Gly281, with and without an N-terminal Met Accession #:Q6IBA9), Human plasma derived TRAIL, Human serum derived TRAIL, recombinant human TRAIL where first amino acid is between position 85-151 and the last amino acid is at position 249-281.

Examples of monoclonal antibodies for measuring CRP include without limitation: Mouse, Monoclonal (108-2A2); Mouse, Monoclonal (108-7G41D$_2$); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG, Human C-Reactive Protein/CRP Biot MAb (C1 232024), Mouse IgG2B, Human C-Reactive Protein/CRP MAb (Clone 232007), Mouse IgG2B, Human/Mouse/Porcine C-Reactive Protein/CRP MAb (C1 232026), Mouse IgG2A.

Antibodies for measuring CRP include monoclonal antibodies for measuring CRP and polyclonal antibodies for measuring CRP.

Antibodies for measuring CRP also include antibodies that were developed to target epitopes from the list comprising of: Human plasma derived CRP, Human serum derived CRP, Mouse myeloma cell line NS0-derived recombinant human C-Reactive Protein/CRP (Phe17-Pro224 Accession #P02741).

Examples of monoclonal antibodies for measuring IP-10 include without limitation: IP-10/CXCL10 Mouse anti-Human Monoclonal (4D$_5$) Antibody (LifeSpan BioSciences), IP-10/CXCL10 Mouse anti-Human Monoclonal (A00163.01) Antibody (LifeSpan BioSciences), MOUSE ANTI HUMAN IP-10 (AbD Serotec), RABBIT ANTI HUMAN IP-10 (AbD Serotec), IP-10 Human mAb 6D$_4$ (Hycult Biotech), Mouse Anti-Human IP-10 Monoclonal Antibody Clone B-C50 (Diaclone), Mouse Anti-Human IP-10 Monoclonal Antibody Clone B-C55 (Diaclone), Human CXCL10/IP-10 MAb Clone 33036 (R&D Systems), CXCL10/INP10 Antibody 1E9 (Novus Biologicals), CXCL10/INP10 Antibody 2C1 (Novus Biologicals), CXCL10/INP10 Antibody 6D$_4$ (Novus Biologicals), CXCL10 monoclonal antibody M01A clone 2C1 (Abnova Corporation), CXCL10 monoclonal antibody (M05), clone 1E9 (Abnova Corporation), CXCL10 monoclonal antibody, clone 1 (Abnova Corporation), IP10 antibody 6D$_4$ (Abcam), IP10 antibody EPR7849 (Abcam), IP10 antibody EPR7850 (Abcam).

Antibodies for measuring IP-10 include monoclonal antibodies for measuring IP-10 and polyclonal antibodies for measuring IP-10.

Antibodies for measuring IP-10 also include antibodies that were developed to target epitopes from the list comprising of: Recombinant human CXCL10/IP-10, non-glycosylated polypeptide chain containing 77 amino acids (aa 22-98) and an N-terminal His tag Interferon gamma inducible protein 10 (125 aa long), IP-10 His Tag Human Recombinant IP-10 produced in E. Coli containing 77 amino acids fragment (22-98) and having a total molecular mass of 8.5 kDa with an amino-terminal hexahistidine tag, E. coli-derived Human IP-10 (Val22-Pro98) with an N-terminal Met, Human plasma derived IP-10, Human serum derived IP-10, recombinant human IP-10 where first amino acid is between position 1-24 and the last amino acid is at position 71-98.

It will be appreciated that the expression level of the polypeptides described herein can be an absolute expression level, a normalized expression and/or a relative expression level.

In general scientific context, normalization is a process by which a measurement raw data is converted into data that may be directly compared with other so normalized data. In the context of the present invention, measurements of expression levels are prone to errors caused by, for example, unequal degradation of measured samples, different loaded quantities per assay, and other various errors. More specifically, any assayed sample may contain more or less biological material than is intended, due to human error and equipment failures. Thus, the same error or deviation applies to both the polypeptide of the invention and to the control reference, whose expression is essentially constant. Thus, division of TRAIL, IP-10 or CRP raw expression value by the control reference raw expression value yields a quotient which is essentially free from any technical failures or inaccuracies (except for major errors which destroy the sample for testing purposes) and constitutes a normalized expression value of the polypeptide. Since control reference expression values are equal in different samples, they constitute a common reference point that is valid for such normalization.

According to a particular embodiment, each of the polypeptide expression values are normalized using the same control reference.

It will further be appreciated that absolute expression values are dependent upon the exact protocol used, since each protocol typically leads to different signal to noise ratios, and consequentially to different concentrations being measured. More specifically, while the overall trend of the biomarkers will be preserved regardless of the protocol (e.g. TRAIL increases in viral infections and decreases in bacterial), the measurement scale is protocol dependent.

Such alterations in measured concentrations of proteins across different protocols can be compensated for by correlating the measurements of the two protocols and computing a transformation function, as illustrated in Example 5 herein below.

Typically, the samples which are analyzed are blood sample comprising whole blood, serum, plasma, leukocytes or blood cells. Preferably, the sample is whole blood, serum or plasma.

Of note, TRAIL and IP-10 and CRP are highly expressed in other tissues and samples including without limitation CSF, saliva and epithelial cells, bone marrow aspiration, urine, stool, alveolar lavage, sputum. Thus, some embodiments of the present invention can be used to measure TRAIL, CRP and IP-10 in such tissues and samples.

Preferably, the level of the polypeptides is measured within about 24 hours after the sample is obtained. Alternatively, the concentration of the polypeptides is measured in a sample that was stored at 12° C. or lower, when storage begins less than 24 hours after the sample is obtained.

Once the tests are carried out to determine the level of the polypeptides, a subject specific dataset is optionally generated which contains the results of the measurements.

The subject-specific dataset may be stored in a computer readable format on a non-volatile computer readable medium, and is optionally and preferably accessed by a hardware processor, such as a general purpose computer or dedicated circuitry.

As mentioned, the levels of the polypeptides in the test subjects blood are compared to the levels of the identical polypeptides in a plurality of subjects' blood, when the subjects have already been verified as having a bacterial infection, viral infection or non-bacterial/non-viral disease on the basis of parameters other than the blood level of the polypeptides. The levels of the polypeptides of the plurality of subjects together with their verified diagnosis can be stored in a second dataset, also referred to herein as the "group dataset" or "prediagnosed dataset", as further described herein below.

The phrase "non-bacterial/non-viral disease" refers to disease that is not caused by a bacteria or virus. This includes diseases such as acute myocardial infarction, physical injury, epileptic attack, inflammatory disorders etc, fungal diseases, parasitic diseases etc.

The phrase "viral infection" as used herein refers to a disease that is caused by a virus and does not comprise a bacterial component.

Methods of analyzing a dataset, for example, for the purpose of calculating one or more probabilistic classification function representing the likelihood that a particular subject has a bacterial infection, or the likelihood that a particular subject has a viral infection or the likelihood that a particular subject has a non-bacterial non-viral disease, may be performed as described in Example 1 herein below. For example, diagnosis may be supported using PCR diagnostic assays such as (i) Seeplex® RV15 for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, or (ii) Seeplex® PB6 for detection of *Streptococcus pneumoniae*, *Haemophilus influenzae*, *Chlamydophila pneumoniae*, *Legionella pneumophila*, *Bordetella pertussis*, and *Mycoplasma pneumoniae*.

Blood cultures, urine cultures and stool cultures may be analyzed for *Shigella* spp., *Campylobacter* spp. and *Salmonella* spp.; serological testing (IgM and/or IgG) for cytomegalovirus (CMV), Epstein-Barr virus (EBV), *Mycoplasma pneumonia*, and *Coxiella burnetii* (Q-Fever).

Radiological tests (e.g. chest X-ray for suspected lower respiratory tract infection [LRTI]) may be used to confirm chest infections.

Alternatively, or additionally at least one trained physician may be used to establish the diagnosis.

Methods of determining the expression level of the polypeptides in the pre-diagnosed subjects have been described herein above.

Preferably, the same method which is used for determining the expression level of the polypeptides in the pre-diagnosed subjects is used for determining the level of the polypeptides in the test subject. Thus, for example if an immunoassay type method is used for determining the expression level of the polypeptides in the pre-diagnosed subjects, then an immunoassay type method should be used for determining the level of the polypeptides in the test subject.

It will be appreciated that, the type of blood sample need not be identical in the test subject and the pre-diagnosed subjects. The present inventors were able to show that serum and plasma levels for TRAIL are very similar. Thus, for example, if a serum sample is used for determining the expression level of the polypeptides in the pre-diagnosed subjects, then a plasma sample may be used for determining the level of the polypeptides in the test subject.

The group dataset is preferably stored in a computer readable format on a non-volatile computer readable medium, and is optionally and preferably accessed by a hardware processor, such as a general purpose computer or dedicated circuitry. Both datasets can be stored on the same medium and are optionally and preferably accessed by the same hardware processor.

In the subject-specific dataset, each entry can optionally and preferably be described as a tuple (D, L) where D represents the polypeptide in the dataset and L represents the blood level of the polypeptide D. Thus, the dataset may be a two-dimensional dataset in which all the elements can be described by a vector in a two-dimensional space spanned by the polypeptide and respective response. In the group dataset, each entry can be described as a tuple (S, G, D, L) where S represents the particular subject, G represents the diagnosis of the subject S in the group dataset, D represents the polypeptide and L represents blood level of the polypeptide D. Thus, the exemplified illustration is of a four-dimensional dataset in which all the elements can be described by a vector in a four-dimensional space spanned by the subjects, diagnosis, polypeptide and respective responses. Some embodiments of the present invention contemplate use of datasets of higher dimensions. Such datasets are described hereinafter.

The group dataset may optionally and preferably also include one or more of, more preferably all, the entries of the subject-specific dataset. In embodiments in which group dataset includes all the entries of the subject-specific dataset, it is not necessary to use two separate datasets, since the entire dataset is contained in one inclusive dataset. Yet, such an inclusive dataset is optionally and preferably annotated in a manner that allows distinguishing between the portion of the inclusive dataset that is associated with the subject under analysis, and the portion of the inclusive dataset that is associated only with the other subjects. In the context of the present disclosure, the portion of the inclusive dataset that is associated with the subject under analysis is referred to as the subject-specific dataset even when it is not provided as a separate dataset. Similarly, the portion of the inclusive dataset that is associated only with the other subjects is referred to as the group dataset even when it is not provided as a separate dataset.

The group dataset preferably includes polypeptide levels of many subjects (e.g., at least 10 subjects being prediagnosed as having a viral infection, at least 10 subjects being prediagnosed as having a bacterial infection and at least 10 subjects being prediagnosed as having a non-bacterial/non-viral disease; or at least 20 subjects being prediagnosed as having a viral infection, at least 20 subjects being prediagnosed as having a bacterial infection and at least 20 subjects being prediagnosed as having a non-bacterial/non-viral disease; or at least 50 subjects being prediagnosed as having a viral infection, at least 50 subjects being prediagnosed as having a bacterial infection and at least 50 subjects being prediagnosed as having a non-bacterial/non-viral disease.

The group-specific dataset can include additional data that describes the subjects. Datasets that include additional data may be advantageous since they provide additional information regarding the similarities between the subject under analysis and the other subject, thereby increasing the accuracy of the predictability.

Representative examples of types of data other than the level of the polypeptides include, without limitation traditional laboratory risk factors and/or clinical parameters, as further described herein above.

The present embodiments contemplate subject-specific and group datasets that include additional data, aside from the polypeptides and respective levels. In some embodiments at least one of the datasets comprises one or more (e.g., a plurality of) multidimensional entries, each entry having at least three dimensions, in some embodiments at least one of the datasets comprises one or more (e.g., a plurality of) multidimensional entries, each entry having at least four dimensions, in some embodiments at least one of the datasets comprises one or more (e.g., a plurality of) multidimensional entries, each entry having at least five dimensions, and in some embodiments at least one of the datasets comprises one or more (e.g., a plurality of) multidimensional entries, each entry having more than five dimensions.

The additional dimensions of the datasets provides additional information pertaining to the subject under analysis, to the other subjects and/or to levels of polypeptides other than TRAIL, CRP and IP-10.

In some embodiments of the present invention the additional information pertains to at least one of traditional laboratory risk factors, clinical parameters, blood chemistry and/or a genetic profile.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

Preferably, at least one of the traditional laboratory risk factors of the subject under analysis is included in the subject specific dataset, and at least one of the traditional laboratory risk factors of one or more (more preferably all) of the other subjects is included in the group dataset. When the subject specific dataset includes at least one of the traditional laboratory risk factors, the risk factors can be included as a separate entry. When the group dataset includes the risk factors, the risk factors is optionally and preferably included per subject. Thus, for example, a group dataset entry can be described by the tuple (S, G, D, L {R}), where S, G, D and L have been introduced before and {R} is the at least one risk factor of subject S.

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms"), pregnancy, or family history (abbreviated FamHX).

Preferably, at least one of the clinical parameters of the subject under analysis is included in the subject specific dataset, and at least one of the clinical parameters of one or more (more preferably all) of the other subjects is included in the group dataset. When the subject specific dataset includes at least one of the clinical parameters, the clinical parameters can be included as a separate entry. When the group dataset includes the clinical parameters, the clinical parameters is optionally and preferably included per subject. Thus, for example, a group dataset entry can be described by the tuple (S, G, D, L {C}), where S, G, D and L have been introduced before and {C} is the clinical parameter of subject S.

As used herein "blood chemistry" refers to the concentration, or concentrations, of any and all substances dissolved in, or comprising, the blood. Representative examples of such substances, include, without limitation, albumin, amylase, alkaline phosphatase, bicarbonate, total bilirubin, BUN, C-reactive protein, calcium, chloride, LDL, HDL, total cholesterol, creatinine, CPK, γ-GT, glucose, LDH, inorganic phosphorus, lipase, potassium, total protein, AST, ALT, sodium, triglycerides, uric acid and VLDL.

According to one embodiment, the blood chemistry of the subject under analysis is included in the subject specific dataset, and the blood chemistry of one or more (more preferably all) of the other subjects is included in the group dataset. When the subject specific dataset includes the blood chemistry, the blood chemistry can be included as a separate entry. When the group dataset includes the blood chemistry, the blood chemistry is optionally and preferably included per subject. Thus, for example, a group dataset entry can be described by the tuple (S, G, D, L {C}), where S, G, D and L have been introduced before and {C} is the blood chemistry of subject S.

In some embodiments of the present invention the additional information pertains to a genetic profile of individual.

As used herein "genetic profile" refers to the analysis of a number of different genes. A genetic profile can encompass the genes in an entire genome of the individual, or it can encompass a specific subset of genes. The genetic profile may include genomic profile, a proteomic profile, an epigenomic profile and/or a transcriptomic profile.

Preferably, the genetic profile of the subject under analysis is included in the subject specific dataset, and the genetic profile of one or more (more preferably all) of the other subjects is included in the group dataset. When the subject specific dataset includes the genetic profile, the genetic profile can be included as a separate entry. When the group dataset includes the genetic profile, the genetic profile is optionally and preferably included per subject. Thus, for example, a group dataset entry can be described by the tuple (S, G, D, L {P}), where S, G, D and L have been introduced before and {P} is the genetic profile of subject S.

The method optionally and preferably continues to a step of storing the levels of the polypeptide, at least temporarily, on a non-volatile computer readable medium from which it can be extracted or displayed as desired.

Once the two datasets are accessed, the method continues to the analysis phase in order to diagnose the test subject.

The analysis is performed so as to compute one or more probabilistic classification functions $f(\delta_0,\delta_1)$, $g(\delta_0,\delta_1)$, $h(\delta_0,\delta_1)$, representing the likelihoods that a particular subject has a bacterial infection, viral infection or non-viral, non-bacterial disease, respectively. Typically, f, g and h satisfy the relation $f(\delta_0,\delta_1)+g(\delta_0,\delta_1)+h(\delta_0,\delta_1)=1$. Each classification function is a function of the first coordinate $\delta_0$ and the second coordinate $\delta_1$, wherein each of the coordinates $\delta_0$ and $\delta_1$ is defined by a different combination of the expression values as further detailed hereinabove.

The analysis can be executed in more than one way.

According to one embodiment, the analysis uses a binary or, more preferably, trinary classifier to compute one or more of the probabilistic classification functions.

Preferably, the analysis sums the probability of the viral and the non-viral, non-bacterial disease in order to assign the likelihood of a non-bacterial infection. In another preferred embodiment, the analysis sums the probability of the viral and bacterial to assign the likelihood of an infectious disease. Yet in another preferred embodiment the analysis ignores the probability of the non-viral, non-bacterial disease, and performs a direct comparison of the bacterial and the viral probabilities. Exemplified interpretation functions suitable for analyzing the datasets according to some embodiments of the present invention are provided hereinunder.

The analysis of the datasets according to some embodiments of the present invention comprises executing a machine learning procedure.

As used herein the term "machine learning" refers to a procedure embodied as a computer program configured to induce patterns, regularities, or rules from previously collected data to develop an appropriate response to future data, or describe the data in some meaningful way.

Use of machine learning is particularly, but not exclusively, advantageous when the dataset includes multidimensional entries.

The group and subject datasets can be used as a training set from which the machine learning procedure can extract parameters that best describe the dataset. Once the parameters are extracted, they can be used to predict the type of infection.

In machine learning, information can be acquired via supervised learning or unsupervised learning. In some embodiments of the invention the machine learning procedure comprises, or is, a supervised learning procedure. In supervised learning, global or local goal functions are used to optimize the structure of the learning system.

In other words, in supervised learning there is a desired response, which is used by the system to guide the learning.

In some embodiments of the invention the machine learning procedure comprises, or is, an unsupervised learning procedure. In unsupervised learning there are typically no goal functions. In particular, the learning system is not provided with a set of rules. One form of unsupervised learning according to some embodiments of the present invention is unsupervised clustering in which the data objects are not class labeled, a priori.

Representative examples of "machine learning" procedures suitable for the present embodiments, including, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, instance-based algorithms, linear modeling algorithms, k-nearest neighbors analysis, ensemble learning algorithms, probabilistic models, graphical models, logistic regression methods (including multinomial logistic regression methods), gradient ascent methods, singular value decomposition methods and principle component analysis. Among neural network models, the self-organizing map and adaptive resonance theory are commonly used unsupervised learning algorithms. The adaptive resonance theory model allows the number of clusters to vary with problem size and lets the user control the degree of similarity between members of the same clusters by means of a user-defined constant called the vigilance parameter.

Following is an overview of some machine learning procedures suitable for the present embodiments.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the datasets. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

The aforementioned self-organizing map is an unsupervised learning technique often used for visualization and analysis of high-dimensional data. Typical applications are focused on the visualization of the central dependencies within the data on the map.

The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact.

The term "feature" in the context of machine learning refers to one or more raw input variables, to one or more processed variables, or to one or more mathematical combinations of other variables, including raw variables and processed variables. Features may be continuous or discrete.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the type of infection. Symmetrical uncertainty is an algorithm that can be used by a feature selection algorithm, according to some embodiments of the present invention. Symmetrical uncertainty compensates for information gain's bias towards features with more values by normalizing features to a [0,1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the type of infection, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the datasets or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular portion of the group dataset matches a particular portion of the subject-specific dataset) or a value. The leaf nodes can also contain additional information about the represented classification such as a confidence score that measures a confidence in the represented classification (i.e., the likelihood of the classification being accurate). For example, the confidence score can be a continuous value ranging from 0 to 1, which a score of 0 indicating a very low confidence (e.g., the indication value of the represented classification is very low) and a score of 1 indicating a very high confidence (e.g., the represented classification is almost certainly accurate).

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

Regression techniques which may be used in accordance with the present invention include, but are not limited to linear Regression, Multiple Regression, logistic regression, probit regression, ordinal logistic regression ordinal Probit-Regression, Poisson Regression, negative binomial Regression, multinomial logistic Regression (MLR) and truncated regression.

A logistic regression or log it regression is a type of regression analysis used for predicting the outcome of a categorical dependent variable (a dependent variable that can take on a limited number of values, whose magnitudes are not meaningful but whose ordering of magnitudes may or may not be meaningful) based on one or more predictor variables. Logistic regressions also include a multinomial variant. The multinomial logistic regression model, is a regression model which generalizes logistic regression by allowing more than two discrete outcomes. That is, it is a model that is used to predict the probabilities of the different possible outcomes of a categorically distributed dependent variable, given a set of independent variables (which may be real-valued, binary-valued, categorical-valued, etc.).

The advantage of logistic regression is that it assigns an interpretable measure of prediction confidence—a probability. For example, patients predicted of having a bacterial infection with a probability of 75% and 99%, would both be assigned as bacterial when using an SVM interpretation function but the fact that the latter has a higher probability would be masked. Assigning the likelihood level of confidence adds valuable clinical information that may affect clinical judgment.

Importantly, calculating the likelihood of infection type for each patients, allows to rationally filter out patients for which the system knows that it cannot classify with high certainty. This is demonstrated in FIG. 5, herein. Thus, when the product assigns a likelihood of say 40% bacterial infection (40 out of 100 patients with the "40%" score will be bacterial).

Additionally, by using thresholds on the likelihood scores, one can assign non-binary classifications of the test-subject. By way of example a test-subject with a bacterial likelihood below 30% can be assigned a low probability of bacterial infection; between 30% and 70% an intermediate probability of bacterial infection and above 70% a high probability of a bacterial infections. Other thresholds may be used.

The Least Absolute Shrinkage and Selection Operator (LASSO) algorithm is a shrinkage and/or selection algorithm for linear regression. The LASSO algorithm may minimizes the usual sum of squared errors, with a regularization, that can be an L1 norm regularization (a bound on the sum of the absolute values of the coefficients), an L2 norm regularization (a bound on the sum of squares of the coefficients), and the like. The LASSO algorithm may be associated with soft-thresholding of wavelet coefficients, forward stagewise regression, and boosting methods. The LASSO algorithm is described in the paper: Tibshirani, R, Regression Shrinkage and Selection via the Lasso, J. Royal. Statist. Soc B., Vol. 58, No. 1, 1996, pages 267-288, the disclosure of which is incorporated herein by reference.

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions of the type of infection. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based algorithms generate a new model for each instance, instead of basing predictions on trees or networks generated (once) from a training set.

The term "instance", in the context of machine learning, refers to an example from a dataset.

Instance-based algorithms typically store the entire dataset in memory and build a model from a set of records similar to those being tested. This similarity can be evaluated, for example, through nearest-neighbor or locally weighted methods, e.g., using Euclidian distances. Once a set of records is selected, the final model may be built using several different algorithms, such as the naive Bayes.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device.

Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein.

The health-related data management system of the invention may also be considered to be implemented as a computer-readable storage medium, configured with a computer program, where the storage medium so configured causes a computer to operate in a specific and predefined manner to perform various functions described herein.

The recorded output may include the assay results, findings, diagnoses, predictions and/or treatment recommendations. These may be communicated to technicians, physicians and/or patients, for example. In certain embodiments, computers will be used to communicate such information to interested parties, such as, patients and/or the attending physicians. Based on the output, the therapy administered to a subject can be modified.

In one embodiment, the output is presented graphically. In another embodiment, the output is presented numerically (e.g. as a probability). In another embodiment, the output is generated using a color index (for example in a bar display) where one color indicates bacterial infection and another color non-bacterial infection. The strength of the color correlates with the probability of bacterial infection/non-infection. Such a graphic display is presented in FIGS. 29A-29F.

In some embodiments, the output is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In some embodiments, the methods described herein are carried out using a system 330, which optionally and preferably, but not necessarily, comprises a hand-held device, which comprises at least two compartments the first which measures the amount of polypeptides in the blood (e.g. using an immunohistochemical method) and the second which computationally analyzes the results measured in the first compartment and provides an output relating to the diagnosis.

Figure 34:
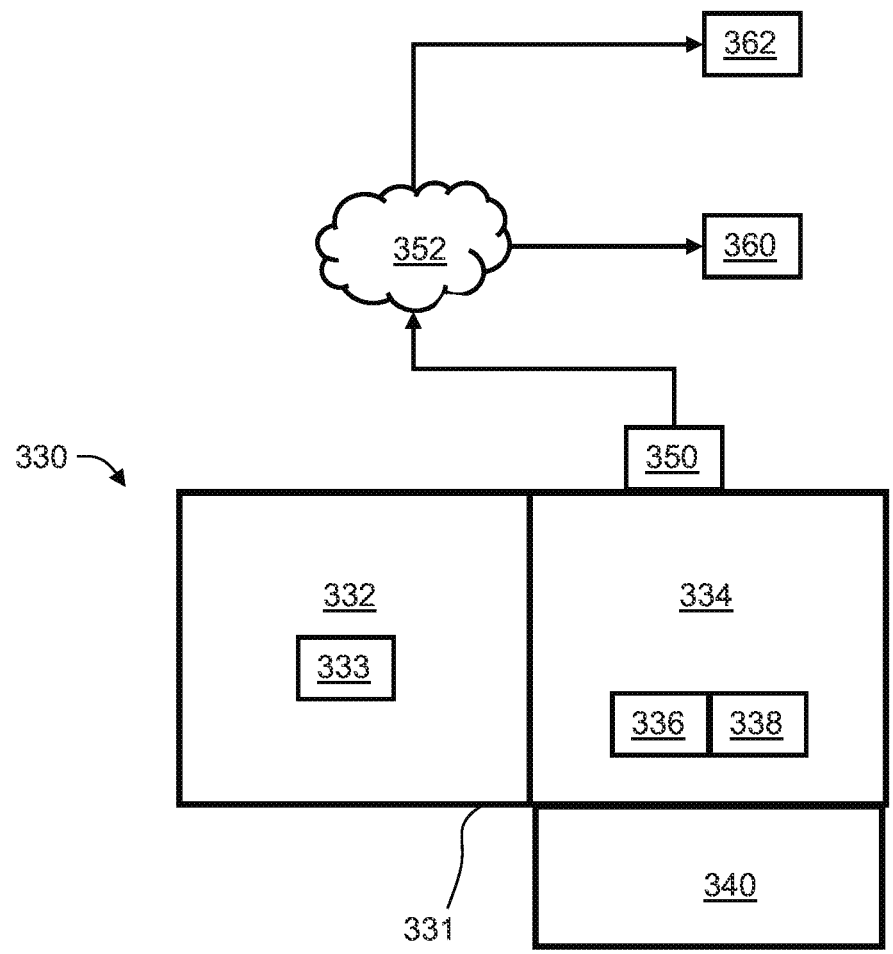
FIG. 34 is a schematic illustration of a block diagram of a system for analyzing biological data, according to some embodiments of the present invention.
Figure 35A:
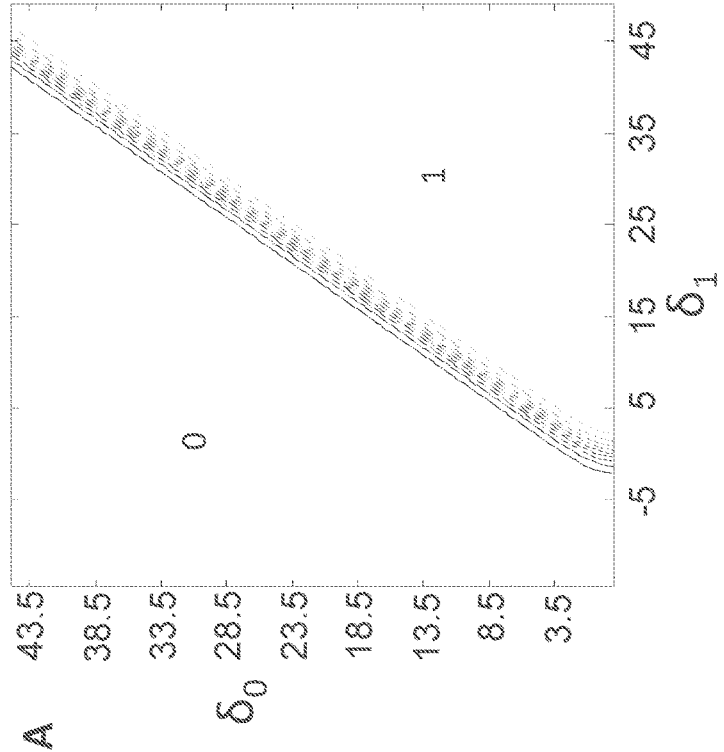
FIGS. 35A-35D are contour plots describing the probability of bacterial (FIG. 35A), viral (FIG. 35B), non-bacterial (FIG. 35C), and non-infectious (FIG. 35D) etiologies as a function of the coordinates $\delta_0$ and $\delta_1$. The probability values range between 0% (black) to 100% (white).
Figure 35B:
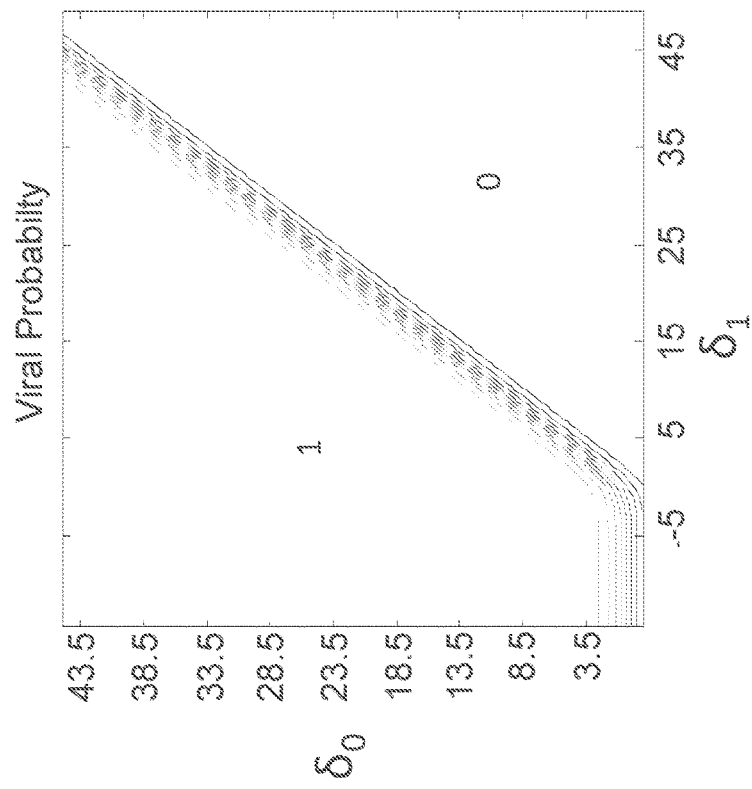
Figure 35C:
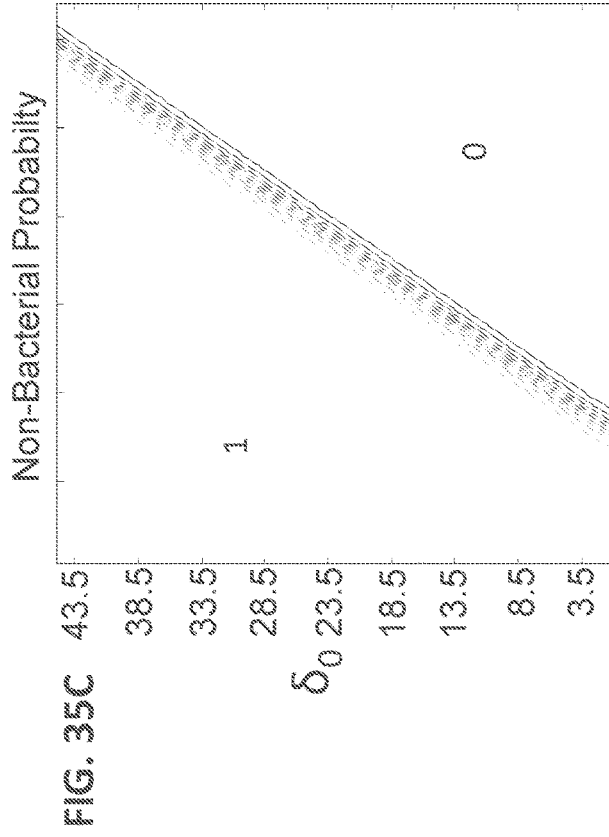
Figure 35D:
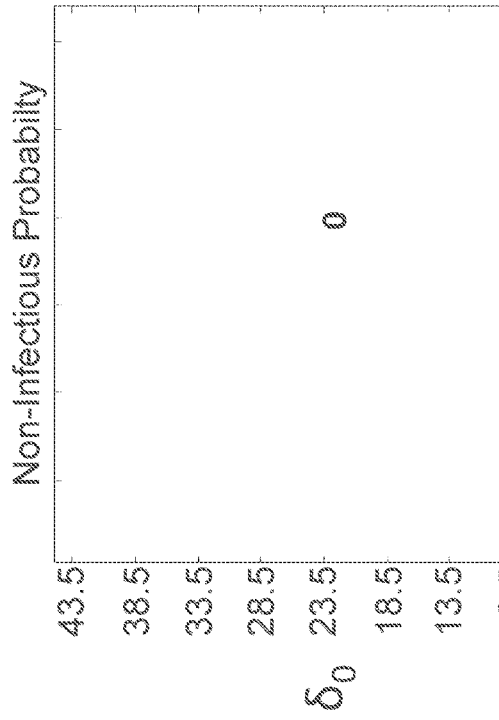

A block diagram of representative example of system 330 according to some embodiments of the present invention is illustrated in FIG. 34. System 330 can comprise a device 331 which can be, but is not necessarily a hand-held device. Alternatively, device 331 which can be a desktop mountable or a desktop placeable device. System 330 can comprise a first compartment 332 having a measuring system 333 configured to measure the expression value of the polypeptides in the blood of a subject. Measuring system 333 can perform at least one automated assay selected from the group consisting of an automated ELISA, an automated immunoassay, and an automated functional assay. System 330 can also comprise a second compartment 334 comprising a hardware processor 336 having a computer-readable medium 338 for storing computer program instructions for executing the operations described herein (e.g., computer program instructions for defining the first and/or second coordinates, computer program instructions for defining the curved line and/or plane, computer program instructions for calculating the first and/or distances, computer program instructions for correlating the calculated distance(s) to the presence of, absence of, or likelihood that the subject has, a bacterial and/or viral infection). Hardware processor 336 is configured to receive expression value measurements from first compartment 332 and execute the program instructions responsively to the measurements. Optionally and preferably hardware processor 336 is also configured to output the processed data to a display device 340.

In some optional embodiments of the present invention, system 330 communicates with a communication network. In these embodiments, system 330 or hardware processor 336 comprises a network interface 350 that communicates with a communication network 352. In the representative illustration shown in FIG. 34, network 352 is used for transmitting the results of the analysis performed by hardware processor 336 (for example, the presence of, absence of, or likelihood that the subject has, a bacterial and/or viral infection) to one or more remote locations. For example, system 330 can transmit the analysis results to at least one of a laboratory information system 360, and/or a central server 362 that collects data from a plurality of systems like system 330.

Figure 39A:
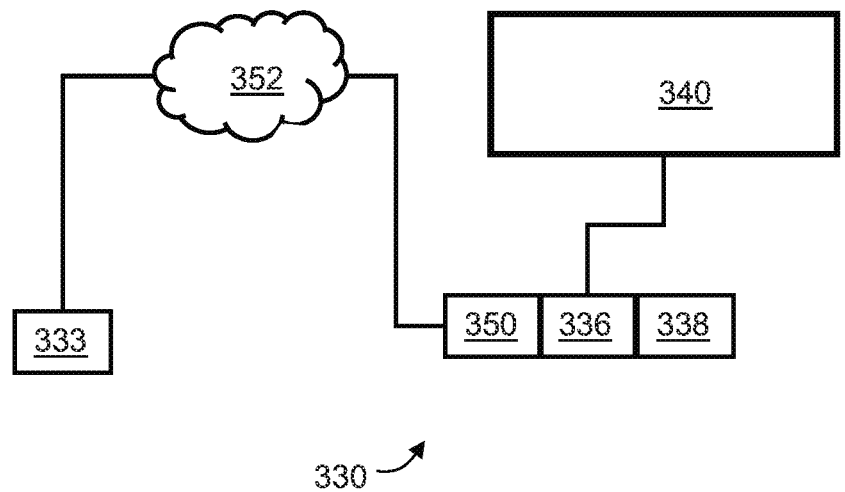
FIGS. 39A and 39B are schematic illustrations of a block diagram of a system for analyzing biological data, in embodiments of the invention in which the system comprises a network interface (FIG. 39A) and a user interface (FIG. 39B).

FIG. 39A is a schematic illustration showing a block diagram of system 330 in embodiments in which communication network 352 is used for receiving expression value measurements. In these embodiments, system 330 can comprise computer-readable medium 338, as further detailed hereinabove, and a hardware processor, such as, but not limited to, processor 336. Hardware processor 336 can comprise network interface 350. Via interface 350, hardware processor 336 receives expression value measurements from a measuring system, such as, but not limited to, measuring system 333, and executes the computer program instructions in computer-readable medium 338, responsively to the received measurements. Hardware processor 336 can then output the processed data to display device 340.

Combinations of the embodiments shown in FIGS. 34 and 39A are also contemplated. For example, interface 350 can be used both for receiving expression value measurements from network 352 and for transmitting the results of the analysis to network 352.

Figure 39B:
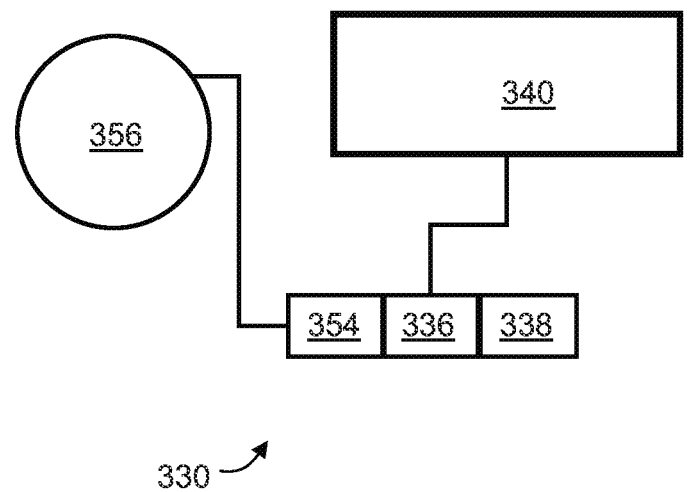

In some embodiments of the present invention system 330 communicates with a user, as schematically illustrated in the block diagram of FIG. 39B. In these embodiments, system 330 can comprise computer-readable medium 338, as further detailed hereinabove, and a hardware processor, such as, but not limited to, processor 336. Hardware processor 336 comprises a user interface 354 that communicates with a user 356. Via interface 350, hardware processor 336 receives expression value measurements from user 356. User 356 can obtain the expression value from an external source, or by executing at least one assay selected from the group consisting of an immunoassay and a functional assay, or by operating system 333 (not shown, see FIGS. 39A and 34). Hardware processor 336 executes the computer program instructions in computer-readable medium 338, responsively to the received measurements. Hardware processor 336 can then output the processed data to display device 340.

Once the diagnosis has been made, it will be appreciated that a number of actions may be taken.

Thus, for example, if a bacterial infection is ruled in, then the subject may be treated with an antibiotic agent.

Examples of antibiotic agents include, but are not limited to Daptomycin; Gemifloxacin; Telavancin; Ceftaroline; Fidaxomicin; Amoxicillin; Ampicillin; Bacampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloradine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Trovafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; Bacitracin; Polymyxin B; Viomycin; Capreomycin.

If a viral infection is ruled in, the subject may be treated with an antiviral agent. Examples of antiviral agents include, but are not limited to Abacavir; Aciclovir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Fusion inhibitor; Ganciclovir; Ibacitabine; Imunovir; Idoxuridine; Imiquimod; Indinavir; Inosine; Integrase inhibitor; Interferon type III; Interferon type II; Interferon type I; Interferon; Lamivudine; Lopinavir; Loviride; Maraviroc; Moroxydine; Methisazone; Nelfinavir; Nevirapine; Nexavir; Oseltamivir; Peginterferon alfa-2a; Penciclovir; Peramivir; Pleconaril; Podophyllotoxin; Raltegravir; Reverse transcriptase inhibitor; Ribavirin; Rimantadine; Ritonavir; Pyramidine; Saquinavir; Sofosbuvir; StavudineTelaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; Zidovudine; RNAi antivirals; inhaled rhibovirons; monoclonal antibody respigams; neuriminidase blocking agents.

The information gleaned using the methods described herein may aid in additional patient management options. For example, the information may be used for determining whether a patient should or should not be admitted to hospital. It may also affect whether or not to prolong hospitalization duration. It may also affect the decision whether additional tests need to be performed or may save performing unnecessary tests such as CT and/or X-rays and/or MRI and/or culture and/or serology and/or PCR assay for specific bacteria and/or PCR assays for viruses and/or perform procedures such as lumbar puncture.

It is often clinically useful to assess patient prognosis, disease severity and outcome. The present inventors have now found that low levels of TRAIL (lower than about 20 μg/ml or about 15 μg/ml or about 10pg/ml or about 5 μg/ml or about 2 μg/ml) are significantly correlated with poor patient prognosis and outcome, and high disease severity. For example, the present inventors showed that adult patients in the intensive care unit (ICU), which are generally severely ill, had significantly lower TRAIL levels compared to all other patients, which were less ill regardless of whether they had an infectious or non-infectious etiology.

Thus, according to another aspect of the present invention there is provided a method of predicting a prognosis for a disease comprising measuring the TRAIL protein serum level in subject having the disease, wherein when the TRAIL level is below a predetermined level, the prognosis is poorer than for a subject having a disease having a TRAIL protein serum level above the predetermined level.

Methods of measuring TRAIL protein serum levels are described herein above.

The disease may be an infectious disease or a non-infectious disease. The subject may have a disease which has been diagnosed or non-diagnosed.

Particular examples of diseases include without limitation bacterial infections (e.g. bacteremia, meningitis, respiratory tract infections, urinal tract infections etc.), sepsis, physical injury and trauma, cardiovascular diseases, multi-organ failure associated diseases, drug-induced nephrotoxicity, acute kidney disease, renal injury, advanced cirrhosis and liver failure, acute or chronic left heart failure, pulmonary hypertension with/without right heart failure, and various types of malignancies.

According to another embodiment, additional polypeptides are measured which aid in increasing the accuracy of the prediction. Thus, for example, other polypeptide which may be measured include IP-10, CRP, IL1RA, PCT and SAA.

According to a particular embodiment, IP-10, CRP and TRAIL are measured.

According to another embodiment, only TRAIL is measured.

The present inventors have found that patients having very low levels of TRAIL (as classified herein above) have lower chance of recovery, and higher chance of complications. Accordingly, the present inventors propose that when π is found that a subject has very low levels of TRAIL they should be treated with agents that are only used as a last resort.

Such agents for example may be for example experimental agents that have not been given full FDA approval. Other last resort agents are those that are known to be associated with severe side effects. Another exemplary last resort agent is an antibiotic such as vancomycin (which is typically not provided so as to prevent the spread of antibiotic resistance).

It will be appreciated that agents that are not typically considered as last resort agents can also be provided, but in doses which exceed the clinically acceptable dose.

According to this aspect of the present invention, if the TRAIL level is above a predetermined level, then the patient should typically not be treated with a last resort agent.

The present inventors have now found that basal levels of TRAIL in healthy individuals or patients with a non-infectious disease are lower in females compared to males during fertility age (t-test P<0.001) (see FIG. 37A), but is invariant in pre- or post-fertility age (t-test P=0.9, FIG. 37A). This trend was not observed in patients with an infectious disease.

This age dependent dynamics can be used to improve models distinguishing between bacterial, viral and non-infectious or healthy individuals, as would be evident to one skilled in the art.

For example, the model can include age and gender parameters. If the subject's age is within a certain range indicative of fertility (e.g. about 13 to 45 years) and the subject is male, then TRAIL model coefficients of males at fertility age can be used. If the subject's age is within the range indicative of fertility and the subject is female then TRAIL model coefficients of females at fertility age can be used. If the subject's age is outside the range indicative of fertility then TRAIL model coefficients that are gender invariant can be used.

Thus, according to another aspect of the invention there is provided a method of determining an infection type in a female subject of fertility age, the method comprising comparing the TRAIL protein serum level in the subject to a predetermined threshold, said predetermined threshold corresponding to the TRAIL protein serum level of a healthy female subject of fertility age, or a group of healthy female subjects of fertility age, wherein a difference between said TRAIL protein serum level and said predetermined threshold is indicative of an infection type.

Thus, according to another aspect of the invention there is provided a method of determining an infection type in a male subject of fertility age, the method comprising comparing the TRAIL protein serum level in the subject to a predetermined threshold, said predetermined threshold corresponding to the TRAIL protein serum level of a healthy male subject of fertility age, or a group of healthy male subjects of fertility age, wherein a difference between said TRAIL protein serum level and said predetermined threshold is indicative of an infection type.

It will be appreciated that predetermined thresholds can be used to either rule in or rule out an infection type.

Thus, for example if the TRAIL protein serum level is above a first predetermined threshold, the infection type is viral.

If, for example the TRAIL protein serum level is above a second predetermined threshold, the infection type is not bacterial.

If for example, the TRAIL protein serum level is below a third predetermined threshold, the infection type is bacterial.

If for example the TRAIL protein serum level is below a fourth predetermined threshold, the infection type is not viral.

Typically, the healthy male or female subject, referred to herein has no known disease. According to a particular embodiment, the control subject has no infectious disease.

Typically, the difference between the TRAIL protein serum level of the subject and the predetermined threshold is a statistically significant difference, as further described herein above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

A Host-Proteome Signature for Distinguishing Between Bacterial and Viral Infections: a Prospective Multi-Center Observational Study Methods Study population: A total of 1002 patients took part in the study. Pediatric patients (≤18 years) were recruited from pediatric emergency departments (PED), pediatric wards and surgical departments, and adults (>18 years) from emergency departments (ED), internal medicine departments and surgical departments. Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection (FIG. 1A). Importantly, in order to enable broad generalization, antibiotic treatment at enrollment did not cause exclusion from the study.

Enrollment process and data collection: For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). Thirty days after enrollment, disease course and response to treatment were recorded. All information was recorded in a custom electronic case report form (eCRF).

Microbiological investigation: Patients underwent two multiplex-PCR diagnostic assays from nasal swab samples:

(i) Seeplex® RV15 (n=713), for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, and (ii) Seeplex® PB6 (n=633) for detection of *Streptococcus pneumoniae, Haemophilus influenzae, Chlamydophila pneumoniae, Legionella pneumophila, Bordetella pertussis,* and *Mycoplasma pneumoniae*. Multiplex-PCR assays were performed by a certified service laboratory. Patients were also tested for additional pathogens according to their suspected clinical syndrome, including: blood culture (n=420), urine culture (n=188) and stool culture for *Shigella* spp., *Campylobacter* spp. and *Salmonella* spp. (n=66); serological testing (IgM and/or IgG) for cytomegalovirus (CMV), Epstein-Barr virus (EBV), *Mycoplasma pneumonia*, and *Coxiella burnetii* (Q-Fever) (n=167, n=130, n=206 and n=41 respectively).

Establishing the reference standard: The Clear Diagnosis, Unanimous and Majority cohorts: A rigorous composite reference standard was created following recommendations of the Standards for Reporting of Diagnostic Accuracy (STARD).[38] First, a thorough clinical and microbiological investigation was performed for each patient as described above. Then, all the data collected throughout the disease course was reviewed by a panel of three physicians. For adult patients (>18 years) the panel included the attending physician and two infectious disease specialists, while for children and adolescents (≤18 years) it included the attending pediatrician, an infectious disease expert and a senior attending pediatrician. Each panel member assigned one of the following diagnostic labels to each patient: (i) bacterial; (ii) viral; (iii) no apparent infectious disease or healthy (controls); and (iv) indeterminate. Patients with mixed infections (bacteria plus virus) were labeled as bacterial because they are managed similarly (e.g. treated with antibiotics). Importantly, the panel members were blinded to the labeling of their peers and to the results of the signature.

This process was used to create three cohorts with an increasing level of diagnostic certainty (FIG. 1A):
  (i) Majority cohort: Patients were assigned the same label by at least two of the three panel members;
  (ii) Unanimous cohort (a subgroup of the Majority cohort): Patients were assigned the same label by all three panel members (the terms "unanimous cohort" and "consensus cohort" are used herein interchangeably); and
  (iii) Clear Diagnosis cohort (a subgroup of the Unanimous cohort): Bacterial labeled patients were unanimously diagnosed by all three panel members, had WBC >15,000/µl (a cutoff indicative of increased bacterial infection risk[11]) and one of the following microbiological confirmations: bacteremia (with positive blood culture), bacterial meningitis (with positive CSF culture), pyelonephritis (with positive urine culture and ultrasound demonstration of renal involvement), UTI (with positive urine culture), septic shock (with positive blood culture), or peritonsillar abscess (proven by surgical exploration or computerized tomography). Viral labeled patients were unanimously diagnosed by panel members and had and a positive test result of a virus.

Additionally, control labeled patients were unanimously diagnosed by all three panel members.

Samples, procedures and protein measurements: Venous blood samples were stored at 4° C. for up to 5 hours on site and subsequently fractionated into plasma, serum and total leukocytes and stored at −80° C. Nasal swabs and stool samples were stored at 4° C. for up to 72 hours and subsequently transported to a certified service laboratory for multiplex PCR-based assay. In the screening phase, host-proteins were measured in serum and leukocytes using enzyme linked immunosorbent assay (ELISA), Luminex technology, protein arrays and Flow cytometry (on freshly isolated leukocytes). After screening and signature construction (see Host-proteome screening section), three proteins were selected and measured as follows: CRP was measured via either Cobas 6000, Cobas Integra 400, Cobas Integra 800, or Modular Analytics P800 (Roche). TRAIL and IP-10 were measured using commercial ELISA λits (MeMed Diagnostics).

Statistical analysis: The primary analysis was based on area under the receiver operating characteristics curve (AUC), Sensitivity (TP/P), Specificity (TN/N), Positive likelihood ratio (LR+=Sensitivity/[1−Specificity]), Negative likelihood ratio (LR−=[1−Sensitivity]/Specificity) and Diagnostic odds ratio (DOR=LR+/LR−), where P, N, TP and TN correspond to positives (bacterial patients), negatives (viral patients), true positives (correctly diagnosed bacterial patients), and true negatives (correctly diagnosed viral patients), respectively. Statistical analysis was performed with MATLAB. Sample size calculations are presented in Example 2 herein below.

Figure 1B:
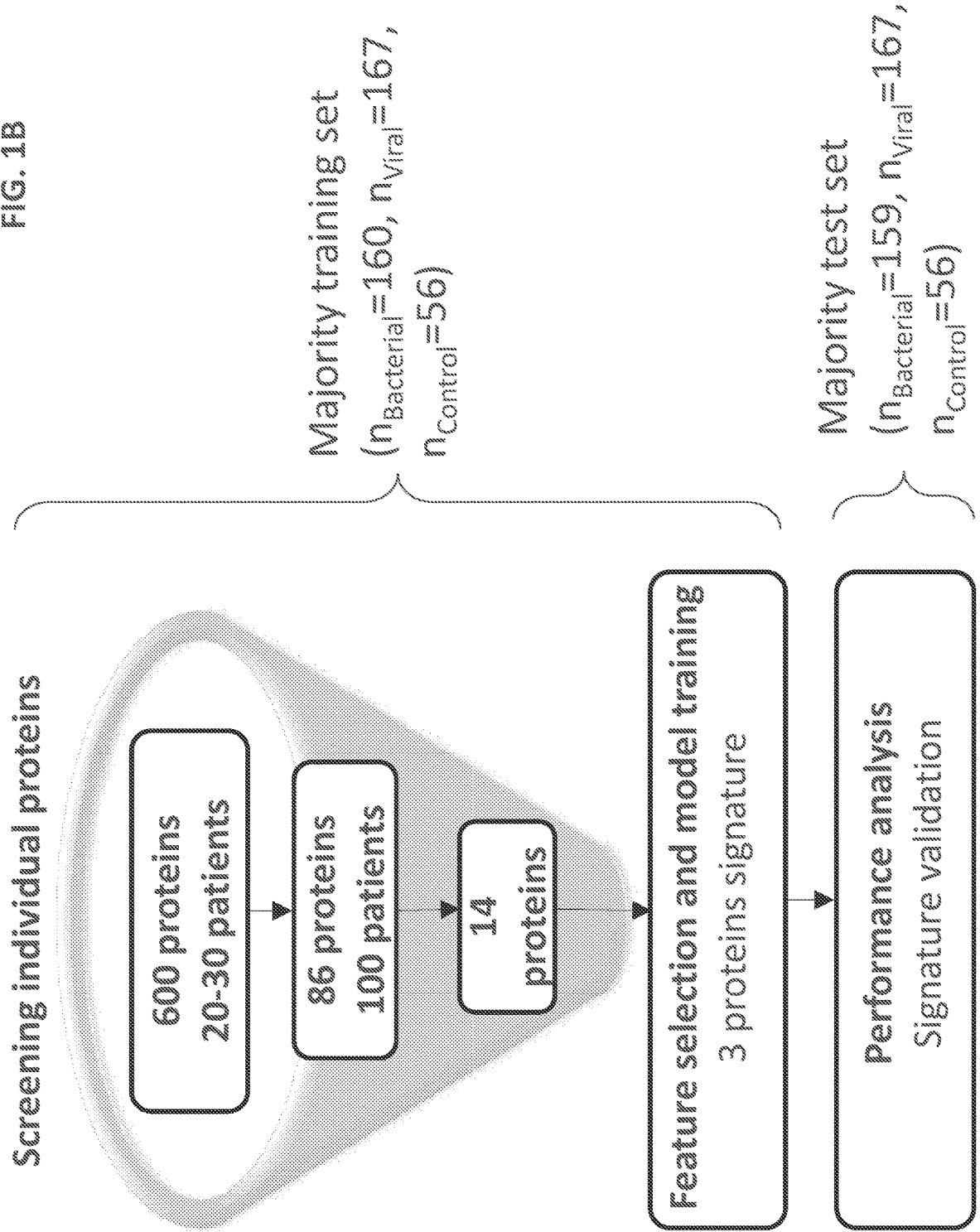

Host-proteome screening: A general overview of the process for developing, training and testing the multivariate logistic model is depicted in FIG. 1B. Briefly, a systematic literature screen and bioinformatics analysis was performed that identified 600 protein candidates that were likely to be differentially expressed in peripheral blood samples of bacterial versus viral patients, some of which have a known role in the host immune response to infection and others with no direct link to the immune system. Next, each protein candidate was measured on 20-30 patients from the training set (50% viral and 50% bacterial) and a Wilcoxon rank-sum (WS) P-value <0.01 was used to screen proteins with statistically significant differential measurements. This resulted in a set of 86 proteins (false discovery rate [FDR] of 0.07). Each of these proteins was then evaluated in 100 additional patients (50% viral and 50% bacterial) and further screened using a t-test cutoff of $P<10^{-4}$, resulting in 14 proteins that were significantly differentially expressed in viral versus bacterial patients (FDR<0.001).

Signature development and validation: A feature selection process was applied to identify the optimal combination of proteins. Two feature selection schemes were used: mutual-information min-max[39] and forward greedy wrapper[40], which use a series of iterations to add or remove features. The process was terminated when the increase in performance on the training set was no longer statistically significant (P>0.05). Both processes converged to the same final set of three proteins. To integrate the protein levels into a single score, multiple computational models were examined. Their performances were not significantly different (P>0.1 as further detailed in Example 2 herein below). A Multinomial Logistic Regression (MLR) model was chosen because provides a probabilistic interpretation by assigning a likelihood score to a patient's diagnosis. The signature uses this property to filter out patients whose probability of bacterial infection is intermediate: between 0.35 and 0.55. The term 'marginal immune response' is used to describe these patients because their profile borders between bacterial and viral host-responses. The patients in the Majority cohort were divided into training and test sets, each comprising 50% of the patients (FIG. 1B). The training set included the 120 patients who participated in the screening process and additional patients that were randomly assigned. The test set included the remaining patients and was used for independent assessment of the signature performance. Importantly, none of the test set patients were used to train the algorithms, or to select the proteins. A leave-10%-out cross-validation was used to estimate model performance. More details on the model construction are provided in Example 2 herein below).

Results

Figure 6A:
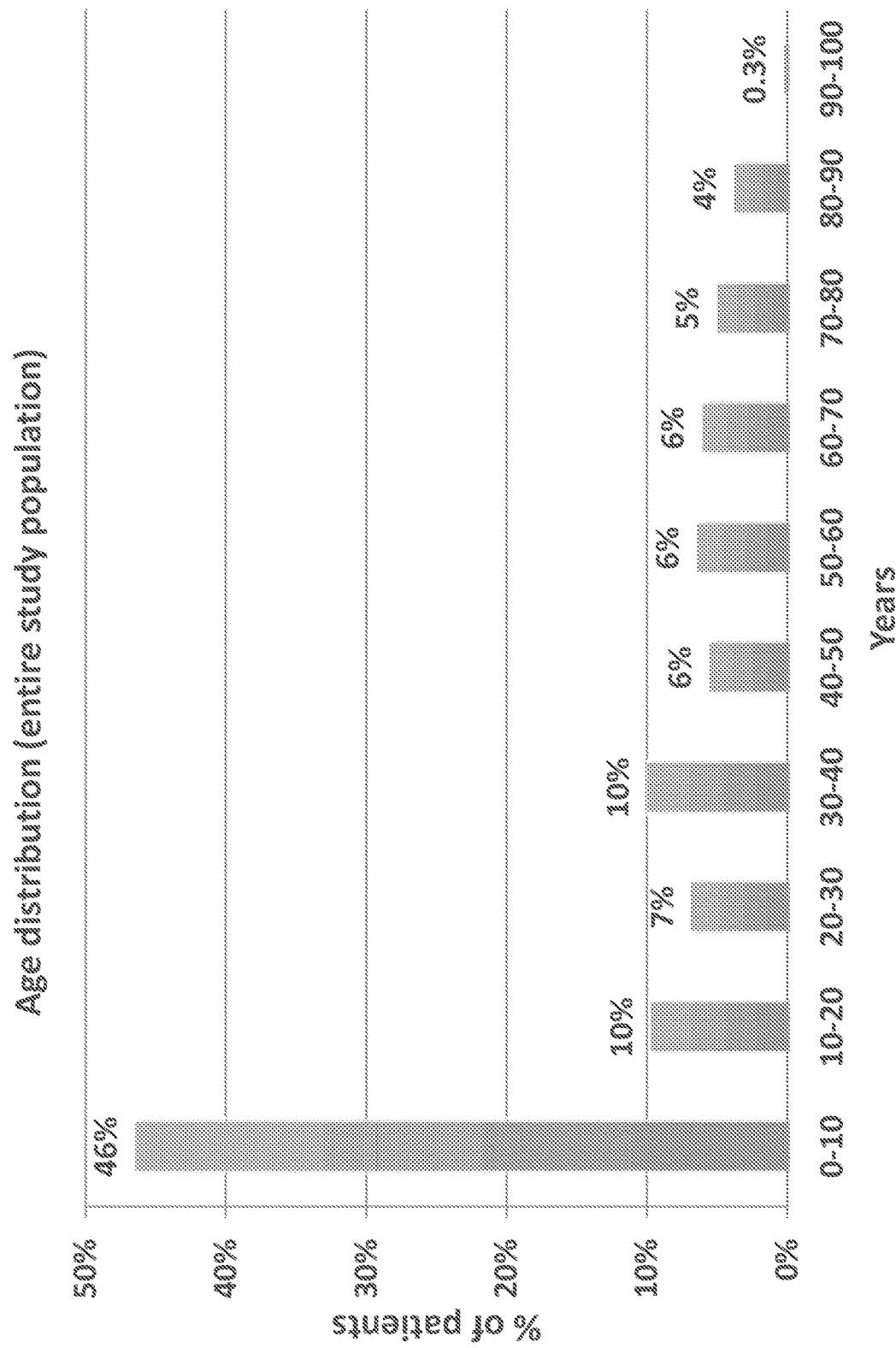
FIGS. 6A-6B. Age distribution of the diagnosed patients. A. The entire study population (n=794); B. Pediatric patients only (n=445).
Figure 6B:
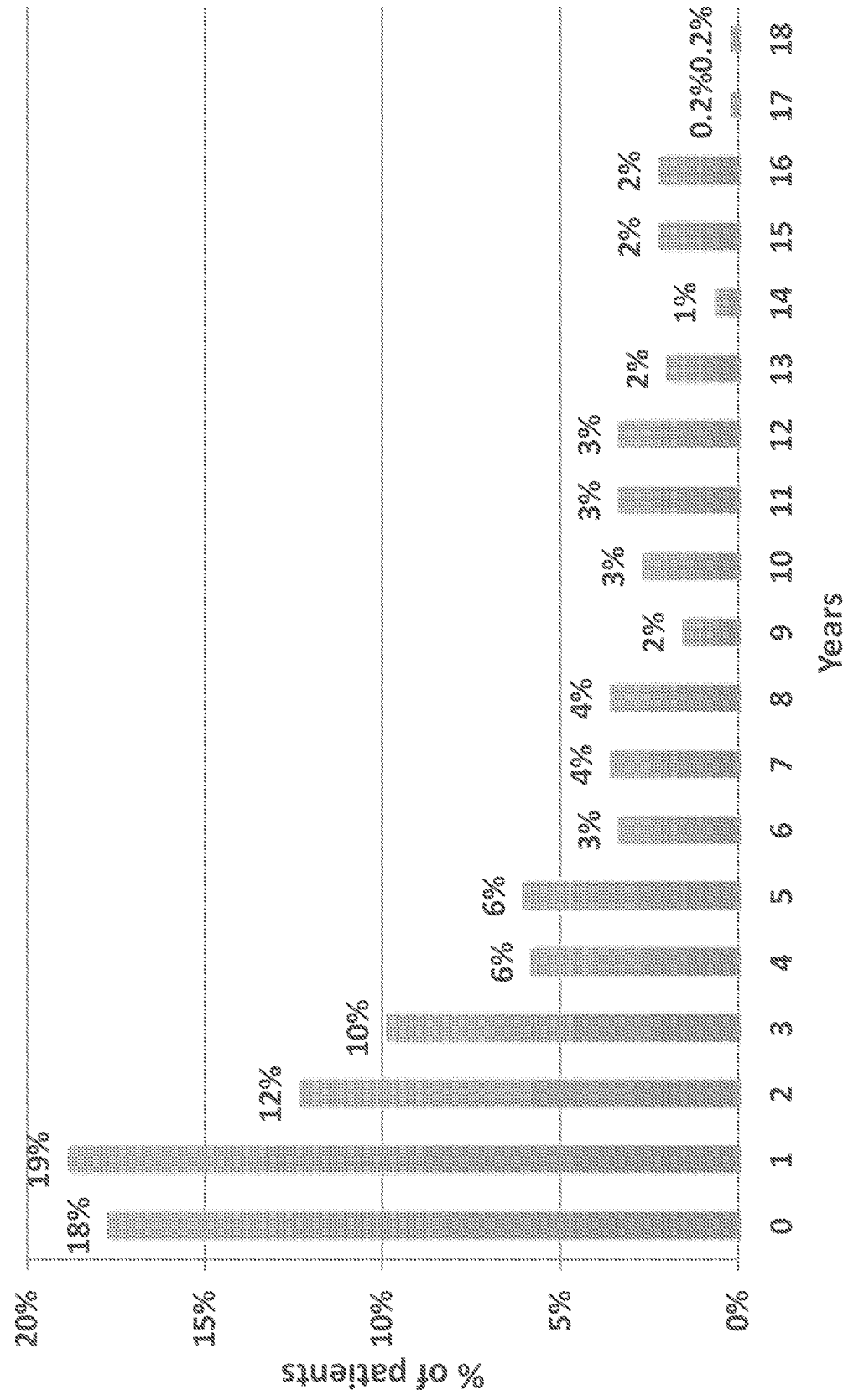
Figure 7A:
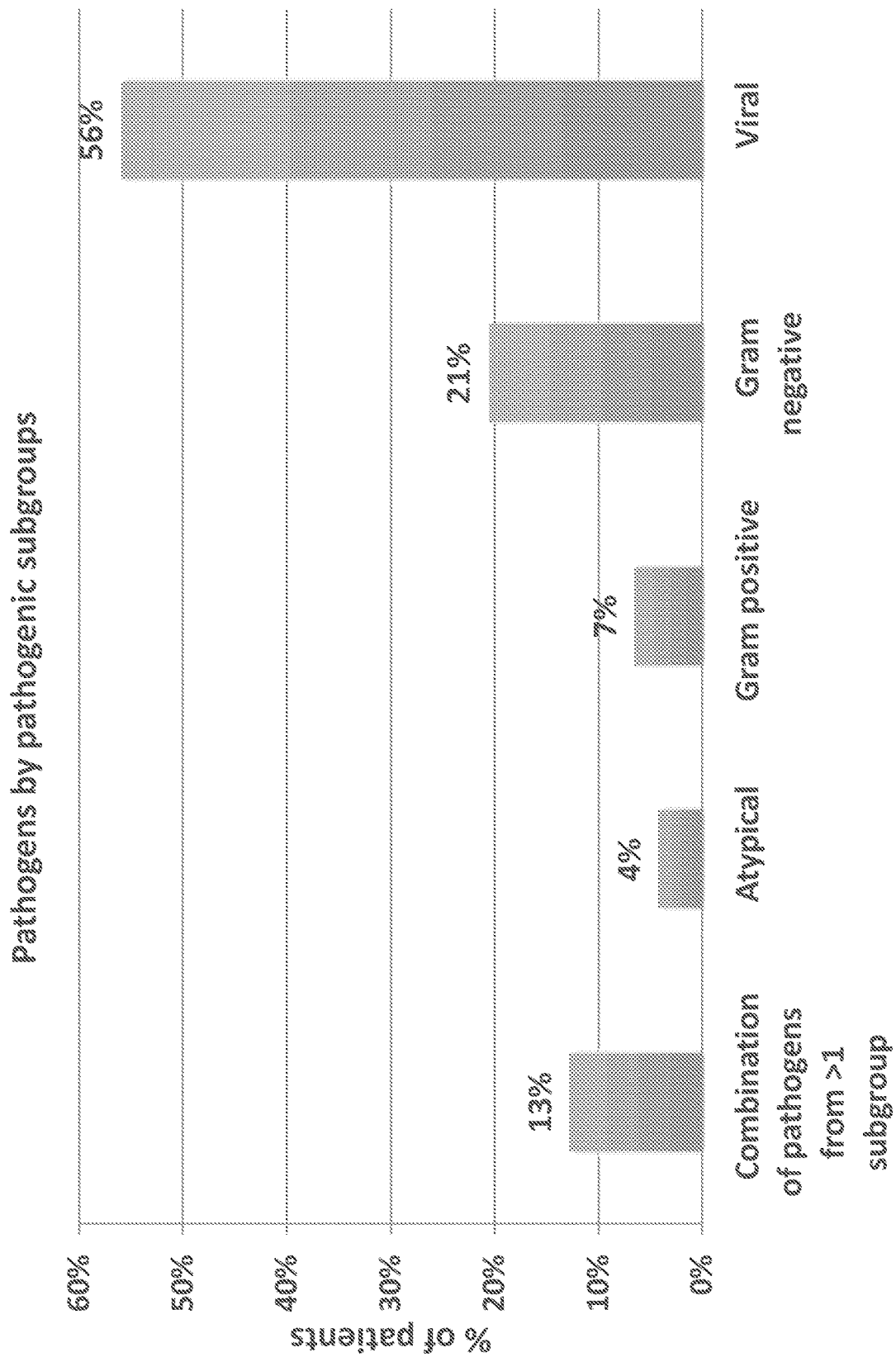
FIGS. 7A-7B. Distribution of detected pathogens in diagnosed patients (n=794). A. Distribution of detected pathogens by pathogenic subgroups; B. Distribution of detected pathogens by strain (strains detected from >1% of patients are presented). Distribution represents % of positive detections in patients with diagnosed infectious disease.
Figure 7B:
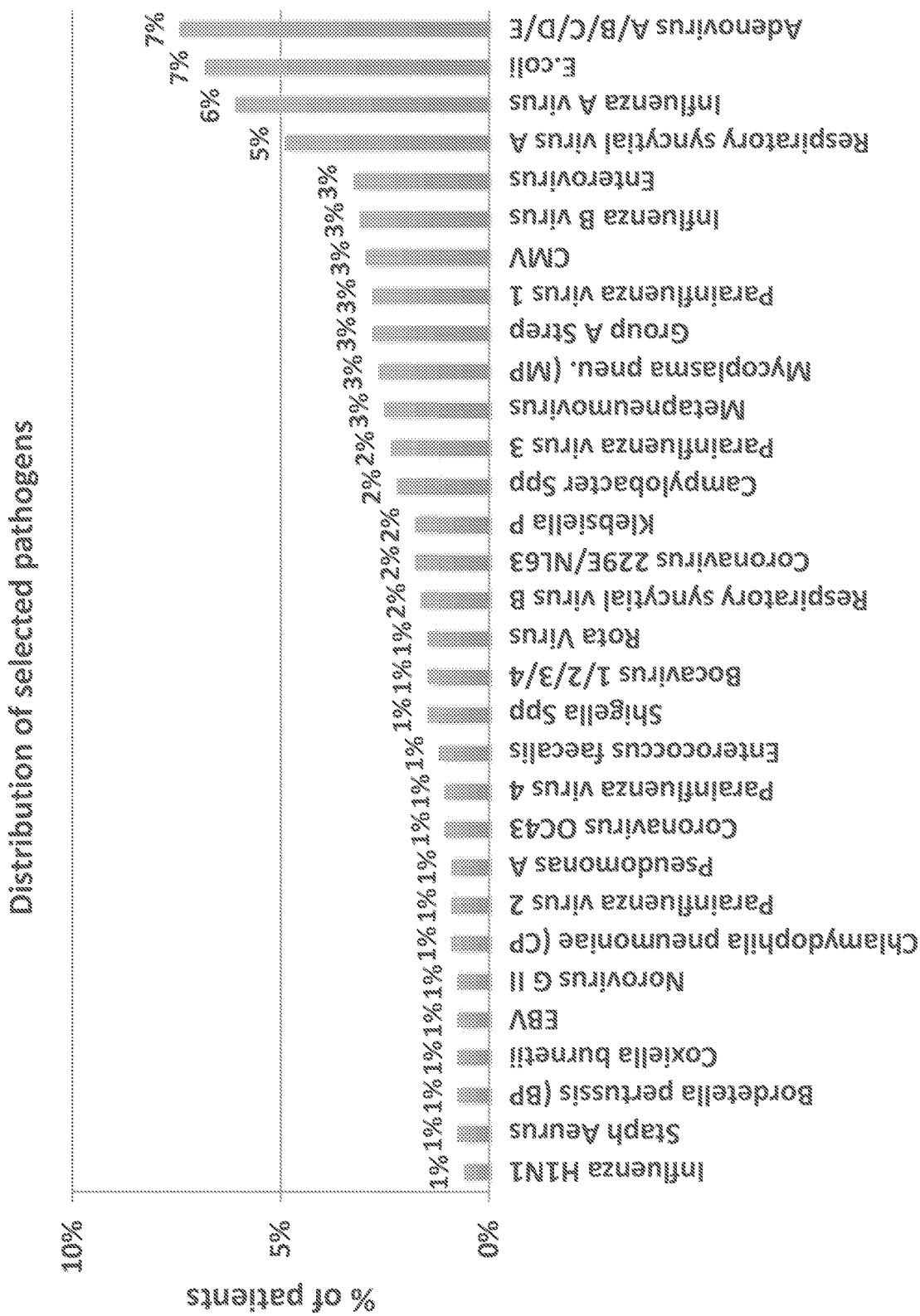

Patient characteristics: Three physicians independently assigned a label to each patient (either bacterial, viral, controls, or indeterminate). The labels were used to create three cohorts with increasing level of diagnostic certainty: Majority (n=765), Unanimous (n=639) and Clear Diagnosis (n=312) cohorts (FIG. 1A). Additionally, 98 patients were labeled as indeterminate, because the physicians could not establish disease etiology or there was no majority labeling. A detailed characterization of the Majority cohort is depicted in Table 1. Briefly, the cohort was balanced with respect to gender (47% females, 53% males) and included 56% pediatric patients (≤18 years) and 44% adults (>18 years). Patients presented with a wide range of clinical syndromes (e.g. RTI, UTI, and systemic infections), maximal temperatures (36-41.5° C.), time from symptoms onset (0-12 days), comorbidities, and medications (Table 1 and FIGS. 6A-12B). Altogether, 56 pathogen species were detected that are responsible for the vast majority of acute infectious diseases in the Western world (FIGS. 7A-7B).

TABLE 1

| Criteria | Total n = 765 | Children (≤18 years) n = 432 | Adults (>18 years) n = 333 |
|---|---|---|---|
| Age (years) | | | |
| <3 | 211 (28) | | |
| 3-6 | 93 (12) | | |
| 6-9 | 46 (6) | | |
| 9-18 | 82 (11) | | |
| 18-30 | 55 (7) | | |
| 30-60 | 161 (21) | | |
| >60 | 117 (15) | | |
| Gender | | | |
| Female | 363 (47) | 205 (47) | 158 (47) |
| Maximal Temperature (° C.) | | | |
| <37.5 | 106 (14) | 28 (6) | 78 (23) |
| 37.5-38.4 | 154 (20) | 68 (16) | 86 (26) |
| 38.5-39.4 | 294 (38) | 164 (38) | 130 (39) |
| 39.5-40.4 | 196 (26) | 157 (36) | 39 (12) |
| >40.5 | 15 (2) | 15 (3) | 0 (0) |
| Time from symptoms onset (days) | | | |
| 0-1 | 175 (24) | 118 (27) | 57 (17) |
| 2-3 | 265 (36) | 161 (37) | 104 (31) |
| 4-5 | 161 (22) | 89 (21) | 72 (22) |
| 6-7 | 109 (15) | 52 (12) | 57 (17) |
| 8-9 | 10 (1) | 2 (0.5) | 8 (2) |
| 10-12 | 14 (2) | 2 (0.5) | 12 (4) |
| N/A | 31 (4) | 8 (2) | 23 (7) |
| Clinical syndrome | | | |
| Cellulitis | 28 (4) | 7 (2) | 21 (6) |
| CNS | 14 (2) | 9 (2) | 5 (2) |
| GI | 89 (11.5) | 66 (15) | 23 (7) |
| LRTI | 158 (21) | 84 (19) | 74 (22) |
| Non-infectious | 112 (14.5) | 29 (7) | 83 (25) |
| Other | 12 (1.5) | 4 (1) | 8 (2.5) |

TABLE 1-continued

| Criteria | Total n = 765 | Children (≤18 years) n = 432 | Adults (>18 years) n = 333 |
|---|---|---|---|
| Systemic | 150 (19.5) | 110 (26) | 40 (12) |
| URTI | 145 (19) | 104 (24) | 41 (12) |
| DTI | 57 (7) | 19 (4) | 38 (11) |
| Recruiting site | | | |
| Pediatrics & Internal | 293 (38) | 137 (32) | 156 (47) |
| PED & ED | 472 (62) | 295 (68) | 177 (53) |
| Hospitalization duration (days) | | | |
| Not hospitalized | 272 (36) | 174 (40) | 98 (29) |
| 1-2 | 206 (28) | 126 (29) | 80 (24) |
| 3-4 | 170 (22) | 94 (22) | 76 (23) |
| 5-6 | 53 (7) | 24 (6) | 29 (9) |
| 7-8 | 31 (4) | 7 (1.5) | 24 (7) |
| >8 | 33 (4) | 7 (1.5) | 26 (8) |
| Season | | | |
| Autumn | 181 (24) | 111 (26) | 70 (21) |
| Spring | 208 (27) | 124 (29) | 84 (25) |
| Summer | 170 (22) | 98 (23) | 72 (22) |
| Winter | 206 (27) | 99 (23) | 107 (32) |
| Smoking | | | |
| Yes | 74 (10) | 0 (0) | 74 (22) |
| No | 691 (90) | 432 (100) | 259 (78) |
| Antibiotic prescription | | | |
| Yes | 432 (56) | 207 (48) | 225 (68) |
| No | 333 (44) | 225 (52) | 108 (32) |
| Detected microorganisms | | | |
| Not detected | 219 (29) | 79 (18) | 140 (42) |
| Viruses | | | |
| Adenovirus A/B/C/D/E | 50 (7) | 47 (11) | 3 (1) |
| Bocavirus 1/2/3/4 | 9 (1) | 9 (2) | 0 (0) |
| CMV & EBV | 25 (3) | 23 (5) | 2 (0.6) |
| Coronavirus 229E/NL63/OC43 | 19 (2) | 14 (3) | 5 (2) |
| Enteric viruses | 19 (2) | 16 (4) | 3 (1) |
| Enterovirus | 21 (3) | 20 (5) | 1 (0.3) |
| Influenza A virus | 45 (6) | 24 (6) | 21 (6) |
| Influenza B virus | 19 (2) | 14 (3) | 5 (2) |
| Metapneumovirus | 17 (2) | 13 (3) | 4 (1) |
| Parainfluenza 1/2/3/4 | 48 (6) | 41 (9) | 7 (2) |
| Respiratory syncytial virus A/B | 40 (5) | 38 (9) | 2 (0.6) |
| Rhinovirus A/B/C | 87 (11) | 73 (17) | 14 (4) |
| Bacteria | | | |
| Atypical bacteria | 27 (4) | 7 (2) | 20 (6) |
| E. coli | 44 (6) | 17 (4) | 27 (8) |
| Enterococcus faecalis | 10 (1) | 0 (0) | 10 (3) |
| Group A Strep | 19 (2) | 16 (4) | 3 (1) |
| Haemophilus influenzae | 179 (23) | 148 (34) | 31 (9) |
| Streptococcus pneumoniae | 306 (40) | 207 (48) | 99 (30) |

Table 1—Baseline characteristics of the majority cohort patients. Values are numbers (percentages). Only microorganisms that were detected in more than 5 patients are presented. CNS—central nervous system, GI—gastroenteritis, LRTI—lower respiratory tract infection, UTRI—upper respiratory tract infection, UTI—urinary tract infection, N/A—healthy controls or patients in which data was not obtained. Influenza A subgroup included H1N1 strains. The atypical bacteria subgroup included *Chlamydophila pneumoniae, Mycoplasma pneumonia* and *Legionella pneumophila*. The Enteric viruses subgroup included Rota virus, Astrovirus, Enteric Adenovirus and Norovirus G I/II. In the clinical syndrome analysis the LRTI group included *pneu-* monia, bronchiolitis, acute bronchitis, and laryngitis; URTI group included pharyngitis, acute otitis media, acute sinusitis and acute tonsillitis.

Signature performance on the Clear Diagnosis, Unanimous and Majority cohorts: Of the 600 screened host-proteins and their combinations, the best signature for discriminating bacterial, viral and control patients in the Majority cohort training set included three soluble proteins: TNF-related apoptosis-inducing ligand (TRAIL), Interferon gamma-induced protein 10 (IP-10), and C-reactive protein (CRP) (FIGS. 2A-2C). Signature AUC for distinguishing between bacterial and viral infections on the test set of the Majority cohort was 0.94±0.04. Similar results were obtained using leave-10%-out cross-validation on the entire Majority cohort (AUC=0.94±0.02). The signature significantly outperformed all the individual proteins evaluated in the screening phase ($P<10^{-6}$). The training and testing procedures were repeated on the Unanimous and Clear Diagnosis cohorts, yielding AUCs of 0.96±0.02 and 0.99±0.01, respectively. This stepwise increase in performance is aligned with the increased certainty of reference standard assignment in the three cohorts (Table 2, herein below).

Comparison with laboratory measurements, clinical parameters, and well-established biomarkers: The signature was compared with well-established clinical parameters and laboratory measurements, including white blood count (WBC), absolute neutrophil count (ANC), percentage neutrophils, maximal temperature, pulse, and respiratory rate (FIG. 3A and Example 2). The signature surpassed all individual parameters ($P<10^{-18}$). Next, the signature was compared to a combination of several clinical parameters. To this end, multinomial logistic models were generated for all combinations of up to four clinical parameters. The best performing pair, triplet and quadruplet are depicted in FIG. 3A (adding a fifth parameter did not improve performance). The signature was significantly better than the best performing clinical parameters combination ($P<10^{-15}$), which consisted of ANC, pulse, % lymphocytes and % monocytes, (AUC=0.94±0.02 vs. 0.77±0.04). Next, the signature performance was compared to PCT and CRP, two proteins routinely used in clinical practice to diagnose sepsis and bacterial infections (Example 2). The signature performed significantly better than both proteins ($P<10^{-8}$ and $P<10^{-6}$, respectively). The signature also performed better than a wide range of host-proteins with an established role in the

TABLE 2

Signature measures of accuracy for diagnosing bacterial vs. viral infections

| B. Marginal immune response filter | | | A. All patients | | | |
| --- | --- | --- | --- | --- | --- | --- |
| Majority cohort | Unanimous cohort | Clear diagnosis cohort | Majority cohort | Unanimous cohort | Clear diagnosis cohort | Accuracy measure |
| 0.94 | 0.97 | 0.99 | 0.94 | 0.96 | 0.99 | AUC |
| (0.92, 0.96) | (0.95, 0.99) | (0.98, 1.00) | (0.92, 0.96) | (0.94, 0.98) | (0.98, 1.00) | |
| 0.91 | 0.93 | 0.96 | 0.88 | 0.90 | 0.94 | Total |
| (0.88, 0.94) | (0.9, 0.96) | (0.93, 0.99) | (0.85, 0.90) | (0.87, 0.92) | (0.91, 0.97) | accuracy |
| 0.92 | 0.94 | 0.96 | 0.87 | 0.88 | 0.96 | Sensitivity |
| (0.88, 0.96) | (0.9, 0.98) | (0.88, 1.00) | (0.83, 0.91) | (0.84, 0.91) | (0.88, 1.00) | |
| 0.89 | 0.93 | 0.97 | 0.90 | 0.92 | 0.93 | Specificity |
| (0.86, 0.89) | (0.9, 0.96) | (0.89, 0.97) | (0.86, 0.93) | (0.89, 0.96) | (0.89, 0.97) | |
| 8.4 | 13.4 | 32.0 | 8.7 | 11.0 | 13.7 | LR+ |
| (6, 12) | (8, 21) | (13, 78) | (6, 12) | (7, 16) | (8, 24) | |
| 0.09 | 0.07 | 0.04 | 0.14 | 0.13 | 0.04 | LR− |
| (0.06, 0.13) | (0.04, 0.11) | (0.01, 0.26) | (0.11, 0.19) | (0.09, 0.18) | (0.01, 0.27) | |
| 93 | 208 | 776 | 60 | 84 | 319 | DOR |
| (53, 164) | (99, 436) | (92, 6528) | (37, 98) | (47, 150) | (43, 2383) | |

A. Performance estimates and their 95% CIs were obtained using a leave-10%-out cross-validation on all patients in the Clear Diagnosis cohort ($n_{Bacterial}$=27, $n_{Viral}$=173), Unanimous ($n_{Bacterial}$=256, $n_{Viral}$=271), and Majority ($n_{Bacterial}$=319, $n_{Viral}$=334) cohorts. B. The analysis was repeated after filtering out patients with a marginal immune response (Clear Diagnosis [$n_{Bacterial}$=27, $n_{Viral}$=159, $n_{marginal}$=14], Unanimous [$n_{Bacterial}$=233, $n_{Viral}$=232, $n_{marginal}$=62], and Majority [$n_{Bacterial}$=290, $n_{Viral}$=277, $n_{marginal}$=88]), which resembles the way clinicians are likely to use the signature.

Figure 3B:
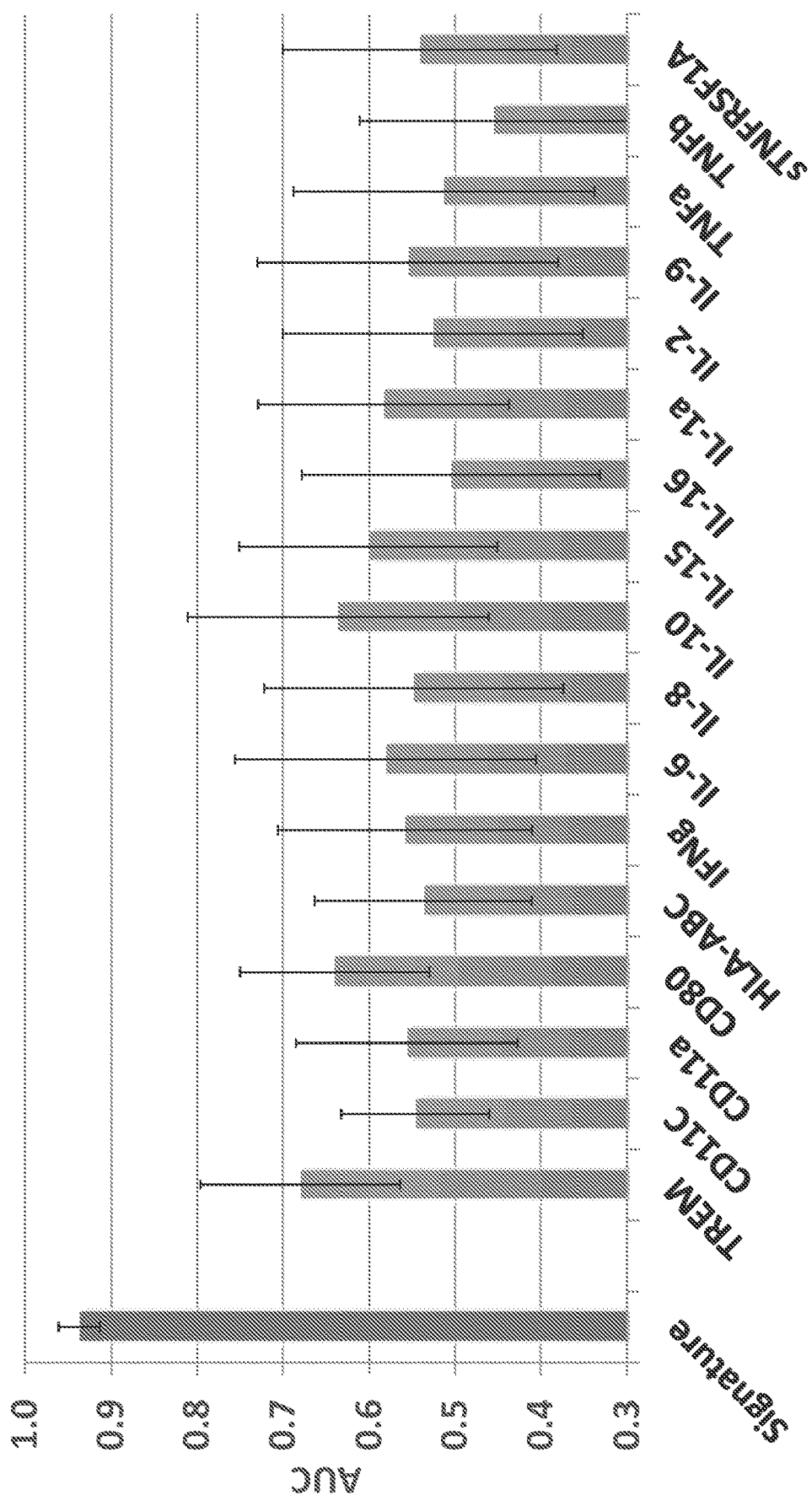

Next, the present inventors used the signature to distinguish between infectious (bacterial or viral) and non-infectious controls on the Majority cohort test set, yielding an AUC of 0.96±0.02. Further evaluation using leave-10%-out cross-validation gave similar results (AUC=0.96±0.01). The signature outperformed any of the individual proteins ($P<10^{-8}$). Again, evaluation on the Unanimous and Clear Diagnosis cohorts showed improved AUCs of 0.97±0.02, and 0.97±0.03, respectively. To obtain conservative estimations of signature performance, the analysis that follows focuses on the Majority cohort.

immune response to infection, including sepsis and bacterial-related (e.g. TREM, IL-6 and IL-8), virus-related (e.g. IFN-γ and IL-2), and inflammation-related (e.g. IL-1a and TNF-α) proteins ($P<10^{-8}$) (FIG. 3B and Example 2, herein below).

Signature performance is robust across different patient subgroups: Patient and pathogen heterogeneity, which are inherent in real-life clinical settings, might negatively affect the diagnostic utility of any individual host-biomarker. To examine whether the signature, a combination of multiple biomarkers, can maintain steady performance despite patient-to-patient variability, subgroup analyses were performed.

Figure 4:
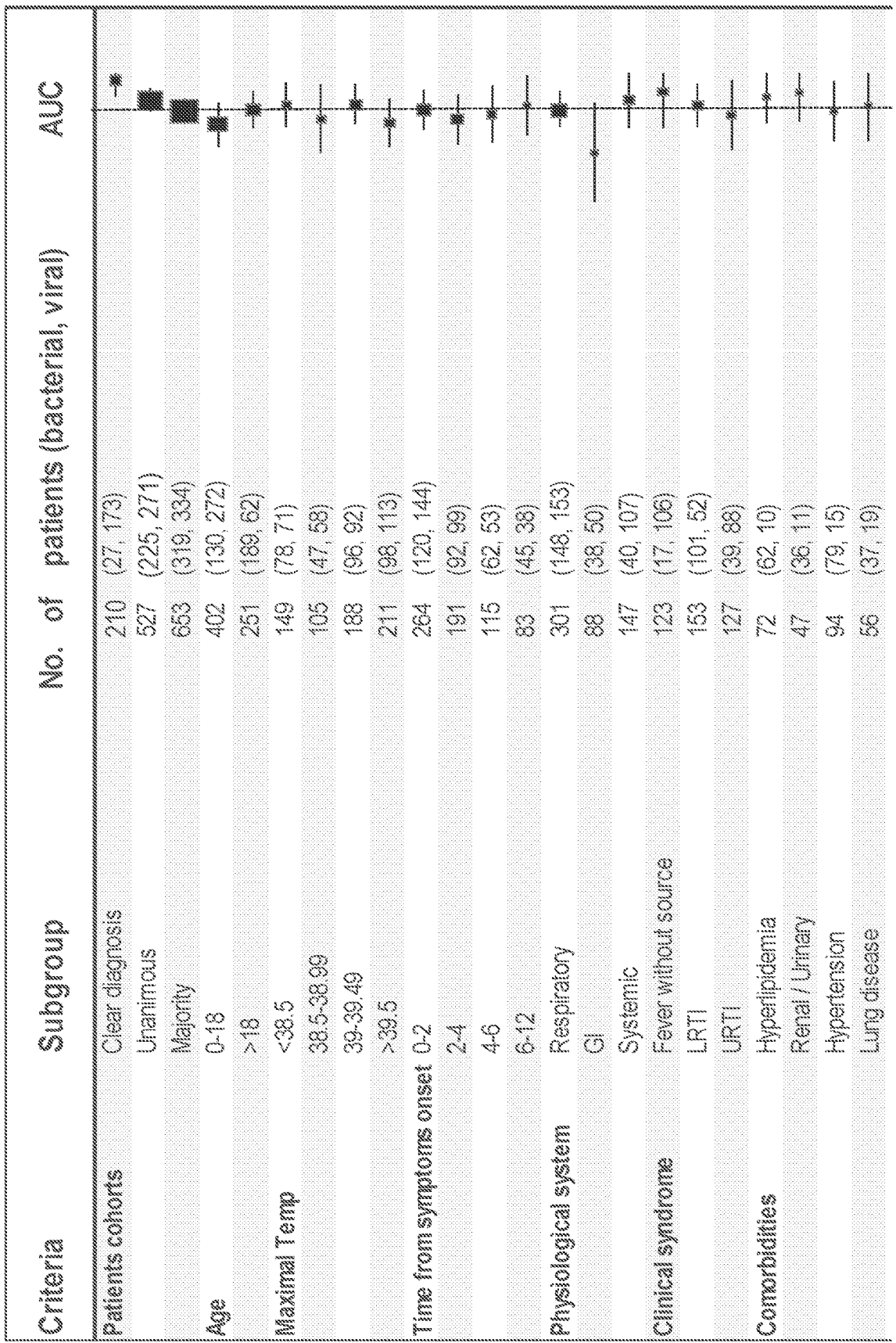
FIG. 4. Signature performance is robust across different patient subgroups. Signature AUC in subgroups of the Majority cohort (bacterial and viral) are depicted. Square size is proportional to number of patients and error bars represent 95% CI. In the Pathogens analysis, each virus was compared to bacteria affecting the same physiological system, indicated in brackets. R-respiratory, S-systemic, C-central nervous system, G-gastrointestinal, U-urinary, K-skin. Only pathogens detected in more than 5 patients are presented. For subgroup definitions see Table 1 in Example 1.

The signature was robust (AUCs between 0.87 and 1.0) across a wide range of patient characteristics, including age, clinical syndrome, time from symptom onset, maximal temperature, pathogen species, comorbidities, treatment with medications for chronic diseases, and clinical site (FIG. 4 and Example 2, herein below). The signature was also tested on the subgroup of patients who were technically excluded, but had unanimous labeling by the expert panel, which yielded an AUC of 0.96±0.06 ($n_{Bacterial}$=27, $n_{Viral}$=14). This might suggest that the signature is applicable more broadly to conditions that were initially excluded (e.g. sub-febrile patients).

Signature performance remains unaffected by the presence of potential colonizers: Many disease-causing bacteria are also part of the natural flora, and are frequently found in asymptomatic subjects.[12,42-44] Such bacteria pose a considerable diagnostic challenge, because merely detecting them does not necessarily imply a causative role in the disease; therefore, appropriate treatment may remain unclear. The present inventors asked whether the signature performance is affected by their presence.

*Streptococcus pneumoniae* (SP) and *Haemophilus influenzae* (HI), detected by PCR on nasal swabs, were the two most common bacteria in the Majority group (Table 1, herein above). High rates of SP and HI were found amongst both bacterial and viral patients (SP: 36% and 47%; HI: 20% and 32%), substantiating the understanding that their mere presence does not necessarily cause a disease.[12] The patients were stratified based on whether or not they had SP (SP+: $n_{Bacterial}$=116, $n_{Viral}$=157; SP−: $n_{Bacterial}$=203, $n_{Viral}$=177) and AUC performance of the two groups was compared. A significant difference was not observed (0.93±0.03 vs. 0.94±0.02, P=0.31). The presence or absence of HI did not affect signature performance either (0.94±0.04 vs. 0.93±0.02; HI+: $n_{Bacterial}$=63, $n_{Viral}$=10⁶; HI−: $n_{Bacterial}$=256, $n_{Viral}$=228, P=0.34). This indicates that the signature remains unaffected by carriage of SP and HI.

Discussion

A rigorous composite reference standard strategy was constructed that included the collection of clinical data, a chemistry panel, and a wide array of microbiological tests, followed by labeling by three independent physicians. This process generated a hierarchy of three sub-cohorts with decreasing size and increasing reference standard certainty: Majority, Unanimous and Clear Diagnosis. The respective signature AUCs were 0.94±0.02, 0.96±0.02, and 0.99±0.01. This stepwise increase in performance may be attributed to the increase in reference standard certainty. However, the increased accuracy, particularly in the Clear Diagnosis cohort, may also be partially due to a selection bias of patients with severe illness or straightforward diagnosis. Therefore, the primary analysis presented herein focused on the Majority cohort, which captures a wider spectrum of illness severity and difficult-to-diagnose cases. This cohort potentially includes some erroneous labeling, thereby leading to conservative estimations of the signature accuracy.

The signature addresses several challenges of current microbiological tests. (i) The difficulty of diagnosing inaccessible or unknown infection sites. The signature accurately diagnosed such cases, including lower respiratory tract infections (AUC 0.95±0.03, n=153) and fever without source (AUC=0.97±0.03, n=123). (ii) Prolonged time to results (hours to days). The signature measures soluble proteins, which are readily amenable to rapid measurement (within minutes) on hospital-deployed automated immunoassay machines and point-of-care devices. (iii) Mixed infections may lead to diagnostic uncertainty, because detection of a virus does not preclude bacterial co-infection.[14,15] The signature addresses this by classifying mixed infections together with pure bacterial infections, thus prompting physicians to manage both groups similarly with regard to antibiotics treatment. The fact that mixed co-infections elicited a proteome host-response that is similar to pure bacterial, rather than a mixture of responses, may indicate pathway dominance of bacterial over viral. (iv) A significant drawback of microbiological tests, PCRs in particular, is detection of potential colonizers in subjects with non-bacterial diseases.[12,13] The signature performance was unaffected by the presence or absence of potential colonizers.

Host-proteins, such as PCT, CRP and IL-6, are routinely used to assist in the diagnosis of bacterial infections because they convey additional information over clinical symptoms, blood counts and microbiology.[11] However, inter-patient and pathogen variability limit their usefullness.[21-27] Combinations of host-proteins have the potential to overcome this, but have thus far yielded insignificant-to-moderate diagnostic improvement over individual proteins.[11,35-37] This modest improvement may be due to the reliance on combinations of bacterial-induced proteins that are sensitive to the same factors, and are therefore less capable of compensating for one another. Accordingly, a larger improvement was observed in combinations that included host-proteins, clinical parameters and other tests.[11,35-37] Obtaining these multiple parameters in real-time, however, is often not feasible.

To address this, a combination of proteins with complementary behaviors was identified. Specifically, it was found that TRAIL was induced in response to viruses and suppressed by bacteria, IP-10 was higher in viral than bacterial infections, and CRP was higher in bacterial than viral infections. While the utility of elevated CRP to suggest bacterial infections is well established[31,45], the inclusion of novel viral-induced proteins, to complement routinely used bacterial-induced proteins, substantially contributed to the signature's robustness across a wide range of subgroups, including time from symptom onset, pathogen species and comorbidities among others. For example, adenoviruses, an important subgroup of viruses that cause 5%-15% of acute infections in children are particularly challenging to diagnose because they induce clinical symptoms that mimic a bacterial infection.[46] Routine laboratory parameters perform poorly on this subgroup compared to the signature (AUCs=0.60±0.10 [WBC], 0.58±0.10 [ANC], 0.88±0.05 [signature]; n=223).

Despite advances in infectious disease diagnosis, timely identification of bacterial infections remains challenging, leading to antibiotic misuse with its profound health and economic consequences. To address the need for better treatment guidance, the present inventors have developed and validated a signature that combines novel and traditional host-proteins for differentiating between bacterial and viral infections. The present finding in a large sample size of patients is promising, suggesting that this host-signature has the potential to help clinicians manage patients with acute infectious disease and reduce antibiotic misuse.

Example 2

A Host-Proteome Signature for Distinguishing Between Bacterial and Viral Infections: a Prospective Multi-Center Observational Study—Supplementary Material Measures of accuracy: The signature integrates the levels of three protein biomarkers measured in a subject, and computes a numerical score that reflects the probability of a bacterial vs. viral infection. To quantify the diagnostic accuracy of the signature a cutoff on the score was used and the following measures were applied: Sensitivity, specificity, positive predictive value (PPV), negative predictive value (NPV), total accuracy, positive likelihood ratio (LR+), negative likelihood ratio (LR−), and diagnostic odds ratio (DOR). These measures are defined as follows:

$$\text{Sensitivity} = \frac{TP}{TP+FN}$$

$$\text{Specificity} = \frac{TN}{TN+FP}$$

$$\text{total accuracy} = \frac{TP+TN}{TP+FN+TN+FP}$$

$$PPV = \frac{TP}{TP+FP} = \frac{\text{sensitivty} \cdot \text{prevalence}}{\text{sensitivity} \cdot \text{prevalence} + (1-\text{specificity}) \cdot (1-\text{prevalence})}$$

$$NPV = \frac{TN}{TN+FN} = \frac{\text{specificity} \cdot (1-\text{prevalence})}{\text{specificity} \cdot (1-\text{prevalence}) + (1-\text{sensitivty}) \cdot (\text{prevalence})}$$

$$LR+ = \frac{\text{Sensitivity}}{1-\text{Specificity}}$$

$$LR- = \frac{1-\text{Sensitivity}}{\text{Specificity}}$$

$$DOR = \frac{LR+}{LR-}$$

P, N, TP, FP, TN, FN are positives, negatives, true-positives, false-positives, true-negatives, and false-negatives, respectively. Prevalence is the relative frequency of the positive class (i.e., prevalence=P/(P+N)). Unless mentioned otherwise, positives and negatives refer to patients with bacterial and viral infections, respectively.

The area under the receiver operating curve (AUC) was also used to perform cutoff independent comparisons of different diagnostic methods. For details on formulation and confidence interval (CI) computation of the AUC see Hanley and McNeil.[1] 95% CIs of the accuracy measures throughout this document are reported.

Sample size: The primary study objective was to obtain the performance of the signature for classifying patients with viral and bacterial etiologies. It was estimated that the sample size required to reject the null hypothesis that the sensitivity and specificity over the entire population, P, are lower than P0=75% with significance level of 1%, power of 90% for a difference of 15% (P1−P0 ≥15%), which yielded 394 patients (197 viral and 197 bacterial). Additionally it was anticipated that roughly 15% of the patients will have an indeterminate source of infection, 10% would be excluded for technical reasons and 10% will be healthy or non-infectious controls. Taken together, the study required the recruitment of at least 607 patients. This requirement was fulfilled because 1002 patients were recruited.

Constructing a computation model logistic model: To integrate the protein levels into a single predictive score, multiple computational models were examined including Artificial Neural Networks (ANN), Support Vector Machines (SVM), Bayesian Networks (BN), K-Nearest Neighbor (KNN) and Multinomial Logistic Regression (MLR).[2,3] The AUCs for distinguishing between bacterial and viral infections obtained on the Majority cohort using a leave-10%-out cross validation were 0.93±0.02 (ANN), 0.93±0.02 (SVM [linear]), 0.94±0.02 [SVM (radial basis function)], 0.92±0.02 (BN), 0.91±0.02 (KNN) and 0.94±0.02 (MLR). Significant difference in the performances of ANN, SVM and MLR models (P>0.1 when comparing their AUCs) were not observed. The present inventors chose to use MLR because it provides a probabilistic interpretation by assigning a likelihood score to a patient's diagnosis.

The present inventors trained and tested the MLR signature for distinguishing between bacterial and non-bacterial etiologies. Since the prevalence of underlying etiologies varies across different clinical settings, the model priors were adjusted to reflect equal baseline prevalence (50% bacterial and 50% non-bacterial). Within the non-bacterial group the priors were adjusted to 45% viral and 5% non-infectious, to reflect the anticipated higher prevalence of viral versus non-infectious patients among subjects with suspicious for acute infection. The MLR weights and their respective 95% confidence intervals, as well as the p-values associated with each coefficient are summarized in Tables 3-4 herein below. In the bacterial versus viral infection analysis the probabilities were adjusted to sum up to 1 ($P_{b\_adjusted}=[P_b+P_v]$ and $P_{b\_adjusted}=[P_b+P_v]$, where $P_b$ and $P_v$ correspond to the probability of bacterial and viral infections respectively).

TABLE 3

MLR coefficients and their respective standard error

| Second Coordinate $\delta_1$ (bacterial) | First Coordinate $\delta_0$ (viral) | |
|---|---|---|
| $b_0 = -0.378 \pm 0.732$ | $a_0 = -1.299 \pm 0.651$ | Constant |
| $b_1 = -0.020 \pm 0.0084$ | $a_1 = 0.0088 \pm 0.0064$ | TRAIL |
| $b_2 = 0.0875 \pm 0.015$ | $a_2 = 0.0605 \pm 0.0145$ | CRP |
| $b_3 = 0.0050 \pm 0.0014$ | $a_3 = 0.0053 \pm 0.0014$ | IP-10 |

TABLE 4

The p-values associated with each MLR coefficient.

| Class (bacterial) | Class (viral) | |
|---|---|---|
| <0.001 | <0.001 | Constant |
| <0.001 | 0.008 | TRAIL |
| <0.001 | <0.001 | CRP |
| <0.001 | <0.001 | IP-10 |

Figure 5:
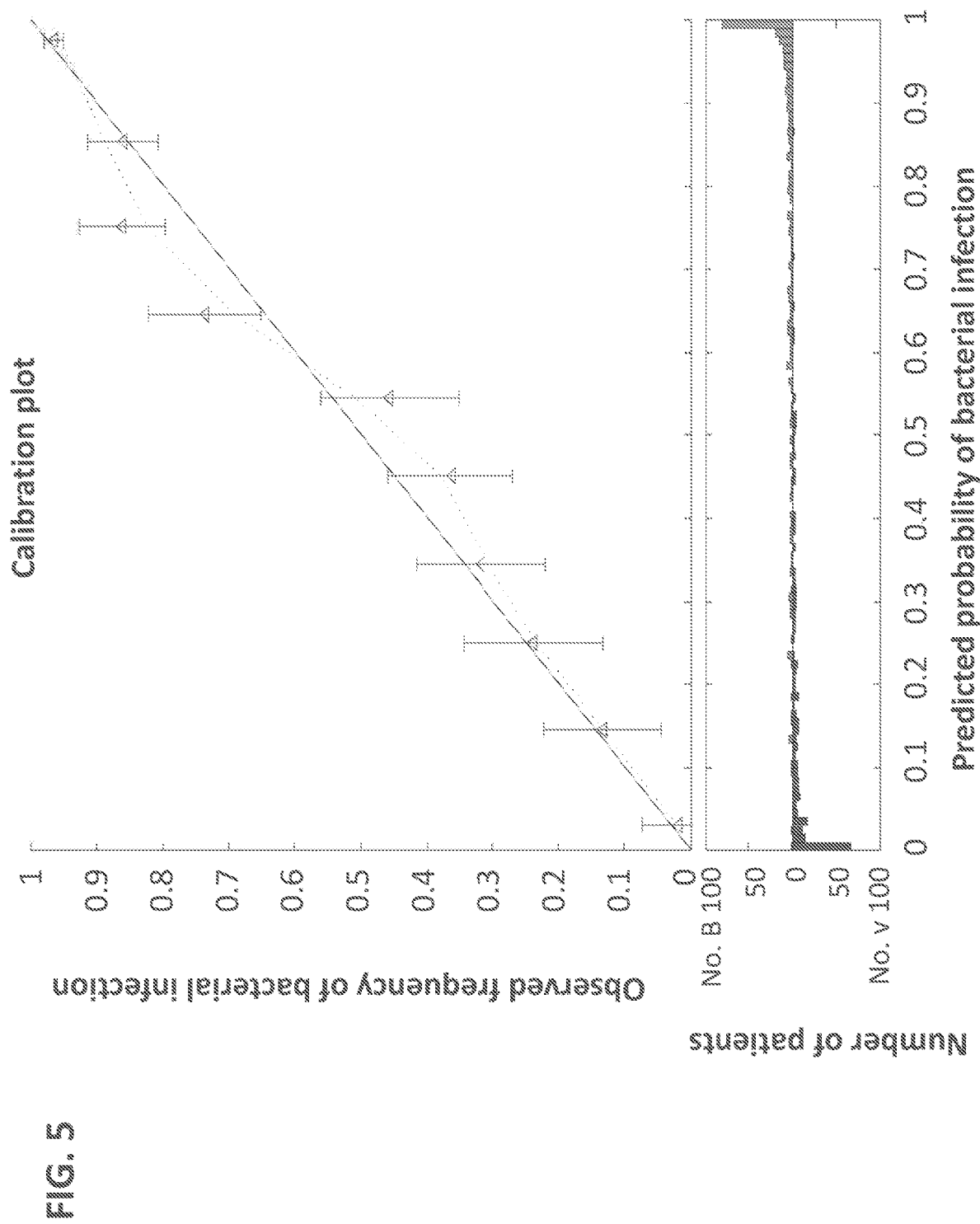
FIG. 5. Calibration plot of the MLR model. In the top panel patients were grouped into 10 bins based on their predicted probabilities of a bacterial infection (x-axis), and compared to the observed fraction of bacterial infections within each bin (y-axis). Dashed line is a moving average (of size 5 bins). The bottom panel shows the distribution of predicted probabilities for bacterial (upper bars) and viral (lower bars).

Logistic calibration curves: In order to assess the validity of the MLR model, the calculated prediction probabilities were compared with the actually observed outcomes (FIG. 5). The predicted probabilities are highly compatible with the observed ones, further demonstrating the model validity.

Summary of the patient cohorts used in this study: A total of 1002 patients were recruited and 892 were enrolled (110 were excluded based on pre-determined exclusion criteria). Based on the reference standard process described in the 'Methods' section of Example 1, patients were assigned to four different diagnosis groups: (i) bacterial; (ii) viral; (iii) no apparent infectious disease or healthy (controls); and (iv) indeterminate. Patients with mixed infections (bacteria plus virus) were labeled as bacterial because they are managed similarly (e.g. treated with antibiotics) (FIG. 1A). In total, 89% of all enrolled patients were assigned a diagnosis, a rate which approaches the literature-documented limit.[4-6] The following sections provide a detailed description of patient characteristics, which includes all the patients with a final diagnosis (n=794): 765 patients of the Majority cohort and 29 patients for which the serum samples were depleted during the screening phase (FIGS. 1A-1B).

Age and gender distribution: Patients of all ages were recruited to the study. The patients with agreed diagnosis (diagnosed patients; n=794) included more pediatric (≤18 years) than adult (>18 years) patients (445 patients [56%] vs. 349 [44%]). The age distribution was relatively uniform for patients aged 20-80 years and peaked at <4 years of age for pediatric patients (FIGS. 6A-6B). The observed age distribution for pediatric patients is consistent with that expected and represents the background distribution in the inpatient setting[7] (e.g., the emergency department [ED], pediatrics departments, and internal departments). Patients of both genders were recruited to the study. The patient population was balanced in respect to gender distribution (47% females, 53% males).

Detected pathogens: A wide panel of microbiological tools were used in order to maximize pathogen detection rate. At least one pathogen was detected in 65% of patients with an acute infectious disease (56% of all 794 diagnosed patients). A total of 36 different pathogens were actively detected using multiplex PCR, antigen detection, and serological investigation. Additional 20 pathogens were detected using standard culture techniques or in-house PCR. Altogether, 56 different pathogens from all major pathogenic subgroups were detected (FIG. 7A). This rate of pathogen identification is similar to that reported in previously published studies and included pathogens from all major pathogenic subgroups (Gram-negative bacteria, Gram-positive bacteria, atypical bacteria, RNA viruses, and DNA viruses). In 13% of the patients, pathogens from more than one of the aforementioned pathogenic subgroups were detected (FIG. 7A).

The pathogenic strains found in this study are responsible for the vast majority of acute infectious diseases in the Western world and included key pathogens such as influenza A/B, respiratory syncytial virus (RSV), parainfluenza, *E. Coli*, Group A *Streptococcus*, etc. Notably, analysis of the detected pathogens revealed that none of the pathogens is dominant (FIG. 7B).

Figure 8:
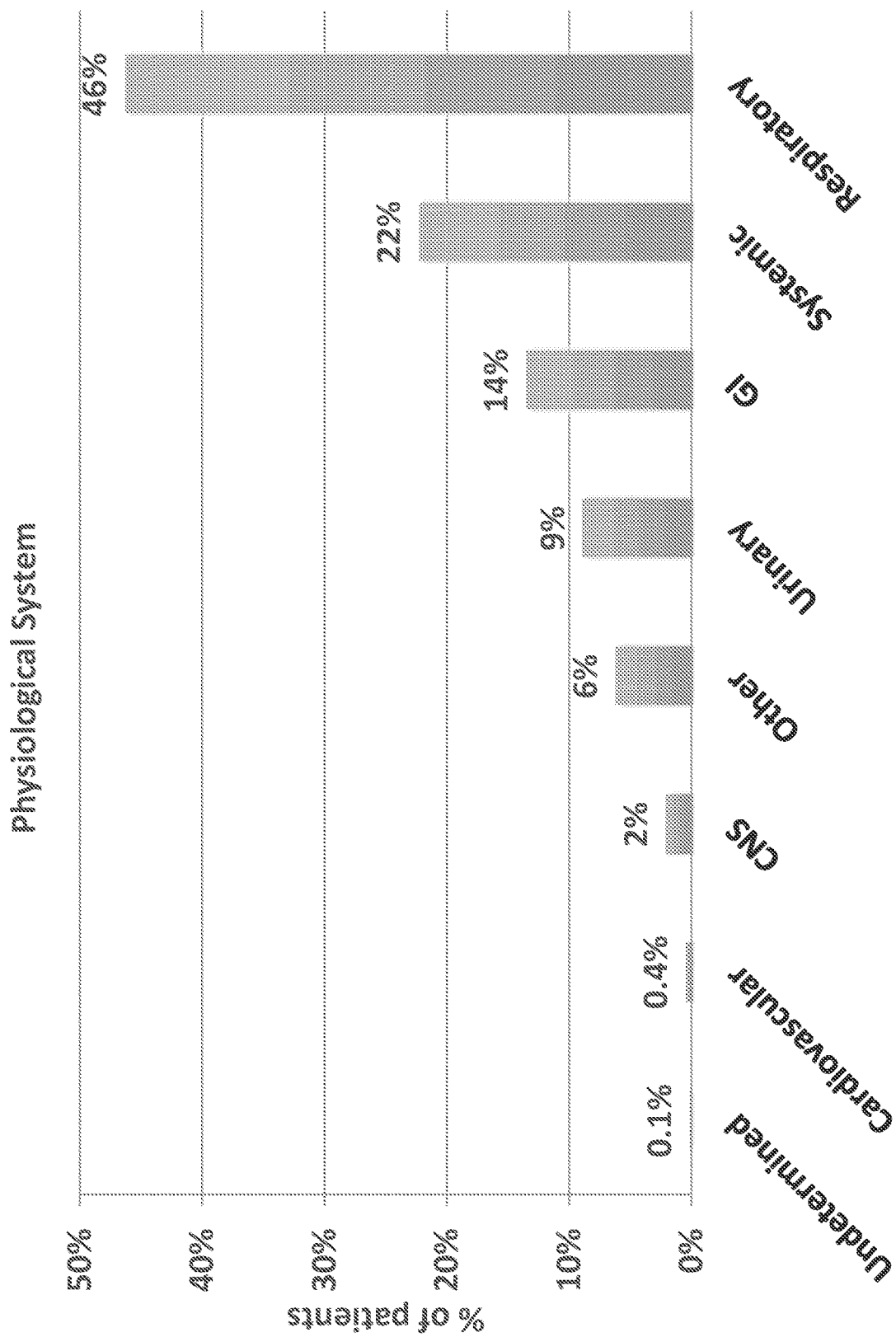
FIG. 8. Distribution of involved physiologic systems in patients diagnosed with an infectious disease (n=673).
Figure 9A:
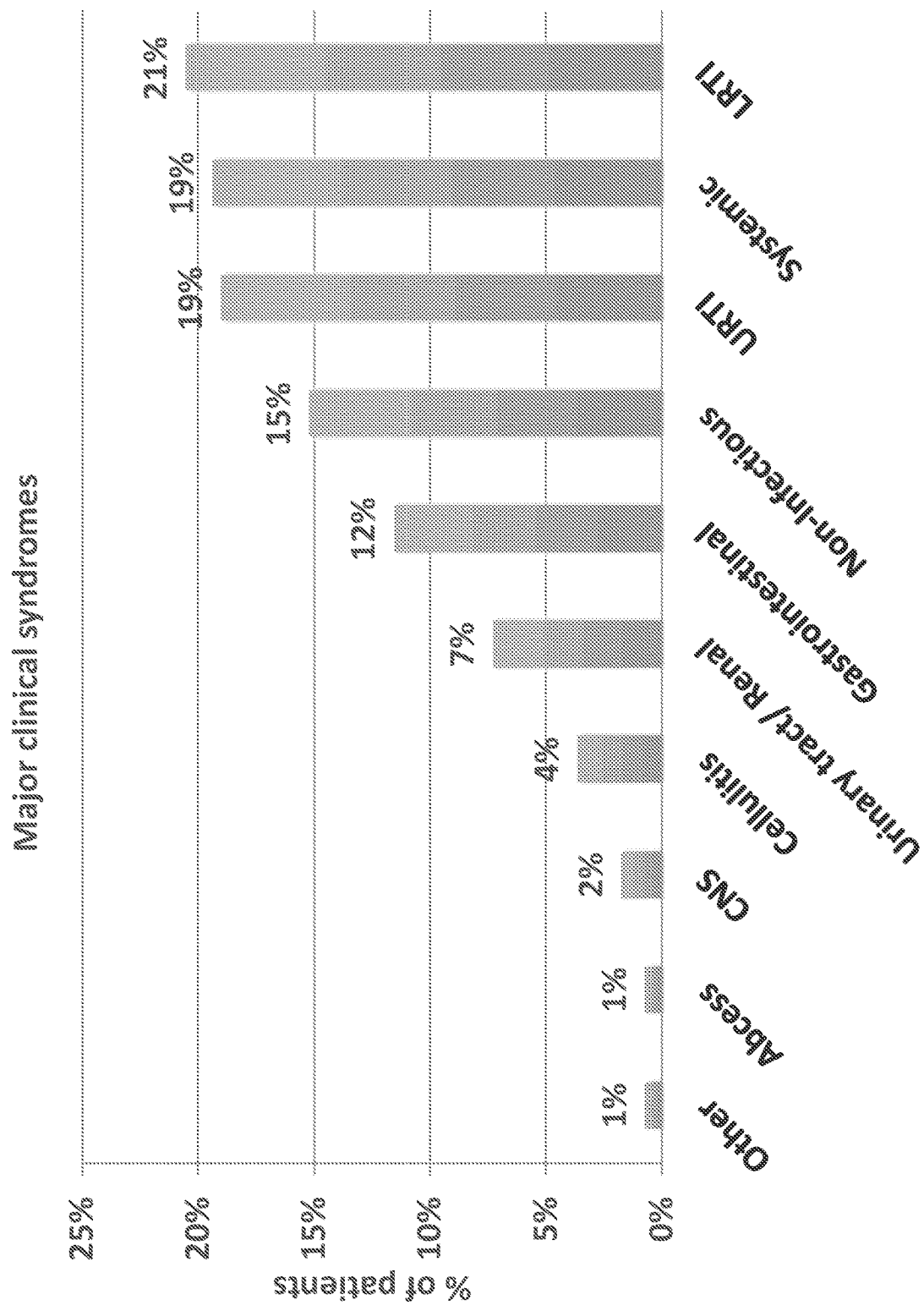
FIGS. 9A-9B. Distribution of clinical syndromes (all diagnosed patients, n=794). A. Major clinical syndromes; B. Specific clinical syndromes.
Figure 9B:
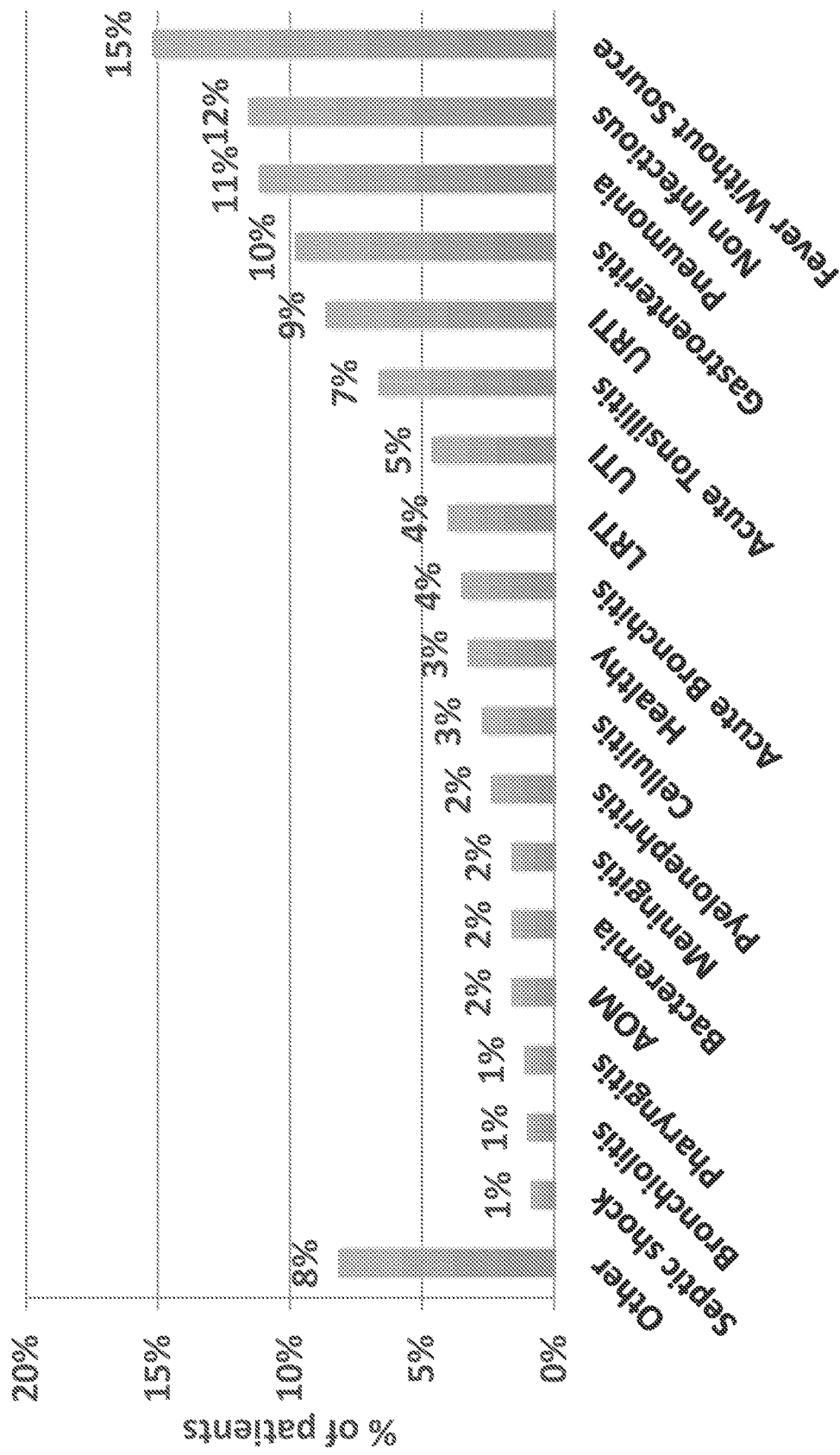

Involved physiologic systems and clinical syndromes: The infectious disease patients (all diagnosed patients [n=794], excluding those with non-infectious diseases or healthy subjects, n=673) presented with infections in a variety of physiologic systems (FIG. 8). The most frequently involved physiologic system was the respiratory system (46%), followed by systemic infections (22%). All infections that did not involve the aforementioned systems and were not gastrointestinal, urinary, cardiovascular, or central nervous system (CNS) infections were categorized as 'Other' (e.g., cellulitis, abscess). The observed distribution of physiologic system involvement represents the natural distribution and is consistent with that reported for large cohorts of patients sampled year-round.

The diagnosed patients in the present study (n=794) presented with a variety of clinical syndromes (FIGS. 9A-9B) that reflects the expected clinical heterogeneity in a cohort of pediatric and adult patients collected year-round. The most frequent clinical syndrome was LRTI (21%) including mainly pneumonia, bronchitis, bronchiolitis, chronic obstructive pulmonary disease (COPD) exacerbation, and non-specific LRTI. The second most frequent syndrome was systemic infection (19%) including mainly fever without a source and occult bacteremia cases. Systemic infections were primarily detected in children <3 years of age but were also detected in a few adult patients. Systemic infections constitute a real clinical challenge as balancing between patient risk and the costs of testing/treatment is unclear. The third most frequent clinical syndrome was URTI (19%) including mainly acute tonsillitis, acute pharyngitis, non-specific URTI, acute sinusitis, and acute otitis media. The next most frequent syndromes were gastroenteritis (12%), UTI (7%), and cellulitis (4%). CNS infections (2%) included septic and aseptic meningitis. Additional clinical syndromes (1%) were classified as 'Other' and included less common infections (e.g., otitis externa, epididymitis, etc.). The observed pattern of clinical syndrome distribution represents most of the frequent and clinically relevant syndromes and is consistent with previously published large studies.

Figure 10:
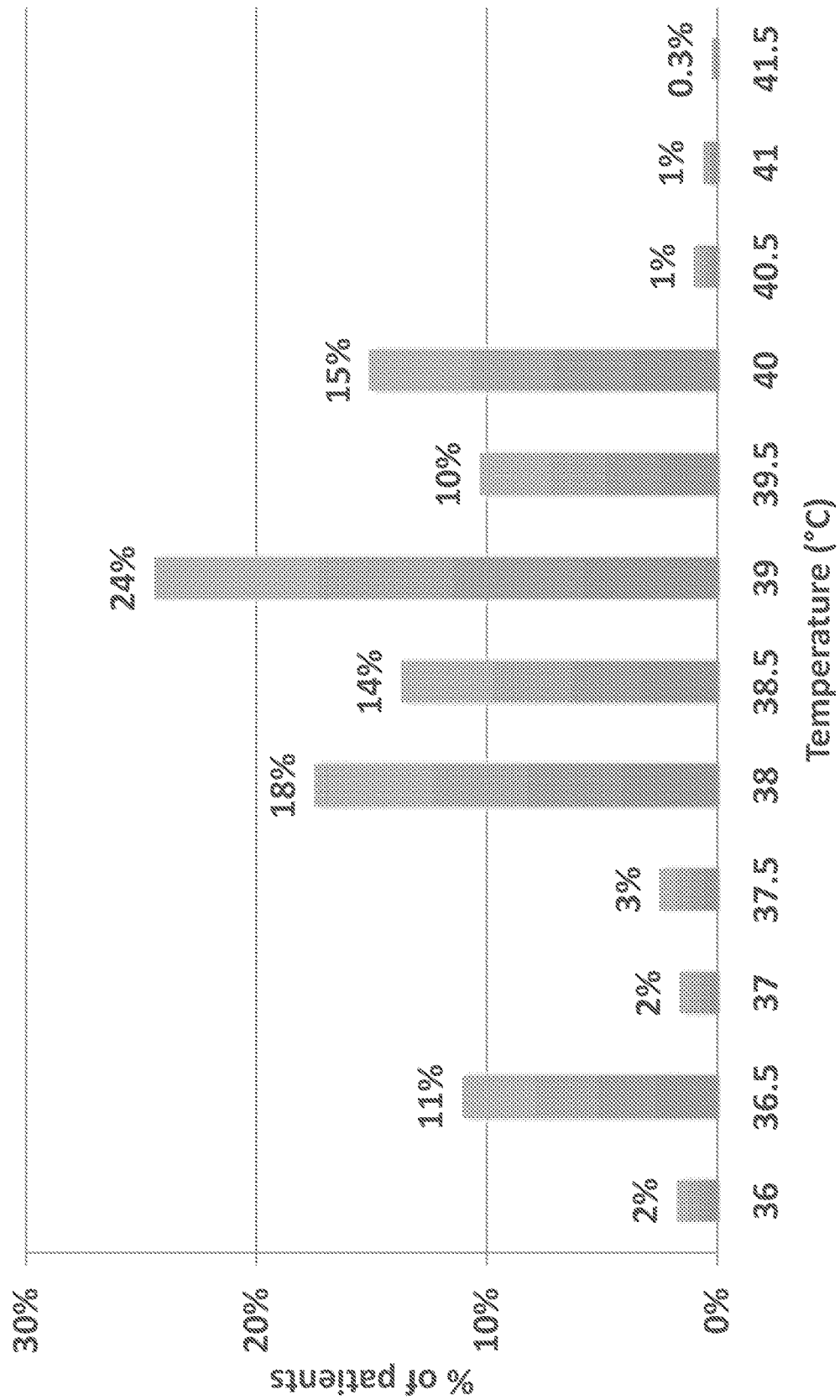
FIG. 10. Distribution of maximal body temperatures (n=794).

Core body temperature: Core body temperature is an important parameter in evaluating infectious disease severity. The distribution of maximal body temperatures was examined in all of the diagnosed patients (n=794) using the highest measured body temperature (per-os or per-rectum). The distribution of the maximal body temperatures was relatively uniform between 38° C. and 40° C. with a peak of at 39° C. (FIG. 10). Body temperature <37.5° C. was reported for 15% of patients (the subgroup of patients with non-infectious diseases or healthy subjects). Body temperature ≥40.5° C. was rare (<3% of patients). Altogether, the observed distribution represents the normal range of temperatures in the clinical setting.

Figure 11:
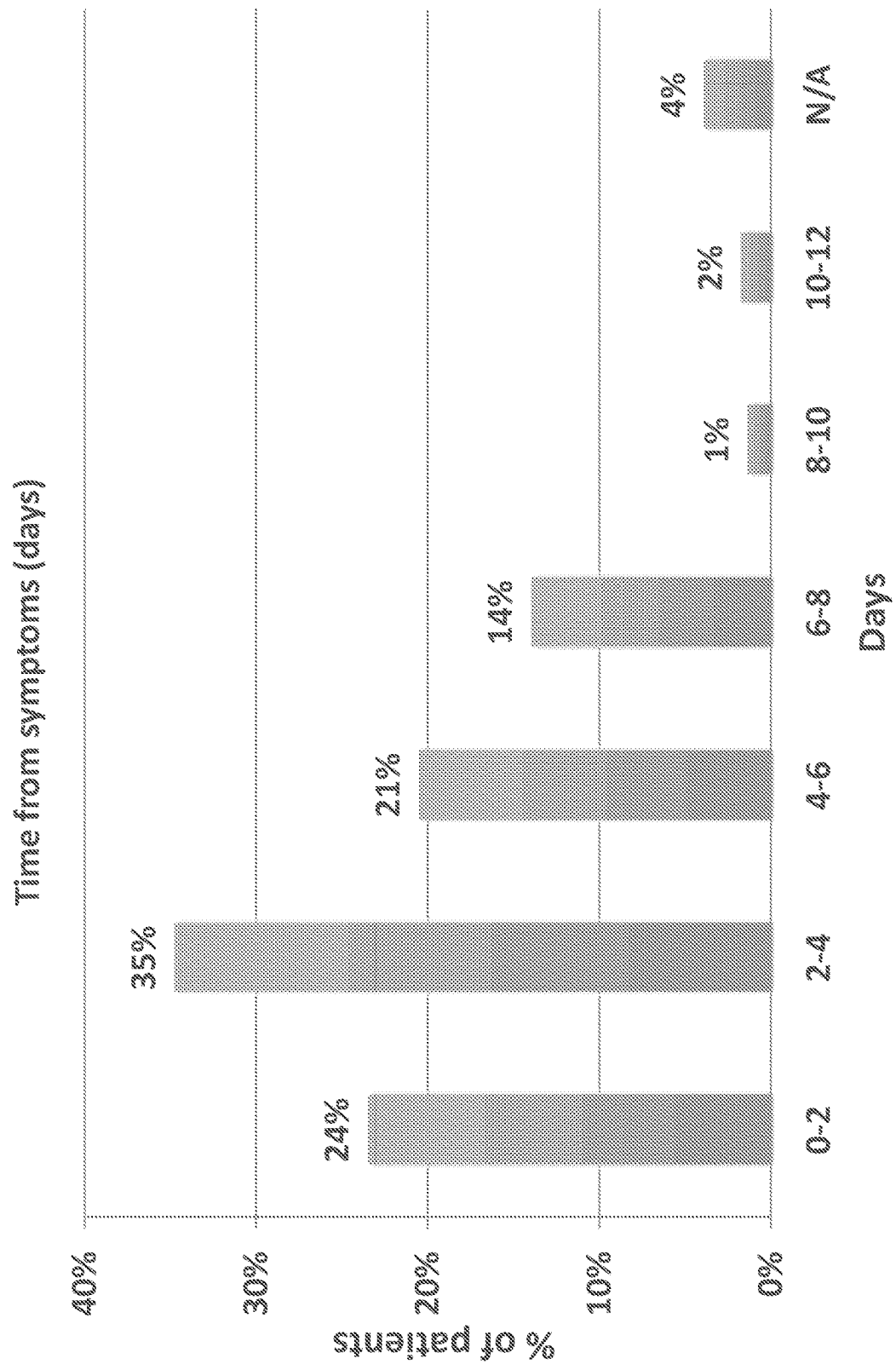
FIG. 11. Distribution of time from initiation of symptoms (n=794). N/A—healthy controls or patients for which data was not obtained.

Time from symptoms onset: 'Time from symptoms' was defined as the duration (days) from the appearance of the first presenting symptom (the first presenting symptom could be fever but could also be another symptom such as nausea or headache preceding the fever). The distribution of 'time from symptoms' in our cohort (all diagnosed patients, n=794) peaked at 2-4 days after the initiation of symptoms (35% of patients) with substantial proportions of patients turning to medical assistance either sooner or later (FIG. 11).

Figure 12A:
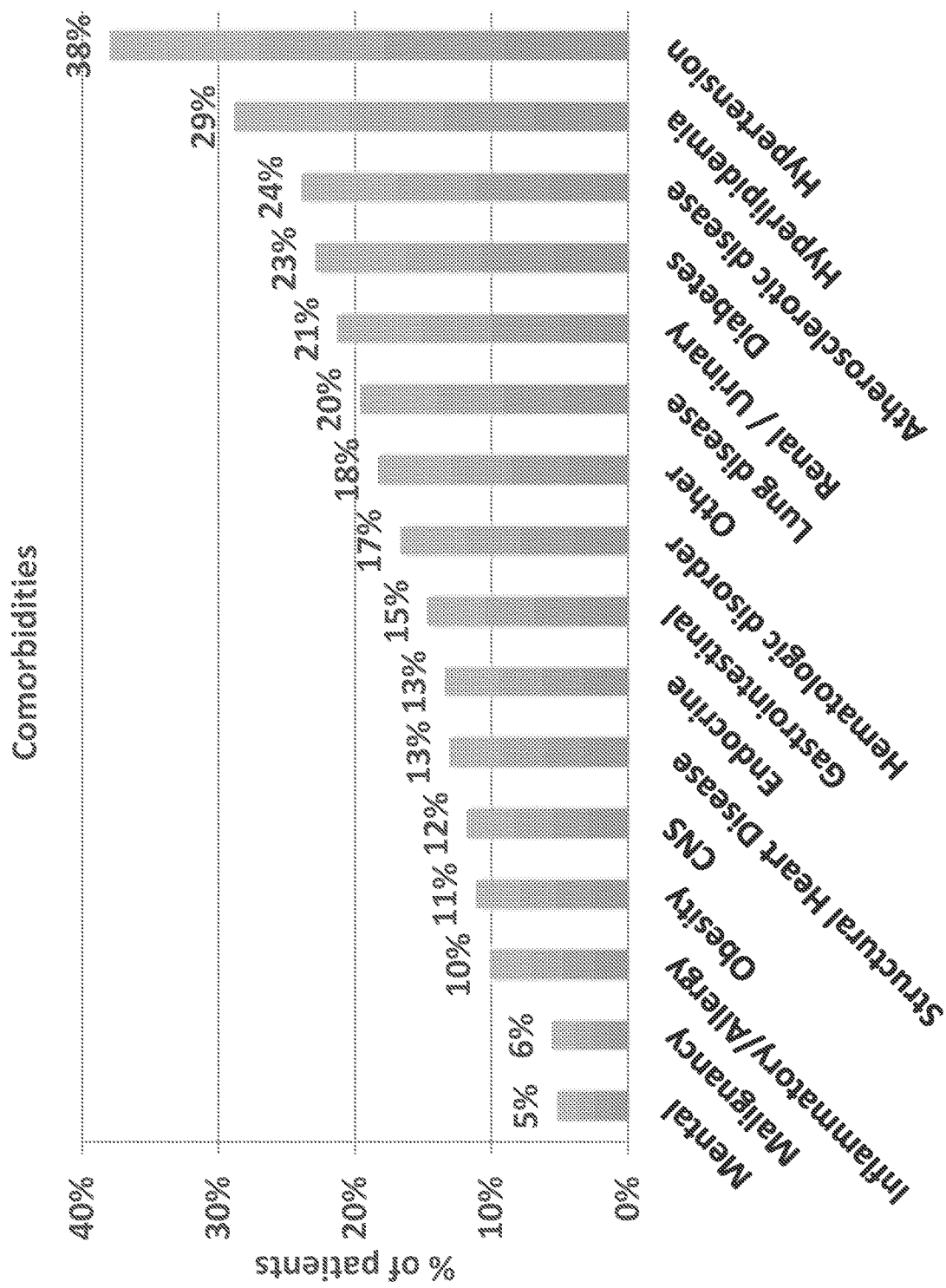
FIGS. 12A-12B. Comorbidities-related characterization of the patient population. A. Distribution of comorbidities (all chronically ill patients, n=305); B. Distribution of chronic medications (all chronically ill patients, n=305). Of note, some of the patients presented with several chronic diseases, and treated with several chronic medications.
Figure 12B:
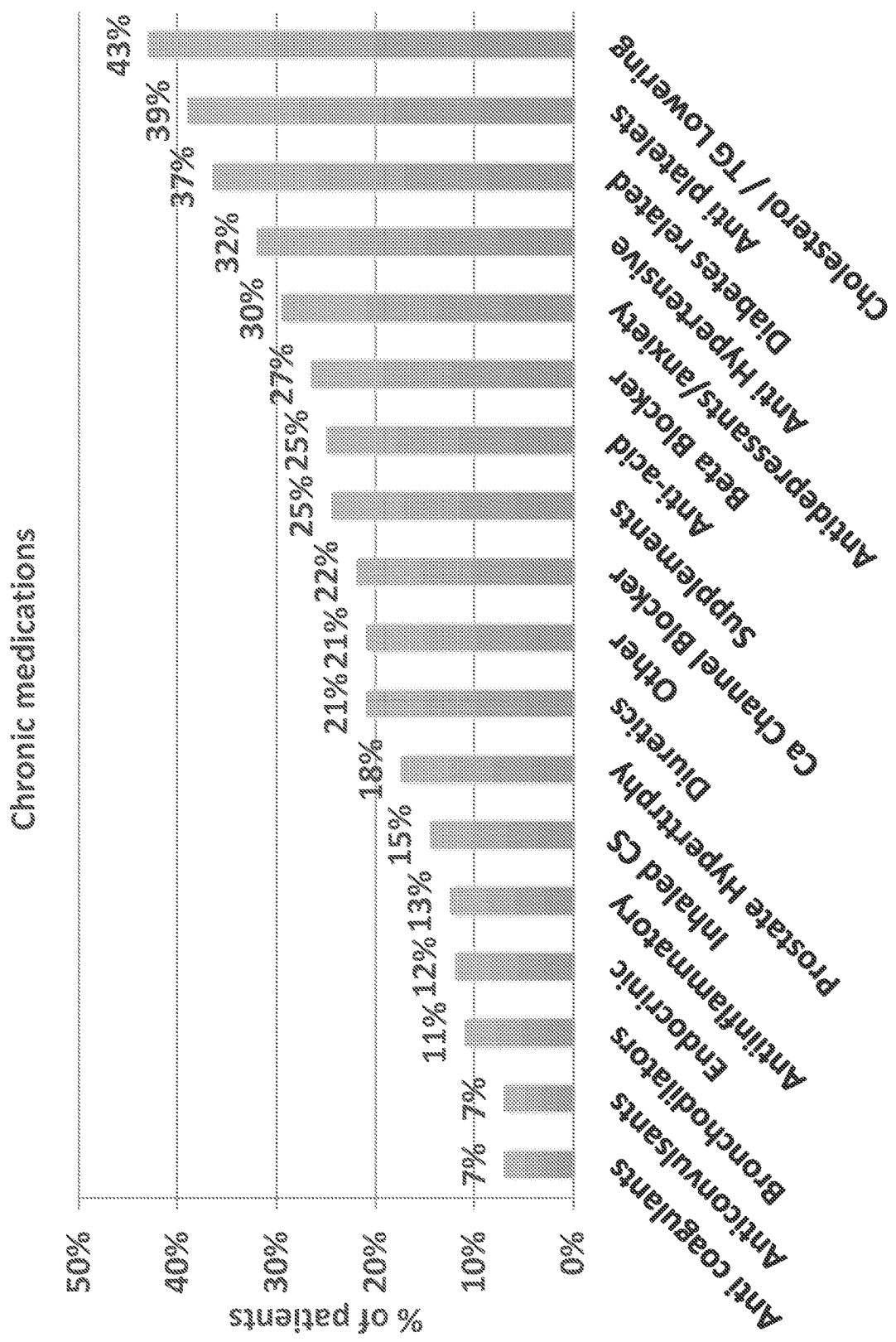

Comorbidities and chronic drug regimens: Comorbidities and chronic drug regimens may, theoretically, affect a diagnostic test. Out of the diagnosed patients 62% had no comorbidities whereas 38% had ≥1 chronic disease. In addition, 75% of patients were not treated with chronic medications and 25% were treated with ≥1 chronic medication. The most frequent chronic diseases in our patient population were hypertension, hyperlipidemia, lung diseases (e.g., COPD, asthma, etc.), diabetes mellitus (mostly type 2), and ischemic heart disease, mirroring the most common chronic diseases in the Western world (FIG. 12A). The distribution of chronic drugs used by our patient population strongly correlated with the range of reported chronic diseases (e.g., 29% of the patients with comorbidities had hyperlipidemia and lipid lowering agents were the most frequently used drugs). Other frequently used drugs included aspirin, blood glucose control drugs, and beta blockers (FIG. 12B).

Figure 13:
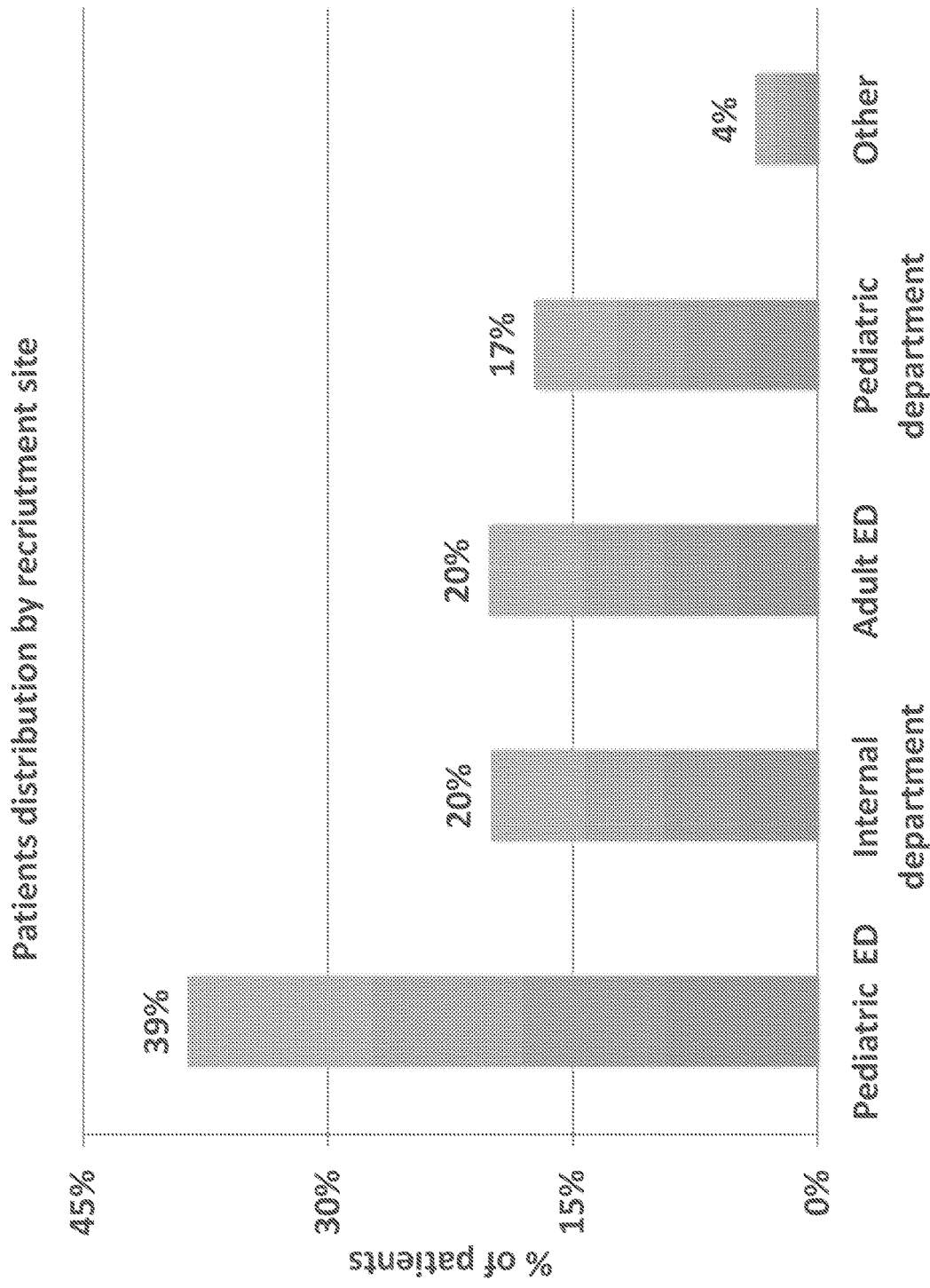
FIG. 13. Distribution of recruitment sites (diagnosed patients, n=794).

Patient recruitment sites: Pediatric patients (≤18 years) were recruited from pediatric emergency departments (PED), pediatric wards and surgical departments, and adults (>18 years) from emergency departments (ED), internal medicine departments and surgical departments. The pediatric ED was the most common recruitment site (39%) and the other sites were comparable (17-20%) reflecting a relatively balanced recruitment process. The ratio between ED patients and hospitalized patients was ~1:1 for adults and ~2:1 for children (FIG. 13).

Characteristics of excluded patients: Of the 1002 patients recruited for the study, 110 patients (11%) were excluded (some patients fulfilled more than one exclusion criterion). The most frequent reason for exclusion was having a fever below the study threshold of 37.5° C. (n=54), followed by time from symptom initiation of >12 days (n=26) and having a recent (in the preceding 14 days) infectious disease (n=22). Other reasons for exclusion included having an active malignancy (n=14), and being immunocompromised (e.g., due to treatment with an immunosuppressive drug; n=2).

Characteristics of indeterminate patients: A total of 98 patients were defined as indeterminate based on the inability of the expert panel to reliably establish a composite reference standard, despite the rigorous collection of laboratory and clinical information. While it is not possible to directly examine the signature performance in these patients in the absence of a reference standard, it is possible to analyze their host-protein response in order to assess whether they differ from patients with a reference standard. We compared the distribution of TRAIL, IP-10 and CRP in acute infection patients with a reference standard (n=653) to those without a reference standard (n=98). No statistically significant difference was observed (Kolmogorov Smirnov test P=0.20, 0.25, 0.46 for TRAIL, IP-10 and CRP, respectively). The similarity in the host-protein response between patients with and without a reference standard implies that the present approach may be useful for diagnosing indeterminate patients in the clinical setting.

The signature performance remains robust across different patient subgroups: In Example 1, the present inventors demonstrated that the signature remained robust across a wide range of patient characteristics including age, clinical syndrome, time from symptom onset, maximal temperature, pathogen species, comorbidities, and the clinical site with AUCs ranging from 0.87 to 1.0 (FIG. 4). In this Example, a review of the performance of the signature across additional patient subgroups is provided.

Stratification by chronic drug regimens: In real-world clinical practice, patients are often under various chronic drug regimens, which could, potentially, affect the level of proteins comprising the signature. The present inventors therefore examined whether the most used drugs (by categories) in our cohort impact the signature's performance. None of the evaluated drug groups were associated with significant alterations in the signature's accuracy (Table 5).

TABLE 5

Evaluation of the signature's sensitivity to various types of chronic drug regimens.

| Viral patients, n | Bacterial patients, n | Total patients, n | AUC [95% CI] | | Drug category |
|---|---|---|---|---|---|
| 7 | 43 | 50 | [0.90, 1.00] | 0.95 | Anti Hypertensive |
| 6 | 48 | 54 | [0.96, 1.00] | 0.99 | Anti platelets |
| 7 | 35 | 42 | [0.80, 1.00] | 0.90 | Anti-acid |
| 4 | 25 | 29 | [0.93, 1.00] | 0.98 | Antidepressants |
| 5 | 35 | 40 | [0.88, 1.00] | 0.95 | Beta Blocker |
| 5 | 34 | 39 | [0.86, 1.00] | 0.94 | Ca Channel Blocker |
| 11 | 53 | 64 | [0.89, 1.00] | 0.94 | Cholesterol/TG Lowering |
| 5 | 35 | 40 | [0.74, 1.00] | 0.87 | Diabetic |
| 5 | 25 | 30 | [0.83, 1.00] | 0.93 | Diuretics |
| 4 | 14 | 18 | [0.93, 1.00] | 0.98 | Hormonal |
| 8 | 18 | 26 | [0.87, 0.99] | 0.95 | Inhaled CS |
| 4 | 21 | 25 | [0.84, 1.00] | 0.94 | Prostate Hypertrophy |

Sepsis based stratification: Sepsis is a potentially fatal medical condition characterized by a whole-body inflammatory state (called systemic inflammatory response syndrome [SIRS]) and the presence of a known or suspected infection. Patients with a bacterial sepsis benefit from early antibiotic therapy; delayed or misdiagnosis can have serious or even fatal consequences. The present inventors focused on adult patients for whom the definition of SIRS is clear and examined the ability of the signature to distinguish between adult patients with bacterial sepsis and those with viral infections as well as between adult patients with bacterial sepsis and those with viral sepsis.

Adult patients with bacterial sepsis were defined according to the American College of Chest Physicians and the Society of Critical Care Medicine. SIRS was defined by the presence of at least two of the following findings: (i) body temperature <36° C. or >38° C., (ii) heart rate >90 beats per minute, (iii) respiratory rate >20 breaths per minute or, on blood gas, a $PaCO_2$<32 mm Hg (4.3 kPa), and (iv) WBC <4,000 cells/$mm^3$ or >12,000 cells/$mm^3$ or >10% band forms. It was found that the signature achieved very high levels of accuracy in distinguishing between adult patients with bacterial sepsis and those with viral sepsis (AUC of 0.97 and 0.93 for the Unanimous [adult bacterial sepsis, adult viral sepsis] and the Majority [adult bacterial sepsis, adult viral sepsis] cohorts, respectively). These results demonstrate the utility of the signature in differentiating adult patients with bacterial sepsis from adult patients with viral infections.

TABLE 6

Signature accuracy in diagnosing bacterial sepsis vs. viral sepsis in adult patients

| Viral patients, n | Bacterial patients, n | Total patients, n | AUC [95% CI] | | |
|---|---|---|---|---|---|
| 21 | 93 | 114 | [0.94, 1.00] | 0.97 | Unanimous |
| 35 | 112 | 147 | [0.89, 0.97] | 0.93 | Majority |

Bacterial vs. non-bacterial patients stratification: Antibiotic misuse typically stems from the use of these drugs to treat non-bacterial (viral or non-infectious) patients or due to delayed or missed diagnosis of bacterial infections.

Therefore, the present inventors further examined the signature performance for distinguishing between bacterial and non-bacterial patients. The entire Majority cohort was evaluated using leave-10%-out cross-validation, yielding an AUC of 0.94±0.02. Improved performances were shown when evaluating the Unanimous cohort (AUC of 0.96±0.02), and after filtering out patients with a marginal immune response (Table 7).

TABLE 7

Signature measures of accuracy for diagnosing bacterial vs. non-bacterial (viral and non-infectious) patients.

| A. All patients | | B. Marginal immune response filter | | Accuracy measure |
|---|---|---|---|---|
| Majority cohort | Unanimous cohort | Majority cohort | Unanimous cohort | |
| 0.95 (0.93, 0.97) | 0.96 (0.94, 0.98) | 0.94 (0.92, 0.96) | 0.96 (0.94, 0.98) | AUC |
| 0.91 (0.89, 0.93) | 0.93 (0.91, 0.95) | 0.88 (0.85, 0.91) | 0.91 (0.89, 0.93) | Total accuracy |
| 0.91 (0.88, 0.93) | 0.92 (0.88, 0.95) | 0.87 (0.83, 0.91) | 0.88 (0.85, 0.91) | Sensitivity |
| 0.92 (0.89, 0.95) | 0.94 (0.91, 0.96) | 0.90 (0.87, 0.93) | 0.93 (0.91, 0.95) | Specificity |
| 11.4 (8, 16) | 15.3 (10, 23) | 8.7 (6, 12) | 12.6 (9, 18) | LR+ |
| 0.1 (0.07, 0.14) | 0.08 (0.05, 0.13) | 0.14 (0.11, 0.19) | 0.13 (0.09, 0.18) | LR− |
| 116 (67, 200) | 180 (94, 344) | 60 (38, 94) | 97 (56, 168) | DOR |

A. Performance estimates and their 95% CIs were obtained using a leave-10%-out cross-validation on all patients in the Unanimous ($n_{Bacterial}$ = 256, $n_{Non-bacterial}$ = 383), and Majority ($n_{Bacterial}$ = 319, $n_{Non-bacterial}$ = 446) cohorts.
B. The analysis was repeated after filtering out patients with a marginal immune response (Unanimous [$n_{Bacterial}$ = 237, $n_{Non-bacterial}$ = 343, $n_{Marginal}$ = 59], and Majority [$n_{Bacterial}$ = 292, $n_{Non-bacterial}$ = 387, $n_{Marginal}$ = 86]), which resembles the way clinicians are likely to use the signature.

Figure 15A:
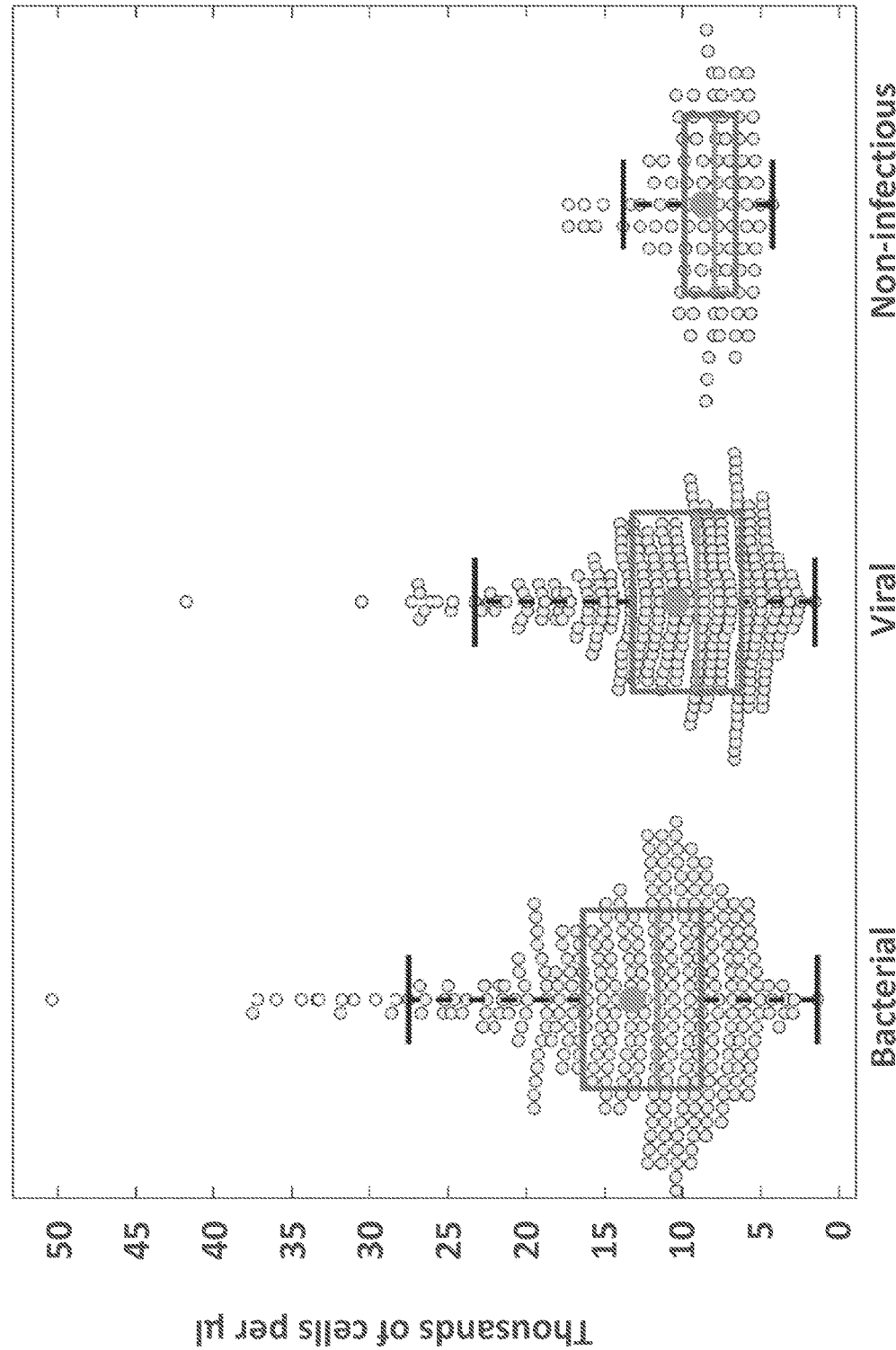
FIGS. 15A-15E. Scatter plots of clinical parameters and laboratory measurements in bacterial, viral, and non-infectious patients (as indicated) in the Majority (bacterial, viral, non-infectious) cohort (n=765). Boxed line and circle correspond to group median and average respectively. T-test p-values between bacterial and viral groups and between infectious (bacterial and viral) vs. non-infectious (including healthy subjects) are depicted.
Figure 15B:
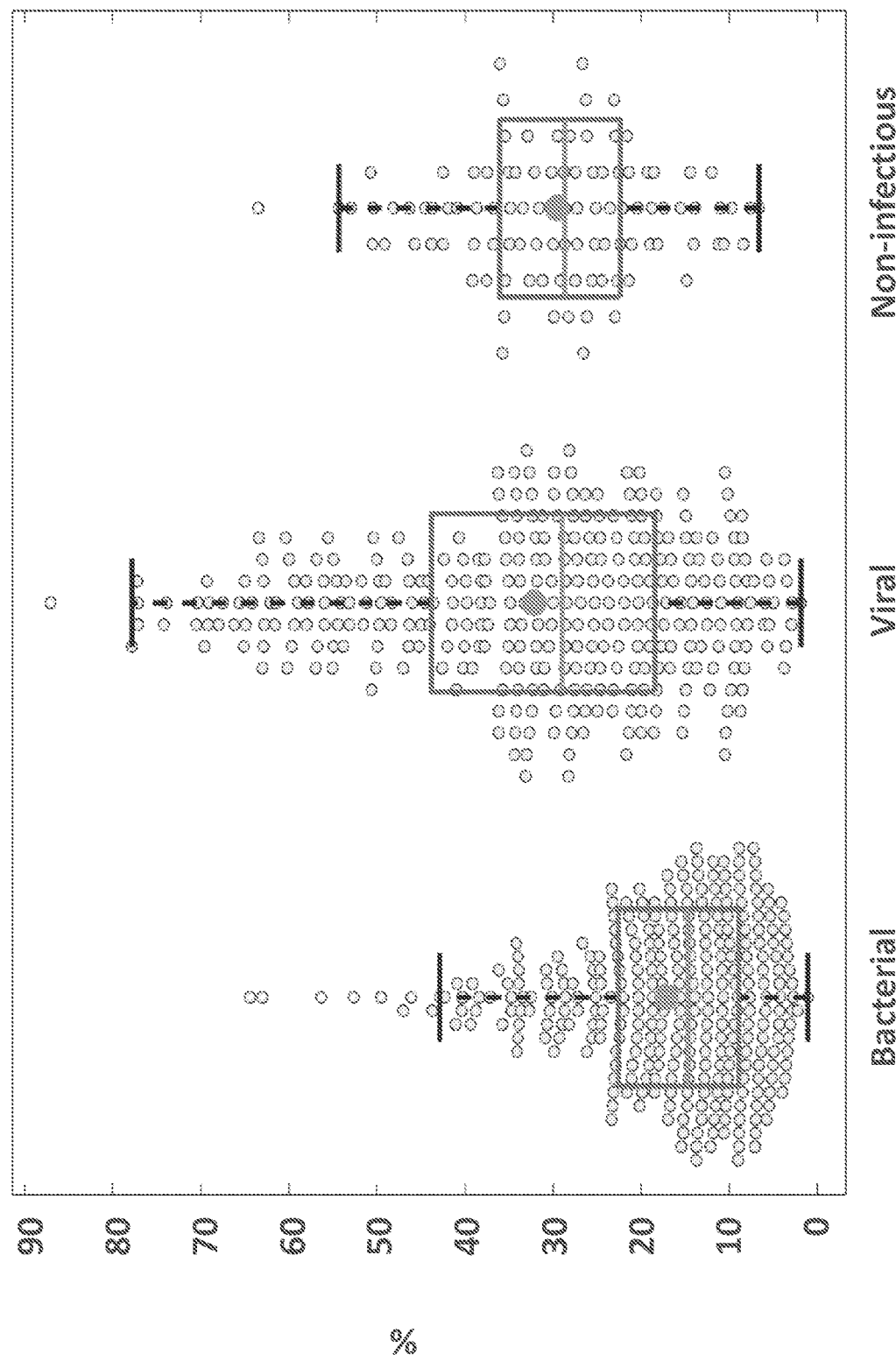
Figure 15C:
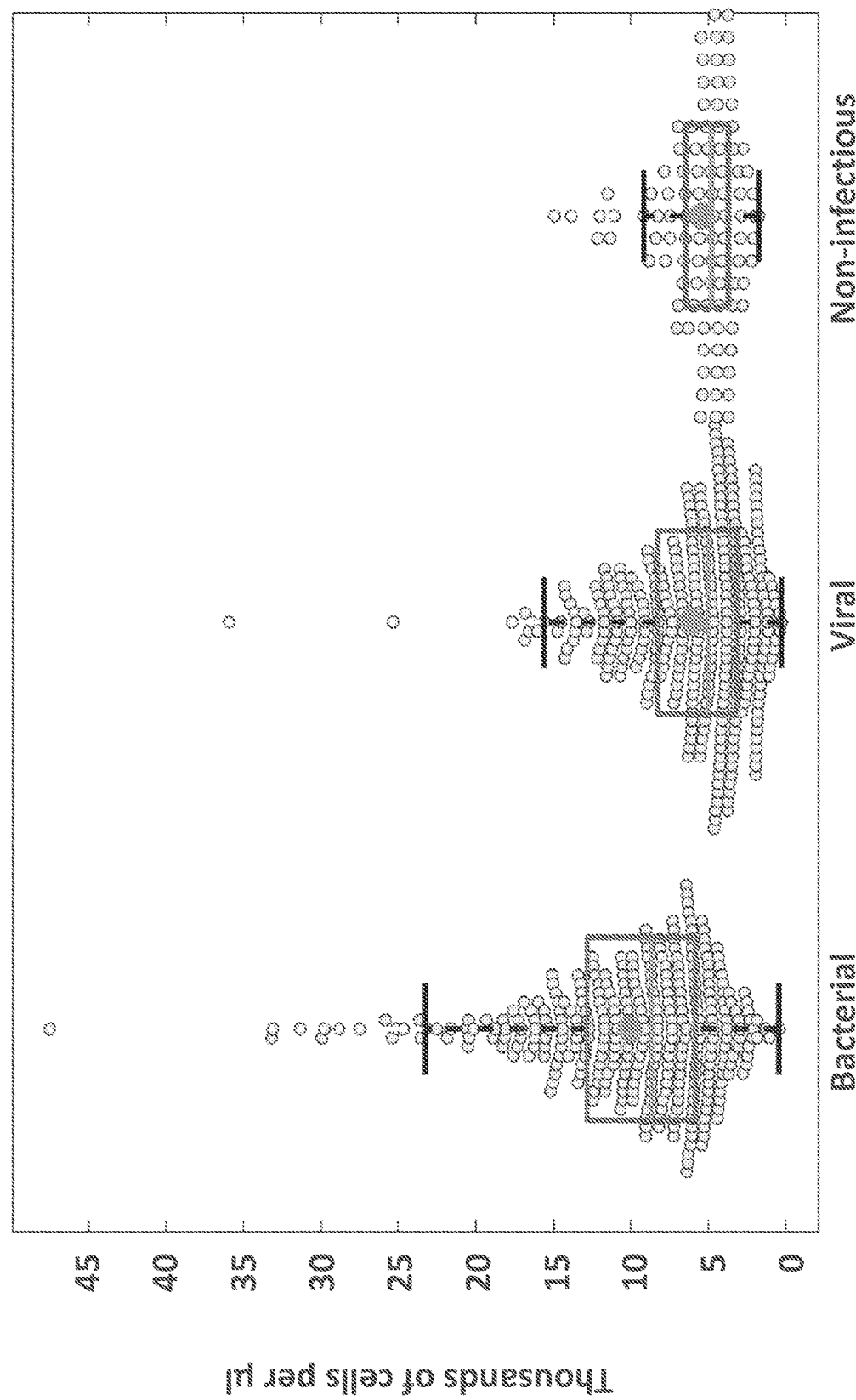
Figure 15D:
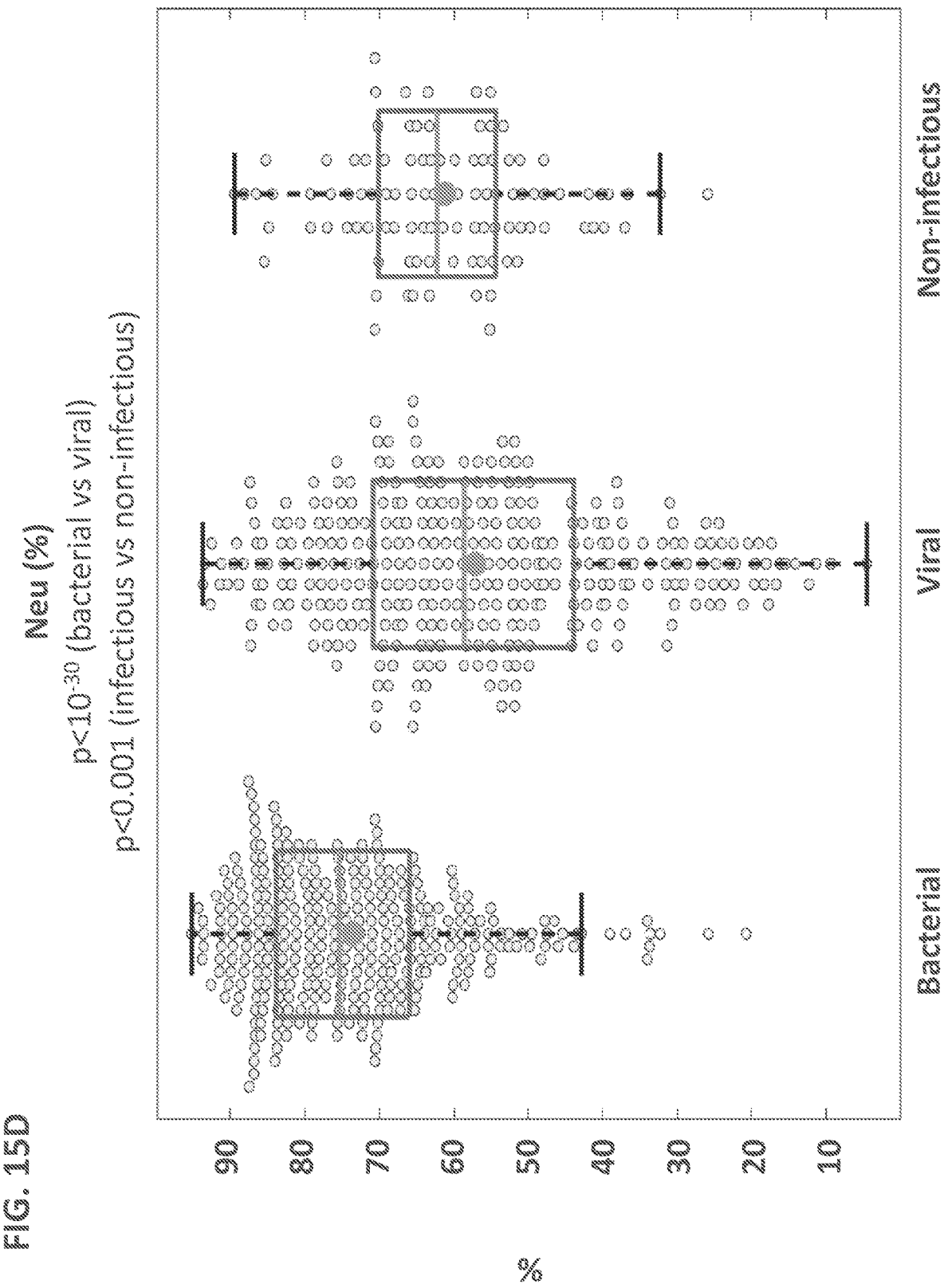
Figure 15E:
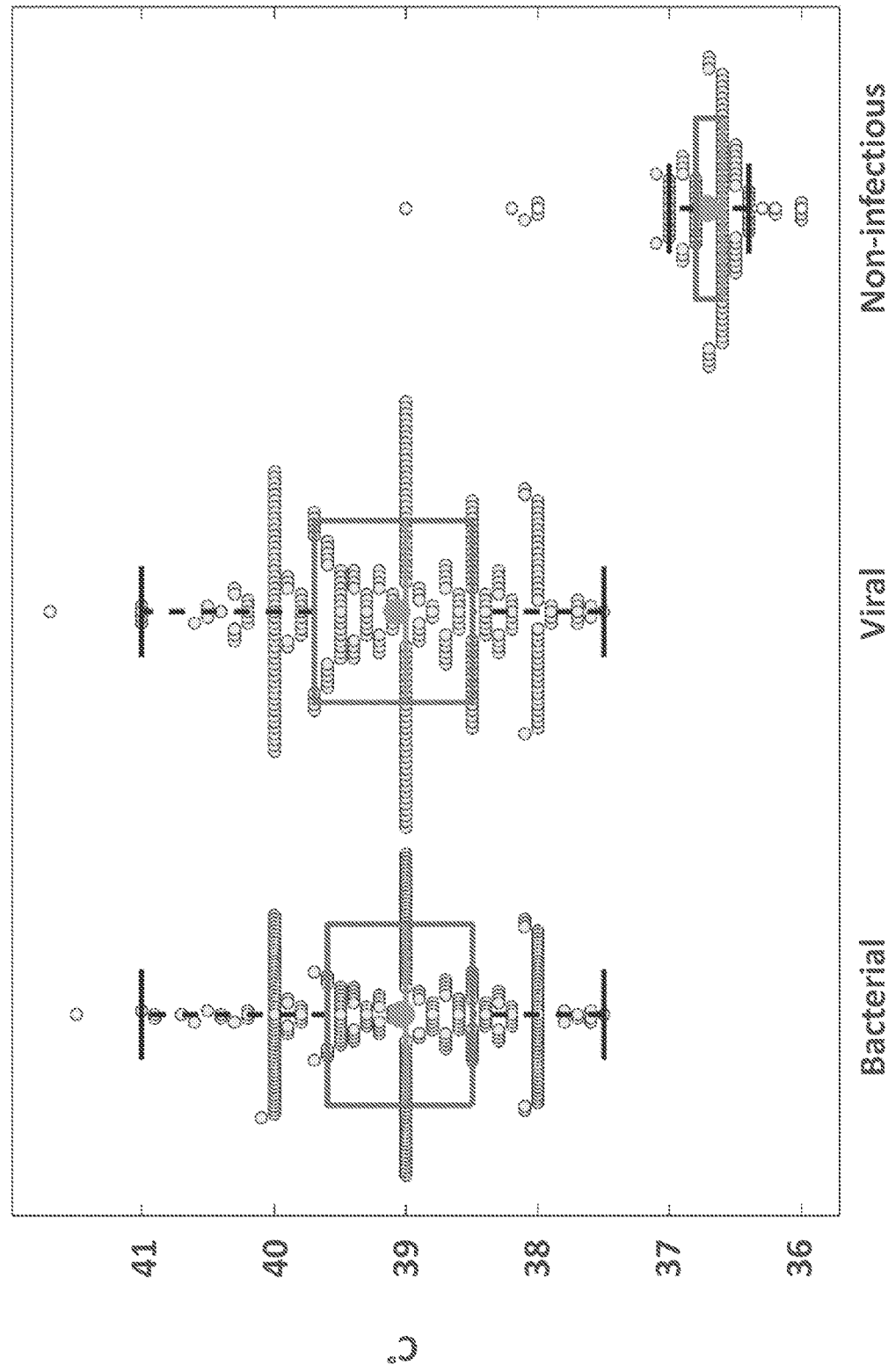

Protein stability at different temperatures can affect the assay performance: The utility of a biomarker depends on its stability in real-life clinical settings (e.g., its decay rate when the sample is stored at room temperature prior to analyte measurement). To address this, we examined the stability of TRAIL, CRP and IP-10 in serum samples from four independent individuals during 24 hours at 4° C. and 25° C. Aliquots of 100 μL from each plasma sample were pipetted into 0.2 mL tubes and kept at 4° C. or 25° C. from 0 to 24 hours. Subsequently, the levels of the analytes were measured (different time-points of the same analytes were measured using the same plate and reagents). The analyte half-lives at 4° and 25° C. were greater than 72 hours for TRAIL, CRP and IP-10 (FIGS. 15A-15C). Of note, in the real clinical setting, if the samples are stored at room temperature, the concentrations of TRAIL, IP-10 and CRP should be measured within about 24 after the sample is obtained. Preferably they should be measured within 5 hours, 4 hours, 3 hours, 2 hours, 1 hour, or even immediately after the sample was obtained. Alternatively, the sample should be stored at a temperature lower than 10° C., and then TRAIL can be measured more than 24 after obtaining the sample.

The three protein combination outperforms any individual and pairs of proteins: The combination of the three proteins outperforms that of the individual and pairs of proteins for distinguishing bacterial vs. viral and infectious vs. non-infectious patients.

TABLE 8

Bacterial vs. viral

| AUC | Proteins #3 | Protein #2 | Protein #1 |
|---|---|---|---|
| 0.89 | — | — | TRAIL |
| 0.88 | — | — | CRP |
| 0.66 | — | — | IP-10 |
| 0.95 | — | CRP | TRAIL |
| 0.93 | — | IP-10 | CRP |
| 0.90 | — | IP-10 | TRAIL |
| 0.96 | IP-10 | CRP | TRAIL |

TABLE 9

Infectious vs. Noninfectious

| AUC | Proteins #3 | Protein #2 | Protein #1 |
|---|---|---|---|
| 0.60 | — | — | TRAIL |
| 0.87 | — | — | CRP |
| 0.89 | — | — | IP-10 |
| 0.90 | — | CRP | TRAIL |
| 0.95 | — | IP-10 | CRP |
| 0.89 | — | IP10 | TRAIL |
| 0.96 | IP-10 | CRP | TRAIL |

Performance analysis as a function of the prevalence of bacterial infections: The prevalence of bacterial and viral infections is setting dependent. For example, in the winter, a pediatrician in the outpatient setting is expected to encounter substantially more viral infections than a physician in the hospital internal department during the summer. Notably, some measures of diagnostic accuracy such as AUC, sensitivity, and specificity are invariant to the underlying prevalence, whereas other measures of accuracy, such as PPV and NPV are prevalence dependent. In this section, the expected signature performance in terms of PPV and NPV in clinical settings with different prevalence of bacterial and viral infections is reviewed.

As the basis for this analysis the signature accuracy measures were used that were obtained using the Unanimous (bacterial, viral) and Majority (bacterial, viral) cohorts. The prevalence of bacterial infections in the Unanimous cohort was 51.7% yielding a PPV of 93%±3% and NPV of 93%±3%. The prevalence of bacterial infections in the Majority cohort was 48.7% yielding a PPV of 89%±3% and NPV of 92%±3%.

Figure 14A:
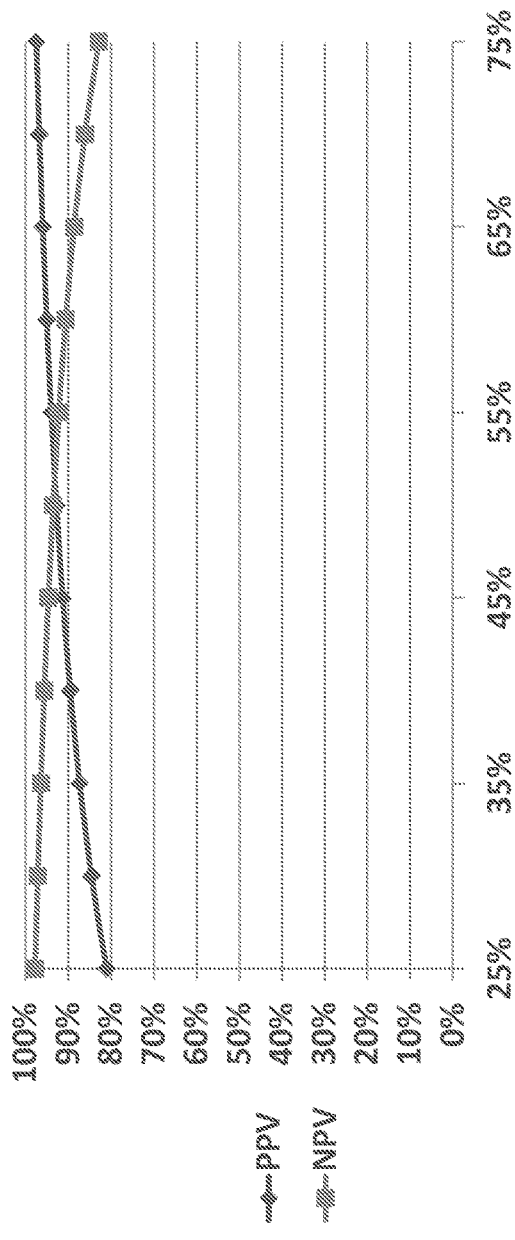
FIGS. 14A-14B. Extrapolated PPV and NPV values for the signature as a function of the prevalence of bacterial infections, A. Unanimous (bacterial, viral) cohort (n=527), B. Majority (bacterial, viral) cohort (n=653).
Figure 14B:
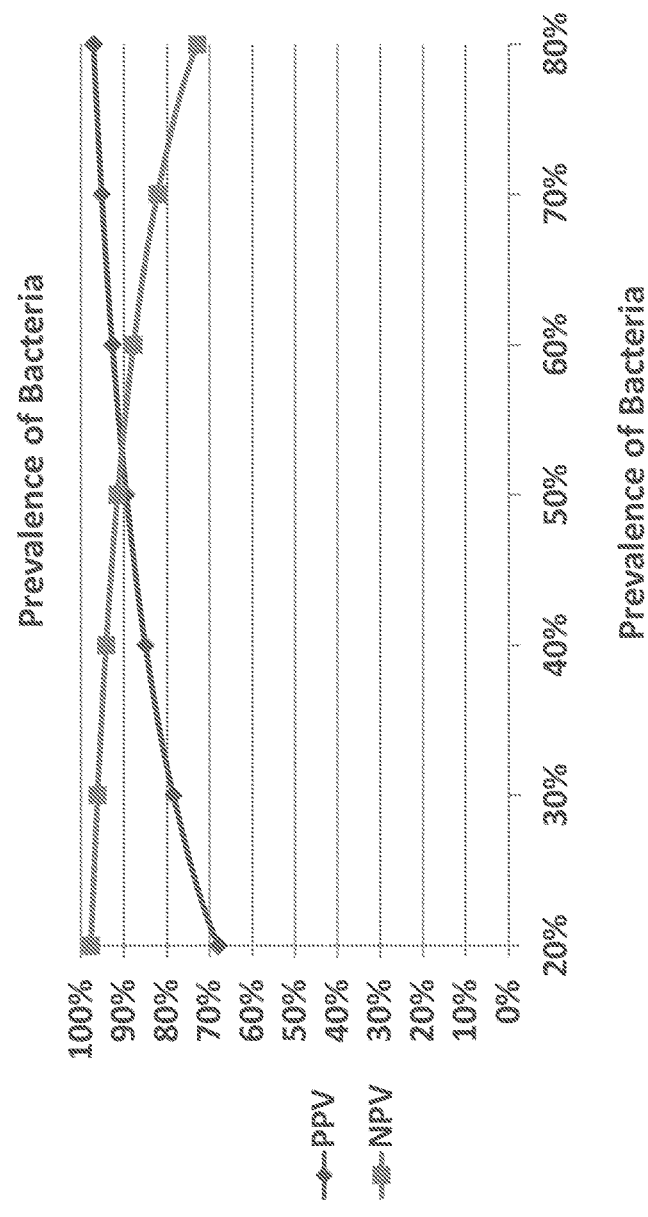

The measured sensitivity and specificity was used to compute the expected changes in the signature PPV and NPV as a function of the prevalence of bacterial infections (FIGS. 14A-14B).

Examples of different clinical settings and the extrapolated signature PPV and NPV for each of them are presented in Table 10A.

TABLE 10A

Extrapolated signature PPV and NPV in different clinical settings, based on the Unanimous cohort.

| NPV | PPV | Prevalence of Bacterial infections* | Age | Setting |
|---|---|---|---|---|
| 98% | 76% | 20% | Children | Outpatient |
| 97% | 85% | 35% | Adults | Outpatient |
| 94% | 93% | 50% | Children | Inpatient |
| 78% | 98% | 80% | Adults | Inpatient |

*An average annual prevalence. Estimates of bacterial infection prevalence are based on data reported in the Bacterial etiology chapter, Part 7 of Harrison's Internal Medicine 17$^{th}$ Edition.

The signature outperforms standard laboratory and clinical parameters for diagnosing bacterial vs. viral infections: Standard laboratory and clinical parameters, some of which are routinely used in clinical practice to aid in the differential diagnosis of an infection source, were evaluated in the Majority cohort (bacterial, viral, non-infectious, n=765). The evaluated parameters included ANC, % neutrophils, % lymphocytes, WBC, and maximal temperature. In accordance with the well-established clinical role of these parameters, we observed a statistically significant difference in their levels between bacterial and viral patients (FIGS. 15A-15E). For example, bacterial patients had increased levels of ANC ($P<10^{-24}$), and WBC ($P<10^{-10}$), whereas viral patients had a higher % lymphocytes ($P<10^{-31}$). The signature was significantly more accurate than any of the individual features ($P<10^{-18}$) and their combinations ($P<10^{-15}$), see FIG. 3A.

The signature outperforms protein biomarkers with a well-established immunological role: The signature outperformed all clinical parameters and the 600 proteins that were evaluated during the screening phase (see FIGS. 3A-3B). The following section further compares the signature to selected proteins that are routinely used in the clinical setting or that have an immunological role.

Figure 16A:
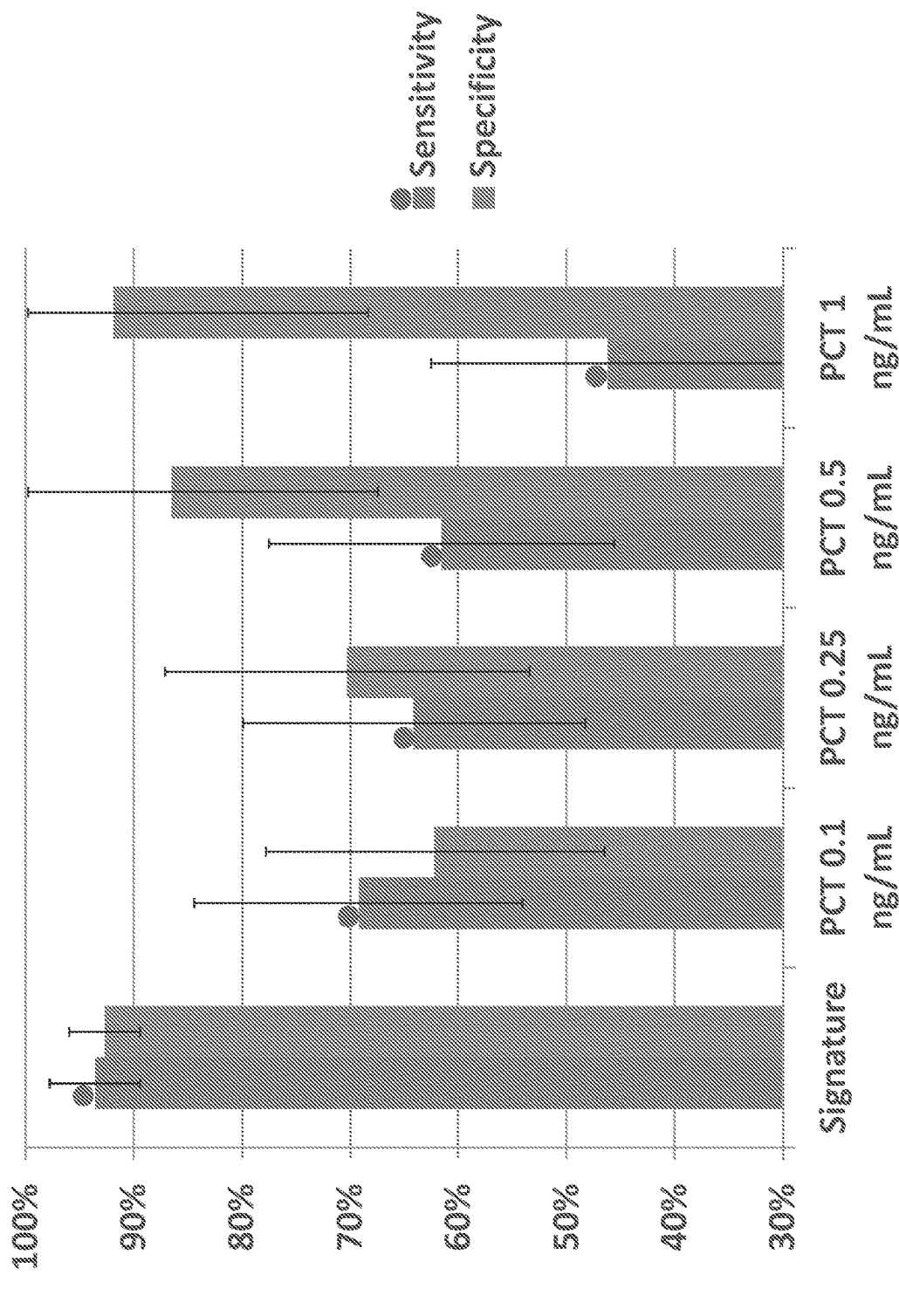
FIGS. 16A-16B. Comparison of the performance of the signature and PCT using different cutoffs. A. Performance measured in 76 patients from the Unanimous (bacterial, viral) cohort; B. Performance measured in 101 patients from the Majority (bacterial, viral) cohort. Error bars represent 95% CI. Signature sensitivity (left) and specificity (right) were calculated after filtering out 14% of the patients with a marginal immune response.
Figure 16B:
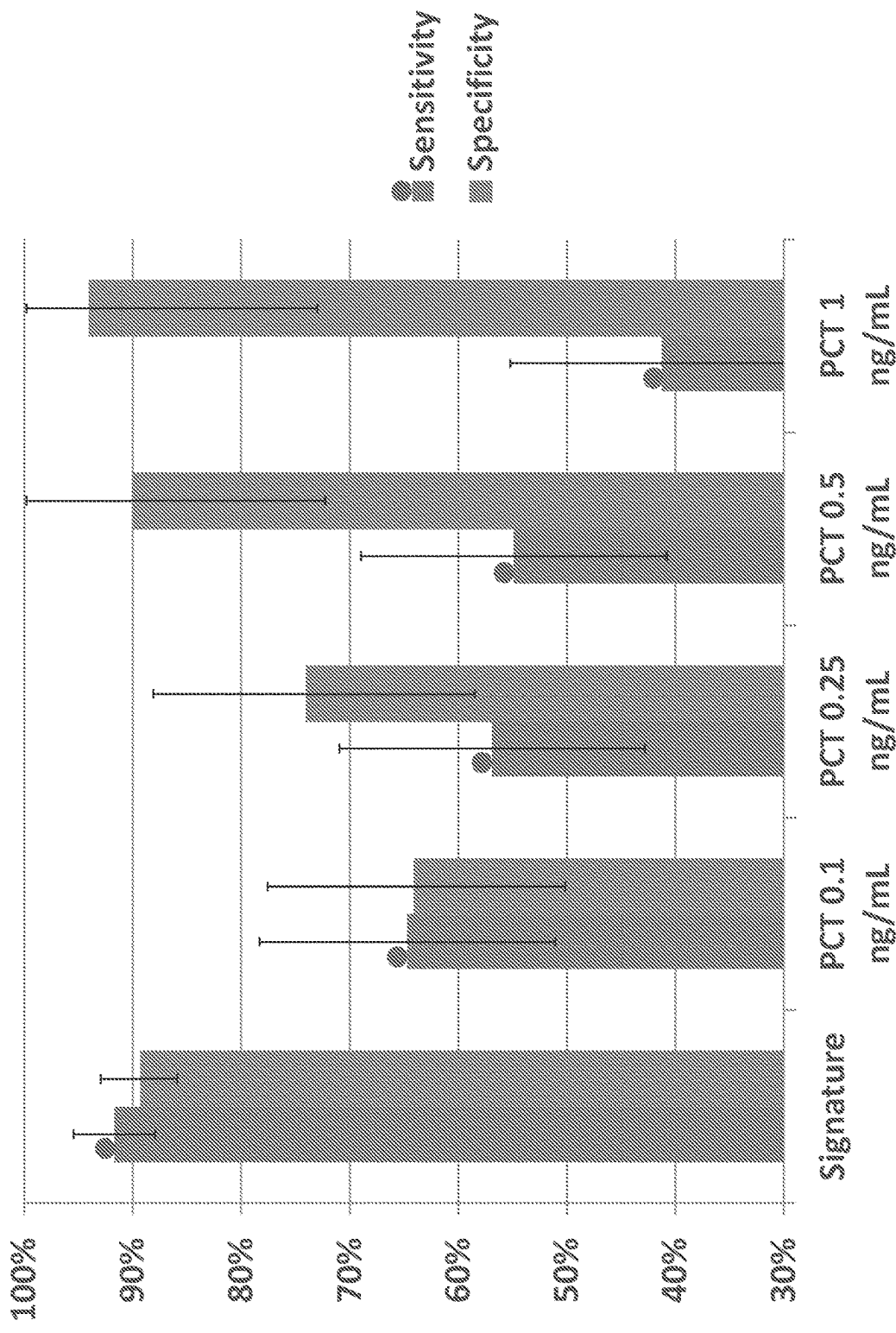

One of the most widely used and useful protein biomarkers for differentiating sepsis from other non-infectious causes of SIRS in critically ill patients is procalcitonin (PCT). Whether PCT can be used to distinguish between local bacterial and viral infections is less clear. To test this, we measured PCT concentrations in 76 randomly selected patients from the Unanimous (bacterial, viral) cohort ($n_{Bacterial}$=39, $n_{viral}$=37) and 101 randomly selected patients from the Majority (bacterial, viral) cohort ($n_{Bacterial}$=51, $n_{Viral}$=50) and compared the diagnostic accuracy based on PCT levels to that of the signature. PCT accuracy was calculated using the standard cutoffs routinely applied in the clinical setting (0.1 ng/mL, 0.25 ng/mL, 0.5 ng/mL, and 1 ng/mL).[19-23] Maximal PCT sensitivity of 69% was attained at a cutoff of 0.1 mg/mL and resulted in a specificity of 62% (for the Unanimous [bacterial, viral] cohort). For the same cohort, the signature showed significantly higher sensitivity of 94% ($P<0.001$) and specificity of 93% ($P<0.001$) (FIG. 16A). A comparison using the patients from the Majority (bacterial, viral) cohort showed similar results (FIG. 16B).

Overall, despite its high diagnostic and prognostic value for sepsis detection in critically ill patients, our results indicate that PCT is less accurate in distinguishing between patients with local infections (bacterial vs. viral).

Figure 17B:
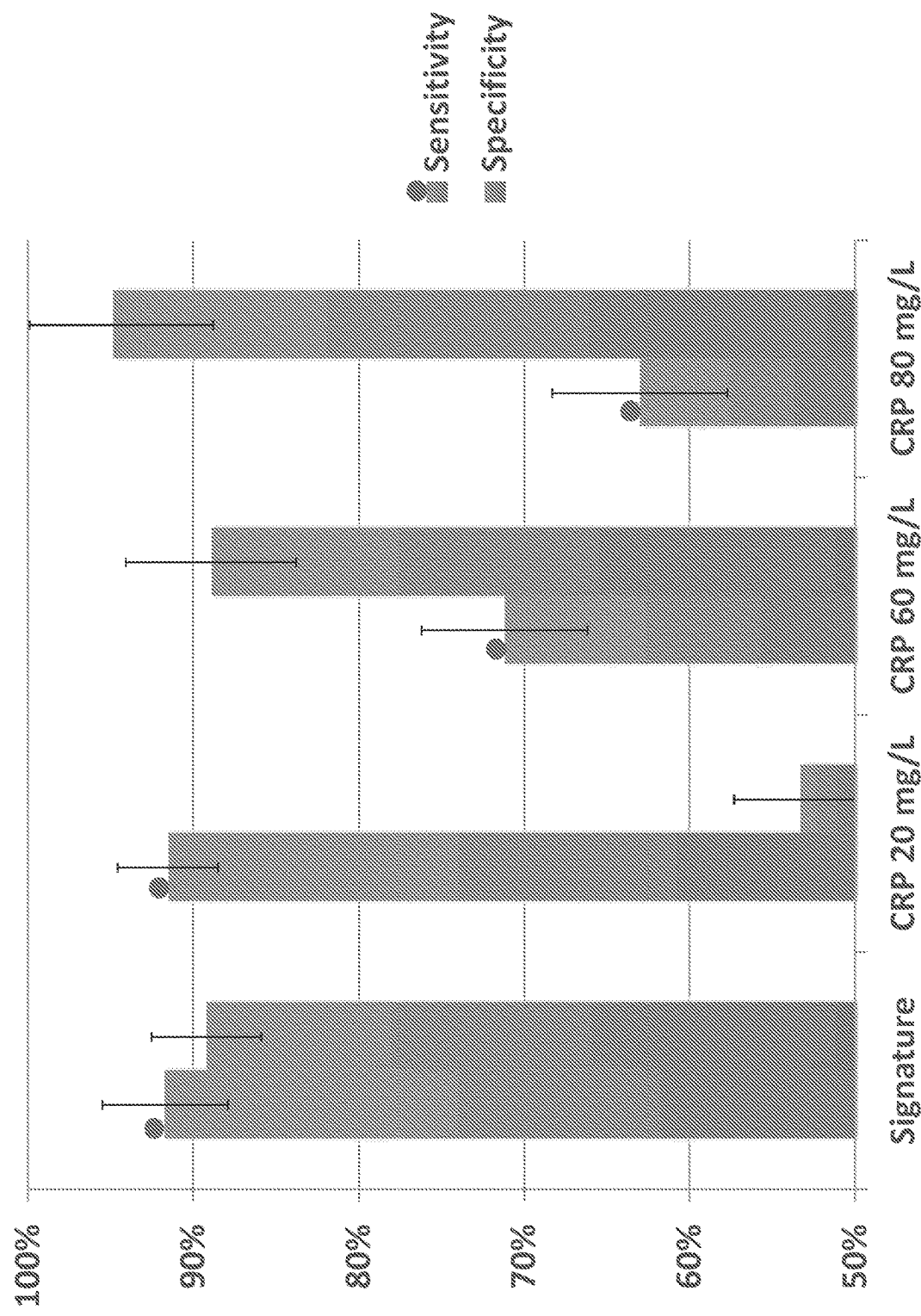
Figure 18C:
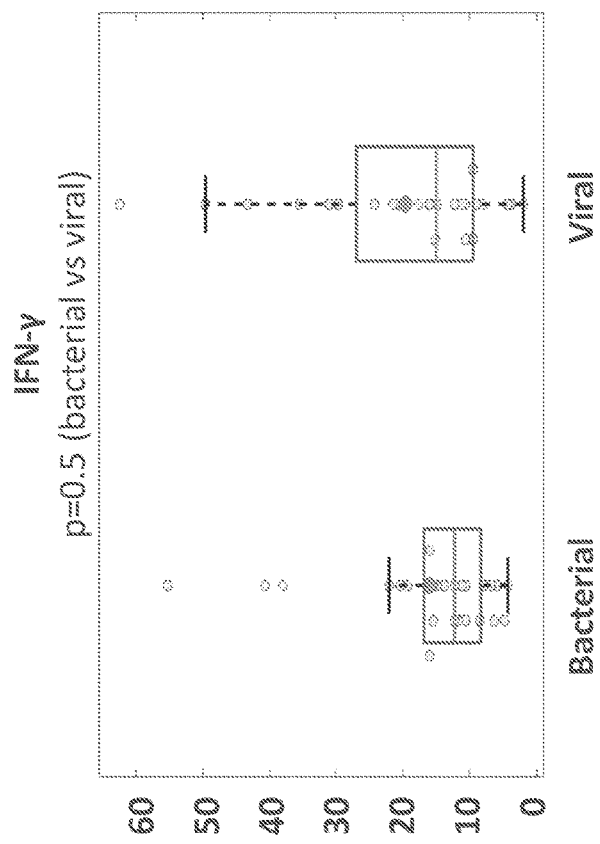
Figure 18D:
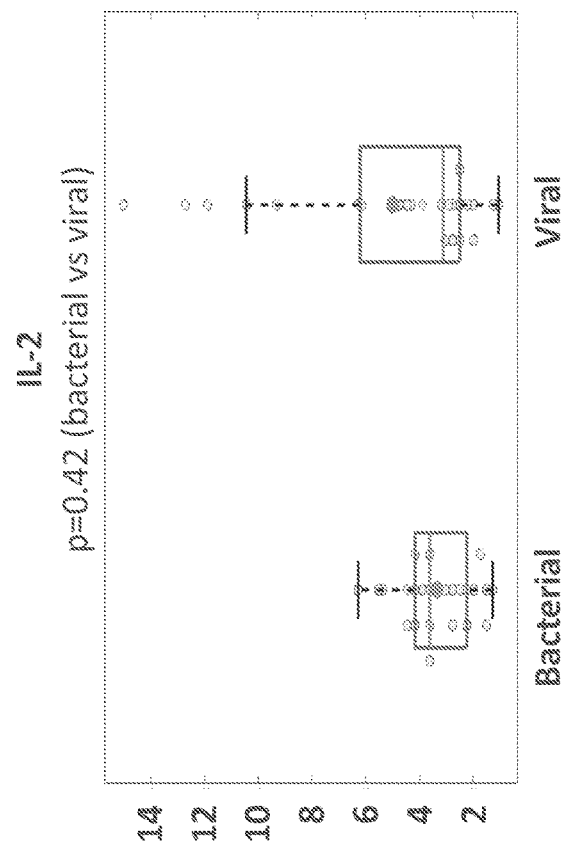
Figure 18E:
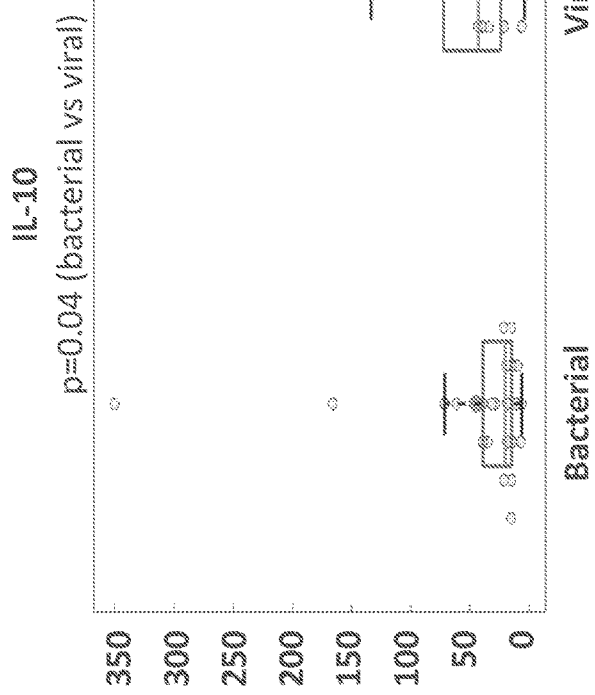
Figure 18F:
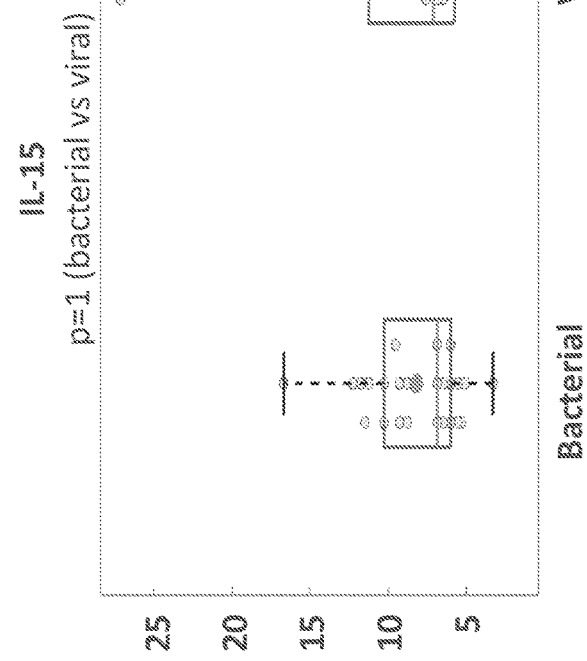
Figure 18G:
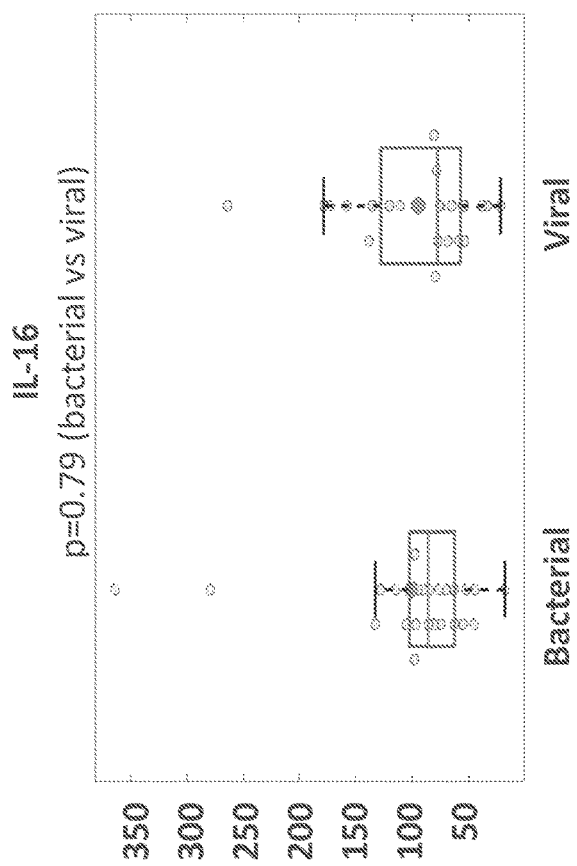
Figure 18H:
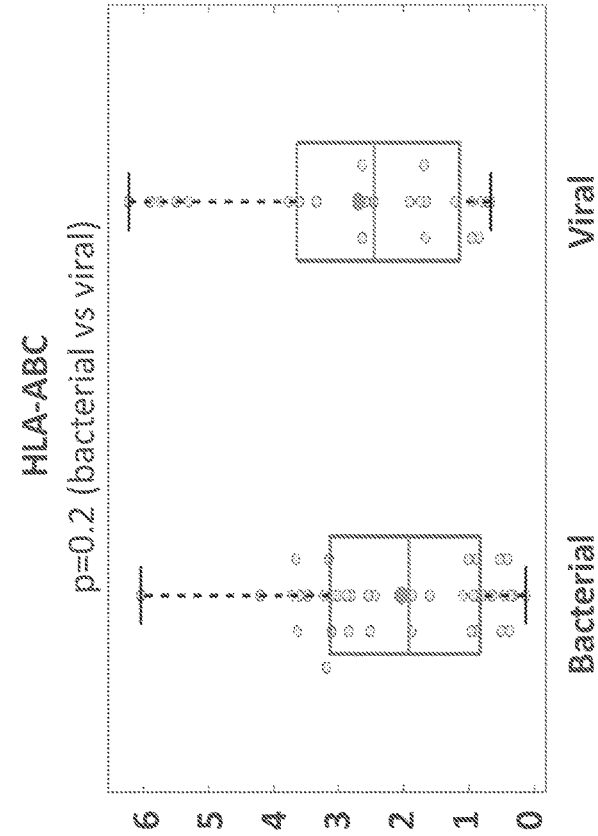

Another protein biomarker used in the clinical setting is the C-reactive protein (CRP), an acute phase response protein that is up-regulated in infections and other inflammatory conditions. The performance of CRP was compared to that of the signature using the entire Unanimous (bacterial, viral) and Majority (bacterial, viral) cohorts. CRP accuracy was determined using several standard cutoffs applied in the clinical setting.[24-26] Maximal CRP sensitivity of 92% was attained at 20 mg/mL cutoff resulting in a specificity of 60% (for the Unanimous [bacterial, viral] cohort) (FIG. 17A). The signature had a similar sensitivity (94%) and a significantly higher specificity (93%, $P<10^{-9}$) in the same cohort. Similar results were observed using the Majority (bacterial, viral) cohort (FIG. 17B). Overall, the signature has a similar sensitivity to CRP with a 20 mg/L cutoff but a considerably higher specificity for distinguishing bacterial from viral patients.

Next, the differential response of protein biomarkers with a well-established role in the host response to infections was examined (Table 10B and FIGS. 18A-18H). Each biomarker was tested on at least 43 patients (about half bacterial and half viral), and if it showed promising results, it was further tested on additional patients (up to 150).

TABLE 10B

A list of protein biomarkers with a well-established role in the host response against infections, and the number of patients used to test each biomarker (for each analysis the analyzed patients included approximately half bacterial and half viral patients).

| No. of patients | Short description | Protein biomarker |
|---|---|---|
| 120 | CD11a is expressed by all leukocytes as part of the integrin lymphocyte function-associated antigen-1 (LFA-1). LFA-1 plays a central role in leukocyte intercellular adhesion through interactions with its ligands, ICAMs 1-3 (intercellular adhesion molecules 1 through 3). CD11a also functions in lymphocyte co-stimulatory signaling. | CD11a |
| 79 | CD11C is an integrin α X chain protein and mediates cell-cell interactions during inflammatory responses. | CD11C |
| 82 | CD80 is a membrane receptor involved in the co-stimulatory signal essential for T-lymphocyte activation. The binding of CD28 or CTLA-4 to CD80 induces T-cell proliferation and cytokine production. | CD80 |
| 65 | These are MHC class I antigens associated with β2-microglobulin and are expressed by all human nucleated cells. HLA-A, B, C are central in cell-mediated immune response and tumor surveillance. | HLA-A, B, C |
| 49 | IFN-γ is a soluble cytokine. IFN-γ participates in innate and adaptive immunity against viral and intracellular bacterial infections and in tumor control. | IFN-γ |
| 43 | IL-1a is a member of the IL-1 cytokine family. IL-1a is a pleiotropic cytokine involved in various immune responses, inflammatory processes, and hematopoiesis. IL-1a is produced by monocytes and macrophages as a proprotein, which is proteolytically processed and released in response to cell injury, thereby inducing apoptosis. | IL-1a |
| 49 | IL-2 is produced by T-cells in response to antigenic or mitogenic stimulation. IL-2 is required for T-cell proliferation and other activities crucial for regulation of the immune response. | IL-2 |
| 43 | IL-6 is a cytokine that functions in inflammation and maturation of B cells. IL-6 is an endogenous pyrogen capable of inducing fever in people with autoimmune diseases or infections. | IL-6 |
| 43 | IL-8 is a member of the CXC chemokine family and functions as one of the major mediators of the inflammatory response. | IL-8 |
| 43 | IL-9 is a cytokine that acts as a regulator of a variety of hematopoietic cells. IL-9 supports IL-2 independent and IL-4 independent growth of helper T-cells. | IL-9 |
| 48 | IL-10 is a cytokine produced primarily by monocytes and to a lesser extent by lymphocytes. IL-10 has pleiotropic effects in immunoregulation and inflammation. | IL-10 |
| 49 | IL-15 is a cytokine that stimulates the proliferation of T-lymphocytes. | IL-15 |
| 49 | IL-16 functions as a chemo-attractant, a modulator of T cell activation, and an inhibitor of HIV replication. | IL-16 |
| 54 | sTNFRSF1A is a receptor for TNFSF2/TNF-α and homo-trimeric TNFSF1/lymphotoxin-α that contributes to the induction of non-cytocidal TNF effects including anti-viral state and activation of the acid sphingomyelinase. | sTNFRSF1A |
| 43 | TNF-α is a cytokine secreted mainly by macrophages. TNF-α can induce cell death of certain tumor cell lines. It is a potent pyrogen causing fever directly or by stimulation of IL-1 secretion. | TNF-α |

TABLE 10B-continued

A list of protein biomarkers with a well-established role in the host response against infections, and the number of patients used to test each biomarker (for each analysis the analyzed patients included approximately half bacterial and half viral patients).

| No. of patients | Short description | Protein biomarker |
|---|---|---|
| 43 | TNF-β is a potent mediator of inflammatory and immune responses. It is produced by activated T and B lymphocytes and is involved in the regulation of various biological processes including cell proliferation, differentiation, apoptosis, lipid metabolism, coagulation, and neurotransmission. | TNF-β |
| 150 | TREM is a pro-inflammatory amplifier present on neutrophils and monocytes. | TREM |

Since these biomarkers do not have a well-established cutoff in the clinical setting, we used their AUCs as a basis for comparison (FIG. 3B) The most informative biomarker was TREM (AUC of 0.68±0.09). The accuracy of TREM was significantly lower than that of the signature ($P<10^{-9}$ when comparing the two AUCs; FIG. 3B). These results demonstrate that mere participation of a protein in the host response to an infection does not necessarily imply diagnostic utility. For example, although IFN-γ has a well-established role in the immune response to viruses and intracellular bacteria, its short half-life (<20 h)[27] limits its diagnostic utility (as its concentration in the blood is highly dependent on the time from infection onset).

Example 3

Trinary Classifier Outperforms a Binary Classifier

In the binary model the classifier is trained by classifying all samples as either 'Bacterial' or 'Non-bacterial' ('Viral' and 'Non-infectious' are grouped). In the trinary model, the classifier learns to distinguish between three classes 'Bacterial', 'Viral' and 'Non-infectious'. The probability of the viral and the non-infectious are then grouped together to give the probability of 'non-bacterial'. This was demonstrated on the present data.

Both of the above classifiers were evaluated using a leave 10%-out cross-validation on both the Majority and Unanimous cohorts.

Results

Running the binary classifier on the majority cohort yields the results as summarized in Table 10C, herein below:

TABLE 10C

| Reference class | | |
|---|---|---|
| Bacterial (B) | Viral and non-infectious (V + NI) | |
| 63 | 411 | V + NI |
| 256 | 35 | B |

The sensitivity of the classifier on the Majority cohort is 80.3% and the specificity is 92.2%.

Running the multinomial based classifier on the same dataset yields the following results summarized in Table 10D.

TABLE 10D

| Reference class | | |
|---|---|---|
| (B) | (V + NI) | |
| 54 | 417 | V + NI |
| 265 | 29 | B |

It can be seen that this classifier outperforms the previous one both in terms of sensitivity and in terms of specificity. The sensitivity was improved to 83.1% and the specificity to 93.5%.

Running the binary classifier on the Unanimous cohort yields the results summarized in Table 11.

TABLE II

| Reference class | | |
|---|---|---|
| (B) | (V + NI) | |
| 39 | 358 | V + NI |
| 217 | 25 | B |

The sensitivity of the classifier on the Unanimous cohort is 84.8% and the specificity is 93.5%.

Running the multinomial based classifier on the same dataset yields the results summarized in Table 12.

TABLE 12

| Reference class | | |
|---|---|---|
| (B) | (V + NI) | |
| 38 | 364 | V + NI |
| 218 | 19 | B |

This classifier outperforms the previous one both in terms of sensitivity and in terms of specificity. The sensitivity was improved to 85.2% and the specificity to 95.0%.

In summary, the trinary classifier outperforms the binary based classifier both in terms of sensitivity and in terms of specificity on both datasets tested.

Example 4

The Clinical Accuracy of the Signature Remains Robust Even when Analytical Accuracy is Reduced It is important to assess how clinical accuracy is affected by the increase in the CV (std/mean) of the proteins measurements, because often different measurement devices, particularly those that are useful at the point-of-care, show increased CVs (i.e. reduced analytical accuracy).

Figure 19A:
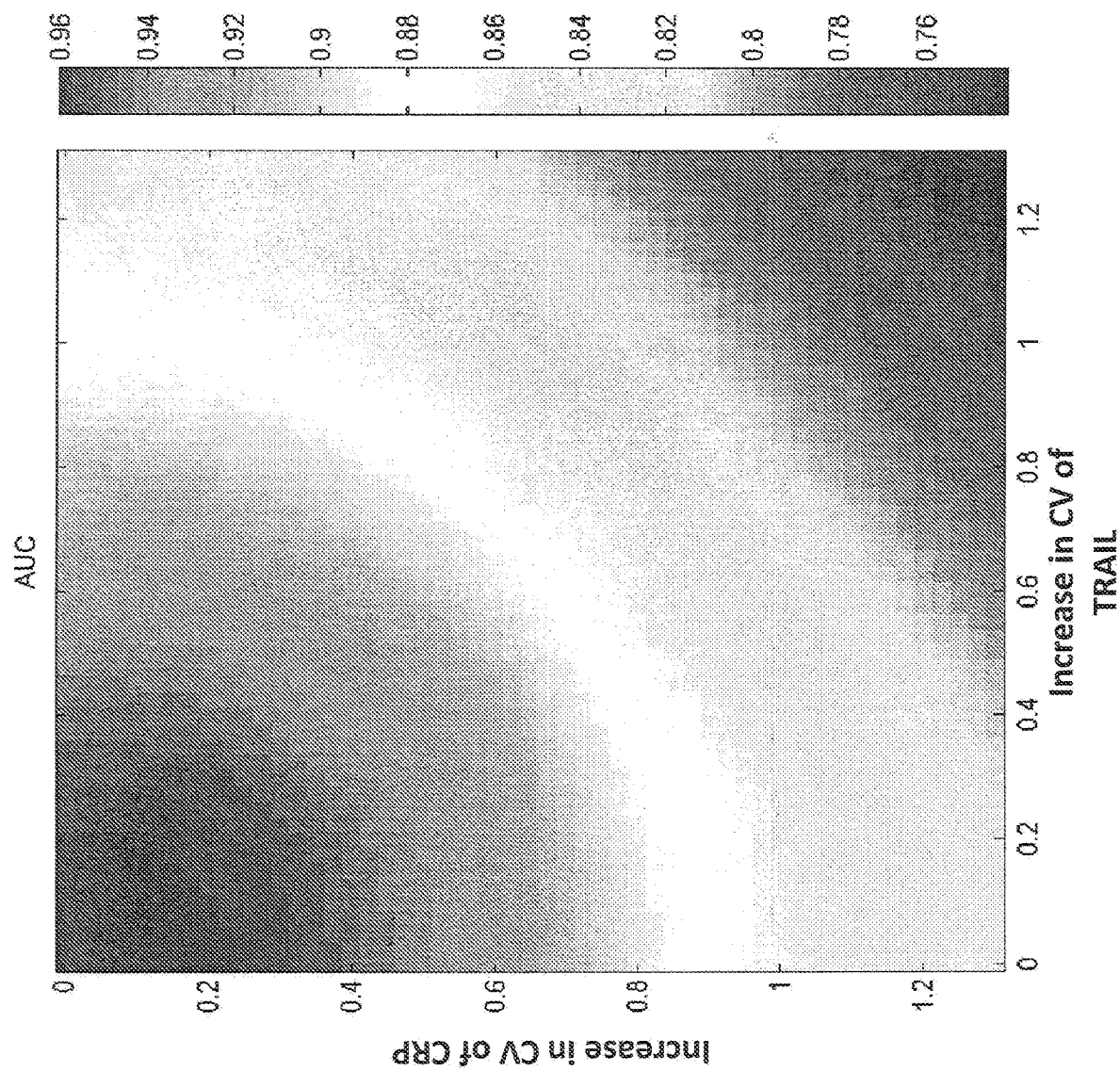
FIGS. 19A-19B. The clinical accuracy of the signature is robust to reduction in the technical accuracy of protein measurements. (A) The AUCs of the signature distinguishing bacterial from viral infection are estimated using a grayscale map as a function of CVs (std/mean) of TRAIL (y-axis) and CRP (x-axis) measurement. (B) AUC values on the diagonal of FIG. 19A presented such that CV of TRAIL and CRP are equal.
Figure 19B:
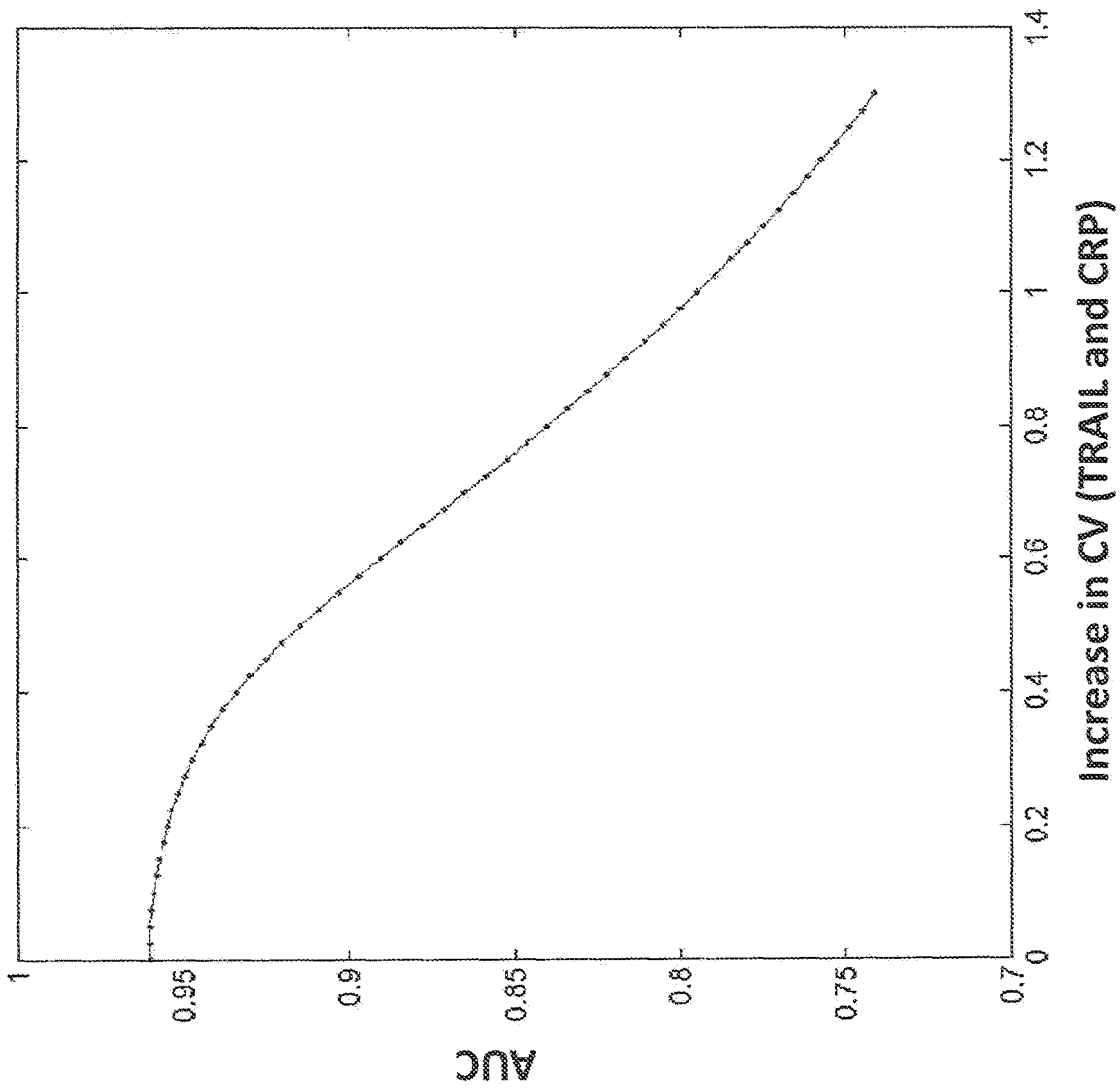

The present inventors examined the change in AUC of the signature for distinguishing bacterial from viral infection as a function of the increase in CV of both TRAIL and CRP. This was done by taking the original patient data of the Unanimous cohort and simulating an increase in CV using monte-carlo simulations (FIGS. 19A-19B). Specifically, for each combination of TRAIL and CRP CVs, 100 simulated measurements were assigned to each of the patients and the AUC in each case was recomputed. The average AUC per CV combination is depicted. It can be seen that the signature clinical accuracy (in terms of AUC) is robust to the increases in technical CV. For example, increasing the ELISA CV by 0, 0.24 and 0.4 leads to a reduction in AUCs of 0.96, 0.95 and 0.94 respectively. Similar results are obtained when increasing the CV of IP-10, and when repeating the simulations on the Majority cohort.

This result may be explained by the usage of multiple biomarkers that compensate for one another. This surprising finding is useful because it opens the way to perform measurements of the proteins on cheap and rapid technologies (such as POC technologies), which often show reduced analytical sensitivity (compared for example to automated immunoassays or ELISA), without losing clinical accuracy.

Example 5

Different ELISA protocols can be applied for measuring TRAIL and IP-10, which would lead to different signal to noise ratios, and consequentially to different concentrations being measured. More specifically, while the overall trend of the biomarkers will be preserved regardless of the protocol (e.g. TRAIL increases in viral infections and decreases in bacterial), the measurement scale is protocol dependent. In the following subsections, examples of protocols are described that lead to different measured concentrations of IP-10 and TRAIL.

Measurements of soluble IP-10 and TRAIL using ELISA—Protocol no. 1: To determine the concentrations of soluble IP-10 and TRAIL in human plasma and serum samples, a standard Sandwich ELISA (Enzyme-linked immunosorbent assay) was used. Briefly, the wells of 96-well plate were coated with capture-antibody specific to TRAIL and IP-10 and diluted in coating buffer (e.g. 1×PBS) followed by overnight incubation at 4° C. The wells were washed twice with washing buffer (e.g. 1×PBS with 0.2% Tween-20) and subsequently blocked with blocking buffer containing proteins (e.g. 1×PBS with 0.2% Tween-20 and 5% non-fat milk) for at least 2 hours at room temperature or overnight at 4° C. Wells were then washed twice with washing buffer. Protein standards and plasma or serum samples were incubated for two hour at room temperature. Then, the wells were washed three times with a washing buffer and subsequently incubated with an HRP conjugated detection-antibody specific to TRAIL and IP-10, diluted in blocking buffer for two hours at room temperature.

The wells were washed four times with a washing buffer and incubated with a reaction solution that contained an HRP substrate (e.g. TMB; 3, 3', 5,5'-Tetramethylbenzidine). After adequate color development, a stop solution was added to each well. The absorbance of the HRP reaction product in 450 nm was determined using standard spectrophotometer. This protocol took 5 (TRAIL) and 4.75 (IP10) hours respectively and is referred to herein as the slow protocol.

Measurements of Soluble IP-10 and TRAIL Using ELISA—Protocol No. 2:

Reducing assay time allows for increased clinical utility. To further reduce the protocol run time, the protocol was optimized for measuring TRAIL and IP10 and reduced to less than 100 minutes. The rapid protocol was performed as follows:

50 µl of assay diluent and 50 µl of Standards was added to samples or controls per well. The reaction was incubated for 30 minutes at room temperature on a horizontal orbital microplate shaker (3 mm orbit) set at 550 rpm. Each well was then aspirated and washed four times by using a wash buffer. Next, 200 µl of Conjugate was added to each well and the reactions were incubated for 45 minutes at room temperature on the shaker. The wells were washed four times with a washing buffer and incubated with a reaction solution that contained an HRP substrate (e.g. TMB; 3, 3', 5,5'-Tetramethylbenzidine). After 10-25 minutes, a stop solution was added to each well. The absorbance of the HRP reaction product in 450 nm was determined using a standard spectrophotometer. This protocol took 99 (TRAIL) and 85 (IP-10) minutes respectively and is referred to herein as the rapid protocol.

Figure 30A:
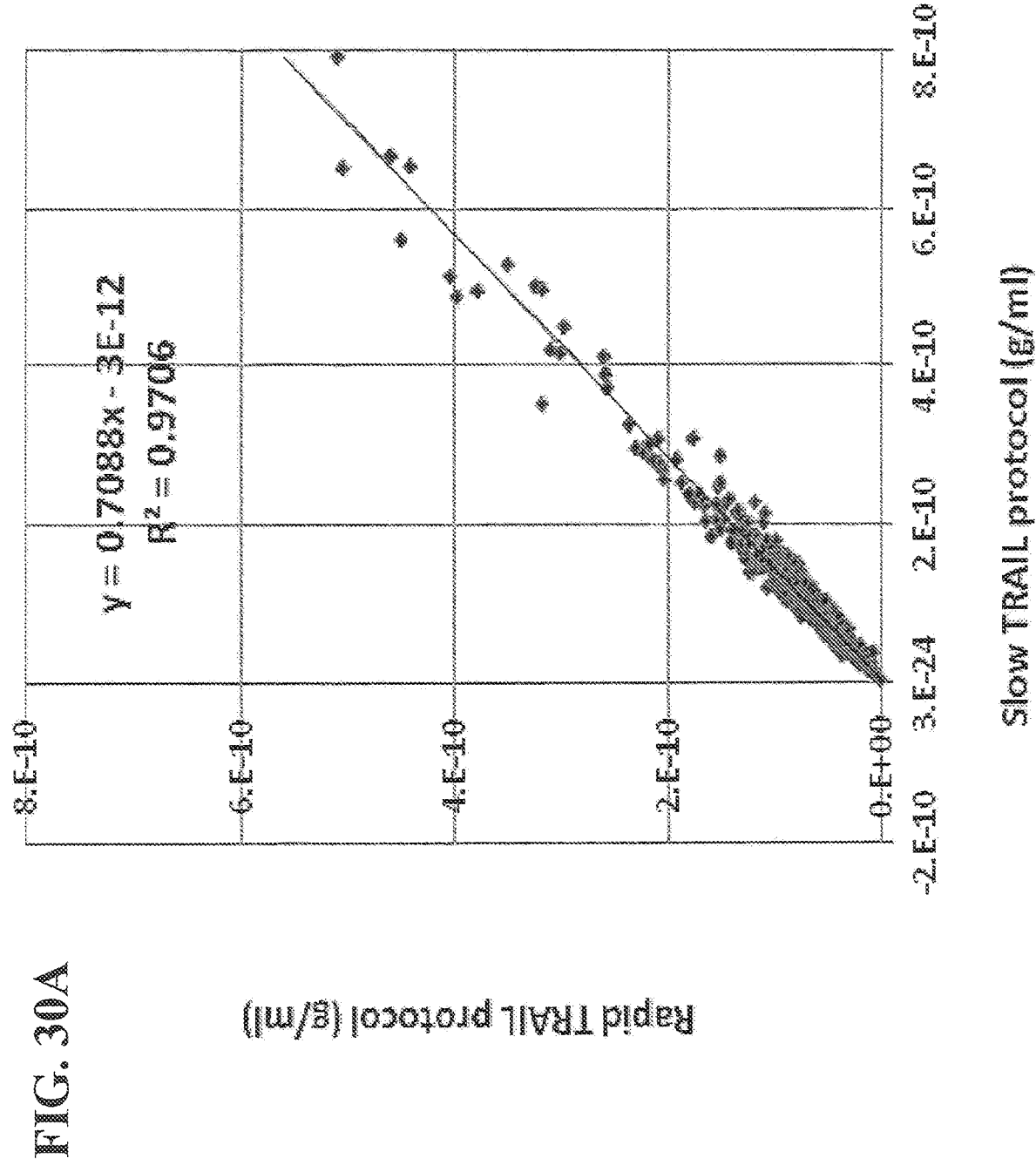
FIGS. 30A-30B are graphs illustrating the correlation between the rapid and slow protocol for measurement of TRAIL (FIG. 30A) and IP-10 (FIG. 30B).
Figure 30B:
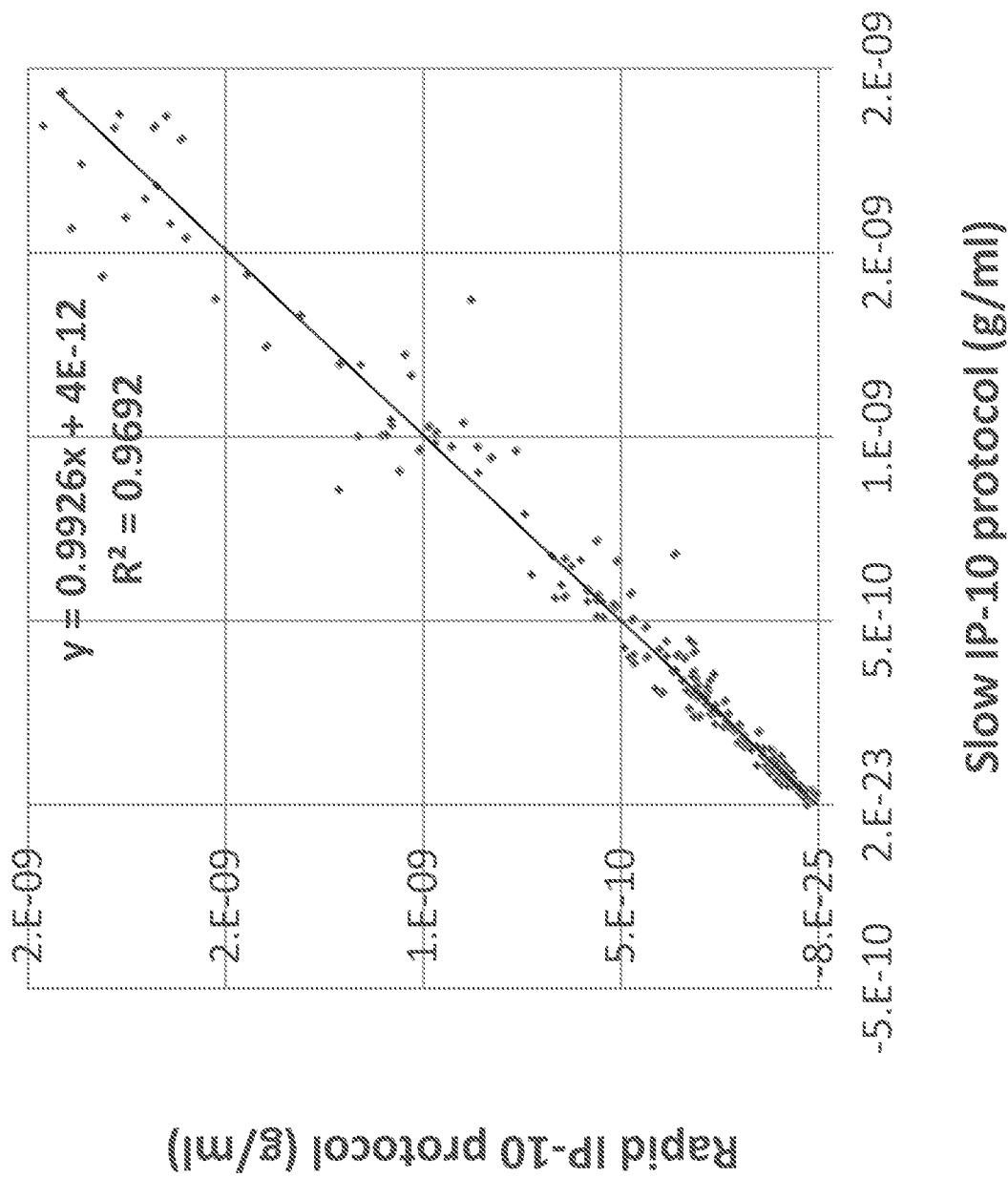

The slow and the rapid protocol measurements were compared using 357 samples for TRAIL and 189 samples for IP-10, and showed highly correlated results (FIGS. 30A-30B).

Of note, the average TRAIL concentration obtained using the rapid protocol was roughly 70 percent less than that obtained using the slow protocol concentration. Such alterations in measured concentrations of proteins across different protocols often occur and can be compensated for by correlating the measurements of the two protocols and computing a transformation function. For example, the transformation function y_slow=0.709×y_rapid−3e−12 may be used to translate the concentrations of the rapid protocol and the slow protocol. This translation preserves TRAIL's accuracy. Other, translation functions and protocols can be developed by one skilled in the art that also preserve the accuracy. In summary, the behavior of TRAIL remains the same across the two protocols (i.e. highest in viral, lower in non-infectious and lowest in bacterial), despite a shift in the calculated concentrations.

Different Protocols and Cohorts Lead to Different Model Coefficients:

An example of the multinomial logistic model coefficients generated on the majority patients cohort when measuring IP-10 and TRAIL with the slow protocol is shown in Table 13:

TABLE 13

| Second Coordinate $\delta_1$ (bacterial) | First Coordinate $\delta_0$ (viral) | |
| --- | --- | --- |
| $b_0 = -1.5389 \pm 0.75676$ | $a_0 = -1.7331 \pm 0.62936$ | Const |
| $b_1 = 0.0851 \pm 0.015288$ | $a_1 = 0.0514 \pm 0.014896$ | CRP (mg/ml) |
| $b_2 = 0.0046 \pm 0.001372$ | $a_2 = 0.0049 \pm 0.001372$ | IP10 (pg/ml) |
| $b_3 = -0.0155 \pm 0.007056$ | $a_3 = 0.0048 \pm 0.005096$ | TRAIL (pg/ml) |

An example of the multinomial logistic model coefficients generated on the consensus patients cohort when measuring IP-10 and TRAIL with the slow protocol is shown in Table 14.

TABLE 14

| Second Coordinate $\delta_1$ (bacterial) | First Coordinate $\delta_0$ (viral) | |
|---|---|---|
| $b_0 = 2.6091 \pm 0.9357$ | $a_0 = -2.6866 \pm 0.75048$ | Const |
| $b_1 = 0.0866 \pm 0.016856$ | $a_1 = 0.0499 \pm 0.016464$ | CRP (mg/ml) |
| $b_2 = 0.0052 \pm 0.001568$ | $a_2 = 0.0059 \pm 0.001568$ | IP10 (pg/ml) |
| $b_3 = -0.0115 \pm 0.008232$ | $a_3 = 0.0084 \pm 0.005684$ | TRAIL (pg/ml) |

Since the frequency of the subgroups in the patient cohort deviates from the anticipated frequency in the general population, one can further adjust the model coefficients to reflect a predetermined prior probability using standard techniques for coefficient adjustment (for example see G. King and L Zeng, Statistics in Medicine 2002). For example, the following examples show multinomial logistic model coefficients generated on the majority patients cohort when measuring IP-10 and TRAIL with the slow protocol, reflecting prior probability of 45% bacterial, 45% viral and 10% non-infectious.

Model coefficients (trained on majority cohort) after prior adjustment are summarized in Table 15:

TABLE 15

| Second Coordinate $\delta_1$ (bacterial) | First Coordinate $\delta_0$ (viral) | |
|---|---|---|
| $b_0 = -1.1302 \pm 0.75676$ | $a_0 = -1.4151 \pm 0.62936$ | Const |
| $b_1 = 0.0851 \pm 0.015288$ | $a_1 = 0.0514 \pm 0.014896$ | CRP (mg/ml) |
| $b_2 = 0.0046 \pm 0.001372$ | $a_2 = 0.0049 \pm 0.001372$ | IP10 (pg/ml) |
| $b_3 = -0.0155 \pm 0.007056$ | $a_3 = 0.0048 \pm 0.005096$ | TRAIL (pg/ml) |

Model coefficients (trained on consensus cohort) after prior adjustment are summarized in Table 16.

TABLE 16

| Second Coordinate $\delta_1$ (bacterial) | First Coordinate $\delta_0$ (viral) | |
|---|---|---|
| $b_0 = -1.7833 \pm 0.9357$ | $a_0 = -2.083 \pm 0.75048$ | Const |
| $b_1 = 0.0866 \pm 0.016856$ | $a_1 = 0.0499 \pm 0.016464$ | CRP (mg/ml) |
| $b_2 = 0.0052 \pm 0.001568$ | $a_2 = 0.0059 \pm 0.001568$ | IP10 (pg/ml) |
| $b_3 = -0.0115 \pm 0.008232$ | $a_3 = 0.0084 \pm 0.005684$ | TRAIL (pg/ml) |

Of note, other combinations of coefficients can be chosen to produce similar results, as would be evident to one skilled in the art. Other protocols for measuring proteins that affect the measured protein concentrations would yield different model coefficients. For example, the rapid protocol for measuring TRAIL reduces the computed concentrations to roughly 70% of the concentrations computed in the slow protocol. Thus, one way to adjust for this is to alter the model coefficients of TRAIL to account for this change. Another way is to divide the rapid protocol measurements of TRAIL by 70% and plug in to the above mentioned models that were developed for the slow protocol.

It is often preferable to use a log transformation on the protein measurements in order to improve model accuracy and calibration (i.e. better fit between the predicted risk of a certain infection and the observed risk).

An example of a model with log transformation of TRAIL and IP-10 is depicted in Table 17 (model was trained on the consensus cohort):

TABLE 17

| Second Coordinate $\delta_1$ (bacterial) | First Coordinate $\delta_0$ (viral) | |
|---|---|---|
| $b_0 = -5.9471 \pm 3.3391$ | $a_0 = -14.8487 \pm 3.3839$ | Const |
| $b_1 = 0.0833 \pm 0.016856$ | $a_1 = 0.0437 \pm 0.017052$ | CRP (mg/ml) |
| $b_2 = 1.3868 \pm 0.48608$ | $a_2 = 2.0148 \pm 0.4408$ | IP10 (pg/ml) |
| $b_3 = -0.788 \pm 0.60505$ | $a_3 = 0.8946 \pm 0.61348$ | TRAIL (pg/ml) |

Example 6

Hypersurface Parameterization

Given the concentrations of CRP [C], TRAIL [T] and IP-10 [P] we define:

$$\delta_0 = -1.299 + 0.0605 \times [C] + 0.0053 \times [P] + 0.0088 \times [T]$$

$$\delta_1 = -0.378 + 0.0875 \times [C] + 0.0050 \times [P] - 0.0201 \times [T]$$

The probabilities can then be calculated by:

$$P(\text{Viral}) = \frac{e^{\delta_0}}{1 + e^{\delta_0} + e^{\delta_1}}$$

$$P(\text{Bacterial}) = \frac{e^{\delta_1}}{1 + e^{\delta_0} + e^{\delta_1}}$$

$$P(\text{Non-infectious}) = \frac{1}{1 + e^{\delta_0} + e^{\delta_1}}$$

We define the hyper surface in the [C], [T], [P] space:

$$\frac{e^{\delta_1}}{1 + e^{\delta_0} + e^{\delta_1}} = \omega$$

that is used to distinguish between bacterial and non-bacterial patients. In one preferred embodiment. In other preferred embodiments. Given a patient's [C], [T], [P] values that patient is classified as bacterial if $$\frac{e^{\delta_1}}{1 + e^{\delta_0} + e^{\delta_1}} > \omega,$$

else he/she are classified as non-bacterial.

We define the set all hyper plains that can be used to distinguish between bacterial and non-bacterial infections as those that reside within the following two hyper surfaces:

$$\frac{e^{\delta_1}}{1 + e^{\delta_0} + e^{\delta_1}} = \omega + \epsilon_1$$

$$\frac{e^{\delta_1}}{1 + e^{\delta_0} + e^{\delta_1}} = \omega - \epsilon_0$$

$\epsilon_1$ can be any number between 0 and 1–. In some preferred embodiments $\epsilon_1$ is smaller then 0.5, 0.4, 0.3, 0.2 or 0.1.

$\epsilon_0$ can be any number between 0 and a. In some preferred embodiments $\epsilon_0$ is smaller then 0.5, 0.4, 0.3, 0.2 or 0.1.

Illustrated examples of surfaces are provided in Example 7.

Example 7

Graphical Representation Of Classification

Figure 20:
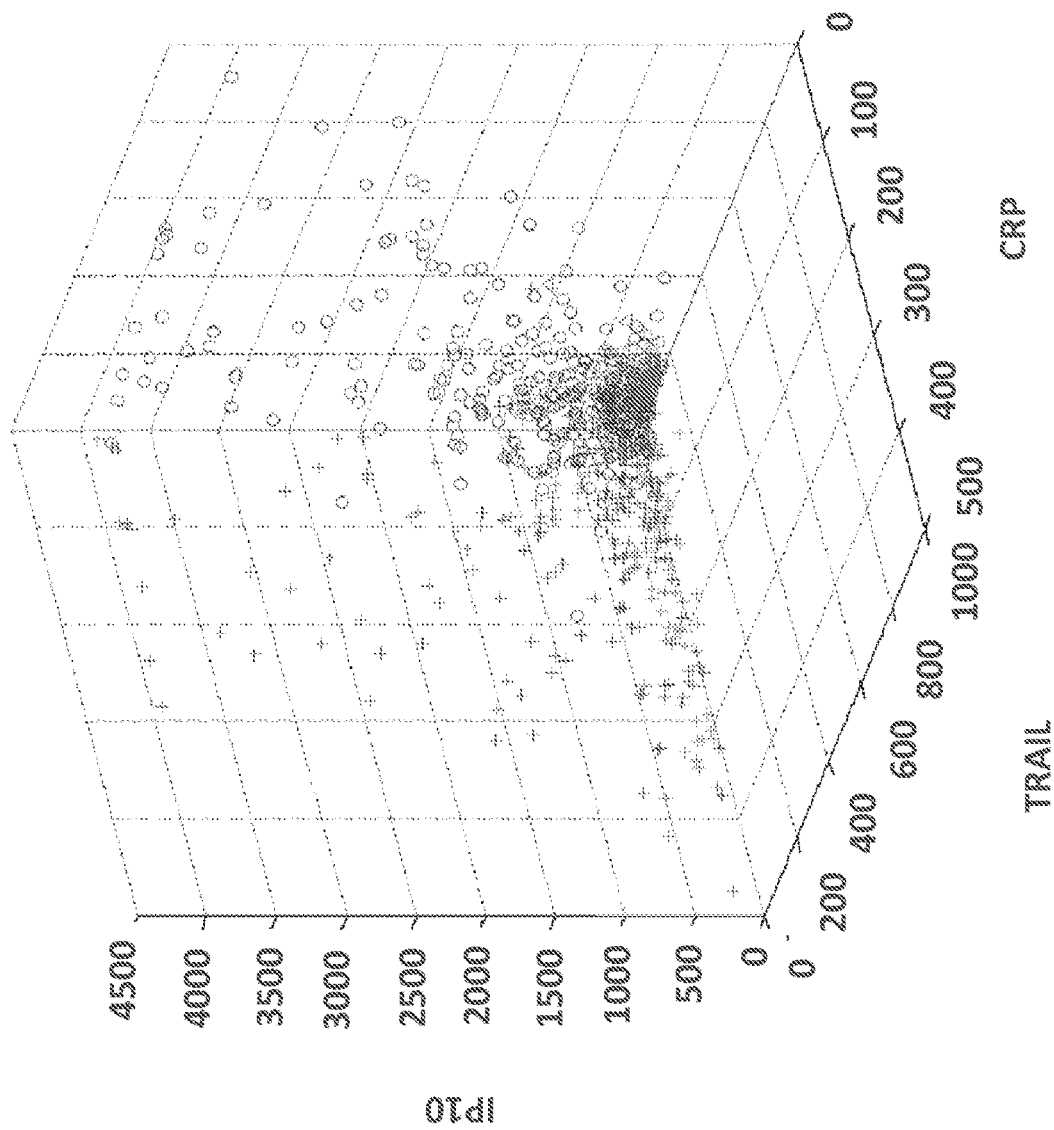
FIG. 20 is a 3-dimensional visualization of bacterial ('+'), viral ('o') and non-infectious ('^') patients. Different patients types are mapped to distinct regions in the CRP (pg/ml), TRAIL and IP-10 (pg/ml) concentration map.
Figure 29D:
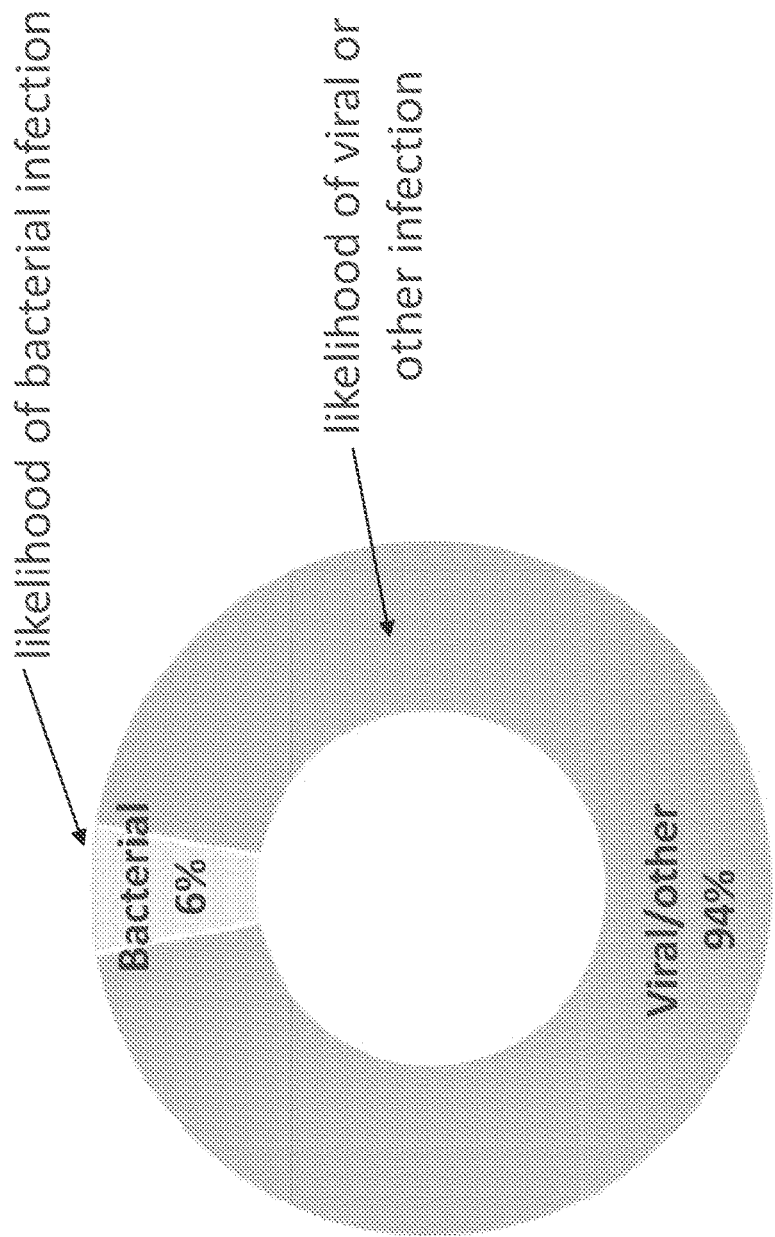
Figure 29E:
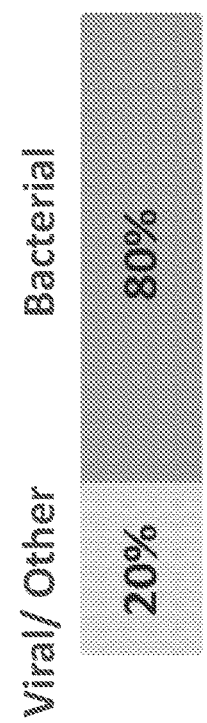
Figure 29F:

FIG. 20 is a 3-dimensional visualization of bacterial ('+'), viral ('o') and non-infectious ('^') patients. Different patients types are mapped to distinct regions in the CRP (pg/ml), TRAIL and IP-10 (pg/ml) concentration map.

By way of example probability surfaces were generated using a multinomial logistic regression. Contour plots of the surfaces are shown in FIGS. 21A-28C, as a function of TRAIL (y-axis), CRP (x-axis), and IP-10 concentrations. FIGS. 21A, 22A, 23A, 24A, 25A, 26A, 27A, 28A, show probabilities of viral infectious, FIGS. 21B, 22B, 23B, 24B, 25B, 26B, 27B, 28B, show probabilities of bacterial or mixed infectious, and FIGS. 21C, 22C, 23C, 24C, 25C, 26C, 27C, 28C, show probabilities of non-infectious or healthy. FIGS. 21A-21C correspond to $IP10_pg$ ranging from 0 to 100, FIGS. 22A-22C correspond to $IP10_pg$ ranging from 100 to 200, FIGS. 23A-23C correspond to $IP10_pg$ ranging from 200 to 300, FIGS. 24A-24C correspond to $IP10_pg$ ranging from 300 to 400, FIGS. 25A-25C correspond to $IP10_pg$ ranging from 400 to 500, FIGS. 26A-26C correspond to $IP10_pg$ ranging from 500 to 1000, FIGS. 27A-27C correspond to $IP10_pg$ ranging from 1000 to 2000 and FIGS. 28A-28C correspond to $IP10_pg$ which is 2000 or above.

Patients with bacterial or mixed are marked with a '+'; viral with a 'o' and non-infectious or healthy with a '^'. It can be seen in that low levels of IP-10 are associated with non-infectious disease, higher levels with bacterial and highest with viral. Low levels of TRAIL are associated with bacterial infections, higher with non-infectious and healthy, and highest with viral. Low levels of CRP are associated with non-infectious disease and healthy subjects, higher with viral infection and highest with bacterial. The combination of the three proteins generates a probability function whose diagnostic performance outperforms any of the individual or pairs of proteins.

FIGS. 35A-35D are contour plots describing the probability of bacterial (FIG. 35A), viral (FIG. 35B), non-bacterial (FIG. 35C), and non-infectious (FIG. 35D) etiologies as a function of the coordinates $\delta_0$ and $\delta_1$. The probability values range between 0% (black) to 100% (white).

Example 8

Exemplified Protocols for Measuring Expression Levels

In general, without limitation expression value of TRAIL can be measured using an ELISA or automated immunoassay; expression value of IP-10 can be measured using an ELISA assay; and expression value of CRP can be measured using an ELISA or automated immunoassay. The expression value of CRP can also be measured using a functional assay based on its calcium-dependent binding to phosphorylcholine.

Protocol A:

Suitable Protocol for Measuring an Expression Value of TRAIL
  (a) immobilize TRAIL present in a sample using an antibody to a solid support;
  (b) contact immobilized TRAIL with a second antibody that specifically binds to TRAIL; and
  (c) quantify the amount of antibody that binds to the immobilized TRAIL.

Suitable Protocol for Measuring an Expression Value of IP-10
  (a) immobilize IP-10 present in a sample using a capture antibody to a solid support;
  (b) contact immobilized IP-10 with a second antibody that specifically binds to IP-10; and
  (c) quantify the amount of antibody that binds to the immobilized IP-10.

Suitable Protocol for Measuring an Expression Value of CRP
  (a) immobilize CRP present in a sample using a capture antibody to a solid support;
  (b) contact immobilized CRP with a second antibody that specifically binds to I CRP; and
  (c) quantify the amount of antibody that binds to the immobilized CRP.

Protocol B:

Suitable Protocol for Measuring an Expression Value of TRAIL
  (a) Incubate a sample with a first antibody that specifically binds to TRAIL, wherein the said first antibody is immobilized to a solid phase;
  (b) Wash;
  (c) Add second antibody that specifically binds to TRAIL, wherein the second antibody is conjugated to an enzyme; wash
  (d) Add enzyme substrate and quantify the amount of antibody that binds to the immobilized sample.

Suitable Protocol for Measuring an Expression Value of IP-10
  (a) Incubate a sample with a first antibody that specifically binds to IP-10, wherein the said first antibody is immobilized to a solid phase;
  (b) Wash;
  (c) Add second antibody that specifically binds to IP-10, wherein the second antibody is conjugated to an enzyme; wash
  (d) Add enzyme substrate and quantify the amount of antibody that binds to the immobilized sample.

Suitable Protocol for Measuring an Expression Value of CRP
  (a) Incubate a sample with a first antibody that specifically binds to CRP, wherein the said first antibody is immobilized to a solid phase;
  (b) Wash;
  (c) Add second antibody that specifically binds to CRP, wherein the second antibody is conjugated to an enzyme; wash
  (d) Add enzyme substrate and quantify the amount of antibody that binds to the immobilized sample.

Protocol C:

Suitable Protocol for Measuring an Expression Value of CRP
  (a) measure the turbidity of a mixture of lipids;
  (b) contact sample with a known amount of the lipids (preferably phosphorylcholine) in the presence of Calcium; and
  (c) measure the turbidity of the solution, wherein increase in turbidity correlates with the amount of CRP.

Example 9

Detailed Description of ELISA for Analyzing the Amount of TRAIL and IP-10

Sample collection and storage: Exposure of samples to room temperature should be minimized (less than 6 hours). A serum separator tube (SST) is used and the samples are allowed to clot for at least 30 minutes before centrifugation (5 minutes at 1200×g). Serum may be assayed immediately, or aliquoted and stored at 4-8° C. for up to 24 hours or at ≤−20° C. for up to 3 months. Repeated freeze-thaw cycles should be avoided.

Reagent preparation: All reagents should be brought to room temperature before use.

Substrate solution: Color Reagents A and B should be mixed together in equal volumes within 10 minutes of use. Protect from light.

QC-1V, QC-2B and Standards: Thaw all QC and Standards and remove 150 uL from each vial to a separate marked Polypropylene test tube. Move back to −20° C. immediately after use.

Trail Measurements:

The materials used for analyzing TRAIL are provided in Table 18, herein below.

TABLE 18

| Storage conditions | Description | Part |
|---|---|---|
| Store at 2-8° C. | 96 well microplate (12 strips of 8 wells) coated with anti-TRAIL antibody | TRAIL Microplate |
| | 21 ml of anti-TRAIL specific antibody conjugated to horseradish peroxidase with preservatives | TRAIL Conjugate |
| | 11 ml of a buffered protein base with preservatives | Assay diluent MM1S |
| | 21 mL of a 25-fold concentrated solution of buffered surfactant with preservative | Wash Buffer Concentrate |
| | 12 mL of stabilized hydrogen peroxide | Color reagent A |
| | 12 mL of tetramethylbenzidine (TMB) | Color reagent B |
| | 6 mL of 2N sulfuric acid | Stop solution |
| | 4 adhesive strips | Plate sealer |
| Store at −20° C. immediately after receiving. | 6 vials containing 0.7 ml of recombinant human TRAIL in buffered protein base with preservatives at the following concentrations 500, 250, 125, 62.5, 31.2 and 0 [pg/mL] | 6 TRAIL Standards |
| | 1 ml | QC-1V |
| | 1 ml | QC-2B |

TRAIL ELISA Procedure a) Prepare samples, reagents and standards as indicated above.
b) Remove excess microplate strips from the plate frame, return them to the foil pouch containing the desiccant pack, and reseal.
c) Add 50 μL of Assay Diluent MM1S to each well.
d) Add 50 μL of Standard, samples, or QC per well. Cover with the adhesive strip provided.
e) Incubate for 30 minutes at room temperature on a microplate shaker (3 mm orbit) set at 550 rpm.
f) Aspirate each well and wash, repeating the process 4 times. Wash by filling each well with Wash Buffer (300 μL). After the last wash, remove any remaining Wash Buffer by aspirating or decanting. Invert the plate and blot it against clean paper towels.
g) Add 200 μL of TRAIL Conjugate to each well. Cover with a new adhesive strip. Incubate for 45 minutes at room temperature on a microplate shaker (3 mm orbit) set at 550 rpm.
h) Repeat the aspiration/wash as in step (g).
i) Add 200 μL of Substrate solution to each well. Incubate for 24 to 30 minutes at room temperature. Protect from light.
j) Add 50 μL of Stop solution to each well. The color in the wells should change from blue to yellow. If the color in the wells is green or the color change does not appear uniform, gently tap the plate to ensure thorough mixing.
k) Determine the optical density of each well immediately, using a microplate reader set to 450 nm. Set wavelength correction to 570 nm, which will correct for optical imperfections in the plate.

TRAIL calculation of concentrations: Average the duplicate readings for each sample and subtract the average zero standard optical density (O.D.). Create a standard curve by plotting the mean absorbance for each standard (γ-axis) against the concentration (x-axis) and draw a best-fit linear curve. The minimal $r^2$ should not fall below 0.96. In case lower $r^2$ values are present, repeat the experiment to get reliable results.

Precision: Precision was evaluated based on the CLSI (formerly NCCLS) EP05-A2 guidelines. Three samples with concentrations at the low (11.4pg/ml), intermediate (58.8 pg/ml), and high (539.0 pg/ml) physiological concentrations were used to assess precision. Results are summarized in Table 19, where $S_r$ is within-run precision and $S_T$ is within-device precision:

TABLE 19

| High (539.0 pg/ml) | Medium (58.8 pg/ml) | Low (11.4 pg/ml) | |
|---|---|---|---|
| 18 | 18 | 18 | # of runs |
| 36 | 36 | 36 | # of duplicates |
| 13.2 | 2.45 | 0.84 | $S_r$ pg/mL |
| 2.5% | 4.2% | 7.3% | $S_r$ CV (%) |
| 29.7 | 3.6 | 1.3 | $S_T$ pg/mL |
| 5.5% | 6.1% | 11.5% | $S_T$ CV (%) |

Recovery: Recovery was evaluated by spiking three levels of human recombinant TRAIL (250, 125 and 62.5pg/mL) into 5 human serum samples with no detectable levels of TRAIL. The spiked values and the average recovery was then measured and calculated, as shown in Table 20 below.

TABLE 20

| Range | Average % Recovery | Sample |
|---|---|---|
| 75-78% | 77% | Serum (n = 5) |

Linearity: To assess the linearity of the assay, five clinical samples containing high concentrations of TRAIL were serially diluted using a serum substitute to produce samples with values within the physiological range of the assay. Linearity was, on average, 97%, 100% and 105% for 1:2, 1:4 and 1:8 dilutions, respectively, as summarized in Table 21 below.

TABLE 21

| Serum (n = 5) | | |
|---|---|---|
| 97% | Average % of expected | 1:2 |
| 90-104% | Range % | |
| 100% | Average % of expected | 1:4 |
| 90-108% | Range % | |
| 105% | Average % of expected | 1:8 |
| 90-121% | Range % | |

Sensitivity: To estimate the Limitation of Blank (LOB), we tested 72 blank samples of serum substitute. The mean of the blank samples was 0.78 pg/ml and the standard deviation was 1.39 pg/ml. Therefore, the calculated LOB is 3.07 pg/ml. To estimate the Limitation of Detection (LOD), the CLSI EP17-A guidelines were followed. Briefly, the measurement distribution around seven predetermined concentrations were characterized, each with 30 independent measurements (210 measurements) yielding an LOD of 10 pg/ml.

Calibration: This immunoassay is calibrated against a purified NS0-expressed recombinant human TRAIL.

Expected values: Samples from apparently healthy adult (>18 years) were measured for the presence of TRAIL. The range and mean values are summarized in Table 22.

TABLE 22

| Range pg/ml | Mean pg/ml | Sample Type |
|---|---|---|
| 17-157 | 90 | Serum (n = 34) |

Cross reactivity and interference: This assay recognizes natural and recombinant human TRAIL. The factors 4-1BB Ligand, APRIL, BAFF/BLyS, CD27 Ligand, CD30 Ligand, CD40 Ligand, Fas Ligand, GITR Ligand, LIGHT, LT α1/β2, LT α2/β1, OPG, OX40 Ligand, TNF-α, TNF-β, TRAIL R3, TRAIL R4, TRANCE and TWEAK were prepared at 50 ng/mL in serum substitution and assayed for cross-reactivity. Additionally, preparations of these factors at 50 pg/mL in a mid-range recombinant human TRAIL control were tested for interference. No significant cross-reactivity or interference was observed.

IP-10 measurements: The materials used for analyzing IP-10 are provided in Table 23, herein below.

e) Incubate for 30 minutes at room temperature on a microplate shaker (3 mm orbit) set at 550 rpm.

f) Aspirate each well and wash, repeating the process 4 times. Wash by filling each well with Wash Buffer (300 μL). After the last wash, remove any remaining Wash Buffer by aspirating or decanting. Invert the plate and blot it against clean paper towels.

g) Add 200 μL of IP-10 Conjugate to each well. Cover with a new adhesive strip. Incubate for 45 minutes at room temperature on a microplate shaker (3 mm orbit) set at 550 rpm.

h) Repeat the aspiration/wash as in step (g).

i) Add 200 μL of Substrate solution to each well. Incubate for 10 minutes at room temperature. Protect from light.

j) Add 50 μL of Stop solution to each well. The color in the wells should change from blue to yellow. If the color in the wells is green or the color change does not appear uniform, gently tap the plate to ensure thorough mixing.

k) Determine the optical density of each well immediately, using a microplate reader set to 450 nm. Set wavelength correction to 570 nm, which will correct for optical imperfections in the plate.

IP-10 calculation of concentrations: Average the duplicate readings for each sample and subtract the average zero standard optical density (O.D.). Create a standard curve by plotting the mean absorbance for each standard (y-axis) against the concentration (x-axis) and draw a best-fit linear curve. The minimal $r^2$ should not fall below 0.96. In case

TABLE 23

| Storage conditions | Description | Part |
|---|---|---|
| Store at 2-8° C. | 96 well microplate (12 strips of 8 wells) coated with anti-IP-10 antibody | IP-10 Microplate |
| | 21 ml of anti-IP-10 specific antibody conjugated to horseradish peroxidase with preservatives | IP-10 Conjugate |
| | 11 ml of a buffered protein base with preservatives | Assay diluent MM56 |
| | 21 mL of a 25-fold concentrated solution of buffered surfactant with preservative | Wash Buffer Concentrate |
| | 12 mL of stabilized hydrogen peroxide | Color reagent A |
| | 12 mL of tetramethylbenzidine (TMB) | Color reagent B |
| | 6 mL of 2N sulfuric acid | Stop solution |
| | 4 adhesive strips | Plate sealer |
| Store at −20° C. immediately after receiving | 6 vials containing 0.7 ml of recombinant human IP-10 in buffered protein base with preservatives at the following concentrations 1000, 500, 250, 125, 62.5 and 0 [pg/mL] | 6 IP-10 Standards |
| | 1 ml | QC-1V |
| | 1 ml | QC-2B |

IP-10 ELISA Procedure a) Prepare samples, reagents and standards as indicated herein above.

b) Remove excess microplate strips from the plate frame, return them to the foil pouch containing the desiccant pack, and reseal.

c) Add 50 μL of Assay Diluent MM56 to each well.

d) Add 50 μL of Standard, sample or QC per well. Cover with the adhesive strip provided.

lower $r^2$ values are present, repeat the experiment to get reliable results.

Precision: Precision was evaluated based on the CLSI (formerly NCCLS) EP05-A2 guidelines. Three samples with concentrations at the low (69.4 pg/ml), intermediate (228.2 pg/ml), and high (641.5 pg/ml) physiological concentrations were used to assess precision. Results are summarized in Table 24 where $S_r$ is within-run precision and $S_T$ is within-device precision:

TABLE 24

| High (641.5 pg/ml) | Medium (228.2 pg/ml) | Low (69.4 pg/ml) | |
|---|---|---|---|
| 18 | 18 | 18 | # of runs |
| 36 | 36 | 36 | # of duplicates |
| 21.1 | 5.6 | 4.0 | $S_r$ pg/mL |
| 3.3% | 2.4% | 5.8% | $S_r$ CV (%) |
| 37.2 | 12.9 | 4.9 | $S_T$ pg/mL |
| 5.8% | 5.7% | 7.1% | $S_T$ CV (%) |

Recovery: Recovery was evaluated by spiking three levels of human IP-10, 500, 250 and 125pg/mL into 5 human serum samples with no detectable levels of IP-10. The spiked values and the average recovery was than measured and calculated as illustrated in Table 25 below.

TABLE 25

| Range | Average % Recovery | Sample |
|---|---|---|
| 72-80% | 77 | Serum/plasma (n = 5) |

Linearity: To assess the linearity of the IP-10 assay, 5 clinical samples containing high concentrations of IP-10 ranging between 873.7 to 1110.4 pg/mL were serially diluted with a serum substitute to produce samples with values within the physiological range of the assay. Linearity was, on average, 98%, 102% and 104% in 1:2, 1:4 and 1:8 dilutions, respectively, as summarized in Table 26 herein below.

TABLE 26

| Serum (n = 5) | | |
|---|---|---|
| 98% | Average % of expected | 1:2 |
| 93-102% | Range % | |
| 102% | Average % of expected | 1:4 |
| 97-107% | Range % | |
| 104% | Average % of expected | 1:8 |
| 96-111% | Range % | |

Sensitivity: To estimate the Limitation of Blank (LOB), we tested 72 blank samples of serum substitute. The mean of the blank samples was 0.23 pg/ml and the standard deviation was 1.26 pg/ml, yielding an LOB of 2.29 pg/ml.

To estimate the Limitation of Detection (LOD), the CLSI EP17-A guidelines were applied. Briefly, the measurement distribution around seven predetermined concentrations were characterized, each with 30 independent measurements (210 measurements) yielding an LOD of 10pg/ml.

Calibration: This immunoassay is calibrated against a highly purified E-coli-expressed recombinant human IP-10.

Expected values: Samples from apparently healthy adult volunteers were measured for the presence of IP-10. The range and mean values are shown in Table 27 below.

TABLE 27

| Range pg/ml | Mean pg/ml | Sample Type |
|---|---|---|
| 29-525 | 119 | Serum (n = 34) |

Cross reactivity and interference: This assay recognizes natural and recombinant human IP-10. The factors BLC/BCA-1, ENA-78, GCP-2, GROα, GRO γ, IFN-γ, IL-8, I-TAC, MIG, NAP-2, SDF-1α and SDF-1β were prepared at 50 ng/mL in serum substitution and assayed for cross-reactivity. Additionally, preparations of these factors at 50 pg/mL in a mid-range recombinant human IP-10 control were tested for interference. No significant cross-reactivity or interference was observed.

Example 10

Trail and Disease Prognosis

It is often clinically useful to assess patient prognosis, disease severity and outcome. The present inventors found that low levels of TRAIL are significantly correlated with poor patient prognosis and outcome, and high disease severity. For example, adult patients in the intensive care unit (ICU) had significantly lower TRAIL levels compared to all other patients, which were less ill regardless of whether they had an infectious or non-infectious etiology. Median serum concentrations were 9pg/ml vs. 80pg respectively, (ranksum P<0.001, FIG. 36A), for severely ill and all other patients respectively.

Figure 36B:
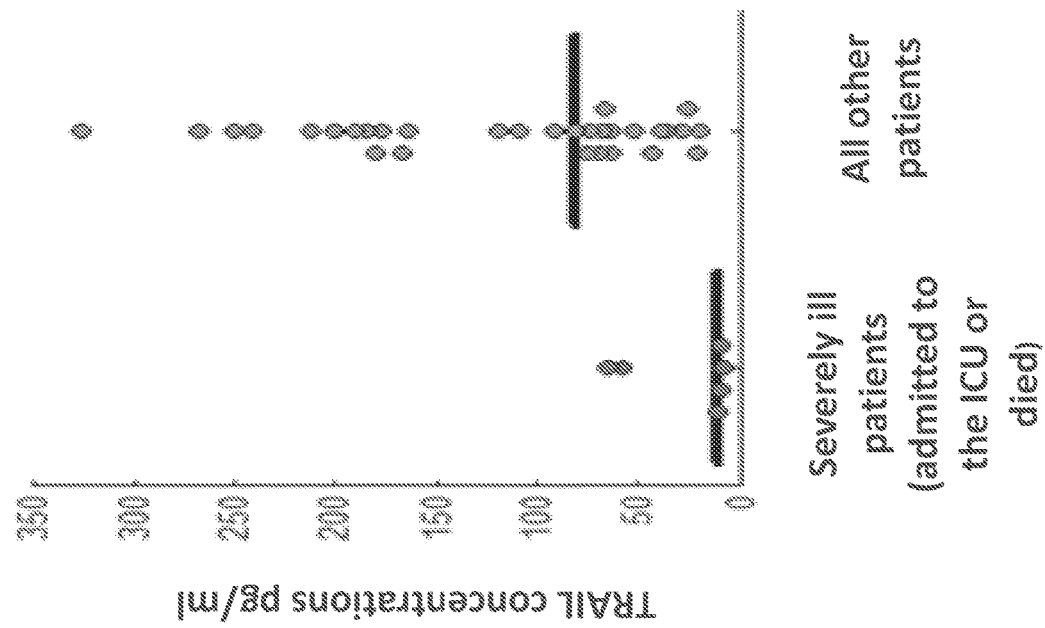
FIGS. 36A-36B. Low TRAIL levels are indicative or poor patient prognosis and outcome and high disease severity. (A) TRAIL concentrations in the serum of patients that were admitted to the ICU compared to all other patients (with infectious or non-infectious etiology). (B) TRAIL concentrations in the serum of pediatric patients that were admitted to the ICU or died compared to all other patients with infectious or non-infectious etiology.
Figure 36A:
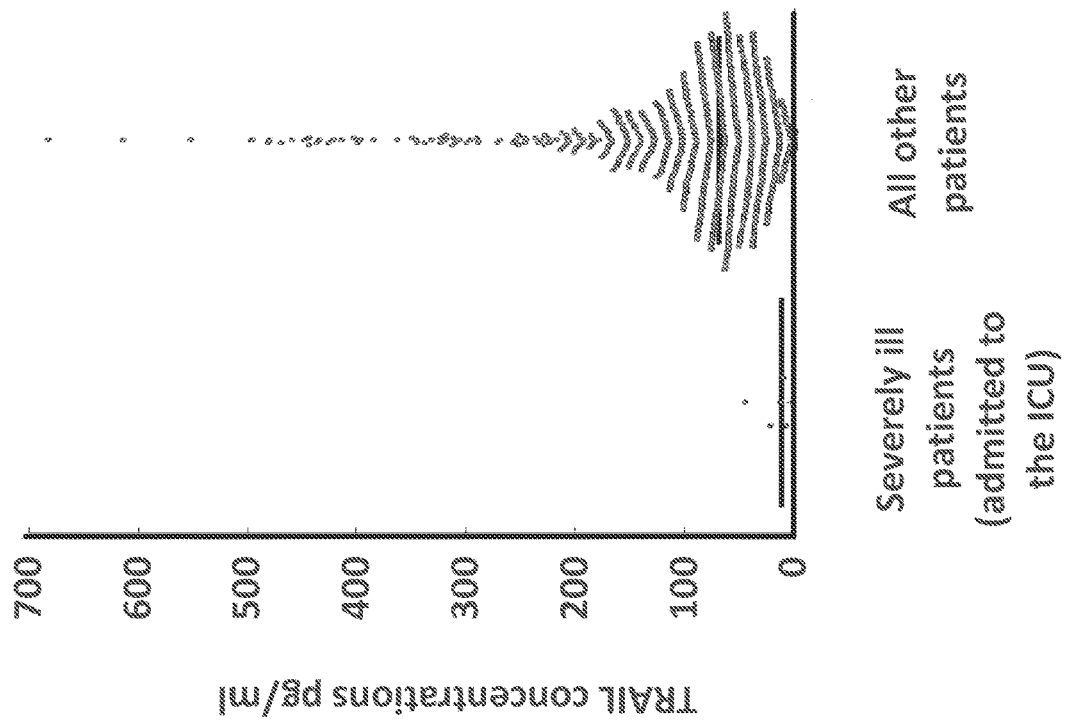

40 Dutch pediatric patients, 3 months to 5 years of age. The TRAIL serum level was measured in 40 Dutch pediatric patients, 3 months to 5 years of age. It was found that those patients that were eventually admitted to the ICU (an indication of disease complication and poor prognosis) or even died had significantly lower TRAIL serum concentrations compared to the rest of the patients (median of 11 vs. 85, respectively; ranksum P<0.001) as depicted in FIG. 36B. Strikingly, the lowest TRAIL levels (≤5 pgml) were measured in the only two children that died in the entire cohort. These results indicate that TRAIL could be used as a prognostic marker for predicting disease severity and outcome.

Example 11

Trail Age and Gender Parameters

Basal levels of TRAIL in healthy individuals or patients with a non-infectious disease are lower in females compared to males during fertility age (t-test P<0.001) (FIG. 37A), but is invariant in pre- or post-fertility age (t-test P=0.9, FIG. 37B). This trend was not observed in patients with an infectious disease.

Example 12

Exemplified Manifolds, Hyperplanes and Coordinates
One-Dimensional Manifold

When n=1, the manifold S is a curved line and the hyperplane π is an axis defining a single direction $\underline{\delta}_1$. The coordinate $\delta_1$ in this Example is optionally and preferably a linear combination $b_0+b_1D_1+b_2D_2+\ldots$, of the polypeptides $D_1, D_2$, etc.

Table 28 below lists diagnostic performance (in AUCs) attained for n=1. The performance were computed using a leave-10%-out cross validation on the cohort specified in each row. In rows 1-4, the analyzed subjects had either bacterial or viral infections and the coordinate $\delta_1$ was calculated so that the probabilistic classification function $f(\delta_1)$ represented the likelihood that the test subject had a bacterial infection. In rows 5-8, the analyzed subjects were infectious or non-infections and the coordinate $\delta_1$ was calculated so that the probabilistic classification function $f(\delta_1)$ represented the likelihood that the test subject had an infection. In rows 10-12, the analyzed subjects had either bacterial or non-bacterial infection and the coordinate $\delta_1$ was calculated so that the probabilistic classification function $f(\delta_1)$ represented the likelihood that the test subject had a bacterial infection. In rows 1-4, the columns P and N correspond to the number of Bacterial and Viral patients respectively, in rows 5-8, the columns P and N correspond to the number of infectious and non-infectious patients, respectively, and in rows 9-12, the columns P and N correspond to the number Bacterial and non-Bacterial patients respectively. Majority and Consensus indicate the type of cohort on which the model was validated.

TABLE 28

| N | P | AUC | Polypeptides | | | Cohort | No. |
|---|---|---|---|---|---|---|---|
| 334 | 319 | 0.93 |  | TRAIL | CRP | Majority | 1 |
| 334 | 319 | 0.94 | TRAIL | IP-10 | CRP | Majority | 2 |
| 271 | 256 | 0.95 |  | TRAIL | CRP | Consensus | 3 |
| 271 | 256 | 0.96 | TRAIL | IP-10 | CRP | Consensus | 4 |
| 112 | 653 | 0.93 |  | TRAIL | CRP | Majority | 5 |
| 112 | 653 | 0.96 | TRAIL | IP-10 | CRP | Majority | 6 |
| 112 | 527 | 0.93 |  | TRAIL | CRP | Consensus | 7 |
| 112 | 527 | 0.97 | TRAIL | IP-10 | CRP | Consensus | 8 |
| 446 | 319 | 0.94 |  | TRAIL | CRP | Majority | 9 |
| 446 | 319 | 0.94 | TRAIL | IP-10 | CRP | Majority | 10 |
| 383 | 256 | 0.95 |  | TRAIL | CRP | Consensus | 11 |
| 383 | 256 | 0.96 | TRAIL | IP-10 | CRP | Consensus | 12 |

Table 29 below lists the coefficients $b_0$, $b_1$, $b_2$, etc that were used to define the coordinate $\delta_1$, for each of the 12 cases listed in Table 28, respectively. The first coefficient on the left is $b_0$, and then from left to right, the coefficients correspond to the order of the polypeptides in each row of Table 28. The coefficients correspond to the following concentration scales for each polypeptide: TRAIL (pg/ml), IP-10 (pg/ml) and CRP (ug/ml).

For a given set of polypeptides, the obtained coefficients have small variations among the different cohorts. Nevertheless, the coefficients for the probabilistic classification functions and coordinates of the present embodiments preferably correspond to those obtained for the Majority Cohort.

TABLE 29

| Coefficients | | | | No. |
|---|---|---|---|---|
|  | −0.029953 | 0.027472 | 0.64814 | 1 |
| −0.029013 | −0.00028168 | 0.028119 | 0.71542 | 2 |
|  | −0.033669 | 0.034565 | 0.636 | 3 |
| −0.03195 | −0.00058691 | 0.035748 | 0.79543 | 4 |
|  | 0.016837 | 0.17237 | −2.0549 | 5 |
| 0.005213 | 0.00592 | 0.1263 | −2.3344 | 6 |
|  | 0.018624 | 0.16625 | −2.3469 | 7 |
| 0.0079169 | 0.0061124 | 0.12261 | −2.7949 | 8 |
|  | −0.027839 | 0.034954 | −0.08503 | 9 |
| −0.027916 | 2.2524e−05 | 0.034878 | −0.088207 | 10 |
|  | −0.030997 | 0.044289 | −0.26606 | 11 |
| −0.03042 | −0.00018635 | 0.044938 | −0.23907 | 12 |

Table 30 below lists diagnostic performance (in AUCs) attained for one-dimensional manifold. The performance were computed using a leave-10%-out cross validation on the Majority cohort. In rows 1-55, the analyzed subjects had either bacterial or viral infections and the probabilistic classification function $f(\delta_1)$ represented the likelihood that the test subject had a bacterial infection. In rows 56-110, the analyzed subjects were infectious or non-infections and the probabilistic classification function $f(\delta_1)$ represented the likelihood that the test subject had an infection. In rows 1-55, the columns P and N correspond to the number of Bacterial and Viral patients respectively, and in rows 56-110, the columns P and N correspond to the number of infectious and noninfectious patients respectively.

TABLE 30

| N | P | AUC | Polypeptides | | | | No. |
|---|---|---|---|---|---|---|---|
| 141 | 142 | 0.88 |  |  |  | IL1ra | CRP | 1 |
| 299 | 295 | 0.90 |  |  |  | IP-10 | CRP | 2 |
| 50 | 51 | 0.87 |  |  |  | PCT | CRP | 3 |
| 241 | 255 | 0.90 |  |  |  | SAA | CRP | 4 |
| 142 | 142 | 0.64 |  |  |  | IP-10 | IL1ra | 5 |
| 14 | 19 | 0.62 |  |  |  | PCT | IL1ra | 6 |
| 122 | 124 | 0.83 |  |  |  | SAA | IL1ra | 7 |
| 142 | 142 | 0.88 |  |  |  | TRAIL | IL1ra | 8 |
| 49 | 51 | 0.74 |  |  |  | PCT | IP-10 | 9 |
| 242 | 251 | 0.85 |  |  |  | SAA | IP-10 | 10 |
| 297 | 295 | 0.88 |  |  |  | TRAIL | IP-10 | 11 |
| 40 | 45 | 0.78 |  |  |  | SAA | PCT | 12 |
| 50 | 51 | 0.87 |  |  |  | TRAIL | PCT | 13 |
| 244 | 255 | 0.90 |  |  |  | TRAIL | SAA | 14 |
| 141 | 142 | 0.90 |  |  | IP-10 | IL1ra | CRP | 15 |
| 14 | 19 | 0.82 |  |  | PCT | IL1ra | CRP | 16 |
| 121 | 124 | 0.89 |  |  | SAA | IL1ra | CRP | 17 |
| 141 | 142 | 0.94 |  |  | TRAIL | IL1ra | CRP | 18 |
| 49 | 51 | 0.89 |  |  | PCT | IP-10 | CRP | 19 |
| 239 | 251 | 0.91 |  |  | SAA | IP-10 | CRP | 20 |
| 40 | 45 | 0.88 |  |  | SAA | PCT | CRP | 21 |
| 50 | 51 | 0.93 |  |  | TRAIL | PCT | CRP | 22 |
| 241 | 255 | 0.94 |  |  | TRAIL | SAA | CRP | 23 |
| 14 | 19 | 0.62 |  |  | PCT | IP-10 | IL1ra | 24 |
| 122 | 124 | 0.85 |  |  | SAA | IP-10 | IL1ra | 25 |
| 142 | 142 | 0.88 |  |  | TRAIL | IP-10 | IL1ra | 26 |
| 13 | 17 | 0.76 |  |  | SAA | PCT | IL1ra | 27 |
| 14 | 19 | 0.71 |  |  | TRAIL | PCT | IL1ra | 28 |
| 122 | 124 | 0.92 |  |  | TRAIL | SAA | IL1ra | 29 |
| 39 | 45 | 0.81 |  |  | SAA | PCT | IP-10 | 30 |
| 49 | 51 | 0.86 |  |  | TRAIL | PCT | IP-10 | 31 |
| 242 | 251 | 0.91 |  |  | TRAIL | SAA | IP-10 | 32 |
| 40 | 45 | 0.86 |  |  | TRAIL | SAA | PCT | 33 |
| 14 | 19 | 0.83 |  | PCT | IP-10 | IL1ra | CRP | 34 |
| 121 | 124 | 0.92 |  | SAA | IP-10 | IL1ra | CRP | 35 |
| 141 | 142 | 0.94 |  | TRAIL | IP-10 | IL1ra | CRP | 36 |
| 13 | 17 | 0.74 |  | SAA | PCT | IL1ra | CRP | 37 |
| 14 | 19 | 0.90 |  | TRAIL | PCT | IL1ra | CRP | 38 |
| 121 | 124 | 0.94 |  | TRAIL | SAA | IL1ra | CRP | 39 |
| 39 | 45 | 0.88 |  | SAA | PCT | IP-10 | CRP | 40 |
| 49 | 51 | 0.92 |  | TRAIL | PCT | IP-10 | CRP | 41 |
| 239 | 251 | 0.94 |  | TRAIL | SAA | IP-10 | CRP | 42 |
| 40 | 45 | 0.92 |  | TRAIL | SAA | PCT | CRP | 43 |
| 13 | 17 | 0.70 |  | SAA | PCT | IP-10 | IL1ra | 44 |
| 14 | 19 | 0.70 |  | TRAIL | PCT | IP-10 | IL1ra | 45 |
| 122 | 124 | 0.91 |  | TRAIL | SAA | IP-10 | IL1ra | 46 |
| 13 | 17 | 0.82 |  | TRAIL | SAA | PCT | IL1ra | 47 |
| 39 | 45 | 0.85 |  | TRAIL | SAA | PCT | IP-10 | 48 |
| 13 | 17 | 0.82 | SAA | PCT | IP-10 | IL1ra | CRP | 49 |
| 14 | 19 | 0.75 | TRAIL | PCT | IP-10 | IL1ra | CRP | 50 |
| 121 | 124 | 0.94 | TRAIL | SAA | IP-10 | IL1ra | CRP | 51 |
| 13 | 17 | 0.78 | TRAIL | SAA | PCT | IL1ra | CRP | 52 |
| 39 | 45 | 0.92 | TRAIL | SAA | PCT | IP-10 | CRP | 53 |
| 13 | 17 | 0.62 | TRAIL | SAA | PCT | IP-10 | IL1ra | 54 |
| 13 | 17 | 0.74 | TRAIL | SAA | PCT | IP-10 | IL1ra | CRP | 55 |
| 87 | 283 | 0.91 |  |  |  | IL1ra | CRP | 56 |
| 102 | 594 | 0.96 |  |  |  | IP-10 | CRP | 57 |
| 6 | 101 | 0.85 |  |  |  | PCT | CRP | 58 |
| 78 | 496 | 0.91 |  |  |  | SAA | CRP | 59 |
| 87 | 284 | 0.89 |  |  |  | IP-10 | IL1ra | 60 |
| 6 | 33 | 0.79 |  |  |  | PCT | IL1ra | 61 |
| 64 | 246 | 0.91 |  |  |  | SAA | IL1ra | 62 |
| 87 | 284 | 0.86 |  |  |  | TRAIL | IL1ra | 63 |
| 6 | 100 | 0.73 |  |  |  | PCT | IP-10 | 64 |
| 81 | 493 | 0.96 |  |  |  | SAA | IP-10 | 65 |
| 107 | 592 | 0.91 |  |  |  | TRAIL | IP-10 | 66 |
| 3 | 85 | 0.89 |  |  |  | SAA | PCT | 67 |
| 7 | 101 | 0.60 |  |  |  | TRAIL | PCT | 68 |
| 81 | 499 | 0.93 |  |  |  | TRAIL | SAA | 69 |
| 87 | 283 | 0.95 |  |  | IP-10 | IL1ra | CRP | 70 |
| 6 | 33 | 0.76 |  |  | PCT | IL1ra | CRP | 71 |
| 64 | 245 | 0.92 |  |  | SAA | IL1ra | CRP | 72 |
| 87 | 283 | 0.93 |  |  | TRAIL | IL1ra | CRP | 73 |
| 6 | 100 | 0.81 |  |  | PCT | IP-10 | CRP | 74 |

TABLE 30-continued

| N | P | AUC | Polypeptides | | | | | No. |
|---|---|---|---|---|---|---|---|---|
| 78 | 490 | 0.97 | | | SAA | IP-10 | CRP | 75 |
| 3 | 85 | 0.88 | | | SAA | PCT | CRP | 76 |
| 6 | 101 | 0.87 | | | TRAIL | PCT | CRP | 77 |
| 78 | 496 | 0.95 | | | TRAIL | SAA | CRP | 78 |
| 6 | 33 | 0.77 | | | PCT | IP-10 | IL1ra | 79 |
| 64 | 246 | 0.94 | | | SAA | IP-10 | IL1ra | 80 |
| 87 | 284 | 0.90 | | | TRAIL | IP-10 | IL1ra | 81 |
| 3 | 30 | 0.72 | | | SAA | PCT | IL1ra | 82 |
| 6 | 33 | 0.67 | | | TRAIL | PCT | IL1ra | 83 |
| 64 | 246 | 0.90 | | | TRAIL | SAA | IL1ra | 84 |
| 3 | 84 | 0.98 | | | SAA | PCT | IP-10 | 85 |
| 6 | 100 | 0.68 | | | TRAIL | PCT | IP-10 | 86 |
| 81 | 493 | 0.96 | | | TRAIL | SAA | IP-10 | 87 |
| 3 | 85 | 0.98 | | | TRAIL | SAA | PCT | 88 |
| 6 | 33 | 0.77 | | PCT | IP-10 | IL1ra | CRP | 89 |
| 64 | 245 | 0.95 | | SAA | IP-10 | IL1ra | CRP | 90 |
| 87 | 283 | 0.95 | | TRAIL | IP-10 | IL1ra | CRP | 91 |
| 3 | 30 | 0.73 | | SAA | PCT | IL1ra | CRP | 92 |
| 6 | 33 | 0.74 | | TRAIL | PCT | IL1ra | CRP | 93 |
| 64 | 245 | 0.92 | | TRAIL | SAA | IL1ra | CRP | 94 |
| 3 | 84 | 0.98 | | SAA | PCT | IP-10 | CRP | 95 |
| 6 | 100 | 0.77 | | TRAIL | PCT | IP-10 | CRP | 96 |
| 78 | 490 | 0.97 | | TRAIL | SAA | IP-10 | CRP | 97 |
| 3 | 85 | 0.80 | | TRAIL | SAA | PCT | CRP | 98 |
| 3 | 30 | 0.91 | | SAA | PCT | IP-10 | IL1ra | 99 |
| 6 | 33 | 0.67 | | TRAIL | PCT | IP-10 | IL1ra | 100 |
| 64 | 246 | 0.94 | | TRAIL | SAA | IP-10 | IL1ra | 101 |
| 3 | 30 | 0.78 | | TRAIL | SAA | PCT | IL1ra | 102 |
| 3 | 84 | 0.65 | | TRAIL | SAA | PCT | IP-10 | 103 |
| 3 | 30 | 0.91 | SAA | PCT | IP-10 | IL1ra | CRP | 104 |
| 6 | 33 | 0.66 | TRAIL | PCT | IP-10 | IL1ra | CRP | 105 |
| 64 | 245 | 0.95 | TRAIL | SAA | IP-10 | IL1ra | CRP | 106 |
| 3 | 30 | 0.73 | TRAIL | SAA | PCT | IL1ra | CRP | 107 |
| 3 | 84 | 0.97 | TRAIL | SAA | PCT | IP-10 | CRP | 108 |
| 3 | 30 | 0.78 | TRAIL | SAA | PCT | IP-10 | IL1ra | 109 |
| 3 | 30 | 0.73 | TRAIL | SAA | PCT | IP-10 | IL1ra | CRP 110 |

Table 31 below list the coefficients $b_0, b_1, b_2$, etc that were used to define the coordinate $\delta_1$, for each of the 110 cases listed in Table 30, respectively. The first coefficient on the left is $b_0$, and then from left to right, the coefficients correspond to the order of the polypeptides in each row of Table 30. The coefficients correspond to the following concentration scales for each polypeptide: TRAIL (pg/ml), IP-10 (pg/ml), CRP (ug/ml), PCT (ng/ml), SAA (g/ml) and IL1ra (g/ml).

TABLE 31

| Coefficients | | | | | No. |
|---|---|---|---|---|---|
| | | | -9849178.8 | 0.0363 | -1.997 | 1 |
| | | | -0.0009 | 0.039722 | -1.6069 | 2 |
| | | | 0.6405 | 0.054137 | -2.9681 | 3 |
| | | | 1098.3777 | 0.034353 | -2.33196 | 4 |
| | | | -0.00089 | 47954608.09 | 0.4715979 | 5 |
| | | | 4.5607 | -69280395.624 | -0.74822 | 6 |
| | | | 5283.68 | -33345728.8342 | -1.706206 | 7 |
| | | | -0.03151 | 43833567.7377 | 3.0601663 | 8 |
| | | | 0.86013 | -0.00060898 | -0.13268 | 9 |
| | | | 4677.8311 | -0.0009684361 | -1.01872 | 10 |
| | | | -0.0288 | 0.00031349 | 2.5632 | 11 |
| | | | 2349.8702 | 1.1895403 | -1.35195 | 12 |
| | | | -0.019169 | 0.4382 | 1.4742 | 13 |
| | | | -0.02176 | 2962.7685 | 1.08972 | 14 |
| | | -0.00165 | 6.264E+7 | 0.039986 | -1.27532 | 15 |
| | | 1.07655 | -8.42E+7 | 0.0475326 | -2.3376 | 16 |
| | | 2098.4 | -2.22E+7 | 0.027867 | -2.23709 | 17 |
| | | -0.0266 | 2.0497E+7 | 0.030146 | 0.9001561 | 18 |
| | | 0.65349 | -0.0005 | 0.051698 | -2.5383 | 19 |
| | | 1378.2 | -0.00109 | 0.034481544 | -1.6940577 | 20 |
| | | -1243.01 | 1.4735726 | 0.054245413 | -2.7487888 | 21 |
| | | -0.010529 | 0.42793 | 0.04535 | -1.421 | 22 |
| | | -0.01891 | 183.3117 | 0.0312776 | 0.1044034 | 23 |
| | | 4.8755 | -0.001241 | -4107077 | -0.0013248 | 24 |
| | | 5777 | -0.001377 | 21179055 | -1.054077 | 25 |
| | | -0.03151 | -1.118-06 | 43882108 | 3.0605 | 26 |
| | | 4823 | 2.91 | -68741718 | -1.9806377 | 27 |
| | | -0.0342 | 1.941 | 113905139.6 | 2.844483 | 28 |
| | | -0.0264 | 3745.49 | -7296968.1 | 1.4399 | 29 |
| | | 2427.6 | 1.3263344 | -0.000765 | -0.8562752 | 30 |
| | | -0.020588 | 0.38993 | 0.00045394 | 1.357 | 31 |
| | | -0.021174 | 3048.4182 | -0.000163 | 1.0917705 | 32 |
| | | -0.013629 | 1431.011 | 0.89320046 | 0.48274 | 33 |
| | 1.5 | -0.003888 | 75533424 | 0.07214 | -0.6620 | 34 |
| | 2425.771 | -0.002 | 59894763 | 0.034006 | -1.433018 | 35 |
| | -0.0251 | -0.00084 | 50294164 | 0.03259 | 1.074937 | 36 |
| | 893.395 | 1.1316 | -70994467 | 0.038 | -2.302 | 37 |
| | -0.0477 | -0.084 | -81575254 | 0.061632 | 1.903272 | 38 |
| | -0.02483 | 1236 | 10145313 | 0.025 | 0.65146 | 39 |
| | -949.2 | 1.528887 | -5.5688E-4 | 0.04984696 | -2.32016 | 40 |
| | -0.011113 | 0.40033 | 0.00021523 | 0.045264 | -1.4662 | 41 |
| | -0.0177 | 329.7448 | -0.0003975 | 0.03169 | 0.14333 | 42 |
| | -0.011 | -1930.2 | 1.24 | 0.050385 | -1.109923 | 43 |
| | 6082.17 | 4.286 | -0.002014 | 2715886 | -1.087150 | 44 |
| | -0.0397 | 2.126 | 0.00092636 | -1508120 | 2.9154 | 45 |
| | -0.0252 | 4082.939 | -0.00062 | 17100158 | 1.55114 | 46 |
| | -0.0560 | 7639.7 | 0.68134 | -27909258 | 2.85226 | 47 |

TABLE 31-continued

| | | Coefficients | | | | | No. |
|---|---|---|---|---|---|---|---|
| | | −0.0134 | 1423.99 | 0.87764371 | 6.13e−05 | 0.446 | 48 |
| | 4736.86 | 1.250 | −0.00652 | 172681901 | 0.07676 | −0.3021 | 49 |
| | | −0.044 | −0.121 | −0.000873 | −4.62E+7 | 0.0671 | 1.937 | 50 |
| | | −0.0219 | 1576.6 | −0.00134 | 54069432 | 0.029267 | 0.78878 | 51 |
| | | −0.055 | 3598 | −0.098620 | −74159142 | 0.041577 | 2.309 | 52 |
| | | −0.0116 | −2055 | 1.188 | 0.00023 | 0.0512 | −1.1542 | 53 |
| | | −0.055 | 8903.82 | 1.03 | −0.0012627 | 14035678 | 3.2 | 54 |
| −0.078 | 14133 | −0.687 | −0.009695 | 1.062E+8 | 0.10 | 5.59 | 55 |
| | | | | 3.996E+8 | 0.11089 | −1.021759 | 56 |
| | | | 0.0063336 | | 0.11347 | −1.9467 | 57 |
| | | | | 860.3249 | 0.0639025 | −84.98948 | 58 |
| | | | | 9898.8177 | 0.091563631 | −0.3299621 | 59 |
| | | | 0.00721 | 107920251.6624 | | −1.0006445 | 60 |
| | | | | 419.2 | 596535240 | −41.585735 | 61 |
| | | | | 14320 | 234257296.8937 | −0.4789050 | 62 |
| | | | 0.00066 | 812307573.5455 | | 0.09918792 | 63 |
| | | | 1089.4251 | | 0.00069423293 | −107.18015 | 64 |
| | | | 12590.5 | | 0.00967490979 | −2.05501 | 65 |
| | | | −0.00905 | | 0.0092076 | 0.19189 | 66 |
| | | | 165893.71 | | 122.7205081 | −11.30895 | 67 |
| | | | 0.0041105 | | 6.5788 | 0.98581 | 68 |
| | | | 0.010541 | | 19453.2163 | −1.366750 | 69 |
| | | | | | 0.10876 | −2.301980 | 70 |
| | | | 393.7 | 559628637 | 0.048935 | −39.915 | 71 |
| | | | 8656.83 | 244256710 | 0.0663 | −0.885780 | 72 |
| | | | 0.0129 | 157875482 | 0.142003 | −2.694252 | 73 |
| | | | 846.608 | 0.0014 | 0.07831107 | −84.66684 | 74 |
| | | | 5900.1661 | 0.00927 | 0.081369191 | −2.5885198 | 75 |
| | | | 131629 | 108.84 | 0.06793071342 | −10.12169 | 76 |
| | | | 0.011421 | 822.6365 | 0.08303337 | −82.88872 | 77 |
| | | | 0.013257 | 10662.5415 | 0.106214424 | −2.33978 | 78 |
| | | | 417.43 | −0.000381 | 744190123.3893 | −41.369532 | 79 |
| | | | 12128 | 0.0091619 | −130390666 | −2.266204 | 80 |
| | | | −0.005459 | 0.007583 | 82287681 | −0.50010 | 81 |
| | | | 377360 | −8.1908 | 6837963488 | −2.47028 | 82 |
| | | | 0.00099 | 418.212 | 560182293 | −41.5502 | 83 |
| | | | 0.011194 | 17111.2 | 29398797 | −1.8577 | 84 |
| | | | 21649017 | 28.96307 | 0.4328 | −156.16 | 85 |
| | | | 0.00330 | 1086.1672 | 0.00029753173 | −107.01823 | 86 |
| | | | −9.3941e−05 | 12572.6828 | 0.00969 | −2.0464 | 87 |
| | | | 24.2 | 80696477 | 471.6 | −2614.99 | 88 |
| | | 392.929 | −0.0001 | 611767730 | 0.0491 | −39.82 | 89 |
| | | 6854 | 0.00937 | −157521601 | 0.070555 | −2.81351 | 90 |
| | | 0.005871 | 0.00552 | −61236289 | 0.118 | −2.9416 | 91 |
| | | 403954 | −8.6576 | 7107285383 | −0.07356 | −2.349 | 92 |
| | | 0.00857 | 373.75 | 383823513 | 0.05763 | −38.781 | 93 |
| | | 0.013998 | 9692.125 | −4665192.1 | 0.0965657 | −2.782 | 94 |
| | | 4998296 | −132.70 | 0.3202 | 10.567847038 | −132.7427 | 95 |
| | | 0.00927 | 827.6066 | 0.000498 | 0.08349426 | −83.41464 | 96 |
| | | 0.00369 | 6461.9905 | 0.008696 | 0.084631596 | −2.9639303 | 97 |
| | | 2.32E+12 | 4.83248e+18 | −1.05E+14 | 9037614498892 | 1.185E+14 | 98 |
| | | 9471186 | −296 | 0.196688 | 116933544267 | −99.64 | 99 |
| | | 0.002761 | 413.88 | −0.00058 | 713679677.7954 | −41.177966 | 100 |
| | | 0.00349 | 12684.8 | 0.0088176 | −124943185 | −2.6391378 | 101 |
| | | 1.3718 | 8853215 | −272.0191 | 68076716508 | −163.16785 | 102 |
| | | 0.9352 | 11007611 | 24.21772 | 0.09197 | −134.8402 | 103 |
| | 5448434 | −195 | 0.1975318 | 32157214873 | 5.367 | −82.7 | 104 |
| | 0.024158 | 327.2 | −0.002344 | 823767988 | 0.0803 | −35.325 | 105 |
| | 0.0065 | 7390.9 | 0.008791 | −151905670 | 0.080040 | −3.579 | 106 |
| | 2.78 | −1129873 | −106.418 | 43593035460 | 29.2 | −338.972 | 107 |
| | 1.563 | −96788.08 | −22.217 | 0.4843 | 8.2370 | −237.8248 | 108 |
| | 4.06E+12 | 1.757e+18 | 2.798E+13 | 3.97E+12 | −5.96133e+22 | −8.51E+14 | 109 |
| 1.839 | −9.83E+5 | −16.687 | 0.58062 | −4575512593 | 9.549 | −276.3 | 110 |

Two-Dimensional Manifold

When n=2, the manifold S is a curved surface and the hyperplane $\pi$ is a flat plane defined by the first direction $\delta_0$ and the second direction $\delta_1$. The coordinate $\delta_0$ in this Example is optionally and preferably a linear combination $a_0 + a_1 D_1 + a_2 D_2 + \ldots$, of the polypeptides $D_1, D_2$, etc; and the coordinate $\delta_1$ in this Example is optionally and preferably a linear combination $b_0 + b_1 D_1 + b_2 D_2 + \ldots$, of the polypeptides $D_1, D_2$, etc.

Tables 32-35 below list diagnostic performance (in AUCs) attained for n=2. The performance were computed using a leave-10%-out cross validation on a subset of the majority cohort that had sufficient serum to measure all the proteins. The coordinates $\delta_0$ and $\delta_1$ were calculated so that the probabilistic classification function $f(\delta_0, \delta_1)$ represented the likelihood that the test subject had a bacterial infection. The AUC values correspond to classifications according to Bacterial versus Viral (second column from right—B vs. V) and infectious vs. non-infectious (rightmost column—I vs. NI). Shown are results for the embodiments in which the plurality of polypeptides includes two polypeptides (Table 32), three polypeptides (Table 33), four polypeptides (Table 34) and five polypeptides (Table 35). The coefficients for the coordinates $\delta_0$ and $\delta_1$ are presented for each polypeptide, wherein "const" correspond to $\alpha_0$ when applied to the coordinate $\delta_0$ and $b_0$ when applied to the coordinate $\delta_1$. The coefficients correspond to the following concentration scales for each protein: TRAIL (pg/ml), IP-10 (pg/ml), CRP (ug/ml), PCT (ng/ml), SAA (g/ml) and IL1ra (g/ml).

TABLE 32

| AUC (I vs. NI) | AUC (B vs. V) | | | | |
|---|---|---|---|---|---|
| 0.91 | 0.88 | TRAIL | IP-10 | Const | |
| | | 0.0006 | 0.0086 | −0.3333 | $\delta 0$ |
| | | −0.0294 | 0.0089 | 2.4481 | $\delta 1$ |
| 0.95 | 0.89 | IP-10 | CRP | Const | |
| | | 0.0055 | 0.0517 | −0.474 | $\delta 0$ |
| | | 0.0046 | 0.0902 | −1.9201 | $\delta 1$ |
| 0.96324 | 0.85647 | SAA | IP-10 | Const | |
| | | 9623.7195 | 0.0089 | −1.0634 | $\delta 0$ |
| | | 14280.3897 | 0.0079 | −2.0098 | $\delta 1$ |
| 0.89408 | 0.63901 | IP-10 | IL1ra | Const | |
| | | 0.0077 | 77589304.64 | −0.2347 | $\delta 0$ |
| | | 0.0069 | 122880671.4 | 0.3245 | $\delta 1$ |
| 0.735 | 0.70468 | PCT | IP-10 | Const | |
| | | 0.1778 | 0.0012 | 1.3717 | $\delta 0$ |
| | | 0.9426 | 0.0007 | 1.3073 | $\delta 1$ |
| 0.93 | 0.94 | TRAIL | CRP | Const | |
| | | 0.0129 | 0.0647 | −0.551 | $\delta 0$ |
| | | −0.0077 | 0.0953 | −0.1177 | $\delta 1$ |
| 0.92719 | 0.90714 | TRAIL | SAA | Const | |
| | | 0.0146 | 15457.6689 | −1.0101 | $\delta 0$ |
| | | −0.0081 | 18311.8735 | 0.2736 | $\delta 1$ |
| 0.85523 | 0.88673 | TRAIL | IL1ra | Const | |
| | | 0.0118 | 660539652.3 | −0.1638 | $\delta 0$ |
| | | −0.0224 | 691029794.9 | 3.3011 | $\delta 1$ |
| 0.69731 | 0.86706 | TRAIL | PCT | Const | |
| | | 0.0095 | 0.6699 | 0.7941 | $\delta 0$ |
| | | −0.0105 | 1.0871 | 2.4419 | $\delta 1$ |
| 0.92 | 0.89 | SAA | CRP | Const | |
| | | 7927.9578 | 0.0371 | 0.9937 | $\delta 0$ |
| | | 9043.9184 | 0.0704 | −1.2549 | $\delta 1$ |
| 0.93 | 0.87 | IL1ra | CRP | Const | |
| | | 357544464 | 0.0549 | 0.9321 | $\delta 0$ |
| | | 345095895 | 0.0895 | −0.8849 | $\delta 1$ |
| 0.85 | 0.88 | PCT | CRP | Const | |
| | | 0.1493 | 0.0543 | 1.225 | $\delta 0$ |
| | | 0.71 | 0.1052 | −1.48 | $\delta 1$ |
| 0.9154 | 0.82529 | SAA | IL1ra | Const | |
| | | 11965 | 233885248 | 0.9453 | $\delta 0$ |
| | | 17194.2625 | 201037678 | −0.6599 | $\delta 1$ |
| 0.84314 | 0.78722 | SAA | PCT | Const | |
| | | 6627 | −0.6192 | 1.4185 | $\delta 0$ |
| | | 8964 | 0.2744 | 0.1417 | $\delta 1$ |
| 0.82323 | 0.58647 | PCT | IL1ra | Const | |
| | | −1.0932 | 601268546 | 1.3547 | $\delta 0$ |
| | | 0.7431 | 600085479 | 0.7175 | $\delta 1$ |

TABLE 33

| AUC (I vs. NI) | AUC (B vs. V) | | | | | |
|---|---|---|---|---|---|---|
| 0.96 | 0.94 | TRAIL | IP-10 | CRP | Const | |
| | | 0.005 | 0.0053 | 0.0555 | −1.0317 | $\delta 0$ |
| | | −0.0143 | 0.005 | 0.0884 | −0.6693 | $\delta 1$ |
| 0.96 | 0.91 | TRAIL | SAA | IP-10 | Const | |
| | | 0.0047 | 9804.469 | 0.0087 | −1.636 | $\delta 0$ |
| | | −0.0167 | 12810.9197 | 0.0085 | −0.435 | $\delta 1$ |
| 0.90 | 0.89 | TRAIL | IP-10 | IL1ra | Const | |
| | | 0.0056 | 0.0072 | 24233992.13 | −0.7474 | $\delta 0$ |
| | | −0.0282 | 0.0073 | 57162308.55 | 2.6252 | $\delta 1$ |
| 0.66 | 0.85 | TRAIL | PCT | IP-10 | Const | |
| | | 0.008 | 0.7463 | 0.0005 | 0.71 | $\delta 0$ |
| | | −0.0136 | 1.1103 | 0.001 | 2.1832 | $\delta 1$ |
| 0.97318 | 0.91325 | SAA | IP-10 | CRP | Const | |
| | | 4964.9078 | 0.0079 | 0.0389 | −1.1506 | $\delta 0$ |
| | | 6345.7097 | 0.0069 | 0.0729 | −2.7684 | $\delta 1$ |
| 0.95695 | 0.90645 | IP-10 | IL1ra | CRP | Const | |
| | | 0.0062 | −72572842.54 | 0.0635 | −0.5109 | $\delta 0$ |
| | | 0.0046 | −16278785.64 | 0.1025 | −1.6901 | $\delta 1$ |

TABLE 33-continued

| AUC (I vs. NI) | AUC (B vs. V) | | | | | |
|---|---|---|---|---|---|---|
| 0.8 | 0.88475 | PCT | IP-10 | CRP | Const | |
| | | 0.1083 | 0.0016 | 0.0598 | 0.1233 | δ0 |
| | | 0.6599 | 0.0011 | 0.1081 | −2.1504 | δ1 |
| 0.94944 | 0.85722 | SAA | IP-10 | IL1ra | Const | |
| | | 9571.3145 | 0.0094 | −141670519.4 | −0.97 | δ0 |
| | | 15309.775 | 0.008 | −119518794.5 | −1.932 | δ1 |
| 0.95635 | 0.79658 | SAA | PCT | IP-10 | Const | |
| | | 6137.1652 | −0.6596 | 0.0047 | −0.5085 | δ0 |
| | | 8580.4524 | 0.2775 | 0.004 | −1.3306 | δ1 |
| 0.73737 | 0.69549 | PCT | IP-10 | IL1ra | Const | |
| | | −1.1448 | 0.0005 | 540518195.3 | 1.0752 | δ0 |
| | | 0.7431 | −0.0003 | 578154355.6 | 0.9893 | δ1 |
| 0.94489 | 0.93838 | TRAIL | SAA | CRP | Const | |
| | | 0.0147 | 8741.563 | 0.0419 | −1.1898 | δ0 |
| | | −0.0045 | 8922.431 | 0.0715 | −0.9205 | δ1 |
| 0.92941 | 0.94316 | TRAIL | IL1ra | CRP | Const | |
| | | 0.0158 | 142723684.3 | 0.0735 | −1.1214 | δ0 |
| | | −0.0124 | 142922206.2 | 0.1005 | 0.254 | δ1 |
| 0.85644 | 0.91373 | TRAIL | PCT | CRP | Const | |
| | | 0.0132 | 0.3236 | 0.066 | −0.695 | δ0 |
| | | 0.0019 | 0.6114 | 0.1084 | −1.7666 | δ1 |
| 0.91298 | 0.91698 | TRAIL | SAA | IL1ra | Const | |
| | | 0.0165 | 13897.6693 | 19314215.49 | −1.1796 | δ0 |
| | | −0.0114 | 17471.1789 | −373899.4284 | 0.5955 | δ1 |
| 0.9451 | 0.85 | TRAIL | SAA | PCT | Const | |
| | | 0.0281 | 13902.8636 | −0.0348 | −2.1844 | δ0 |
| | | 0.0141 | 15302.3132 | 0.7361 | −1.6348 | δ1 |
| 0.73737 | 0.8797 | TRAIL | PCT | IL1ra | Const | |
| | | 0.0126 | 1.6517 | 445497461.8 | −0.3418 | δ0 |
| | | −0.0203 | 2.4203 | 638669048.4 | 2.2766 | δ1 |
| 0.91932 | 0.88856 | SAA | IL1ra | CRP | Const | |
| | | 7641.7563 | 224710899.2 | 0.0265 | 0.8638 | δ0 |
| | | 9730.7248 | 201425116.6 | 0.0536 | −1.256 | δ1 |
| 0.90588 | 0.88556 | SAA | PCT | CRP | Const | |
| | | 8520.704 | −1.4792 | 0.0207 | 1.1579 | δ0 |
| | | 7599.3621 | −0.2234 | 0.0695 | −1.3994 | δ1 |
| 0.84343 | 0.86842 | PCT | IL1ra | CRP | Const | |
| | | −0.6599 | 547844063.4 | 0.0388 | 0.8368 | δ0 |
| | | −0.1506 | 473174484.1 | 0.0873 | −1.6604 | δ1 |
| 0.9 | 0.81448 | SAA | PCT | IL1ra | Const | |
| | | 10349.4815 | −2.3088 | 565967860.9 | 1.0109 | δ0 |
| | | 15172.8663 | −0.2687 | 515166286.4 | −1.0283 | δ1 |

TABLE 34

| AUC (I vs. NI) | AUC (B vs. V) | | | | | | |
|---|---|---|---|---|---|---|---|
| 0.97 | 0.94 | TRAIL | SAA | IP-10 | CRP | Const | |
| | | 0.0058 | 5383.841 | 0.0075 | 0.0394 | −1.7981 | δ0 |
| | | −0.012 | 5731.9467 | 0.007 | 0.0702 | −1.5541 | δ1 |
| 0.96 | 0.94 | TRAIL | IP-10 | IL1ra | CRP | Const | |
| | | 0.0091 | 0.0053 | −6.995E+7 | 0.0703 | −1.5229 | δ0 |
| | | −0.0166 | 0.0046 | −3.228E+7 | 0.101 | −0.2128 | δ1 |
| 0.78667 | 0.903 | TRAIL | PCT | IP-10 | CRP | Const | |
| | | 0.0101 | 0.2921 | 0.0007 | 0.0651 | −0.6733 | δ0 |
| | | −0.0021 | 0.5293 | 0.001 | 0.1077 | −1.8383 | δ1 |
| 0.94957 | 0.91777 | TRAIL | SAA | IP-10 | IL1ra | Const | |
| | | 0.0091 | 10289.5699 | 0.0088 | 153195983.2 | −2.036 | δ0 |
| | | −0.0169 | 14282.9357 | 0.0082 | 138993063.2 | −0.2825 | δ1 |
| 0.93254 | 0.8433 | TRAIL | SAA | PCT | IP-10 | Const | |
| | | 0.0218 | 12161.0003 | −0.2264 | 0.0068 | −3.3387 | δ0 |
| | | 0.0083 | 13578.3133 | 0.5366 | 0.0068 | −2.9001 | δ1 |
| 0.65657 | 0.86842 | TRAIL | PCT | IP-10 | IL1ra | Const | |
| | | 0.0147 | 1.6805 | −0.0004 | 481673333.4 | −0.356 | δ0 |
| | | −0.0268 | 2.4993 | 0.001 | 491494579.8 | 2.4805 | δ1 |
| 0.95829 | 0.92002 | SAA | IP-10 | IL1ra | CRP | Const | |
| | | 6131.1692 | 0.0088 | −1.5446E+8 | 0.028 | −1.0249 | δ0 |
| | | 8579.4749 | 0.0067 | −9.6352E+7 | 0.0614 | −2.3655 | δ1 |
| 0.9881 | 0.8735 | SAA | PCT | IP-10 | CRP | Const | |
| | | 4377.1407 | −1.4641 | 0.0064 | 0.0419 | −1.4913 | δ0 |
| | | 3810.7522 | −0.1982 | 0.0059 | 0.0857 | −3.62 | δ1 |

TABLE 34-continued

| AUC (I vs. NI) | AUC (B vs. V) | | | | | | |
|---|---|---|---|---|---|---|---|
| 0.74242 | 0.89098 | PCT | IP-10 | IL1ra | CRP | Const | |
| | | −0.4843 | 0.0004 | 4.54739E+8 | 0.0378 | 0.6379 | $\delta 0$ |
| | | −0.2044 | −0.0018 | 4.84865E+8 | 0.0969 | −0.7642 | $\delta 1$ |
| 0.94444 | 0.77828 | SAA | PCT | IP-10 | IL1ra | Const | |
| | | 4951.1109 | −2.8236 | 0.0095 | 212692846.6 | −0.802 | $\delta 0$ |
| | | 10430.5725 | −0.1446 | 0.008 | 210027138.1 | −2.0339 | $\delta 1$ |
| 0.92564 | 0.93742 | TRAIL | SAA | IL1ra | CRP | Const | |
| | | 0.0163 | 8701.5399 | 2.10729E+7 | 0.0386 | −1.3076 | $\delta 0$ |
| | | −0.0099 | 9890.6956 | 1.31614E+7 | 0.062 | −0.2694 | $\delta 1$ |
| 0.95294 | 0.91111 | TRAIL | SAA | PCT | CRP | Const | |
| | | 0.0253 | 11551.5028 | −1.3285 | 0.0278 | −1.8221 | $\delta 0$ |
| | | 0.0141 | 9802.9581 | −0.2648 | 0.0748 | −2.7829 | $\delta 1$ |
| 0.79798 | 0.89474 | TRAIL | PCT | IL1ra | CRP | Const | |
| | | 0.0137 | −0.1689 | 2.756E+8 | 0.0476 | −0.6344 | $\delta 0$ |
| | | −0.0264 | −0.236 | 2.7563E+8 | 0.0994 | 0.5587 | $\delta 1$ |
| 0.85556 | 0.92308 | TRAIL | SAA | PCT | IL1ra | Const | |
| | | 0.0343 | 12347.4916 | −0.5098 | 432026875.9 | −2.2741 | $\delta 0$ |
| | | −0.0152 | 19586.5686 | −0.4124 | 426850211.8 | 0.0383 | $\delta 1$ |
| 0.9 | 0.85068 | SAA | PCT | IL1ra | CRP | Const | |
| | | 2665.2949 | −0.5099 | 6.42961E+8 | 0.0552 | 0.5611 | $\delta 0$ |
| | | 3734.4091 | −0.3614 | 5.88426E+8 | 0.0941 | −1.8313 | $\delta 1$ |

TABLE 35

| AUC (I vs. NI) | AUC (B vs. V) | | | | | | | |
|---|---|---|---|---|---|---|---|---|
| 0.95963 | 0.94381 | TRAIL | SAA | IP-10 | IL1ra | CRP | Const | |
| | | 0.0092 | 6688.18 | 0.0082 | −1.6265E+8 | 0.0336 | −2.1333 | $\delta 0$ |
| | | −0.0136 | 8261.93 | 0.0069 | −1.17187E+8 | 0.0619 | −1.1202 | $\delta 1$ |
| 0.95635 | 0.89972 | TRAIL | SAA | PCT | IP-10 | CRP | Const | |
| | | 0.0178 | 6302.89 | −1.297 | 0.0074 | 0.0517 | −3.4117 | $\delta 0$ |
| | | 0.0063 | 4437.96 | −0.249 | 0.0076 | 0.1 | −4.4957 | $\delta 1$ |
| 0.71717 | 0.88346 | TRAIL | PCT | IP-10 | IL1ra | CRP | Const | |
| | | 0.0246 | −0.2302 | −0.0017 | 5.4749E+8 | 0.0616 | −1.3864 | $\delta 0$ |
| | | −0.017 | −0.2819 | −0.0012 | 5.0261E+8 | 0.1096 | −0.1627 | $\delta 1$ |
| 0.85556 | 0.87783 | TRAIL | SAA | PCT | IP-10 | IL1ra | Const | |
| | | 0.0529 | 5922.72 | −0.7334 | 0.0149 | 2530173.292 | −6.1686 | $\delta 0$ |
| | | 0.0043 | 14225.92 | −0.282 | 0.0139 | 32115407.24 | −3.7073 | $\delta 1$ |
| 0.91111 | 0.819 | SAA | PCT | IP-10 | IL1ra | CRP | Const | |
| | | −22863.96 | −0.2611 | 0.0141 | −8.7081E+8 | 0.1586 | −2.8588 | $\delta 0$ |
| | | −18573.7 | −0.3918 | 0.008 | 7.27742E+8 | 0.2362 | −3.2596 | $\delta 1$ |
| 0.87778 | 0.90045 | TRAIL | SAA | PCT | IL1ra | CRP | Const | |
| | | 0.0397 | −7661.57 | −0.4075 | 6.98426E+8 | 0.1355 | −3.522 | $\delta 0$ |
| | | −0.008 | −4178.89 | −0.4915 | 6.53495E+8 | 0.1689 | −1.7514 | $\delta 1$ |

Example 13

Exemplified Coordinates that Include Nonlinear Functions

It was unexpectedly found by the present Inventor that incorporation of the nonlinear functions $\phi_0$ and $\phi_1$ in the calculation of the coordinates $\delta_1$ and $\delta_2$ captures more subtle trends in the data, while retaining a probabilistic framework that allows meaningful interpretation of the results. In this Example, the coordinates $\delta_0$ and $\delta_1$ were calculated according to the following equations:

$$\delta_0 = a_0 + a_1 C + a_2 I + a_3 T + \phi_0$$

$$\delta_1 = b_0 + b_1 C + b_2 I + b_3 T + \phi_1,$$

and the nonlinear functions were defined as:

$$\phi_0 = q_1 C^{\gamma 1} + q_2 C^{\gamma 2} + q_3 T^{\gamma 3}$$

$$\phi_1 = r_1 C^{\gamma 1} + r_2 C^{\gamma 2} + r_3 T^{\gamma 3}.$$

where $\gamma 1 = 0.5$, $\gamma 2 = 2$ and $\gamma 3 = 0.5$.

Table 36 details the coefficients and constants used in this Example.

TABLE 36

| First Coordinate $\delta_0$ (viral) | Second Coordinate $\delta_1$ (bacterial) | |
|---|---|---|
| $a_0 = -0.8388$ | $b_0 = 5.5123$ | Const |
| $a_1 = -0.0487$ | $b_1 = -0.0636$ | CRP (mg/ml) |
| $q_1 = 1.1367$ | $r_1 = 1.4877$ | $CRP^{0.5}$ $(mg/ml)^{0.5}$ |
| $q_2 = -5.14 \times 10^{-05}$ | $r_2 = 3.50 \times 10^{-05}$ | $CRP^2$ $(mg/ml)^2$ |
| $a_2 = 0.0089$ | $b_2 = 0.0085$ | IP10 (pg/ml) |
| $a_3 = 0.0408$ | $b_3 = 0.0646$ | TRAIL (pg/ml) |
| $q_3 = -0.6064$ | $r_3 = -1.8039$ | $TRAIL^{0.5}$ $(pg/ml)^{0.5}$ |

The performance of the model presented in Table 36 was examined on the Microbiologically Confirmed Cohort (AUC of 0.95±0.03), Unanimous Cohort (AUC of 0.95±0.02) and the Study cohort (AUC of 0.93±0.02). The signature performance improved as the size of the equivocal region increases.

Tables 37A-C below detail signature measures of accuracy for diagnosing bacterial versus viral infections when using the nonlinear model of the present Example. Performance estimates and their 95% CIs were obtained on the Microbiologically Confirmed sub-cohort (Table 37A; n=241), Unanimous sub-cohort (Table 37B; n=527), and Study Cohort (Table 37C; n=653), using different sizes of equivocal regions as indicated. Tables 37D-F below detail percentage of patients who had equivocal immune response in the Study Cohort when applying different thresholds, and Tables 37G-H below detail signature sensitivity and specificity when applying different equivocal immune response thresholds obtained on the Study Cohort. In Tables 37D-H the leftmost columns represents a minimal equivocal immune response threshold and the uppermost row represents a maximal equivocal immune response threshold.

TABLE 37A

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.98, (0.96, 1.00) | 0.96, (0.93, 0.99) | 0.94, (0.91, 0.97) | 0.93, (0.90, 0.97) | 0.89, (0.85, 0.93) | Total accuracy |
| 0.96, (0.90, 1.00) | 0.96, (0.91, 1.00) | 0.95, (0.89, 1.00) | 0.93, (0.87, 1.00) | 0.88, (0.80, 0.96) | Sensitivity |
| 0.99, (0.97, 1.00) | 0.96, (0.93, 0.99) | 0.94, (0.90, 0.98) | 0.94, (0.90, 0.97) | 0.90, (0.87, 0.94) | Specificity |
| 65% | 78% | 87% | 90% | 100% | % of patients included |

TABLE 37B

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.97, (0.95, 0.99) | 0.95, (0.93, 0.97) | 0.93, (0.90, 0.95) | 0.92, (0.89, 0.94) | 0.88, (0.85, 0.91) | Total accuracy |
| 0.96, (0.93, 0.99) | 0.93, (0.90, 0.97) | 0.91, (0.87, 0.95) | 0.90, (0.86, 0.94) | 0.85, (0.81, 0.89) | Sensitivity |
| 0.98, (0.96, 1.00) | 0.96, (0.93, 0.99) | 0.94, (0.91, 0.97) | 0.93, (0.90, 0.97) | 0.91, (0.87, 0.94) | Specificity |
| 63% | 76% | 86% | 90% | 100% | % of patients included |

TABLE 37C

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.95, (0.93, 0.98) | 0.92, (0.90, 0.95) | 0.90, (0.87, 0.92) | 0.89, (0.86, 0.91) | 0.85, (0.83, 0.88) | Total accuracy |
| 0.95, (0.91, 0.98) | 0.92, (0.88, 0.95) | 0.89, (0.85, 0.92) | 0.87, (0.83, 0.91) | 0.83, (0.79, 0.87) | Sensitivity |
| 0.95, (0.92, 0.98) | 0.93, (0.89, 0.96) | 0.91, (0.88, 0.95) | 0.90, (0.87, 0.94) | 0.87, (0.84, 0.91) | Specificity |
| 58% | 72% | 84% | 88% | 100% | % of patients included |

TABLE 37D

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 52.8 | 47.2 | 44.0 | 40.9 | 38.6 | 36.3 | 34.8 | 33.2 | 31.2 | 29.1 | 26.3 | 24.0 | 22.7 | 20.5 | 17.6 | 13.9 | 10.4 | 6.6 | 0.05 |
| 46.2 | 40.6 | 37.4 | 34.3 | 32.0 | 29.7 | 28.2 | 26.6 | 24.7 | 22.5 | 19.8 | 17.5 | 16.1 | 13.9 | 11.0 | 7.4 | 3.8 | | 0.1 |
| 42.4 | 36.8 | 33.5 | 30.5 | 28.2 | 25.9 | 24.3 | 22.8 | 20.8 | 18.7 | 15.9 | 13.6 | 12.3 | 10.1 | 7.2 | 3.5 | | | 0.15 |
| 38.9 | 33.2 | 30.0 | 27.0 | 24.7 | 22.4 | 20.8 | 19.3 | 17.3 | 15.2 | 12.4 | 10.1 | 8.7 | 6.6 | 3.7 | | | | 0.2 |
| 35.2 | 29.6 | 26.3 | 23.3 | 21.0 | 18.7 | 17.2 | 15.6 | 13.6 | 11.5 | 8.7 | 6.4 | 5.1 | 2.9 | | | | | 0.25 |
| 32.3 | 26.6 | 23.4 | 20.4 | 18.1 | 15.8 | 14.2 | 12.7 | 10.7 | 8.6 | 5.8 | 3.5 | 2.1 | | | | | | 0.3 |
| 30.2 | 24.5 | 21.3 | 18.2 | 15.9 | 13.6 | 12.1 | 10.6 | 8.6 | 6.4 | 3.7 | 1.4 | | | | | | | 0.35 |
| 28.8 | 23.1 | 19.9 | 16.8 | 14.5 | 12.3 | 10.7 | 9.2 | 7.2 | 5.1 | 2.3 | | | | | | | | 0.4 |
| 26.5 | 20.8 | 17.6 | 14.5 | 12.3 | 10.0 | 8.4 | 6.9 | 4.9 | 2.8 | | | | | | | | | 0.45 |
| 23.7 | 18.1 | 14.9 | 11.8 | 9.5 | 7.2 | 5.7 | 4.1 | 2.1 | | | | | | | | | | 0.5 |
| 21.6 | 15.9 | 12.7 | 9.6 | 7.4 | 5.1 | 3.5 | 2.0 | | | | | | | | | | | 0.55 |
| 19.6 | 13.9 | 10.7 | 7.7 | 5.4 | 3.1 | 1.5 | | | | | | | | | | | | 0.6 |
| 18.1 | 12.4 | 9.2 | 6.1 | 3.8 | 1.5 | | | | | | | | | | | | | 0.65 |
| 16.5 | 10.9 | 7.7 | 4.6 | 2.3 | | | | | | | | | | | | | | 0.7 |
| 14.2 | 8.6 | 5.4 | 2.3 | | | | | | | | | | | | | | | 0.75 |
| 11.9 | 6.3 | 3.1 | | | | | | | | | | | | | | | | 0.8 |
| 8.9 | 3.2 | | | | | | | | | | | | | | | | | 0.85 |
| 5.7 | | | | | | | | | | | | | | | | | | 0.9 |

TABLE 37E

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 53.6 | 43.6 | 38.2 | 33.5 | 29.5 | 26.0 | 23.5 | 21.6 | 18.8 | 16.6 | 13.8 | 11.3 | 10.3 | 9.1 | 7.5 | 5.3 | 3.4 | 2.5 | 0.05 |
| 51.1 | 41.1 | 35.7 | 31.0 | 27.0 | 23.5 | 21.0 | 19.1 | 16.3 | 14.1 | 11.3 | 8.8 | 7.8 | 6.6 | 5.0 | 2.8 | 0.9 | | 0.1 |
| 50.2 | 40.1 | 34.8 | 30.1 | 26.0 | 22.6 | 20.1 | 18.2 | 15.4 | 13.2 | 10.3 | 7.8 | 6.9 | 5.6 | 4.1 | 1.9 | | | 0.15 |
| 48.3 | 38.2 | 32.9 | 28.2 | 24.1 | 20.7 | 18.2 | 16.3 | 13.5 | 11.3 | 8.5 | 6.0 | 5.0 | 3.8 | 2.2 | | | | 0.2 |

TABLE 37E-continued

| | | | | | | | | | | | | | | | | | |
|---|---|---|---|---|---|---|---|---|---|---|---|---|---|---|---|---|---|
| 46.1 | 36.1 | 30.7 | 26.0 | 21.9 | 18.5 | 16.0 | 14.1 | 11.3 | 9.1 | 6.3 | 3.8 | 2.8 | 1.6 | | | | 0.25 |
| 44.5 | 34.5 | 29.2 | 24.5 | 20.4 | 16.9 | 14.4 | 12.5 | 9.7 | 7.5 | 4.7 | 2.2 | 1.3 | | | | | 0.3 |
| 43.3 | 33.2 | 27.9 | 23.2 | 19.1 | 15.7 | 13.2 | 11.3 | 8.5 | 6.3 | 3.4 | 0.9 | | | | | | 0.35 |
| 42.3 | 32.3 | 27.0 | 22.3 | 18.2 | 14.7 | 12.2 | 10.3 | 7.5 | 5.3 | 2.5 | | | | | | | 0.4 |
| 39.8 | 29.8 | 24.5 | 19.7 | 15.7 | 12.2 | 9.7 | 7.8 | 5.0 | 2.8 | | | | | | | | 0.45 |
| 37.0 | 27.0 | 21.6 | 16.9 | 12.9 | 9.4 | 6.9 | 5.0 | 2.2 | | | | | | | | | 0.5 |
| 34.8 | 24.8 | 19.4 | 14.7 | 10.7 | 7.2 | 4.7 | 2.8 | | | | | | | | | | 0.55 |
| 32.0 | 21.9 | 16.6 | 11.9 | 7.8 | 4.4 | 1.9 | | | | | | | | | | | 0.6 |
| 30.1 | 20.1 | 14.7 | 10.0 | 6.0 | 2.5 | | | | | | | | | | | | 0.65 |
| 27.6 | 17.6 | 12.2 | 7.5 | 3.4 | | | | | | | | | | | | | 0.7 |
| 24.1 | 14.1 | 8.8 | 4.1 | | | | | | | | | | | | | | 0.75 |
| 20.1 | 10.0 | 4.7 | | | | | | | | | | | | | | | 0.8 |
| 15.4 | 5.3 | | | | | | | | | | | | | | | | 0.85 |
| 10.0 | | | | | | | | | | | | | | | | | 0.9 |

TABLE 37F

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 52.1 | 50.6 | 49.4 | 47.9 | 47.3 | 46.1 | 45.5 | 44.3 | 43.1 | 41.0 | 38.3 | 36.2 | 34.4 | 31.4 | 27.2 | 22.2 | 17.1 | 10.5 | 0.05 |
| 41.6 | 40.1 | 38.9 | 37.4 | 36.8 | 35.6 | 35.0 | 33.8 | 32.6 | 30.5 | 27.8 | 25.7 | 24.0 | 21.0 | 16.8 | 11.7 | 6.6 | | 0.1 |
| 35.0 | 33.5 | 32.3 | 30.8 | 30.2 | 29.0 | 28.4 | 27.2 | 26.0 | 24.0 | 21.3 | 19.2 | 17.4 | 14.4 | 10.2 | 5.1 | | | 0.15 |
| 29.9 | 28.4 | 27.2 | 25.7 | 25.1 | 24.0 | 23.4 | 22.2 | 21.0 | 18.9 | 16.2 | 14.1 | 12.3 | 9.3 | 5.1 | | | | 0.2 |
| 24.9 | 23.4 | 22.2 | 20.7 | 20.1 | 18.9 | 18.3 | 17.1 | 15.9 | 13.8 | 11.1 | 9.0 | 7.2 | 4.2 | | | | | 0.25 |
| 20.7 | 19.2 | 18.0 | 16.5 | 15.9 | 14.7 | 14.1 | 12.9 | 11.7 | 9.6 | 6.9 | 4.8 | 3.0 | | | | | | 0.3 |
| 17.7 | 16.2 | 15.0 | 13.5 | 12.9 | 11.7 | 11.1 | 9.9 | 8.7 | 6.6 | 3.9 | 1.8 | | | | | | | 0.35 |
| 15.9 | 14.4 | 13.2 | 11.7 | 11.1 | 9.9 | 9.3 | 8.1 | 6.9 | 4.8 | 2.1 | | | | | | | | 0.4 |
| 13.8 | 12.3 | 11.1 | 9.6 | 9.0 | 7.8 | 7.2 | 6.0 | 4.8 | 2.7 | | | | | | | | | 0.45 |
| 11.1 | 9.6 | 8.4 | 6.9 | 6.3 | 5.1 | 4.5 | 3.3 | 2.1 | | | | | | | | | | 0.5 |
| 9.0 | 7.5 | 6.3 | 4.8 | 4.2 | 3.0 | 2.4 | 1.2 | | | | | | | | | | | 0.55 |
| 7.8 | 6.3 | 5.1 | 3.6 | 3.0 | 1.8 | 1.2 | | | | | | | | | | | | 0.6 |
| 6.6 | 5.1 | 3.9 | 2.4 | 1.8 | 0.6 | | | | | | | | | | | | | 0.65 |
| 6.0 | 4.5 | 3.3 | 1.8 | 1.2 | | | | | | | | | | | | | | 0.7 |
| 4.8 | 3.3 | 2.1 | 0.6 | | | | | | | | | | | | | | | 0.75 |
| 4.2 | 2.7 | 1.5 | | | | | | | | | | | | | | | | 0.8 |
| 2.7 | 1.2 | | | | | | | | | | | | | | | | | 0.85 |
| 1.5 | | | | | | | | | | | | | | | | | | 0.9 |

TABLE 37G

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 98.0 | 98.3 | 98.5 | 98.6 | 98.7 | 98.7 | 98.8 | 98.8 | 98.8 | 98.9 | 95.6 | 92.9 | 92.0 | 90.7 | 89.2 | 87.1 | 85.4 | 84.6 | 0.05 |
| 92.9 | 94.1 | 94.6 | 95.0 | 95.3 | 95.5 | 95.6 | 95.7 | 95.9 | 96.0 | 92.9 | 90.4 | 89.5 | 88.3 | 86.8 | 84.8 | 83.2 | | 0.1 |
| 91.2 | 92.7 | 93.3 | 93.7 | 94.1 | 94.3 | 94.5 | 94.6 | 94.8 | 94.9 | 92.0 | 89.5 | 88.6 | 87.4 | 85.9 | 84.0 | | | 0.15 |
| 87.9 | 89.8 | 90.7 | 91.3 | 91.7 | 92.1 | 92.3 | 92.5 | 92.8 | 92.9 | 90.1 | 87.7 | 86.8 | 85.7 | 84.3 | | | | 0.2 |
| 84.3 | 86.8 | 87.8 | 88.6 | 89.2 | 89.6 | 89.9 | 90.1 | 90.5 | 90.7 | 88.0 | 85.7 | 84.8 | 83.8 | | | | | 0.25 |
| 81.9 | 84.7 | 85.8 | 86.7 | 87.4 | 87.9 | 88.3 | 88.5 | 88.9 | 89.2 | 86.5 | 84.3 | 83.5 | | | | | | 0.3 |
| 80.1 | 83.1 | 84.3 | 85.3 | 86.0 | 86.6 | 87.0 | 87.3 | 87.7 | 88.0 | 85.4 | 83.2 | | | | | | | 0.35 |
| 78.8 | 81.9 | 83.3 | 84.3 | 85.1 | 85.7 | 86.1 | 86.4 | 86.8 | 87.1 | 84.6 | | | | | | | | 0.4 |
| 75.5 | 79.0 | 80.5 | 81.6 | 82.5 | 83.2 | 83.7 | 84.0 | 84.5 | 84.8 | | | | | | | | | 0.45 |
| 72.1 | 76.0 | 77.6 | 78.9 | 79.9 | 80.6 | 81.1 | 81.5 | 82.1 | | | | | | | | | | 0.5 |
| 73.1 | 76.7 | 78.2 | 79.4 | 80.4 | 81.1 | 81.6 | 81.9 | | | | | | | | | | | 0.55 |
| 74.2 | 77.5 | 78.9 | 80.1 | 81.0 | 81.6 | 82.1 | | | | | | | | | | | | 0.6 |
| 74.9 | 78.0 | 79.4 | 80.5 | 81.3 | 82.0 | | | | | | | | | | | | | 0.65 |
| 75.8 | 78.7 | 80.0 | 81.0 | 81.8 | | | | | | | | | | | | | | 0.7 |
| 76.9 | 79.6 | 80.8 | 81.7 | | | | | | | | | | | | | | | 0.75 |
| 78.0 | 80.5 | 81.6 | | | | | | | | | | | | | | | | 0.8 |
| 79.3 | 81.5 | | | | | | | | | | | | | | | | | 0.85 |
| 80.5 | | | | | | | | | | | | | | | | | | 0.9 |

TABLE 37H

| 0.95 | 0.9 | 0.85 | 0.8 | 0.75 | 0.7 | 0.65 | 0.6 | 0.55 | 0.5 | 0.45 | 0.4 | 0.35 | 0.3 | 0.25 | 0.2 | 0.15 | 0.1 | |
|---|---|---|---|---|---|---|---|---|---|---|---|---|---|---|---|---|---|---|
| 97.5 | 94.5 | 92.3 | 89.7 | 88.6 | 86.7 | 85.7 | 83.9 | 82.1 | 79.2 | 80.1 | 80.8 | 81.3 | 82.1 | 83.1 | 84.2 | 85.2 | 86.3 | 0.05 |
| 97.9 | 95.5 | 93.6 | 91.4 | 90.5 | 88.8 | 88.0 | 86.4 | 84.9 | 82.3 | 83.0 | 83.5 | 83.9 | 84.5 | 85.3 | 86.1 | 86.9 | | 0.1 |
| 98.2 | 95.9 | 94.2 | 92.2 | 91.4 | 89.9 | 89.1 | 87.7 | 86.2 | 83.9 | 84.4 | 84.8 | 85.1 | 85.7 | 86.3 | 87.1 | | | 0.15 |
| 98.3 | 96.2 | 94.7 | 92.7 | 92.0 | 90.6 | 89.8 | 88.5 | 87.1 | 84.9 | 85.4 | 85.7 | 86.0 | 86.5 | 87.1 | | | | 0.2 |

TABLE 37H-continued

| | | | | | | | | | | | | | | |
|---|---|---|---|---|---|---|---|---|---|---|---|---|---|---|
| 98.4 | 96.5 | 95.0 | 93.2 | 92.5 | 91.1 | 90.5 | 89.2 | 87.9 | 85.8 | 86.2 | 86.5 | 86.8 | 87.2 | 0.25 |
| 98.5 | 96.7 | 95.3 | 93.5 | 92.9 | 91.6 | 90.9 | 89.7 | 88.5 | 86.4 | 86.8 | 87.1 | 87.3 | | 0.3 |
| 98.5 | 96.8 | 95.4 | 93.8 | 93.1 | 91.9 | 91.2 | 90.0 | 88.9 | 86.9 | 87.2 | 87.5 | | | 0.35 |
| 98.6 | 96.9 | 95.5 | 93.9 | 93.3 | 92.0 | 91.4 | 90.2 | 89.1 | 87.1 | 87.5 | | | | 0.4 |
| 98.6 | 96.9 | 95.6 | 94.0 | 93.4 | 92.2 | 91.6 | 90.4 | 89.3 | 87.4 | | | | | 0.45 |
| 98.7 | 97.0 | 95.8 | 94.2 | 93.6 | 92.4 | 91.8 | 90.7 | 89.6 | | | | | | 0.5 |
| 96.4 | 94.8 | 93.6 | 92.1 | 91.6 | 90.4 | 89.9 | 88.8 | | | | | | | 0.55 |
| 95.1 | 93.6 | 92.4 | 91.0 | 90.4 | 89.3 | 88.8 | | | | | | | | 0.6 |
| 93.9 | 92.4 | 91.3 | 89.9 | 89.3 | 88.3 | | | | | | | | | 0.65 |
| 93.3 | 91.8 | 90.7 | 89.3 | 88.8 | | | | | | | | | | 0.7 |
| 92.1 | 90.7 | 89.6 | 88.3 | | | | | | | | | | | 0.75 |
| 91.6 | 90.2 | 89.1 | | | | | | | | | | | | 0.8 |
| 90.2 | 88.8 | | | | | | | | | | | | | 0.85 |
| 89.1 | | | | | | | | | | | | | | 0.9 |

The signature performance was further examined on the Study Cohort when excluding the following two subgroups: (i) patients whose blood sample was taken after more than 3 days of antibiotic treatment in the hospital and (ii) patients with a suspected gastroenteritis. Details of the model performance on the Microbiologically Confirmed Cohort (AUC of 0.96±0.04), Unanimous Cohort (AUC of 0.96±0.02) and the Study cohort (AUC of 0.95±0.02) is further depicted in Table 38A-C.

Tables 38A-C detail signature measures of accuracy for diagnosing bacterial vs. viral infections using the non-linear MLR model. Performance estimates and their 95% CIs were obtained on the Microbiologically Confirmed sub-cohort (Table 38A; n=200), Unanimous sub-cohort (Table 38B; n=402), and Study Cohort (Table 38C; n=491), when excluding patients with over 3 days of antibiotics treatment at the hospital and/or suspicion of gastroenteritis.

TABLE 38A

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.98, (0.96, 1) | 0.96, (0.93, 0.99) | 0.95, (0.92, 0.99) | 0.95, (0.92, 1) | 0.91, (0.86, 0.95) | Total accuracy |
| 0.94, (87, 1) | 0.95, (0.89, 1) | 0.96, (0.89, 1) | 0.96, (0.89, 1) | 0.90, (0.82, 0.99) | Sensitivity |
| 1, (1, 1) | 0.97, (0.93, 1) | 0.95, (0.92, 0.99) | 0.95, (0.91, 0.99) | 0.91, (0.86, 0.95) | Specificity |
| 65% | 80% | 88% | 90% | 100% | % of patients included |

TABLE 38B

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.98, (0.96, 1) | 0.96, (0.94, 0.98) | 0.95, (0.93, 0.97) | 0.94, (0.92, 0.97) | 0.91, (0.88, 0.94) | Total accuracy |
| 0.98, (0.95, 1) | 0.95, (0.92, 0.99) | 0.94, (0.90, 0.98) | 0.93, (0.89, 0.97) | 0.89, (0.85, 0.94) | Sensitivity |
| 0.99, (0.97, 1) | 0.97, (0.94, 0.99) | 0.95, (0.93, 0.98) | 0.95, (0.92, 0.98) | 0.92, (0.88, 0.96) | Specificity |
| 65% | 79% | 88% | 91% | 100% | % of patients included |

TABLE 38C

| Equivocal immune response filter (10-90) | Equivocal immune response filter (20-80) | Equivocal immune response filter (30-70) | Equivocal immune response filter (35-65) | All patients | Accuracy measure |
|---|---|---|---|---|---|
| 0.97, (0.95, 0.99) | 0.94, (0.92, 0.97) | 0.93, (0.90, 0.95) | 0.91, (0.89, 0.94) | 0.88, (0.85, 0.91) | Total accuracy |
| 0.97, (0.94, 1) | 0.95, (0.91, 0.98) | 0.92, (0.88, 0.96) | 0.91, (0.87, 0.95) | 0.87, (0.83, 0.92) | Sensitivity |
| 0.97, (0.94, 1) | 0.94, (0.91, 0.97) | 0.93, (0.90, 0.96) | 0.92, (0.89, 0.96) | 0.89, (0.85, 0.92) | Specificity |
| 59% | 74% | 85% | 88% | 100% | % of patients included |

Example 14

Antibiotics Based Stratification

Of the 653 patients with suspicion of acute infection, 427 received antibiotics (299 had bacterial diagnosis and 128 had viral diagnosis). The AUC of the signature for distinguishing between the bacterial and viral infected patients in the antibiotics treated patients sub-cohort was 0.93±0.02. No statistically significant difference was observed between the performance on the antibiotics treated patients and the general cohort (0.94±0.02 versus 0.93±0.02; P=0.5).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method for analyzing biological data, the method comprising:
   displaying on a display device a graphical user interface (GUI);
   receiving values of biomarkers in the blood of a subject;
   responsively to an activation of a calculation activation control by a user, automatically calculating a score based on said values;
   generating on said GUI a graphical scale indicative of likelihoods for viral infections; and
   generating a mark on said scale at a location corresponding to said score.

2. The method of claim 1, wherein said scale has a first end identified as corresponding to a higher likelihood for a non-viral infection of said subject, and a second end identified as corresponding to a higher likelihood for a viral infection.

3. The method of claim 1, wherein said likelihoods are presented using a color index.

4. The method of claim 1, wherein said receiving said values comprises communicating with a machine that measures said values.

5. The method of claim 4, wherein said GUI further comprises a communication control, wherein said communicating with said machine is in response to an activation of said communication control by the user.

6. The method of claim 1, wherein said GUI comprising a plurality of value input fields, wherein said receiving said values is via said input fields.

7. The method of claim 6, wherein said GUI comprises a clearing control, and the method comprises clearing said value input fields responsively to an activation of said clearing control by said user.

8. The method of claim 6, comprising clearing said value input automatically.

9. The method of claim 1, comprising displaying said score numerically on said GUI.

10. The method according to claim 1, wherein said score is a likelihood that the subject has bacterial infection.

11. The method according to claim 1, wherein said score is a likelihood that the subject has viral infection.

12. The method according to claim 1, wherein said calculating said score comprises calculating a distance between a segment of a curved surface and a plane defined by a first direction and a second direction, said distance being calculated at a point over said surface defined by first coordinate $\square_0$ along said first direction and a second coordinate $\square_1$ along said second direction; and using said distance for calculation said score;

wherein each of said coordinates is defined by a different combination of said values.

13. The method according to claim 12, wherein for at least one of said coordinates, said combination of said values comprises a linear combination of said values.

14. The method according to claim 13, wherein for at least one of said coordinates, said combination of the values includes at least one nonlinear term corresponding to at least one of said values.

15. The method according to claim 12, comprising calculating an additional distance between a segment of an additional curved surface and said plane, and using said additional distance for calculation said score.

16. The method according to claim 15, comprising comparing each of said distance and said additional distance to a respective predetermined threshold, and, generating on said GUI an output indicative of said comparison.

17. The method according to claim 1, comprising displaying on said GUI an output that summarizes scores calculated for previous blood samples.

18. A system for analyzing biological data, the system comprising a display device and a data processor, wherein said data processor is configured to display on said display device a graphical user interface (GUI), to receive values biomarkers in the blood of a subject, to automatically calculate a score based on said values, responsively to an activation of a calculation activation control by a user, to generate on said GUI a a graphical scale indicative of likelihoods for viral infections, and to generate a mark on said scale at a location corresponding to said score.

19. The system according to claim 18, wherein said data processor is configured to communicate with a machine that measures said values, and to receive said values from said machine.

20. The system according to claim 19, wherein said GUI further comprises a communication control, wherein said data processor is configured to communicate with said machine in response to an activation of said communication control by the user.

21. The system according to claim 18, wherein said GUI comprising a plurality of value input fields, and said data processor is configured to receive said values is via said input fields.

22. The system according to claim 18, wherein said data processor is configured to display on said GUI an output that summarizes scores calculated for previous blood samples.

* * * * *

```
                           SEQUENCE LISTING

Sequence total quantity: 38
SEQ ID NO: 1              moltype = DNA   length = 1953
FEATURE                   Location/Qualifiers
source                    1..1953
                          mol_type = genomic DNA
                          organism = Homo sapiens
mRNA                      1..1953
SEQUENCE: 1
acagaaccca gaaaaacaac tcattcgctt tcatttcctc actgactata aaagaataga    60
gaaggaaggg cttcagtgac cggctgcctg gctgacttac agcagtcaga ctctgacagg   120
atcatggcta tgatggaggt ccagggggga cccagcctgg gacagacctg cgtgctgatc   180
gtgatcttca cagtgctcct gcagtctctc tgtgtggctg taacttacgt gtactttacc   240
aacgagctga agcagatgca ggacaagtac tccaaaagtg gcattgcttg tttcttaaaa   300
gaagatgaca gttattggga ccccaatgac gaagagagta tgaacagccc ctgctggcaa   360
gtcaagtggc aactccgtca gctcgttaga aagatgattt tgagaacctc tgaggaaacc   420
atttctacag ttcaagaaaa gcaacaaaat atttctcctc tagtgagaga aagaggtcct   480
cagagagtag cagctcacat aactgggacc agaggaagaa gcaacacatt gtcttctcca   540
aactccaaga atgaaaaggc tctgggccgc aaaataaact cctgggaatc atcaaggagt   600
gggcattcat tcctgagcaa cttgcacttg aggaatggtg aactggtcat ccatgaaaaa   660
gggttttact acatctattc ccaaacatac tttcgatttc aggaggaaat aaaagaaaac   720
acaaagaacg acaaacaaat ggtccaatat atttacaaat acacaagtta tcctgaccct   780
atattgttga tgaaaagtgc tagaaatagt tgttggtcta aagatgcaga atatggactc   840
tattccatct atcaagggg aatatttgag cttaaggaaa atgacagaat ttttgtttct   900
gtaacaaatg agcacttgat agacatggac catgaagcca gttttttgg ggcttttta   960
gttggctaac tgacctggaa agaaaaagca ataacctcaa agtgactatt cagttttcag  1020
gatgatacac tatgaagatg tttcaaaaaa tctgaccaaa acaaacaaac agaaaacaga  1080
aaacaaaaaa acctctatgc aatctgagta gagcagccac aaccaaaaaa ttctacaaca  1140
cacactgttc tgaaagtgac tcacttatcc caagagaatg aaattgctga aagatcttc  1200
aggactctac ctcatatcag tttgctagca gaaatctaga agactgtcag cttccaaaca  1260
ttaatgcaat ggttaacatc ttctgtcttt ataatctact ccttgtaaag actgtagaag  1320
aaagagcaac aatccatctc tcaagtagtg tatcacagta gtagcctcca ggtttcctta  1380
agggacaaca tccttaagtc aaaagagaga agaggcacca ctaaaagatc gcagtttgcc  1440
tggtgcagtg gctcacacct gtaatcccaa cattttggga acccaaggtg ggtagatcac  1500
gagatcaaga gatcaagacc atagtgacca acatagtgaa accccatctc tactgaaagt  1560
acaaaaatta gctgggtgtg ttggcacatg cctgtagtcc cagctacttg agaggctgag  1620
gcaagagaat tgtttgaacc cgggaggcag aggttgcagt gtggtgagat catgccacta  1680
cactccagcc tggcgacaga gcgagacttg gtttcaaaaa aaaaaaaa aaaaacttca  1740
gtaagtacgt gttattttt tcaataaaat tctattacag tatgtcatgt ttgctgtagt  1800
gctcatattt attgttgttt ttgttttagt actcacttgt ttcataatat caagattact  1860
aaaaatgggg gaaaagactt ctaatctttt tttcataata tctttgacac atattacaga  1920
agaaataaat ttcttacttt taatttaata tga                                1953

SEQ ID NO: 2              moltype = DNA   length = 1805
FEATURE                   Location/Qualifiers
source                    1..1805
                          mol_type = other DNA
                          note = cDNA
                          organism = Homo sapiens
SEQUENCE: 2
acagaaccca gaaaaacaac tcattcgctt tcatttcctc actgactata aaagaataga    60
gaaggaaggg cttcagtgac cggctgcctg gctgacttac agcagtcaga ctctgacagg   120
atcatggcta tgatggaggt ccagggggga cccagcctgg gacagacctg cgtgctgatc   180
gtgatcttca cagtgctcct gcagtctctc tgtgtggctg taacttacgt gtactttacc   240
aacgagctga agcagatgca ggacaagtac tccaaaagtg gcattgcttg tttcttaaaa   300
gaagatgaca gttattggga ccccaatgac gaagagagta tgaacagccc ctgctggcaa   360
gtcaagtggc aactccgtca gctcgttaga aagactccaa gaatgaaaag gctctgggcc   420
gcaaaataaa ctcctgggaa tcatcaagga gtgggcattc attcctgagc aacttgcact   480
tgaggaatgg tgaactggtc atccatgaaa aagggtttta ctacatctat tcccaaacat   540
actttcgatt tcaggaggaa ataaaagaaa acacaaagaa cgacaaacaa atggtccaat   600
atatttacaa atacacaagt tatcctgacc ctatattgtt gatgaaaagt gctagaaata   660
gttgttggtc taaagatgca gaatatggac tctattccat ctatcaaggg gaatatttg   720
agcttaagga aaatgacaga ttttgtttgtt ctgtaacaaa tgagcacttg atagacatgg   780
accatgaagc cagttttttt ggggccttt tagttgctta actgacctgg aaagaaaaag   840
caataacctc aaagtgacta ttcagttttc aggatgatac actatgaaga tgtttcaaaa   900
aatctgacca aacaaacaa acagaaaaca gaaaacaaaa aaacctctat gcaatctgag   960
tagagcagcc acaaccaaaa aattctacaa cacacactgt tctgaaagtg actcacttat  1020
cccaagagaa tgaaattgct gaaagatctt tcaggactct acctcatatc agtttgctag  1080
cagaaatcta gaagactgtc agcttccaaa cattaatgca atggttaaca tcttctgtct  1140
ttataatcta ctccttgtaa agactgtaga agaaagagca acaatccatc tctcaagtag  1200
tgtatcacag tagtagcctc caggtttcct taagggacaa catccttaag tcaaaagaga  1260
gaagaggcac cactaaaaga tcgcagtttg cctggtgcag tggctcacac ctgtaatccc  1320
```

```
aacattttgg gaacccaagg tgggtagatc acgagatcaa gagatcaaga ccatagtgac   1380
caacatagtg aaaccccatc tctactgaaa gtacaaaaat tagctgggtg tgttggcaca   1440
tgcctgtagt cccagctact tgagaggctg aggcaagaga attgtttgaa cccgggaggc   1500
agaggttgca gtgtggtgag atcatgccac tacactccag cctggcgaca gagcgagact   1560
tggtttcaaa aaaaaaaaaa aaaaaaactt cagtaagtac gtgttatttt tttcaataaa   1620
attctattac agtatgtcat gtttgctgta gtgctcatat ttattgttgt ttttgtttta   1680
gtactcactt gtttcataat atcaagatta ctaaaaatgg gggaaaagac ttctaatctt   1740
tttttcataa tatctttgac acatattaca gaagaaataa atttcttact tttaatttaa   1800
tatga                                                                1805

SEQ ID NO: 3           moltype = DNA   length = 1334
FEATURE                Location/Qualifiers
source                 1..1334
                       mol_type = other DNA
                       note = cDNA
                       organism = Homo sapiens
SEQUENCE: 3
atttcctcac tgactataaa agaatagaga aggaagggct tcagtgaccg gctgcctggc   60
tgacttacag cagtcagact ctgacaggat catggctatg atggaggtcc agggggggacc   120
cagcctggga cagacctgcg tgctgatcgt gatcttcaca gtgctcctgc agtctctctg   180
tgtggctgta acttacgtgt actttaccaa cgagctgaag cagtttgcag aaaatgattg   240
ccagagacta atgtctgggc agcagacagg gtcattgctg ccatcttgaa gtctacccttg   300
ctgagtctac cctgctgacc tcaagcccca tcaaggactg gttgaccctg cctagacaa   360
ccaccgtgtt tgtaacagca ccaagagcag tcaccatgga aatccacttt tcagaaccaa   420
gggcttctgg agctgaagaa caggcaccca gtgcaagagc tttctttcca gaggcacgca   480
aatgaaaata atccccacac gctacctcc tgcccccaatg cccaagtgtg gttagttaga   540
gaatatagcc tcagcctatg atatgctgca ggaaactcat attttgaagt ggaaaggatg   600
ggaggaggcg ggggagacgt atcgtattaa ttatcattct tggaataacc acagcacctc   660
acgtcaaccc gccatgtgtc tagtcaccag cattggccaa gttctatagg agaaactacc   720
aaaattcatg atgcaagaaa catgtgaggg tggagagagt gactggggct tcctctctgg   780
atttctattg ttcagaaatc aatatttatg cataaaaagg tctagaaaga gaaacaccaa   840
aatgacaatg tgatctctag atggtatgat tatgggtact tttttttcctt ttattttttc   900
tatattttac aaattttcta cagggaatgt tataaaaata tccatgctat ccatgtataa   960
ttttcataca gatttaaaga acacagcatt tttatatagt tctatgagaa acaaccata   1020
ctcaaaatta tgcacacaca cagtctgatc tcacccctgt aaacaagaga tatcatccaa   1080
aggttaagta ggaggtgaga atatagctgc tattagtggt tgtttttgttt tgttttttgtg   1140
atttacttat ttagtttttg gagggttttt ttttttctttt agaaaagtgt tctttacttt   1200
tccatgcttc cctgcttgcc tgtgtatcct gaatgtatcc aggctttata aactcctggg   1260
taataatgta gctacattaa cttgttaacc tcccatccac ttatacccag gaccttactc   1320
aattttccag gttc                                                      1334

SEQ ID NO: 4           moltype = AA   length = 281
FEATURE                Location/Qualifiers
source                 1..281
                       mol_type = protein
                       organism = Homo sapiens
SEQUENCE: 4
MAMMEVQGGP SLGQTCVLIV IFTVLLQSLC VAVTYVYFTN ELKQMQDKYS KSGIACFLKE   60
DDSYWDPNDE ESMNSPCWQV KWQLRQLVRK MILRTSEETI STVQEKQQNI SPLVRERGPQ   120
RVAAHITGTR GRSNTLSSPN SKNEKALGRK INSWESSRSG HSFLSNLHLR NGELVIHEKG   180
FYYIYSQTYF RFQEEIKENT KNDKQMVQYI YKYTSYPDPI LLMKSARNSC WSKDAEYGLY   240
SIYQGGIFEL KENDRIFVSV TNEHLIDMDH EASFFGAFLV G                       281

SEQ ID NO: 5           moltype = AA   length = 101
FEATURE                Location/Qualifiers
source                 1..101
                       mol_type = protein
                       organism = Homo sapiens
SEQUENCE: 5
MAMMEVQGGP SLGQTCVLIV IFTVLLQSLC VAVTYVYFTN ELKQMQDKYS KSGIACFLKE   60
DDSYWDPNDE ESMNSPCWQV KWQLRQLVRK TPRMKRLWAA K                       101

SEQ ID NO: 6           moltype = AA   length = 65
FEATURE                Location/Qualifiers
source                 1..65
                       mol_type = protein
                       organism = Homo sapiens
SEQUENCE: 6
MAMMEVQGGP SLGQTCVLIV IFTVLLQSLC VAVTYVYFTN ELKQFAENDC QRLMSGQQTG   60
SLLPS                                                                65

SEQ ID NO: 7           moltype = AA   length = 223
FEATURE                Location/Qualifiers
source                 1..223
                       mol_type = protein
                       organism = Homo sapiens
SEQUENCE: 7
QDHGYDGGPG GTQPGTDLRA DRDLHSAPAV SLCGCNLRVL YQRAEAEKQQ NISPLVRERG   60
PQRVAAHITG TRGRSNTLSS PNSKNEKALG RKINSWESSR SGHSFLSNLH LRNGELVIHE   120
```

```
KGFYYIYSQT YFRFQEEIKE NTKNDKQMVQ YIYKYTSYPD PILLMKSARN SCWSKDAEYG    180
LYSIYQGGIF ELKENDRIFV SVTNEHLIDM DHEASFFGAF LVG                    223

SEQ ID NO: 8            moltype = AA  length = 178
FEATURE                 Location/Qualifiers
source                  1..178
                        mol_type = protein
                        organism = Homo sapiens
SEQUENCE: 8
KEKQQNISPL VRERGPQRVA AHITGTRGRS NTLSSPNSKN EKALGRKINS WESSRSGHSF    60
LSNLHLRNGE LVIHEKGFYY IYSQTYFRFQ EEIKENTKND KQMVQYIYKY TSYPDDPILLM   120
KSARNSCWSK DAEYGLYSIY QGGIFELKEN DRIFVSVTNE HLIDMDHEAS FFGAFLVG     178

SEQ ID NO: 9            moltype = DNA  length = 2421
FEATURE                 Location/Qualifiers
source                  1..2421
                        mol_type = other DNA
                        note = cDNA
                        organism = Homo sapiens
SEQUENCE: 9
caccctcatg agccccgggt acgtttaact attgagggcc aggaaattgc cttcctcctg    60
gacactggcg cagccttctc agggttaatc tcctgtcctg gatgactgtc ttcaaggtcc   120
gttaccaccc gaggaatcct gggacagcct ataaccaggt attttctccca catcctcagt   180
tgtaattgag agactttaat cttttcacat gccttttttg ttattcctga agtcccaca    240
cccttattaa ggagggatat attagccaag gctggagcta ttatctacat gaatatgggg   300
aaaaagttac ccatttgctg tcccctactt gaggaggaa tcaaccctga agtctgggca    360
ttggaaggac aatttggaag ggcaaaaaat gcctgcccag tccaaatcag gttaaaagat   420
cccaccactt ttccgtatca aaggcaatat cccttaaggc ctgaagctca taaggatta    480
tagaatattg ttaaacattt aaaagctcaa ggcttagtga ggaaatgcag cagtccctgc    540
aacacccag ttctaggagt acaaaaacca aacagtcagt gggagactagt gcaagatctt    600
agactcatta atgaggcagt aattcctcta tatccagttg tacccaaccc ctataccctg    660
ctctctcaaa taccagggga agcagaatgg ttcacggttc tggacctcaa ggatgccttc    720
ttctttatt ccctgcactc tgactccag tttctctttg cttttgagga tcccacagac     780
cacacgtccc aacttacaca gatggtcttg ccccaagggt ttagggatag ccctccatctg   840
tttggtcagg cactgggccca agatctatag gccacttctc aagtccaggc actctggtcc   900
ttcaatatgt ggatgattta ctttttggcta ccagtttgga agcctcgtgc cagcaggcta   960
ctctggatct cttgaactttt ctggctaatc aagggtacaa ggtgtctagg tcgaaggccc  1020
agcttttgcct acagcaggtt aaatatctaa gcctaatctt agccaaaggg accagggccc  1080
tcagcaagga atgaatacag cctatactgg cttatcctca ccctaagaca ttaaaacagt   1140
tgcggggatt ccttggaatt actggctttt gctgactatg gatctccaga tacagcgaga   1200
cagccaggcc cctctatact ctaatcaagg aaacccagag ggcaaatact catctagtcg   1260
aaagggaacc agaggcagaa acagccttca aaagcttaaa gcaggctcta gtacaagctc   1320
cagctttaag ccttcccaca ggacagaact tctctttata catcacagag agagccaaga   1380
tagctcttgg agtccttaga ctcgtgggac aaccccacaa ccagtggcat acctaagtaa   1440
ggaaattgat gtagtagcaa aaggctggcc tcactgttta agggtagttg cagcagcggc   1500
cgtcttagcg tcagaggcta tcagaataat acaaggaaag gatctcactg tctggactac   1560
tcatgatgta aatggcatac taggtgccaa aggaagttta tggctatcag acaaccgctt   1620
cttagatgcc aggcactact ccttgaggga ctggtgctta aaatatgcac gtgcgtggcc   1680
ctcaaccctg ccactttct cccagaggat ggggaaccaa ttgagcatga ctgccaacaa    1740
attatagtcc agcttatgc cgcccagat gatctcttag aagtccccttt aactaatcct    1800
gaccttaacc tatataccga cggaagttca tttgtggaga atgggatacg aagggcaggt   1860
tacgccatag tgatgtaacc acacttgaaa gcaagcctct tccccaggg accagtgccc    1920
agttagcaga actagtggca cttacccgag ccttagaact gggaaaggga aaaagaataa   1980
atgtgtatac agataacaag tatgcttatc taatcctaca tgcccatgct gcaatatgga  2040
aagaatggga gttcctaacc tctgggaacc cccgctggga gccacaggga agttatggag  2100
ttattgcaca tggtgcagga acccaaagag gtgggagtct tacactacca aggccatcaa   2160
aatgggaagg agaggggaga acagcagcat aagcggctgg cagaggtagg gaaagaccag  2220
caagaaggaa agagagaaag agaaagtcag agaaagagac agagagagga agagacagag   2280
agacagaacg ttaagaggg tgtcagaaac agagacaaac aaaaggagtc agaaagaagg    2340
acagacacag aaagtcaaag agagagttaa aaagagagga agagacaaag aagtcgaaga   2400
gagaaagaga gagatggaag t                                            2421

SEQ ID NO: 10           moltype = DNA  length = 2421
FEATURE                 Location/Qualifiers
source                  1..2421
                        mol_type = other DNA
                        note = cDNA
                        organism = Homo sapiens
SEQUENCE: 10
ctttgcagat aaatatggca cactagcccc acgttttctg agacattcct caattgctta    60
gacatattct gagcctacag cagaggaacc tccagtctca gcaccatgaa tcaaactgcc   120
attctgattt gctgccttat ctttctgact ctaagtggca ttcaaggtaa ggaacatcaa   180
aggatactta atttgtaaaa tgagaaatag gaataggtat aaattctaaa aatacagaaa   240
taatgtattt gtaaaagttt cactgcatgc ttataaataa gagggaaata aatagagatt   300
ccctcagatc ataaaactta tatgaattga agtgagagaa acaaatgaaa taagaaaag    360
agaaggaaaa aggaaggag gacagaagag atggggaaga gggaggatag agagagaaaa   420
tgtgagggaa tgcggacaga gatgagatac agatacttcc ttacctaact aagctcaatg   480
aaccacatga actgtgctta agggttttgac tttataatca acaagctgca attctttct    540
tccagataat caactcttta atcatttaca gttgtgttat gatgtgatcc attcctcctc   600
```

```
agattaagtg actatttgct gatatgggga tataggttct gctaaatacc accagtctac   660
attaaatgcc taaatgaac  actgtgctaa ccttctctgc tgttcctctt ttcctacagg   720
agtacctctc tctagaactg tacgctgtac ctgcatcagc attagtaatc aacctgttaa   780
tccaaggtct ttagaaaaac ttgaaattat tcctgcaagc caattttgtc cacgtgttga   840
gatcatgtga gtgaaatccc atctgattat cacttccctg gttgtaatta tatactgtat   900
taaatatgta atgataataa aaaaagatca gtaaagggtt tgtgatgatt ctaaaactaa   960
tgtacagcaa acaaaaacat gcagagtgaa acttaaatgt ctgacttcag aactgcgtat  1020
gccatctgtt ttattgaccc aacacagttt taaatatttt catccctatt tatttctaca  1080
gtgctacaat gaaaaagaag ggtgagaaga gatgtctgaa tccagaatcg aaggccatca  1140
agaatttact gaaagcagtt agcaaggaaa ggtaggtttg ctgttgcctg cagaagaatt  1200
gctctttagg aaacggcaat cttgggagtc agaaatactt gcattgtggt ttgctgtgca  1260
atcgctggtt taaaagtatg ttaccaccac gccctcccct acctccattt atttaaatgc  1320
tgaggcacca tcttgtgtga taagtatcag aagttaccct gattaccagt caaccttgaa  1380
gtacagctat aactatctaa gcaaaactga caacattttc cccaagtctt tcatggttga  1440
aaaaagcaac ccctataatc cataatgaat gcatagcagc aggaaagctc agttatctat  1500
tctatgaact cggtactttc caaacacaac ccaatctgaa gccagagtca gactatcaca  1560
cttttatatc cccttttctct tcttacaggt ctaaaagatc tccttaaaac cagaggggag  1620
caaaatcgat gcagtgcttc caaggatgga ccacacagag gctgcctctc ccatcacttc  1680
cctacatgga gtatatgtca agccataatt gttcttagtt tgcagttaca ctaaaaggtg  1740
accaatgatg gtcaccaaat cagctgctac tactcctgta ggaaggttaa tgttcatcat  1800
cctaagctat tcagtaataa ctctaccctg gcactataat gtaagctcta ctgaggtgct  1860
atgttcttag tggatgttct gaccctgctt caaatatttc cctcacctt cccatcttcc   1920
aagggtacta aggaatcttt ctgctttggg gtttatcaga attctcagaa tctcaaataa  1980
ctaaaaggta tgcaatcaaa tctgcttttt aagaatgct  ctttacttca tggacttcca  2040
ctgccatcct cccaagggggc ccaaattctt tcagtggcta cctacataca attccaaaca  2100
catacaggaa ggtagaaata tctgaaaatg tatgtgtaag tattcttatt taatgaaaga  2160
ctgtacaaag tagaagtctt agatgtatat atttcctata ttgttttcag tgtacatgga  2220
ataacatgta attaagtact atgtatcaat gagtaacagg aaaattttaa aaatacagat  2280
agatatatgc tctgcatgtt acataagata aatgtgctga atggttttca aaataaaaat  2340
gaggtactct cctggaaata ttaagaaaga ctatctaaat gttgaaagat caaaaggtta  2400
ataaagtaat tataactaag a                                            2421

SEQ ID NO: 11         moltype = DNA  length = 2421
FEATURE               Location/Qualifiers
source                1..2421
                      mol_type = other DNA
                      note = cDNA
                      organism = Homo sapiens
SEQUENCE: 11
agatgacttt tttctatta  tatttaataa gatgatgaac ccttcttgca ttcccgaaat    60
aaacctcaac tgttacagtg ttttattctt taaatatgta cgaagtacat gttaagcaag   120
ttatttccta agcagcccca caaactgggc actactacca tcctgctctg cccctcccctc  180
actctacttc agccacttca gccacaatgg cctctcctca ctgcccctct gatgcaccaa   240
gcttgttctc acctcaggaa tgtgcaacac ctgccagact tgctgttccc cggagcctcc   300
atccccagat atcctcatat atcatcctcc tcttcatttg tgtctctgct tacatatgac   360
ctatttacag aagcctttcc tgtctacccc ccatgaaata gaaatcgcat tccaatcttg   420
tctctacccc aatgctgttt cattttgtct gtagcaattg tcatcatctc atatatattc   480
acatgtggaa aatacacaaa atgtttaact tcttttaatt tacattccat ttcccccatga  540
attgaagctc catgacagcg gagatttttc tctgctttcc ctgttgctca cttcccagca   600
ccaagagcag gcctggcaca tgggaagtac ttactattta ttgaatggat gaatgaacaa   660
atgaatgaat ggatacttat tttacacata agaaaactga agcttataga aattaagtaa   720
ctaaaatcac acagaagcac agctgaaact aaaacctacg tctaactttc aattcctgac   780
ccttaaccat taaaacaaat gacaggtgac tttaggccac tgaaaatgct catataatct   840
tatgaattct aaagcacaag ttaatcacac cattgattga aagtctgagg aatactgtat   900
agacaagccc ctgtacaagg taagcaaaag aatcagagga tggcctccaa agaattccct   960
ggacattatg ggaattacat tgttagcctt cctactgata cccataagcc tcacagcaag  1020
catcatgaag ctgtgacctt catctgcaca tgcccttgta tacccaaaag ataaaactgg  1080
atgcttcagg gccgaatggc caataaacac gtgtttatta ctggcatggg cagacacaca  1140
tactgaaagt accatttccc agcggactag ccatatatg  atcagtacag acactaaaga  1200
tttagctttg aaaaaactat ttgctcttcc aaagctgaag aatcttctgt gatttcaaca  1260
ggcaagttac agtcaggtat tcttaatgtt cttttcctcc tctctcactg ggatactttc  1320
tttccttcag acaacgtcaa gcgaaaaaca aaatttcaca aatctccatt tctgacacta  1380
aacagtacag tatcttttatt tttttttataa tttaatcaaa ccctgtattt tagaactgtg  1440
gggctgatcc aacattgcaa tgtgtcacat ttaattccat caatgtaaag cataatgagc  1500
aaagattaag gtagtgaggc ataactaaat gttttgaacc tgtgaattc  aaaagcaagg  1560
cccatttgtg ttattttcta aatagtaaat aaaatcattt tccaacattt cactatcaaa  1620
ttacagtaat ttttccacca gtacacactt gaggaaagcc acaaaaagac ttttccaaca  1680
gttcattctg ttattgctca taaccttcta aatacttctc ctcattggct tctattcaaa  1740
gtaaatggaa aagcagtaaa atttatggaa aatatattca actgcttaaa atacatcaac  1800
caaaaaaaaag attttagagc tgtattatga gttgtgaaat tgcattgcct tcacttacct  1860
ttcagttttca ctggtaggta acaaaactga cagactggtc aagttccaaa catcccccta  1920
tatagagcct gactcttcca tctcaaattc tcaccttggt caaggccaga gtaaacacct  1980
gtccttcaca ttttttacaca acatcacttt gtatgctaca aatataagct ttcataccag  2040
ggaggaagca aattccagga cactggaaac atttctgct tcttaaacca gtctgttgat   2100
tgttcccttg actttctcag ctgtcaggat agtgaaagga ggaaaactgc aaaactgtaa  2160
agtataaccct gataagtttg cccctttaagc ttttcacaca gagagaggta aaataaaact  2220
caagtctaag gtttaaaatt gagctatgaa tattatattc tagcactaga caaaaatgtt  2280
gcaagatttt aataaaataa gattattaaa atcaattttc acatttcatg ggccaaggag  2340
agacatcaaa gaatgtttaa ctaacatttt aaagatacta tactttataa agttaagaag  2400
```

```
aaaaatgaca actgcaccag t                                                  2421

SEQ ID NO: 12           moltype = DNA  length = 1227
FEATURE                 Location/Qualifiers
source                  1..1227
                        mol_type = other DNA
                        note = cDNA
                        organism = Homo sapiens
SEQUENCE: 12
ctttgcagat aaatatggca cactagcccc acgttttctg agacattcct caattgctta         60
gacatattct gagcctacag cagaggaacc tccagtctca gcaccatgaa tcaaactgcc        120
attctgattt gctgccttat ctttctgact ctaagtggca ttcaaggagt acctctctct        180
agaactgtac gctgtacctg catcagcatt agtaatcaac ctgttaatcc aaggtcttta        240
gaaaaacttg aaattattcc tgcaagccaa ttttgtccac gtgttgagat cattgctaca        300
atgaaaaaga agggtgagaa gagatgtctg aatccagaat cgaaggccat caagaattta        360
ctgaaagcag ttagcaagga aaggtctaaa agatctcctt aaaaccagag gggagcaaaa        420
tcgatgcagt gcttccaagg atggaccaca cagaggctgc ctctcccatc acttccctac        480
atggagtata tgtcaagcca taattgttct tagtttgcag ttacactaaa aggtgaccaa        540
tgatggtcac caaatcagct gctactactc ctgtaggaag gttaatgttc atcatcctaa        600
gctattcagt aataactcta ccctggcact ataatgtaag ctctactgag gtgctatgtt        660
cttagtggat gttctgaccc tgcttcaaat atttccctca cctttcccat cttccaaggg        720
tactaaggaa tctttctgct ttggggttta tcagaattct cagaatctca aataactaaa        780
aggtatgcaa tcaaatctgc ttttttaaga atgctctttta cttcatggac ttccactgcc        840
atcctcccaa ggggcccaaa ttctttcagt ggctacctac atacaattcc aaacacatac        900
aggaaggtag aaatatctga aatgtatgt gtaagtattc ttatttaatg aaagactgta        960
caaagtagaa gtcttagatg tatatatttc ctatattgtt ttcagtgtac atggaataac       1020
atgtaattaa gtactatgta tcaatgagta acaggaaaat tttaaaaata cagatagata       1080
tatgctctgc atgttacata agataaatgt gctgaatggt tttcaaaata aaaatgaggt       1140
actcctctgg aaatattaag aaagactatc taaatgttga aagatcaaaa ggttaataaa       1200
gtaattataa ctaagaaaaa aaaaaaa                                           1227

SEQ ID NO: 13           moltype = AA   length = 98
FEATURE                 Location/Qualifiers
source                  1..98
                        mol_type = protein
                        organism = Homo sapiens
SEQUENCE: 13
MNQTAILICC LIFLTLSGIQ GVPLSRTVRC TCISISNQPV NPRSLEKLEI IPASQFCPRV         60
EIIATMKKKG EKRCLNPESK AIKNLLKAVS KERSKRSP                                 98

SEQ ID NO: 14           moltype = DNA  length = 2301
FEATURE                 Location/Qualifiers
source                  1..2301
                        mol_type = other DNA
                        note = cDNA
                        organism = Homo sapiens
SEQUENCE: 14
aaggcaagag atctaggact tctagcccct gaactttcag ccgaatacat ctttttccaaa         60
ggagtgaatt caggcccttg tatcactggc agcaggacgt gaccatggag aagctgttgt        120
gtttcttggt cttgaccagc ctctctcatg cttttggcca gacaggtaag ggccacccca        180
ggctatggga gagatttgat ctgaggtatg ggggtgggc ctaagactgc atgaacagtc        240
tcaaaaaaaa aaaaaaaaga ctgtatgaac agaacagtga agcatccttc atggtgtgtg        300
tgtgtgtgtg tgtgtgtgtg tgtgtgtgtg tggtgtgtaa ctggagaagg ggtcagtctg        360
tttctcaatc ttaaattcta tacgtaagtg agggatagaa tctgtgtgat ctgagaaacc        420
tctcacattt gcttgtttt ctggctcaca gacatgtga ggaaggcttt tgtgtttccn        480
aaagagtcgg atacttccta tgtatccctc aaagcaccgt taacgaagcc tctcaaagcc        540
ttcactgtgt gcctccactt ctacacgaa ctgtcctcga cccgtgggta cagtattttc         600
tcgtatgcca ccaagagaca agacaatgag attctctat tttggtctaa ggatataggg         660
tacagttta cagtgggtgg gtctgaaata ttattcgagg ttcctgaagt cacagtagct         720
ccagtacaca tttgtacaag ctgggtgtcc gcctcaggga tcgtggagtt ctggagtagat        780
gggaagccca gggtgaggaa gagtctgaag aagggataca ctgtgggggc agaagcaagc        840
atcatcttgg ggcaggagca ggattccttc ggtgggaact tgaaggaag ccagtccctg          900
gtgggagaca ttgaaatgt gaacatgtgg gactttgtgc tgtcaccaga tgagattaac          960
accatctatc ttggcgggcc cttcagtcct aatgtcctga actggcgggc actgaagtat         1020
gaagtgcaag gcgaagtgtt caccaaaccc cagctgtggc cctgaggccc agctgtgggt        1080
cctgaaggta cctcccggtt ttttacaccg catgggcccc acgtctctgt ctctggtacc        1140
tcccgctttt ttacactgca tggttcccac gtctctgtct ctgggccttt gttccctat         1200
atgcattgca ggcctgctcc accctcctca gcgcctgaga atggaggtaa agtgtctggt        1260
ctgggagctc gttaactatg ctgggaaacg gtccaaaaga atcagaattt gaggtgtttt        1320
gttttcattt ttatttcaag ttggacagat cttggagata atttcttacc tcacatagat        1380
gagaaaacta acacccagaa aggagaaatg atgtttataaa aaactcataa ggcaagagct        1440
gagaaggaag cgctgatctt ctatttaatt ccccacccat gacccccaga aagcaggagg        1500
gcattgccca cattcacagg gctcttcagt ctcagaatca ggacactggc caggtgtctg        1560
gtttgggtcc agagtgctca tcatcatgtc atagaactgc tgggcccagg tctcctgaaa        1620
tgggaagccc agcaataccca cgcagtccct ccactttctc aaagcacact ggaaaggcca        1680
ttagaattgc cccagcagag cagatctgct ttttttccag agcaaaatga agcactaggt        1740
ataaaatgt tgttactgcc aagaacttaa atgactggtt tttgtttgct tgcagtgctt        1800
tcttaatttt atggctcttc tgggaaactc ctccccttt ccacgcgaac cttgtggggc        1860
tgtgaattct ttcttcatcc ccgcattccc aatataccca ggcacaagaa gtggacgtga        1920
```

```
accacagggt gtcctgtcag aggagcccat ctcccatctc cccagctccc tatctggagg    1980
atagttggat agttacgtgt tcctagcagg accaactaca gtcttcccaa ggattgagtt    2040
atggactttg ggagtgagac atcttcttgc tgctggattt ccaagctgag aggacgtgaa    2100
cctgggacca ccagtagcca tcttgtttgc cacatggaga gagactgtga ggacagaagc    2160
caaactggaa gtggaggagc caagggattg acaaacaaca gagccttgac cacgtggagt    2220
ctctgaatca gccttgtctg gaaccagatc tacacctgga ctgcccaggt ctataagcca    2280
ataaagcccc tgtttacttg a                                              2301

SEQ ID NO: 15           moltype = DNA  length = 2301
FEATURE                 Location/Qualifiers
source                  1..2301
                        mol_type = other DNA
                        note = cDNA
                        organism = Homo sapiens
SEQUENCE: 15
aggaattgaa ctcagctctg ccccaagcgg acctaataga catctacaga actctccacc    60
ccaaatcaac agaatataca tttttttcag caccacacca cacctattcc aaaattgatc    120
acatagttgg cagtaaagct ctcctcagca aatgtaaagg aacagaaatt ataacaaact    180
atctctcaga ccacagtgca atcaaattag aactcagaat taagaatctc actcaaaacc    240
gcacaactac atgaaactg aacaacctgc ttctgaatga ctactgggta cataatgaaa     300
tgaaggcaga aataaagatg ttcttttgaaa tgaacaagaa caaacacaca acataccaga   360
atctctggga cgcattcaaa gcagtgtgta gagggaaatt tatagcacta agtgcccaca    420
agagaaagca ggaaacatcc aaaattgaca tcctaacatc acagttaaaa gaactagaaa    480
agcaagagca aacacattca aaagctagca gaaggcaaga gataactaaa atcagagcag    540
aactgaagga aatagagaca caaaacccct tcaaaaaatt aatgaatcca ggagctggtt    600
ttttgaaagg atcaacaaaa tagatagacc actagcaaga ctaataaaga aaaaagaga    660
gaagaatcaa atagcacaa taaaaaaatg ataaagggga tatcaccacc gatcccacgg     720
aaatacaaac taccatcaga gaatactaca aacacctcta cgcaaataaa ctagaaaatc    780
aagaagaaat ggataaattc ctcgacacat acactctccc aagactaaac caggaagaag    840
ttgaatctct gaatagacca ataacaggat atgaaattgt ggcaataatc aataccttac    900
caacaaaaaa gagtccagga ccagatggat tcacagccga attctaccag aggtacaagg    960
aggaactggt accattcctt ctgaaactat tccaatcaat agaaaaagag ggaatcctcc    1020
ctaactcatt ttatgaggcc agcatcattc tgataccaaa gccgggcaga gacacaacca    1080
aaaaagagaa ttttagacca atcaatatcc ttgatgaaca ttgatgcaaa aatcctcaat    1140
aaaatactgc aaaccaaat ccagcagcac atcaaaaagc ttatccacca tgatcaagtg     1200
ggcttcatcc ctgggatgca aggctggttc aatatacgca aatcaataaa tgtaatccag    1260
catataaaca gagccaaaga caaaaaccac atgattatct caatagatgc agaaaagacc    1320
tttgacaaaa ttcaacaacc cttcatgctc aaaactctca ataaattagg tattgatggg    1380
acgtatttca aaataataag agctatctat gacaaaccca cagccaatat cactactgaat    1440
gggcaaaaac tggaagtatt cactttgaaa actggcacaa gacagggatg ccctctctca    1500
ccactcctat tcaacatagt gttggaagtt ctgccagggc aattaggca ggagaaggaa     1560
ataaagggta ttcaattagg aaaagaggaa gtcaaattgt ccctgtttgc agacgacatg    1620
attgtatatc tagaaaaaccc cattgtctca gcccaaaatc tccttaagca gataagcaac    1680
ttcagcaaaa tctcaggata caaaatcaat gtacaaaaat cacaagcatt cttatacacc    1740
aacaacagac aaacagagag ccaaatcatg agtgaaatcc cattcacaat tgcttttaaag   1800
agaataaaat acctaggaat ccaacttaca agggatgtga aggacctctt caaggagaac    1860
tacaaaccac tgctcaatga aataaaagag gataaaaaca atggaagaa cattccatgc     1920
tcatgggtag gaagaatcaa tatcatgaaa atggccatac tgcccaaggt aatttacaga    1980
ttcaatgcca tccccatcaa gctaccaatg ccttttcttca cagaattgga aaaaactatt    2040
tttagttcat atggaaccaa aaaagagccc gcattgccaa gtcaatccta agccaaaaga    2100
acaaagctgg aggcatcaca ctacctgact tcaaactata ctacaaggct acagtaacca    2160
aaacagcatg gtactggaac caaaacagag atatagatca atggaacaga acagagccct    2220
caaaattaat gccacatatc tacaactatc tgatctttga caaacctgag aaaaaccagc    2280
aatggggaaa ggattcccca t                                              2301

SEQ ID NO: 16           moltype = DNA  length = 2024
FEATURE                 Location/Qualifiers
source                  1..2024
                        mol_type = other DNA
                        note = cDNA
                        organism = Homo sapiens
SEQUENCE: 16
aaggcaagag atctaggact tctagcccct gaactttcag ccgaatacat cttttccaaa    60
ggagtgaatt caggcccttg tatcactggc agcaggacgt gaccatggag aagctgttgt    120
gtttcttggt cttgaccagc ctctctcatg cttttggcca gacagacatg tcgaggaagg    180
cttttgtgtt tcccaaagag tcggatactt cctatgtatc cctcaaagca ccgttaacga    240
agcctctcaa agccttcact gtgtgcctcc acttctacac ggaactgtcc tcgacccgtg    300
ggtacagtat tttctcgtat gccaccaaga gacaagcaa tgagattctc atatttggt     360
ctaaggatat aggatacagt ttacagtgg gtgggtctga aatattattc gaggttcctg     420
aagtcacagt agctccagta cacatttgta caagctggga gtccgcctca gggatcgtgg    480
agttctgggt agatgggaag cccagggtga ggaagagtct gaagaaggga tacactgtgg    540
gggcagaagc aagcatcatc ttggggcagg agcaggattc cttcggtggg aactttgaag    600
gaagccagtc cctggtggga gacattgaa atgtgaacat gtgggacttt gtgctgtcac     660
cagatgagat taacaccatc tatcttggcg ggccttcag tcctaatgtc tgaactggc     720
gggcactgaa gtatgaagtg caaggcgaag tgttccaaa accccagctg tggccctgag    780
gcccagctgt gggtcctgaa ggtacctccc ggttttttac accgcatggg cccacgtct     840
ctgtctctgg tacctcccgc tttttacac tgcatggttc ccacgtctct gtctctggc     900
cttttgttcc ctatatgcat tgcaggcctg ctccaccctc ctcagcgcct gagaatggag    960
gtaaagtgtc tggtctggga gctcgttaac tatgctggga acggtccaa aagaatcaga    1020
```

```
atttgaggtg ttttgttttc attttttattt caagttggac agatcttgga gataatttct  1080
tacctcacat agatgagaaa actaacaccc agaaaggaga aatgatgtta taaaaaactc  1140
ataaggcaag agctgagaag gaagcgctga tcttctattt aattccccac ccatgacccc  1200
cagaaagcag gagggcattg cccacattca cagggctctt cagtctcaga atcaggacac  1260
tggccaggtg tctggtttgg gtccagagtg ctcatcatca tgtcatagaa ctgctgggcc  1320
caggtctcct gaaatgggaa gcccagcaat accacgcagt ccctccactt tctcaaagca  1380
cactggaaag gccattagaa ttgcccccagc agagcagatc tgcttttttt ccagagcaaa  1440
atgaagcact aggtataaat atgttgttac tgccaagaac ttaaatgact ggttttttgtt  1500
tgcttgcagt gctttcttaa ttttatggct cttctgggaa actcctcccc ttttccacac  1560
gaaccttgtg gggctgtgaa ttctttcttc atccccgcat tcccaatata cccaggccaa  1620
aagagtggac gtgaaccaca gggtgtcctg tcagaggagc ccatctccca tctcccagc   1680
tccctatctg gaggatagtt ggatagttac gtgttcctag caggaccaac tacagtcttc  1740
ccaaggattg agttatggac tttgggagtg agacatcttc ttgctgctgg atttccaagc  1800
tgagagacg tgaacctggg accaccagta gccatcttgt ttgccacatg gagagagact   1860
gtgaggacag aagccaaact ggaagtggag gagccaaggg attgacaaac aacagagcct  1920
tgaccacgtg gagtctctga atcagccttg tctggaacca gatctacacc tggactgccc  1980
aggtctataa gccaataaag cccctgttta cttgaaaaaa aaaa                   2024

SEQ ID NO: 17          moltype = AA   length = 224
FEATURE                Location/Qualifiers
source                 1..224
                       mol_type = protein
                       organism = Homo sapiens
SEQUENCE: 17
MEKLLCFLVL TSLSHAFGQT DMSRKAFVFP KESDTSYVSL KAPLTKPLKA FTVCLHFYTE   60
LSSTRGYSIF SYATKRQDNE ILIFWSKDIG YSFTVGGSEI LFEVPEVTVA PVHICTSWES  120
ASGIVEFWVD GKPRVRKSLK KGYTVGAEAS IILGQEQDSF GGNFEGSQSL VGDIGNVNMW  180
DFVLSPDEIN TIYLGGPFSP NVLNWRALKY EVQGEVFTKP QLWP                   224

SEQ ID NO: 18          moltype = DNA   length = 26803
FEATURE                Location/Qualifiers
source                 1..26803
                       mol_type = other DNA
                       note = cDNA
                       organism = Homo sapiens
SEQUENCE: 18
cttgctctgt cacccaggct ggagtgcagt gctgtgatca tggttcactg cagccttgaa    60
ctcctgggct ctggcaatcc tcctgcctga gccttctgag tagctgagac tatagatatg   120
ggccaccaca cctggctaat tttaattttt ttttagtaga gatgaagtct tgctatgttg   180
accaggcttg tgggagttca gtcaggctgg tggaaaaaat tttaaagata gttataagaa   240
atagacacaa accttcttgt aaggctggag agggttaca ttgcttcagt aacagatttg    300
gctgaaagca gcctaatcct ctctaccttt agctgatagc aaaaatgaaa ataacaaggg   360
aatgtgagga agtttatcta aatgcttgc ttactcagtg ggtcctaaaa ccaaacttg     420
atcaacctca ggtgcataat tgctctctac tcagggggtg agcaatgtta attaccctct   480
agtggtgttt actcgagacc tttgtcattt aatctgtatt aaataaatgt gaactttgct   540
agcttattga ggtgatgctc cagatgcaga gcagagcccc ttagccagac tgacaggcaa   600
aatatctgtg tcagtgtatg tctctcatcc atcactggtt caggtgtctgc gggctggatt   660
cctgcacagg ctggtcttga actcctgggc tcaagcaatc ctcccgcctg agccttctga   720
gtagctgaga ctacagatat gggccaccac acctggctat ttttaacatt ttttagtaga   780
gatgaagtct tgctgtgttg cccaggctgg tcttaaactc ctgggctcaa gagctcctcc   840
tgccttggcc tcccaaagtg ctgggagtac aggcatgagt catggtgccc agacggacat   900
tttttttaaa ataaggaat actcctgaaa cgctgaagtc ttctttgtac ccctctgtga    960
taacatgaat agcctcttaa tgcaccaag gagcaagaca agttagtccc aaagtagctc    1020
acatagatga tgataaagga atgagggggtg ggtgtgatct atgcaaaaaa cccttactct  1080
ttaatgggtt gctgtttcta acataattgc aacagtacca tacattgcta taatgcatta   1140
tagttttcaa agtgcttttg tggcctccat aatagagagg ttgtgaggta agcttcaacc   1200
acggctgccc tactacccaa gagtggacac acaatgatga ataggtcaat ttctgcctct   1260
tagtttctta gctagggagg ggcacttact ggaacagcac agaaaacaga gtctttggcc   1320
cagttggaga atcttatca ggttatgcta cttcaagctt tcctcctgct aaatgtgaga    1380
ggaataaatc cctgttcctt ggatcagtgt gactctgaaa cagctggagg agagacagct   1440
ttaggcaggt tgaaacagag agctccagca tatgtacttt tttttttttt ttgagatgga   1500
gtctcgctct gtctcccagg ctggagtgca gtggctcgat cttggctcac tgcaagctct   1560
gcctcccagg ttcatgccat tctccgcct cagcctccct agtagctggg actacaggg    1620
cccgccacca cgcccggcta attttttttgt attttagta gacagggtt ttcaccatgt     1680
tggccaggcc agtcttgaac tcctgacctg aggtgatcca cctgcctcag tctcccaaag   1740
tgctgggatt acaggcgtga gccactgaac ttggccaagt gcactacttt taaaagttaa   1800
agtattatgc agccatgagg gaatattgtg caagaagaaa gcttttacaa gaaaaacttg   1860
aaacattggt attttttgcct cctttttaac aactgagagc gtttgggag ttgtttcttg    1920
tcgaagaaac aacccatgtt tattttccca gtatggcagg accatgtagg aaagcaaaat   1980
taccctcag gagagggaaat tctctgacac tctataagc tccataaccc tcctctgaac    2040
tgtggccaac aagattgggt agcactttt aaggtagttt aagaaaaata ggctgtgcat    2100
ggtggtttat gcctgtaatc ccagcacttt ggaggccga ggtgagtgga tcacctgagg    2160
tcaggagttt gagaccagcc tgaccaatat ggtgaaaccc catctctact gaaaatacaa   2220
aaattagccg ggtgtggtgg cgggcacctg tagtcccagc tactcgggga gctgaggcag   2280
gagaattgct tgaacctggg aggcggaggt tgcagtgagc cgagactgtg ccactgcact   2340
ccagcctggg tgcagagca ggactccatc tcaaaaaaaa aaaaaaaaa aagaaagaaa     2400
gaaaaatata tagtgagccc aataaagctg tataatctaa atcaaacatg acttgcatgc   2460
ctggagactt tgcactagaa aaatatttct acctaaaaaa tcaattttta ttttcttct    2520
cacaaatatt caatctgctt tcatctcagt tcttcctacc ttgtcaaacc tctccccaca   2580
```

```
tttcctattc ttttctctc cagcctgata tctctcatta tactgcttaa gagaaatgtt    2640
atgttactat tcttttctcc cagaactgtt tctctggttc tttaaggtgt ctgagtacac    2700
actgtgcctt cttcctttta gccctctctt ctccttgttc cctgagcctt acctttatga    2760
ccttagaact tcaagttccc actacaattt taaatataga ctattttgct tttcctccta    2820
ctagggagct taaattgcct ctaattacac tgttttcccg agtccttcct ctccttttgca   2880
atttagatat agcacagaag cacattttgc ttgactgtcc tctgaactgt catgctgttt    2940
tgatgtggtt ctattgtcca agagtcttgg ttaaataata gcccagcatc ccacctgtgt    3000
ttaaaagaac tgcttcacag gcaaatcaaa aagcccatgg atccgaagtc acaatgggcg    3060
ttgctattca aacagcacca gattgctatt caacgcttgg ttgaaaaata aatttcagtt    3120
tcattcacct aatatatttc cttctatttt gtaggatggt atgctcttac ttcaatttgg    3180
acttgttcac aattgaacgt taacatagcc ttatagatta gcctgttttc attggtccag    3240
agtattctcc aaataaagca gggtctgtgc attttaagca actccctga acaatttcat     3300
gggcattctc aaatttgaga actacctgaa aagctgtgtt ggagaaaaga acaaccaatg    3360
aatgttgcag gacagaatat tgaacattaa cttccctttt cctcttctcc catctgttct    3420
cttccattat ccctacccgt ccgctcagtc tcgttattca ggcaacagtt attttgccat    3480
tatttcctca agaaaggaac aaaagtaaac acaattgctt tctgattttt ttttttttt     3540
tgcattttaa aatggacttt gaaaccataa gcaaagaggt gtttaagagt ctttccaaag    3600
ccaaaaatga aggttttgaa atttcaaagt cactgccttg aagagactcg aggtttggag    3660
tgtgtacagt atgtcggagc tggacttttc tccttcctga gactagataa cggtctgaat    3720
ccaagacagt tttcatgatt tcagaggaag tggtcaagtg gtctgtgagg tagaccttct    3780
gcttaagagc agtcaggagg ccgggtgccg tggctcacgc ctgtaatccc agcactttgg    3840
gagaccgagg tgggcggatc acctgaggtc aggagttcaa gaccaagcct gaccaacatgc  3900
agaaaccctg tctctactaa aaatacaaaa aattggccgg gcacggtggc acatgcactc    3960
cagcctgggc aacaatagtg aaactccatc tcaaaaaaaa aacaaaaaaa agagaagaaa    4020
agaaaagaaa aggagcagtc aggatgtgtg cctccaaagc tgaggtagac aaaaagatac    4080
cagagttcta gaggcctgcc aggcacagca gcagcagcaa aggaaaggtg tgggcgagaa    4140
cagggcagcc aggcgtgtgc cacctcccag acacaattat tgggaatgga gggcaagtgg    4200
tgatgggaga aaatcttgac ttaattgatg tcaagattaa agaaatgcca cctggtggca    4260
tttaagttca cacataggta aagaaagtta tgcatttact gtgaaagtca tcccactatt    4320
tagtagaaac aggagatctg gattctggtc aagagtctct tttgccaact gtggcaccac    4380
tgagcagcgg cacagctttt gtgaatcctg ggttcttcat tattaaaatg gggacattag    4440
cgttgggttg agtataagaa atggacattt ttgcaggtca aaaatggttg aatatttgca    4500
ttttcatatg attcaaccga atacttactt cacaggcata aggaaaaaaa tagaataaca    4560
tactaacaac tgtccctgga gtaagtactt aacaaataca tgatttataa agaagatatg    4620
tgaaagatat ttgtaagtac atgatttata gaaagatatg aaagtatgta aaccccttgtg  4680
gtctaatggt cacagaataa tctgagctta atatccctgc tccctaccat acagaaggca    4740
aaatgcctat tagggtttt cttttcttcac cctctccttc ttttcctcc tcctcttgac      4800
tcctcctcat cctcctcttt cttcttcccc ttattaatgt ctaaaaaggg gctgagcatg    4860
gtggctcatg cctgtaatcc tagcactctg ggaagctgcg gcaggtggat cacctgaggc    4920
caggagtttg aaaccagcct ggtcaacatg gcaaaacccc atccctacta aaaatacaaa    4980
aattacccag gtgtggtggc aggcacctgt aattccaact acccgggagg ctgaggcagg    5040
agaatcgctt aaacccggga ggcagaggtt gcagtgagcc aagattgtgc cactgttgtc    5100
catcctgggt gacagaggga gactctgtct caagataaat aataataa ataataattt      5160
ctaaaaaggt aatacatttt catagttcaa aaaccaaaag gtataaaagg aaatacagta    5220
aaaaatttcc tatcatatca ctgtctagag tactattcct tatatatttt cctgattttt    5280
gagtatttta aaatgtgagt gttggatatg agtgttggat ttaaaaagtt ttatgataat    5340
ttgtgtatat ttgtgtgtgt gtgtgtgtgt gtgtgtgtgt agtagtcc aagactatca      5400
gtttatgaat aataagagga gacccatgga aaaccagtcc ctttgaccaa gttcactcag    5460
ataatcagca gcagggcttg gacattaatt acagttatcc aacatccttt gaggtctcac    5520
atgacaaatt acaaatatgg agtgtaaatg taacccactt tgctaggcaa aaaaagccct    5580
gtttttttaa aaaatatata ttttggctt atgggcaaca gaagccaggg agacgtacag     5640
tcaaacctca tttctcatgg ctttcatatc tgcaaattct cctactcatt aaaagttatt    5700
tataactccc gaatcaatac ccacagcact tttgtgatca ttggcagaca tgtgcagaaa    5760
agaaaaaaaa attgagttgt tgattgcaca cattcccagc tgaatttcaa caaagcaaca    5820
ctctgcctc ccacttcagc tttccttacta tatgtgtgtc cttttcttgt ttattttagta    5880
ccatgttttt cacactttcg ttcttttttgg tggtgatttt gctgtttaaa atggccaaca    5940
agtgtagtgc taagtgctgc gtagggttct taagcacaag aaggctatga tgtgccttat    6000
ggagaaaata cgtgtgttgg atcagtttca ctcaagcatg agttatgcg ctattagctg     6060
tgagttcaat gttaacaaat caacaatata tgctaaagtg tcttttaaaca gaaacacaca   6120
taaaacaagg ttatatgttt ggttggcaaa aatgttataa ccagaagctt gcagaaacct    6180
aaccctgtat ttcccttaag agcaatggtt cattattcac taattcaatg tttacagcaa    6240
ctttataaac tataactacc atgaataatg agaattgact atgttttaga tcataatacc    6300
tgaagtgaag ttttccatca tggttttag ttcttagagt ccatttaagt tttttaaaaa      6360
tatgatagct atcctattca atcccacatt cttgagatta aaaaattaat cttttatttg    6420
gtacagaaaa ggctcctgcg tgcatttttg gaggggctgg accgctgagg aagtcatggt    6480
tggctcaagt ggtttaaatg cattgctaat ttcatagcct ctgaaccact tatgaaacaa    6540
tactgatgat atgtcagtag ctatgtttgc agctccttca ggaatgctta tatcttttac    6600
tgctggtaaa gaagaaattt atagtaatag atttttttt tttttagata gagtctcact     6660
ctgtcgccta ggctgagtta cagcggcttg atcacggttt actgcagcct ggatctccca    6720
ggctctccta ctgtagcctc cccagtaact agggccccca cacaggcatc accacaccca    6780
gctcattttt ttatgttta tagagacagg tcttactat gttttccagg ctggtctcaa      6840
acttctgggc tcaagcaatc ctcctacttt ggcctccaa agtgctgaaa ttacaggcat      6900
gaaccactgc acctggttta tggtcatctt aagtagagac ttatgagtgc gtatcattgt    6960
atcaccaatc tgagactcaa tttatcttt ctgttaatg acaatgcagt tttctgtta       7020
attacaatga aaatcaaggg ttgcttagca agttttact cataactcca agttttgtga     7080
cttatagtga gaaatgggta taattctttg tgatttgtta aaatgcagta tttcgaggag    7140
ggataacata taaaatttaa cagtttccta tcattatttt tatcctttg aaccactgta     7200
tactacagat agacaaaggc agctttgcc acttactcct cagtgtgact aagttgacca     7260
gatgttttcc agaccacagg ttctgtcaag agacagtgtg gagagaaatg ggtaggcagg    7320
```

```
tatggaaaga agagtcagaa acagatagtg agctaatctc tacaaatggc tcgttatggc   7380
ctgagctgtg ttctcctccc cgcaaaaaga tatgttggag tcgtaatccc cagtacctca   7440
gaatgtggcc ttatttggag attcgatatt tacagaggta agcaagttaa aatgagatca   7500
ctatagtggg tcctaattca atacgactgg tatccttaca aaaaggggga aatttaacca   7560
cagatacaga cacacacata gggagagtgc tagtgaaggt gaagtcagag attggaatga   7620
tgtagcagaa gcctaggaat gccaaagatt gccagcaaac caccagaagc tgggagagcc   7680
acatggaaca gattctcctt cacagtcccc tgaaagaacc aactctcctg acacctcgat   7740
ttcagacttc tagcctccag agctggggtc aatgagcttc tctcattaag ccatcatcca   7800
gtgtatggta ctttgttaca gcagtcttag caaatgcatg gttcctcact ggaaccatga   7860
atttccatgc atttatttca tttaaataat aaaacggatc cccttttgtg cttgtagttc   7920
tgttccattt caaaaatcca gaaaaaagat ttgttcagaa gctagaaatg atgaactgga   7980
tcttgcccaa ggtcataaaa ccacaaaacc ctttacagag cacaaaagtc tgattttcta   8040
aagcttctct caaaagatgg gtcactcctt agtcatttag gccactgaca actgccctgg   8100
actctttatt tattttattta tttatttatt ttttgagaca gagtcttgct   8160
ttgtcgccca ggctggagtg cagtggcgtg atctgagctc actgcaagcc ctgcctcccg   8220
ggttgacgcc attctcctgc ctcagcctcc caagtagctg ggactacagg cacccgccac   8280
cacgcccggc taatttttg tatttgtttt agtagagaca gggtttcacc atgttagcca   8340
ggatggtctc gaggtcctga cctttgtgat cacccgcctt ggctcccaa agtgctggga   8400
ttacaggcgt gagccactgc gcctggcctg gactcttaca tataataagc ttgacttatc   8460
gtacaactta taattgatgc tttcacgtca tgggaagatc aaattaatgc agagagcgac   8520
tacgtttctg tgggagagc agcaggggtc ttgagaggaa cagcagtgtt gactgtttcg   8580
ctacctactc tgggtgctga ttacatcttt cctttcgtgca gcaaatcca cttggagcta   8640
tttggggctc actgtgggca tcattctttg tatactctgc tcctttcccc catagtttct   8700
ctattgatgg gggattacta aagaatgaag aaaagaacaa aatgaaagtg gcttttgaaa   8760
aattttaaat gactgtcact atgtaacata ttcattattt catgtctcca ctggacattt   8820
tggagatgtg agccttgcaa tacctacatg aatgcttcta ttgattatgat tattgttttg   8880
ctcttcgcct aacaacttgc caagtattgt caacctcagt gtgtgagatg gggtccactc   8940
aaacatcagg gccgaagtca ggtagttcag ttaagtgaat ttgataccag gaactagtta   9000
caaaggagtt ggaagggctg gaaagccaaa ctggagaaga aggggaaccc cagagtaaca   9060
atagcaggaa gcctctaccg tctacctcta gaactgggga ggagctgagt taacagagtc   9120
ctggagccat tgctggggaa gaagaacccc aactgcagag gaaaagtggc cattgtgaag   9180
aaggtgatgg tggagaagtc gtctgaatca aaggggagag gatatgttgg ctccttttatc   9240
ttttttatctt tcattgtcct aattccttct gggcatggtt aaatgagccc aggaaatgca   9300
gttggcagga atcagcttcc tgtgacatag acagagtaag agaaggacaa aaataatgaa   9360
tctgagagca agcaggcaaa tgaccagcac attaagccta gcacacagta tgttatacgg   9420
gatttggggt agcaaaagat gaaggcaggt cagagaagcc acaactaggg gatgggcaag   9480
gtcaatgagg tatgacgggt attgtataca ggaagagggt cataaacagg agtggagtca   9540
atacaggaga ctaacatata cacatcataa atattagtag agaagcataa aatagtctcc   9600
tggagatcag ggaaacagga aattataggt tttcaggata attcagccat atccaggaaa   9660
cacacacagt gaagtaacaa agagtcaata ggcttagagt ggtacaattc attatgcaca   9720
tgtaggaatt cattccaaat aataggctga aatgtagaca tgagaatcca aaaaagatgt   9780
tttcttagtt tttgccaata tcttagctac gttttttttg gttcaacaaa gtaagttaac   9840
agtcatatct gcttggaaat tgtatttagg ccaggtgcag tgctcacgc ctgtaatccc   9900
agcacttggg gtggctgagg caggaggatc ccttgagccc aggagttaga ggctgcagtg   9960
agcgacaact acaccactgc attccagtct gggtgacaga acaaaaactt attaaaaaaaa   10020
gaaaaaaaaa aggtcgggcg cggtggctca cgcctgtaat cccagcactt tgggaggtcg   10080
aggtgggcgg atcacgagtc aagagatgga gaccatcttg gtcaacatgg tgaaaccccca   10140
tctctactaa aaatacaaaa attagctggg catggtggca tgcacctgta gtcccaccta   10200
ttcaggaggc tgaggcagga gatcgcttg aacccgggaa gcggaggttg cagtgagctg   10260
agattgcacc actgcactcc atcctgtcga gactctgtct caaaaagaaa aaaaggaaa   10320
agaaactatt gaaatagctg atattagttt gcttacttgt cgttactctt tttcatgatg   10380
gattataaag aaaagttata actatttgaa ttttctgctg atttgaagtc tctataaaca   10440
gtacattcct ttttggtaca cagagggcac ttatctgcaa gaaagcaaa gaaaatggaa   10500
aagttaatga aagaggaatc atccaatcca cgaacagaat gaaaccacat acacagtgaa   10560
gaaacttgtc ttacattttc ttcctatat tacttatcat tcatggtagt gactactttg   10620
gggcttgagt aaagcttctc taatttattc catgtagcat catatgtgaa aaagacaaat   10680
agatactttta gacatgataa taacacttta ttttttattt atttgtttat ttgagacag   10740
agttttgctc ttgttgccca ggctggagtg caatggtgca atctcagctc actgcaacct   10800
ctgcctcctg ggttcaagcg actctcctga ctcagcctcc caagtagctg ggattacagg   10860
cacgcatcac cacgcccagc taatttttg taattttagt agagacaggg tttctccgtg   10920
ttggccgggc tggcctcaaa ctcctgacct caggtgatcc acccaccttg gtctcccgaa   10980
gtgctgggat tataggtgtg agccaccatg cctggcccat aacacctat ttaaaaataa   11040
tctgtctgga tccatacaac ttgtctggat aactaaattg gaaattattc cttgttttaa   11100
agtaattcaa ttgaaaattt ttaaattttt ttgttaatca agcatcattt ggtgaatct   11160
aaattaacac atgtaggaga tgcctgtttc actaattaca caggcatctt cagtaatta   11220
atgtctggga ggaaggaatg tcttttgctt actctcttct tcttcacaaa aatgtgaatt   11280
ttggaaagca ataatggaag catgtagaat tatagaaata caaatgtata taactatcac   11340
aaaaaaatga ggccaaagga ctattcagat ataattaggc tatggtagct gtaattatct   11400
aggaaattaa taaaattcat tcacctagaa attattagtg agcatcaaat atgtgtcagc   11460
actaggctag ggtctcagaa cgtacagata aatcatagtt ctggcttcag ggagttatat   11520
agattagaga taaaacctaa ctacaggggc tgggcacggt agctcatacc tgtaatccca   11580
ccactttggg aggccgaggc gggtggatcg cctgaggtca aggagtttga gaccagcctg   11640
gccaacatga taaaatcctg tcactactaa aaatacaaaa gttagccggg aggtagtatg   11700
tgcacctgta atcccagcta ctcgggaggc tgaggcagga gaatcttctt agcctgcggt   11760
ggaggttgtg gtgagctgag atcacgacac tgcactccaa tctgggcgag agagtgagac   11820
cctatctcaa aaccccaaac aaaacaaaca aaaaaaccaa acctaactac agggctatga   11880
gagatgacta ctgcaaggaa gccacaggta gaacaaaggg gatgtgtccc caggcaaagg   11940
gtagtcagca agcctgcaac ctcagggttc ccggatctga gcctctggct cttggctagg   12000
caggccccaa gcgttggcct cctgccatgg caagctccag cctggtctcc caccttgagc   12060
```

```
taacattcat atgttgtaga cacagccacg cttcctgctt acctgtcact tccagttctc   12120
gaaggcaccc tttttcaaatg aaaatccgcc ccttttcaca tcaaacagct catctggtcc   12180
tgtggattac atttctcaga aatgcctctg aacattcgcc tcctctccac ccccactgcc   12240
tctgctacag tgcaggtgct cgccatttct gatttgttct gtcacacact cgtttatcag   12300
gtctcctcca tctcctgtttt gacatgctgt aaagcaattt gccactggaa aaaagggctc   12360
tcttttttttt tttgagacgg agtctcgctc tgctgcccag gctggagtgc aatggcatga   12420
tctcggctca ctgcaacctc tgcctcccaa gttcaagtga ttctcctgcc tcagcctccc   12480
taaagtctgg gattacaggt gcacgccacc aagcccggct aattttttgta tttttagtag   12540
acgtgggggtt tcaccatatt ggccaagctg gtctcgaact cctgacctca ggtgatccac   12600
ccgcctcggc ctcccaaagt gctgggattt caggtgtgag gcatcgtgcc cggcctctct   12660
ttccaaagta tgttattatt ttcccaaga ccctttgacg gatcctcatt tcctacacac   12720
agtggttctc aaacttggat gtactccaga attacatagg aaattcttca tttttttaga   12780
cgaggtcttg ctatgtttct caggttggtc tcaaactctt gacctcgtgt gatcctccgg   12840
ccgcagtctc ccaagtagct gagattatag gcgtgccact gagcccagct ggaaatttt    12900
ttaaaacaca gattcctctg aatcaaaatt tctagaagtg aggtctgagc aatctgtatt   12960
tttaacaagt tatccagatg gctctttact gtcagtctgg ttccagctga gggagtttta   13020
gaattacaag gcaaagtcca aacttagcac acaaagtcat tcacatcaac tcttccccctg  13080
tacacaccct atgtcatagc cagagttgta acccatttct taaacaccca gggttcttt    13140
aagtctctgt gtcattgtat gttatttctt ctagaattgc cttttaacctc ctttccaccc   13200
tggaaagcat tccctaagcc atctttgaag cttttctttga tctctaactt agagtcctcc   13260
tctccttcta aagccctgtg ttaatcactt gtcatggtgt actttaattt ttacttgcct   13320
gtttcttttt acggtactttt gacttcaaag ggtgggggctg caaattagtc atctccttag   13380
agtccagcct tgttcctagt tcctaactgg cacttaatat aaacgaatga atgaatggac   13440
aaaatgaagag aatgctagtt atgataaaga attggccgtg tatgagacta cttctcttta   13500
tgaactaaat aattatatgc ctttcaataa aatactagta cacgtagcta gcacaagctc   13560
atcagcattt gagatgatat ggaaaccaaa ataaacaaat gctaccacaa aaacataatg   13620
actgctttcc ccagtgcagg actgatgaaa tcatcaaaca ttgagattaa tgtaatgttt   13680
ggcagatgtc cagtgttttt attttcatt tgcctttgtg ttcatttatg gactaacaat   13740
ataataaaca cacacatact cacagtacat cttttttttt tttttttttg caaagcccag   13800
ttttcttcat cgcatatctt tgttttcttc aagtatcccc tttcttaatg ttggtagtat   13860
ttttttttaat gaaatataaa tccctaacca ccaagcaaga aatgagactc ttaattgcat   13920
cagtttacag tgcaatgtga gtgtaaatag tgtaaattga attttaatg gactttttt    13980
tttcccgttt ttgcttgcct tacattcatt atccctccct gggtaataaa catttatttt   14040
tcccttttgta accactcctc ccttctgtc catgtggttc tttttagtgg agctggtggt   14100
agggatgtgg catgagattc aagcttggcc acctggagtc actgtgttgt gctccagaag   14160
gacacctgat ccaagtcagc cagtaagagt gagcccagg atttttgctt ggaccactga    14220
ggaaaagtgt actctgccct gtggctgatc aaccattagg atataagcca ttgttgtagc   14280
tgtgtgagtc aagctacctg agaatgagga caacacagtg gcaagcaaca ccaagagaga   14340
aaaagaggca gattctgatg acattttga gcctttgcat ccagctatgc ctgaatccaa    14400
tttatccccct ggaatttaca cttacttgag ctccacccac ttgaaagaaa acatttcttt   14460
ttattcttag cctgatttga atttggcctc tctcatttac tacccaaagt gtcttgacca   14520
ctagaatatt atgccagact ttacagcatc attgaatttg ccactttcca gaagagttgt   14580
gtgaattttc aatgtagctt ttaccttcta tgagtatcta gagatatatt taagtagaag   14640
tactccacta gtttgttgtg agatcttaag tcacttaatt tctctgtacc ctagttccct   14700
catttgctag acctagggag ctataatgtt ccttctgcaa aattcttatt ttgtgaaata   14760
ttctagaatg tctaactgat acactgctag aacaactgac tgctatttaa gaagagttga   14820
ctgctattta aggatcataa ttctctaggc ataagtgctg tgacggcaca gcgtgtgcat   14880
cggggctgag gggtggggtg gagcagaaag taggaggaga aagtttgata aacttccttt   14940
tggataaaatt gaaaacagtc aaataattta aatttctta tattatcatt attagcttct    15000
tctataatta ggagacttgt tccaaaatgt gagaattgtc acaagttgtc aaattcatca   15060
aaggaagaaa atggatgtct cacaaaaaag tatgctcagt ccaattttctt ctcgtcacac   15120
tggaacaaac tgaacagttt tacacagaga tgagaagcct ggacatttt caaatatgtt    15180
ttgaagagaa tggcaatgcc tgagacagaa gtaggaaaaa gcaatgaata tttaaaaatc   15240
tgagctggtg taaaactaga aatagtttta gtaagaacaa tgtgatgtgc tacactaagt   15300
gaaatgtata cattgggcca cattataatc aaaaataaga atgtacttt attcatcttt   15360
tatttaaaca ataatcaagg tggcgggcgc ggtggctcat gcctgtaatc ccagcacttt   15420
gggaggccaa ggtgggtgga tcatgaggtc aggagttcaa gaccagcctg gacaacgtgg   15480
tgaaacccccg tctctactaa aaatacaaaa attagctggg tggggtggca tatgcctgta   15540
ataccagctg ctcgggggggc tgaggcagga gaatcgcttg aacttgggaa gtggaggttg   15600
cagtcagcca agattgtgcc attgcgctcc agcctgggtg acagagcaag agactctgtc   15660
tcaaaaggaa aaaagaaaaa aaaaaaatca aggtaccatt tgtaccatttt cctgaatttt   15720
ctccaaagtg gcaaggtcac atgtttatac attagactcc cagtttaaca cacagcagac   15780
aataactttt tttttttttt tttgagatgg agtctcgctc tgtcacccag gctggagtgc   15840
agtggcacaa tcttggctga ctgcaacctc cgcttcccga gttcaagcga ttctcctgcc   15900
tcagcctccc gagtagctgg gattacaggc atatgccacc atgccagct aattttttgta    15960
tttttagtgg agatggggtt tcaccacatt gtccaggctg gtctcaaact cctgacctca   16020
taatccagcc acctcagcct cccgaagtgc tggtccaccc ttccttcttt tctcccttcc   16080
atccttctcc cttttattcc attttttctaa atattagacc atagtacaaa tcaaaagtca   16140
caaactgata ggctgcaatg tagatacagc tgggaaaatg ttttgtttgc agaacactgg   16200
ggaaatttaa catgaaaaac tggaagatct caatccacat ggccacatgg taatattatt   16260
aatgttgcag gggctttcca attcaacatg tcctctgcat ccctactatt tatactgcca   16320
ctcatccacc tttctgtatt actggcctat cacctataca cgtttgagtt tatattcttc   16380
tggctttact tagcaactta cctttttatat ttaacattac aacatggtat tatcaattag   16440
tattcgattc agttgcatat aaccaaaaat gccaaatat actggcttaa acactaagga   16500
ttttatttttc tgtcatataa aacaagtctg gaggtgggta gtccagggct aatatgacac   16560
tccagtgtca caaggtacct gggctccttc tatttatctt tttttttttt tttttgaga    16620
cggagtcttg ctctgtagcc caggctggag tgcagtggtg cgatctggc tcactgcaag    16680
cttcgcctcc cgggttcaca ccattctcct gcctcagcct ccgagtagc tgggactaca    16740
ggcgcccgcc accacgcccg gctaattttt ttgttatttt taatagagac gaggtttaca   16800
```

```
ccgtgttagc caggatggtc tcgatctcct gacctcgtga tccactcatc tcggcctccc   16860
aaagtgctgg gattagaggc gtgagccacc gcgcctggcc ctatttatct tttataggac   16920
atggcttcca gtctcaagtt cagtttgtca cccataatgg ccaaagagca gtagtcacct   16980
tacctgtttc aggcaggaag ggcagagggc aagaaacaaa atggtgctcc tcctgattga   17040
gtcagcgttc tttaaagatg ttttccagat gttccaccca gccgcgtttt ttttttttg    17100
agagacaggg tcttgctctt gtcacccagg ctggagtaca gtggcatgat catggctcac   17160
tgaggcctca atctcccagg ctcaagcgat ccttccattt tagcctccca agtagctgga   17220
agtagctggg accacaggca catgccacca taccctgcta acttttttcat tttgtgtaga   17280
gacaaggtgt cactgtgttc tccaggctgg tctgcagttt ccaactcctg agtgcaagtg   17340
atcctcctgc tttggcctcc caaagggctg ggattacagg tgtgagccac tgtgtctggc   17400
caagctactt ctacttatat ctcattggtc ataacttgat cacacagcca catccagcta   17460
caatggagat tgaaaatgt agtcttttgg ctgggtacac agcatctgaa taaaatccag    17520
gcattgttac taaggaagaa ggagtaagtg tcaatctcag ctccataact ctctaggtta   17580
atacacacag atgaaggaga ttgctagttg cccctcaaga tccagccttg ccttctgggc   17640
taagaaagcc cctgagattt acctggccat agtggcactg gaacaaaca atgtatttct    17700
aaatcttctg attttaaaat cttcagaat cacgatttct ccgacatcag tattttatg     17760
tctttagaat tcaacaaaat gaaattccta agtctaatat atgtgaatat taagtttag    17820
cagatactgc tacataactt tccagaaggg tgtggcaatt cacatctcca ccagtgatca   17880
gcatgttcat tttccataca gctctggata ttttgtctat tttaaaatat cttcttctaa   17940
tctataattt aaaaatgtaa cttagtagga atttaattgt tcatgtaacc aaatcttccc   18000
attaatggct atgggttct tcttttactt cagaaagtcc tcccccacctt cagagtatat   18060
aaacatttt ttctaaattc ccttctaatt tcttataatt tatagttta ttttgttat      18120
ttgattcatt tattctctca acagatattt attgagcact tattatacgt caggctctct   18180
tcaaactctg gtgagagtat tttctaactg ggagagacaa ccctagttga taagaaacaa   18240
acaaaccaat aagtaaataa gacatttccc ccagataatt aatacttggt gacggggaa    18300
gacagtgaga caggctactt tacactggca gtcaggaaa ggcttctctg aggaggcaag    18360
tgattcagga ttaattgatg actggtggag aagtccgggg agtggacaca ggtgggaaca   18420
gcctggtggg tgtgaacagc aacaagaagg ttaatgtggc ttcatggaac agggtgaaga   18480
tgagacaagc tgaacactga ggtgggcacc agaaacatga gggctttgta ggtcccaata   18540
aggagtatgg attttattgt atactggaga tttgtcatcc atctagaatc tgttttttata  18600
tataagaaaa ggtgtatatg tttgccaag tgtgtgtgtg tgtgtttggg ggggcgggt     18660
ggggcagac agggcgtaac ttttctttaa attagagtca aaatttaatt aaactattca    18720
ttctttacag gcagtgaggg gattaggatc ttatcccaca gaatctcacc tcatttcaaa   18780
tgttgtacag atattatctg agatatattt tcaggccggg tgcggtggct cacgcgtgta   18840
atctcagcac tttgggaagc cgaggcgggt ggatcatttg aggtcaggag ttcaagacca   18900
tcctggccaa catggtgaaa ccccatctct actaaaaata caaaaattag ccgggtgtgg   18960
tggtacacgt ctataatccc agctacttga gaggctgagg caggagaatc gcttgaatcc   19020
aggaggtgga gcttgcagtg agccgagaaa acgccactgc actccagcct gggcgacagg   19080
gcaagactct gtctcaaaaa aaaaaacgaa aaaagaaata tattttcaat gaaatcaagc   19140
atataatgac tatttttatc ccagcatctt ggcttcttca ggctgctata acaaagcatc   19200
cctagtggag catccctaat ctgaaaatcc aaaatccaaa acgttccaaa atctgaaacc   19260
ttctgaacac tgacatgaca ccacaaatgg aaaattctac atgtaaatac acgtaaatac   19320
aaactttgtt tcatgcacaa attaaaaata ttgtataaaa ttaccttcag gctatgcata   19380
taaggcatat atgaaatata aatgaatttt gtgtttaccc atgggtctca tcccaagat    19440
gtttcatttt gtatatgtgc atactcccaa atctgaaaaa atccaaaatc ttaaatatct   19500
gtagtcctaa gcattttaga taaggggatat tcaatccctt atccataaac aatttattta   19560
taaacaacac aaatttaggc tttgtaaaaa atagaaattt ggccgggtgt ggtggctcac   19620
gcttgtaatc ccagcacttt ggaggccgaa ggcaggcaca tcacttgagc tcaggagttt   19680
gagaccagcc tggtcaacat ggtgaaacct tgtctctacc aaaaatacaa aaattagcag   19740
ggcttcgtgg catgcgcctg ttgtcccagc tactcgggag gctgaggcag gagaattgct   19800
tgaaccccga aggcagaggt tgcagtgagc caagattgag ccactgcact ccagcctggg   19860
ggacaagtga gactccacct caaaaaaaca acaatcaaac acaatataaa tttatttctc   19920
atagttctgc aagctgagaa gtccaagatc aagatgtgag cagatccacc tttggtgaag   19980
ggctgctttc catttgatag atggctgtct tcttgtgtcc tcacatggtg gaaagggtga   20040
ggcagttttt tgaggtctct tttaaaagag aactaatccc attcatgtgg gggtctgccc   20100
tcatggccta atcactttcc aaaggcccca cttcctaata ccatcacctt ggggggttaaa  20160
ttttcaacac acaaattggt tggagagtga gcgaacatag acattcagtc tatagccccc   20220
agggatgtag ccactgaata aaataatcta gaacttcatc tagaggcagt ttataagtca   20280
cataagaaaa ccagttttac ttatagtcac ataaaacttt tgataaaaaa caaccctagt   20340
tgataagcca tttgtttact ggacttggct ctgaagaaat gacttttggc taatcctcaa   20400
aatgaaatct actcacagag ggcaagatct gccaccagtg aagatgttta aaacaatgtg   20460
ctgtaggctt tgaaggcaag tctaaagaag agcttctaaa atatttgc acaatggtag    20520
cattaaaaga gtaggcacat gggcccaag ataacatctg tgaagaggag gaccagtgtg    20580
tgtttcctt tgtatgttta agtactaagt cagtgattac tttataatta aaccatattc   20640
ctcttgatct gtccataata aggtcactct gtaatttata ataggcttct taccaaattc   20700
aagctttaca acaaccctat aggttaaata ttcctgtgaa ttttatagat gaagaaacag   20760
agtaagtgaa agagttcata ctcaattcaa gtctcttgag tctaaaatca gtgctctctc   20820
tacataagaa gttagttgct aagatcacac aacttgagaa gagagaagac agttttcaca   20880
gtccctcccc tctgaccact aggctgcttg gggtacttt acaaacttacc tgctctgaat    20940
taaggctctc tgtgaatctg attcatctgc caatttgcaa acagtcagcc ctgtagtacg   21000
tacctaagtt gattttttaaa atactatttc tcatcttaaa ataatggaaa ttgagtgaca   21060
taaatttcct ggacactttt taagatccaa agacaatttg ctaatttgtc gttacaatta   21120
aagagccccc caaaaggcgt aagaactgga ttttgacttg gacttctgtt ccttagtttc   21180
tttaacatat tgggggccgg gagtggtggc tcacacctgt aatcccagca ctttgggagg   21240
ccgaggcggg cagatcacga ggtcaggaga ttgagaccat cctggctaac acagtgaaac   21300
cccgtctcta caaaaaatac aaaaaaaaaa aaaaaaatt agccgggtat ggtggcgggc   21360
gcctgtagtc ccagctactc aggaggctga ggtaggagaa tggcatgaac ccaggaggca   21420
gagcttgcag tgagccgaga tcgcactaca ctgcactcca gcctgggcga cagagcaaga   21480
ttccatctca aaaaaaaaa gaaaaagata ttgggaaaac tcacttaaac tctatgggct   21540
```

```
tctgtaccac taaggcttct caaatttgat gcaagtaatg ggaacttgct gtggctaact   21600
tgagccacag gagaaggata ctgcaagact cacaaatgct tgaaagtttc ggaacaggtt   21660
tggaaatggg taagaaccaa ggaccgggtt gacctgaact gaaaggaaat tgaggtgcta   21720
ttagggacaa atatgaaatg aaggatgaac tgtctctgac atcctttgct tctgtgtttg   21780
gagatgagta agcagggagt gggtgcatat gcaaacaggt tggtcagaaa tgctttggcc   21840
ggatgtgtga ctgaaggcta tgtgcagctg aggaaggctg ggccaccaca gtagcagaga   21900
ggctgaccaa tttggcatgc agcaagcagg aagtagaagg gatcttaagc aagcaaagtg   21960
tttgggtaga caagattatg aggaatgagc accaatgaca tttccaacaa gcactgaaag   22020
cttccaaatg cttctaacag ttactgcctg tacaaacaca ggacagtctt gactatgtga   22080
gactgtgaca gtttcctcat gcctatgaaa tgagagacag tacttagcac tgacatgagc   22140
ttcatatttg aaggcagcaa actactgaac cacatgtagc ttccgaaatc aaaagatgca   22200
aactggcaga ccacaggtca gatatgacat gcagaaaaaa attagttact atcttagcct   22260
agtttgtgct gcttacagaa tatcagagac tgggtacttt atagagaaca caaattattt   22320
ttcatagttt tagaggctgg gaagtccaag atcaaagggc catcatctcg tgaaggcgtc   22380
cctgctgtgt caaaacatgg tggaaggcat cacatgggca aaagagagag agggaagcgg   22440
gggcaaactc cttttatca ggcacccagt cctgtgattc attcatgaag acagtgtcct   22500
cctggcctaa tcacctctta aagctcccac ctctcagcac tgttgcactg gaaattatat   22560
ttctcacaca tgaactttgg ggaacacatt caaaccatta cagttaccaa agataaaaat   22620
gcagatttca gatttctctt ggggaagaaa aaaggctctg gcaataccag ggctgtattt   22680
ccacatggca acagttgtct gttgccttct gttgggttgt gggctctcac attgccatac   22740
cctcctcatg gcccccttca ctcataacag tacctgccta gacctcgaag cactagtttc   22800
caaccctgct tgagttaact acttccatga caactgtgca aggccagagt gtgggcagct   22860
accttgaggg ccaccggcat gggctgccca agtgaccgag ggcactaacc tctgctctcg   22920
aaaacttcttt ggtaggatct cttcactcct gacttactac ttgtaactgc tggaaacaac   22980
catttattct accccctacta aaccacatct gtcttttctg tcagaccaa tcttcaagca   23040
tatgcttcct caaaagactt taattaccag gtagtagaag cggcagcaaa gagtcccccat  23100
ctagcatctt ctaaaatgta gtggagaaac caacgacaac gaatctgaga caaccagttg   23160
tttgacttct ctgaaaacaa cctctaaaaa aagccttctc tcgtgaatag ctgcagacat   23220
gctgggcact aattgatgat gatgccttt agtgagtctc ctctgcacat acctgattcc   23280
atttggatgc tggccctcac atacttctat ctgcgaactc cggaacacag aatatcatac   23340
aatgtatgat tcaatctgga ctctgctgga gccattctct acaaagcaga cacaactttt   23400
tcttgcctaa atcctttcaa gttgctttat ttttattttt aaactaatta ccataaatct   23460
aatttatcaa gctgctttta agataaactt taaaatgctt agagcagtct acaaattctt   23520
gcactgtttc actcttcctt atctctcagt cttcatctcc cattgcatct tctctgactc   23580
tttcatatgg atcttcttt aatttgtgga agaagccaag cttgttcctg cctcaggtcc   23640
ttgacacttg ctgttcactc tcctgggaga ctcttccccc catcttagct tttaaatacc   23700
agctggtcag actccttacc tgccttccac cttcctctca ttctcccact cctcgccttc   23760
atttctcaga gtcctccgct ctcttcttc tattgctctt aacacaattt gtctgttttc   23820
cgctaatctg taaactctac aagagcactt aactattttg catcccaccg aatattcgga   23880
gtcagcacag accccgtcat aatagagtag gtaagcaatg cttacctgtc aaatgaatga   23940
atgaaacacc cgattcatcc cccaagccag cttaatacat tagatgatct tatgggactga  24000
ataagacatc cctcctttta aagaatattt ttgttttagc ttcacatcag caaacccccga  24060
acggttcatc ctaagataag cctggtagag aggaaagata ctaaccttct agggtcctaa   24120
agtggaacta ggaacttatt agatatgcac attctcaggc attatttccg atagcccagt   24180
cagagaattc tgggggtatg gcccagcaat ctgtttaaac aaacctttca ggtaattctg   24240
atacacacta aagtttgaaa ggtttctta aggctttcca gttttcttt cttttttgga   24300
gggatggggg ggggtctccc catgttgccc aggctggtct cgaactccta gcctcaagct   24360
atcctatcct cccaccttcgg ccttccaaag cattgaaatt acaggcatga cccactgcgg   24420
ctcgcctccg tttctaactt aaaaaaattt tctttggagg ggagccttaa tccttttctat   24480
tatcctgcta gtagaatctt actactcctg agggtaatct ttgtcataat ccaaaagcct   24540
tgaataaagg cctatttgta tagttatgca gaatatattc ctgggaggtt tgccttccta   24600
ggagcacagg tcggccctgg gaggtggggg ttgggggggca gggctgcatt ctaaagtcct   24660
gtaacaacgc acaagtacaa ctgaatagaa ctccggaacaa aggcatcagg ccacggtgc   24720
aagtcttgt tcatccgttc cccgactgct caccctgtct gataccgctc ttttccaccc   24780
agaaaagcag ccactcaagt tttaagaatg gatgtatgcc gcggacgttt tcgattaggc   24840
cgttttctct caggcactgg aggatattcg tggctgcagg aggcgcttcc acccttcct   24900
caacctagca aagaagtaac tgaaactaac ccaagggtta caaccgaaaa gcccttcca   24960
gcttcagaag cagaactgga agctcggata gacttctccg cctctacact cctggaaaac   25020
ccgcagtgga tttcaccaac ttcaggatcg gagcccaggc aggcgaacgt accttattgc   25080
gcatgctcgc tagccctcc cgctcggagc ggaaggggga gcgctggggg cctgggcctg   25140
gcctggccgg ggcgtcggca ccggcggcca tcttggcttc ccggggaaag gcggcgtgag   25200
gggaagaagt tgtagggtgg gggcaggagt gaggaggagg gaagagagag ggggaggagg   25260
ccgcggcggg gcagggcggg gactgcctgc ctgcctgggt tgcggaagtg atagccgccg   25320
accggacgtc ctgctttctt gctactgctt cggcttccg gctacccccc gcacggtgaa   25380
ggcggcccag ctgtggatgg tcagatagcc cttgtctccc gccgccaatc tctggccct   25440
agcagcacgg agcagacggc ggcagcagca gcagcaggcg aggaggaaga tggcgggacg   25500
gctgccggcc tgtgtggtgg actgtggcac gggggtaaggg ggcttacggg cggggtggg   25560
gaaactgagg cggaggaagg aagatggcgg gggagggagg aggccgggaa atgaatggtg   25620
cggcgaggtg ccgccgccgg ctgtcagtcc tagaccccgg gccagcgagg gggtggggcc   25680
cgcagccagg gcctcgcggg tcccctcgtt tctccctcct gggactgggg cgggggcgcc   25740
ggcccgagat tcaaccccca acctcccag cggctttctc cgcgcgaccc ctcccggccc   25800
ttccccccact acggtgggca gcgccgccca aagggcgctg gggacggtcg tcttgggggt   25860
ggtccccggg cccgacccat ccggcttttcc tttccctccg cgccgttttt tgccagtcgg   25920
gggaccc cagggggccga gctcggggac tggcctggca tggcgagctag aaaagagaag   25980
cgctcctggt aggtttgaca agatcgctgt gacaacattc tgcccagggt gtgggtgggg   26040
aaagggaaga atcggactct gaaaatggga acctacagtg gggctttcat ttgaccaccc   26100
accttctcct ttcgactcct ggtcatttcc atctccctct gcgttttaac cggtgaacca   26160
agtcacattt taattcgagg gagaaagatg tcatgtgtta cttctgtagc ctcaaaaaag   26220
tccccagtg agcaagcgcg ctgcaacttc cttagttttg tcaaagccgc ttcctgcttt   26280
```

```
cagtctttta taccottata aggtagtttt tagtttccaa cctgagcaca tcttactaga    26340
acttttaagc aggttttaaa gagactgaat taccggtgct tggtgtccat ttatatgact    26400
taaaaaaatg tacttatgtt tcatggagtg ggggaaagga agcaccctgg aaaataaact    26460
aatttaagtt gtattcgttc attctgtgat ggtatcttga aggaagcagg aaggtataga    26520
ggtatatagg agggtgttta agttgcaaat agttactcgt agatatgtag ggtagtttgc    26580
gaaaatgtag agtggcttta aagtgtggtc gttcattttg tattaataga cgttttagag    26640
agttgtacca cactcataac tgcatagaga atagactacc cttattttta tgtagaatca    26700
ctgcttcagg atgacatata ggaaagtggt ttttttttct gtgctgatga catctctcca    26760
attcccagaa cactcccagt ttttttttttt tgaggggggaa gtc                    26803
```

| SEQ ID NO: 19 | moltype = DNA  length = 26803 |
|---|---|
| FEATURE | Location/Qualifiers |
| source | 1..26803 |
|  | mol_type = other DNA |
|  | note = cDNA |
|  | organism = Homo sapiens |

SEQUENCE: 19

```
gccgcaccta ccgctggcct cagacatcag caccccaaag ggtatgttgg agtcccatgg      60
tggaggtgcc ggccgctcct ccacgcactt gatgtatacc gaggatccca tgcttgacgt     120
cgcagggggc attagccagg agcacgttgc tgggatgcca gtccaggctg aggatggtgg     180
agccaatggg cttcttgatg tacttgcaca cccaccagtt attctcccgc tggaaataac     240
agatggcgat gacacacagc tgccgcccac agcaaacttg tcctgtgggc ccagcacaca     300
cagcaggcag tgggtgcggg cttaccctcc tggcccgtca gcgtccacac agaggccttg     360
tggcctgtgc cataggtcac gatgaggtta ctcttggagg cccagttgat gccttttacc     420
tgcccgttgt gctccttgag ctcgggcacc ttggcccact tggccccact cttacagctt     480
cgtggttgtt gaggcagatg gtggccatct gggtgcggcc cttgctccag gttttgcagc     540
aatgggttcc tgcagtcagc tgtgggaggc tgtagttgcc ctccttttca gagtaccoca     600
gctgcagact ctgggcagga cgcacccaac cagtgctctg gttttttgaa gtaaaaaatg     660
cataatgcaa ttttaccatc ttaaccattt tttaattatg aaatccggta gtgttaagta     720
taattgtgtt gttgtgaaac agatctccac aacttttttca ttttgcaaaa ctaaataact     780
cctctttccc cctactccca agctccaggc agctaccatt tctgtttcta tgaatttgac     840
tacttatatt acctcatata aaggggttca taagtatttg tcttttcttg cttggttaca     900
tcacttagca tgatttctta agtttcattc atgttgtagc acatgtcaag atttcctttt     960
ttttttttaa aaaaaaggat gaagactatt cgtttgtata tatatgccac attttgttta    1020
tccatccatt tttcttcaaa tgtttgagtt gtgtgatgtt taattatgtg tcaccttgac    1080
ggggcaaagg gttgcccaga cagctggtaa aacattattt ctgggtatgt tagtgaggct    1140
gtttccagaa gagattagca tttgaattgg caggctgaat aatgaagatc tgccctcatc    1200
aatgtggatg ggcagaaaca aaccaaaaag gtggagaaag gaccagttat ctcccccacca   1260
ccctgtgcc ctttagctgg gacatccatc ttctgccatc agacatcaga gcttctgggtt    1320
ctcaggcctt cagactccag aagttatacc agtggcttcc ctggcttttg gactcagact    1380
ggggtttcac tgtatgtttc cctgattctc aggcctttgg acttgaattg aattacagca    1440
tgaacttttc tagttctcta gcttgcatat ggcatattgt gggacttctt gacctccata    1500
atcatgtgag ctaattccca taatatatct cctcttatgt atctataatt catatagata    1560
tgatatctat atatcaatcc catagataaa tagatgtctc atatatatat caatgtctct    1620
atatgtagat gtctcatata tggtatctat gtatctgtat catctctata tatctaatca    1680
tctaatatag atgtctcatg atatctatat agatatatct atatcataga tgcagagata    1740
tcatatatat gtctgtttct ttggagaatt ctgactgata caggttgctt ccgccttttg    1800
gctatcatga gtaatgccgc tgtaaccatg ggtatgcaaa tacttctttg agaccctgct    1860
ctgagttctt tgggtaaat acccagaagt ggattgctgg atgatttggt ggttctactt     1920
ttaatttttt gaggaaatgc catactgttt tccataatgg ttgcaccatt ttataatctc    1980
accaagagtg cacagggttt caatttctct acatccatac caacacttat tagtgtgtg     2040
gtgtgtgtgt gtgtgtgttt aatggctgtc ctaatgggtg tgaggtgaca tttcactgtg    2100
gttctgattt gcacatctct gataattgct ggtgttgagc atccttccat atgcttgttg    2160
gtcatttata tatcatcttt ggaaaaatg tctattcaag tcttttgtct attttttttc    2220
cttccaactt ttattttagg tctggggta catgtgcaag tttgttacat ggataaattg    2280
tgtgtcatgg gggttgtggg tacagattat ttggtcgcct aggtaaatga gcatagtacc    2340
tgataggtag tttttttgacc ctccccttc tcccacccctc cacctgaag taggccccag    2400
tgtttattgt tcccttcttta gcatctgtgt gtagtcaatg tttagctccc acttataagt    2460
gagaaatgt tggtatttggt tttcgttct tacattaact tgcttagaat gatggcctcc     2520
agcagcatcc atgttgctgc aaaggacatg atttcgttct tcttatagct gtggtgtata    2580
tgtaccacat tttctttacc cagtccactg ctgatgggca tctaggttga ttccatgtct    2640
ttgatattgt gaatagtgct atgatgaaca tatgtgtgca tgtgtcttttg tggcagaaca    2700
atttacatttt ctttgggtat atatccagta atggggttgc taggtggaat gattaattca    2760
cttttaagtt cttttaagaaa tctctaaacc tcttttccca gtggctgaac taacttacat    2820
tcccaccagc agtgtccaag tgtttccttt tctgcacaac cttactaaca tctgttattt    2880
tttgactttt taatgatagc cattctgact catatgagat cgtatctctc tgtgttttttg    2940
acttgcattt ctctgatgat tagtgatgta gagcattttt tcaaatgctt gttggccgca    3000
tgtctcttct tttgagaagt gtctgctcct gtcatttgcc cacttttttaa tgggcttgtt    3060
tgttttttttgc ttgttaattt aagttttcatg tagattctgg atattagacc tttgtcaaat    3120
gcatagtttg tgaatatttt ctcccattcc ataggttgtt tactctgttg atagtttctt    3180
ttgctatgca gaagctcttt agtttagtta ggtactactt gtcaatttttt gttttttgttg    3240
ctttgtccat tttaaaaaat agagtaattt gattattttg ttgttgaatt gtaggaattc    3300
tttatatatt atggatgcta acatcttatc aaatatgatt tgcaaaacat ttccctcat     3360
tctgtaggtt gcctttttcac tattgtgtcc ttcaatgaac aaaatttttt atgttttgatg    3420
cagtcccatt tgtccatttt ttttggttgc ctgtgatttt ggtgtcatat ccaagaatgt    3480
ggaatgtgtc atatccacat tcaatgtcct gacgattttt ttctatgttt tcttccagaa    3540
gttttattgc tttgggtctt tggtttaagt ctttagtcca ttttgagtta atttttgtat    3600
gtggtgtaag aaacaggtcc aactgcattg ttttgcatgt aaatatccag ttttcccagc    3660
atcatttgtt gaccagactg tccttttccc atttagtgct gttggagctc ttcttggagg    3720
```

```
tcagttggcc atgtgtacac aagtttattt ctgggctctt tattctgttc tattgatttg   3780
tatatctgtc tttattccag taccacactg ttttattctt ctttttcaaa attgtttgac   3840
tcttagggcc ctttgagatt ccatatcaat tttaggatga attcttctat ttctgcaaca   3900
aatgctattg gaattttgat aaggattgaa ttgaatctgt agactgtttt gagtgatatt   3960
aacatcttaa taattattaag tctaatccat gaatgtgaga tgtttctatt tatttatctc   4020
ttctttgatt tctttcagta atgttttata gttttcatta tataagtttt tacttcctta   4080
gtcaatttct aagaattgtt ttcttttttga tgccattgca acgggaatca ttttcttaat   4140
tttttcagat gctttcacta tttgtgtata gaaatgtaac tgattttttg tatgtgtgtt   4200
gatttttgtat ctggtaactt tactgaattt ttaaattttgt tctaacctgt tttttttttt   4260
tggtggaatc tttaggattt tctgcatata agatcatgcc atctacaaac agaaattttt   4320
acttctttct tcccaatttg gatgcctttt attgctttt cttgtctaat tgctttggac   4380
tggagttcca atactctgtt gaatagaagt gtccagaaca gacattttg ccttgttctt   4440
aatcttagag gaaaagcttc cagttttca ctgagtatgc cgttagctgt ggacttttcc   4500
taaacaacct ttattatgtg caggtaattt ccttctcttt ccacttttga gtgttttttt   4560
tctttttcttt tctttttttg tgtgtgaaag gatattgaat tttgccaaat gcttttcctg   4620
catcagtgga gatggtcatg tgggttttgt cctttattct gtaaatgtgg tgtactacat   4680
tgattttcat atgttgaacc atccttgcat cccagggata aatcccactt gatcatggtg   4740
aatgatcttt tgagtgtgct gttgaattta ttttgctagt attttttga ctacgttcat   4800
cagacatatt gggtaattat ttattttttc ttgtagtatt tttgcctagc tttgatatca   4860
cactaatgct gcccctcaaa gaatgacctt ggaagtattc ctttctcttc agttttggg   4920
ggattgatgt aaattctttt tttttttttt ttggagacag ggtctcactg tcacccaggc   4980
tggagtgcag cggcacaatc atagctcact gcagcctcca actcctgggc tcaagcaatt   5040
ctgcttcagc ctcctgagta gctgggacta aagcatgtg ccaccatgca cagctaattt   5100
atatatatat aatataatag ataaatatat atatatatat atatattttt                5160
tttttttttt tttttttttt tttttttttt tgcagagaca aggtaggtct tgctatgttg   5220
cccaggctgg tctcagactc ctaggctcaa gtgaacctcc cacctcagtc tcccaaagtt   5280
ctgggattac aggcatgagc caccacgtct ggccagtgtt aattcttcaa tatttggtag   5340
aattcttcag tgaagtcttc tagtcctggg ctttctttg ttgggaggtt tttaattacc   5400
aactcaattt ccttactagt tattggtcta tttatatctt ctatttcttc atgattcagt   5460
cttggcaggt ttggtgttc tagaaattta tccatttctt ataggtcatc cagttttgttg   5520
gtatagttca tagtcttctc ttataatcct ttcttatctg tagctcagta cctcctatct   5580
ggagatgcag aattaggaat tgaaactata ataggccccc cttttataat ggggtgtcct   5640
tatttttacc ttctcacctt gcaatacect tgtcttgcta gtaaagaaag aagggaaatt   5700
tgattcagga ggtaatcata cttttcaatt tgtacaagat ctaatagcca tgaactccta   5760
tgtcattcct caccatccca taattcttag cccagccatc atccttacct caatccctgc   5820
tggtgcagcc tggtttattc tgttaatgtg ctgtactgca ttgaggtaag gacttctgct   5880
cagctttctt cttgatacca ttgtaccttg attcacactt cctcttgtga aataaagttt   5940
agcatgaagc tgctttctta catattttaa gttcggctta aaggttttc tgtacatcgt   6000
gaactgtaac aagtggaata taaccagacc gtagcttaca cttgtgccat ttaccaagtt   6060
ttggccaatc aaatgtagcc aactgtttga actgtattca aataagggaa atgctcagct   6120
gtaaccaagc caactgtttc tgtacctcac ttctgttttc tgtatgtcac tttccttttt   6180
ctgtccataa atcatcttcc atggcgtagg tgtgctggag tctcagagtc tattctggct   6240
caggaggctg cctgattttg aatcattcat ggctcaatta aacttcttta attttttttt   6300
tttttgagat tgagtttcac ccttgttgcc caagttggag tgcaatggtg cagtctctgc   6360
tcactgcagc ctctgcctcc tgggttcaag cgattctcct gcctcagcct cctgagtagc   6420
tgagattaca ggcacatgcc accatgccca gctaattttt ctatttttag tagagacagg   6480
gtttcgccat gttggccagg ctgtctcga actcctgacc tcagcctccc aaagtgctga   6540
gattacagat gtgagccact gcacctggct tcactcctte aaatttaatt cagctaaagt   6600
ttttattttt ttctctttct tttttttttt ttttttgag acagagtcac tgtcacccag   6660
gctgaagtgc agtggcacaa tctcggctca ctgcaacctc cgcctccag actcaagcga   6720
tttctggcta attttttgtgt ttttagtaga gatgggtttt caccatattg gccaggctga   6780
tcttgaactc ctgacctcag gtgatctgcc tgccttggcc tcccaaagtg ctaggattac   6840
aggcatgagc cactgtgccc agcctcaaat ttaagaagaa acagttaaca tggacttgca   6900
tacctccagg atattgtgaa tacctctcaa tatttttcta agttctcaaa gtcaaattag   6960
actctatgac aatcactcaa ggttccctt gtttccaata tgttgatgac ctgctacttt   7020
gcaaccaaag caaacagggt gctcttctgg actcccttac tcaccttaag gcactgactg   7080
actaaggtta taaatcttcc aggtccaaat gccaacaggt acaaaaaatt cttacctact   7140
taggccataa aatattttag ggtactcaaa aactcgtccc aaaatgcctt gaatcaattt   7200
tattcattat ctctcaaaga caaacaatta cgtgaattt taggagcaac tggatattgc   7260
caatggattc ccaattttgc tgcccatgtc taacctttat atgctgtcct cttagataca   7320
accacagagc actttacctg gtactctgag gcaccagcct ccttggaagc attgtccaca   7380
ccccagccct tcgactaccc aactttgaca atctttttta cctatattac tgtgaaaatg   7440
atgggattgt tgtgggtatc ttaggacaat ctttttgtcc cataacatat ttctcatgtc   7500
aacctagata tgtcccacag tacctttctc atgttaagta gcatcaggca ttcctccatg   7560
cttatatgca atagacttag ctgccatcct aattgacaaa gcaagtattc ttatactgcc   7620
ccaccattca cctctctgtt ctccatgctg ttcctctaca ttggtatccc tttcaaagtg   7680
gatcttgcct caactaaccc ttaactgttt tttttttgtt tttgttttt gtttttgac   7740
aattctggca ctaccccaac acctgcttgt tccaatcttt caaagcctgg ccaccttaaa   7800
tagttaatct ggttactggt taggttaaca tctacataat gcagaagagt tttgttcct   7860
accaatgtaa atatacctgg tgaacccatt ctggacaatg gatatataaa agcatatggt   7920
atccataagc aggaagacaa agtcactctg tctcctcctc tggtagatta atttggcact   7980
gggaagcctc catggaagct caaggtcagt gctttaccca agtaagacta ttggaaggaa   8040
atctctctac attgaaaata aatacagtac tggaccttt ctgggtaaca tttcaaaaat   8100
gtaatgcaat caaattcgt gattggctt cacagtggct actaaacaac tccactgt    8160
cattgttact tggattataa ctaagtattt caatgtgagt gaatgtcaga ttacaggata   8220
atattcctgg tttgtaggaa aaagtagtgg gatatgaat agctcaagtg ttcccctagt   8280
tggcttgacc agcacccatg actatagttg gatggatgga ccttaacttg gtcaataaat   8340
aaaatacatt tctatagtaa ccaaggctaa attaaagggt ttctctgcca ggtgtttcac   8400
aacctgtttt acctcatag cctaacagaa gcacattgga agtgaagatg tgcagatgcc   8460
```

```
aacatgattg atgataaggg ttgtgaaaga cacagaattc caacttggtt gttcacaggt   8520
tccaccacta tgaccttgtc tgtaaacaac actggtctct ctctcttttt ttttttttt   8580
agaaggaatc tcactctgtt acccaggctg gagggcagtg gcacaatctc agctcactgc   8640
accctccacc ttccggttca agcgattctc ctgcctcagt ctcccgagta gctgggagta   8700
caggtgccca ccaccatgcc cggcttattt ttgtagtttt agtagagaca ggatttctcc   8760
atgttggcca ggctggtctt cacctcaagt gatccgccag cctcggcctc ccaaagtgct   8820
gggattacaa gcgtgagcca ctgtgcctgg cctggtctca tttttatgta gcaataagat   8880
atataaaagg ttcccaccta agtggtcaga gaaatgtgaa gttggatatc tggtgccttc   8940
ccttaccaga tatcccactt tgaatgctag ccacattaca actgggttc tttatatat   9000
aaattaatgc catgtagatg cacctgatga gacatcatag acaacgcact tatgtattgc   9060
aaccctaagt tctcagtaat gagaatgctt ttcaaagcc tggcaatgta cgatgtagaa   9120
agaacaatcc taagcattcc aaagtaatga acaagcatct ggtgccacta tacagactgg   9180
gaagcctgcc atttacaagt tagcagtgta gcctctgttg cactccaaaa ttgtgtccta   9240
gatatgctga ctgcccaaca gagaggagct tgtacaatca ctggcaacaa tgctacttct   9300
atataaatta gaaaggaaaa attgtgtcta atctatatca tttaaaaaga aaggttggcc   9360
gggcacggtg gctcacgcct gtaatcacag cacttcggga ggccgaagcg ggcggatcat   9420
gaggtcagga gatcgagacc atcctagcta acatggtgaa accctgtctc tactaaaaat   9480
acaaaaaatt agccaggcat ggtggcgggc acctgtagtc ccagctactt gggaggctga   9540
ggcaggagaa tggcgtgaac atgggaggcg gagcttgcag tgagcagaga tcacaccact   9600
gcacccagc ctgggcgaca gaacgagact ccgtctcaaa aaaaaaaaaa aaaaaaaaa   9660
aaaaaaaaaa gaaaggtcaa cattctacgt taggtaaata aggcatagtc caattaactg   9720
aactgaactg acctattccc acgactggga gactggttca acagaatatg gaccagtgtg   9780
ttcagattttt tctctgttgt aatctatgtt cttctttcat tttgcagatc tcttacctcc   9840
cagcacctaa tatgagtctt ttctacatag gaaataatcc aaatatttgt gaaacttcat   9900
gtgaagtttc aaatggggga agtgaaggaa cgaacaaccc acctcctaac cccaatttat   9960
acccacctgt gttagttcat ttgtattgct atgaagagat acctggaggc tgggaaattt   10020
ataaagaaaa gaggcttaat tggctcacag ttctgcaggg tgtataggca tggcatcagt   10080
atgtgctcag ctcctggtga gggcttcagg gagcttacaa tcatagctga aggtgaaggg   10140
ggagcatgca tcttacatgg tgatagaggg agcaagagag agggtcgggg ggtgccaggc   10200
tctttaaaca accagctctc atgtgaaata ccagagccag aactcactca tcaccatgga   10260
gatggcacta agccattcat gagggatctg cctcatcacc caaacacttc ccagtaggcc   10320
ccacctccaa cttggggatt gtatttcaac atgacatttt gaggggacag atatccaata   10380
ttcaaaccat atcaccacca gaaaggcata agattactt taaactgaaa atattggaac   10440
aaacaatcgc tgcggaaagc agccttatct gaccgaaagc agacctgtcc aagagttctg   10500
ctatcatcaa ctccttctga gggacttttcc agacagcgag gtgacagatg tttacaaacg   10560
tgacgttaaa aaataaagtt gtgtaaatga gtcttatcag aaccttttat actttctcac   10620
tgaagcctca gttggtatat aaaccctttac cactggctgt ttgggaagtg actccttaca   10680
gagtgctccc tcaggcatgg agaataaact tttctcctgt taatgtattt tcaactaatt   10740
cgcaggccct agaccactca gatctaagtt gacagatgaa atgtttttcct cccaacatga   10800
ccaagcttat agtgcttttta tggtatatct gtagagattg cggtcaggca taacattgtt   10860
tgttagggtt gcagtacctt tcaggaaatg ctcaaagttt aattgattta ggggactttc   10920
actggatgag atgcctctct gagtcatcat aggttgcaaa gtattagttt tttgccactc   10980
actgtgtgtt gtgatatgac atactcataa tggggtagga caagatgtca gttttgcttc   11040
caaacttttcc ttacttgttt cctttttggt tcaccactaa tgttgaagaa atgcaagatg   11100
gaaaatctca atagttgaca ctgattgatt gattgagatg gagtctcact ctgtcacctg   11160
ggctggagtg cagtggcgtg atatcggctc actgcaacct ccacctccca ggttcaagca   11220
gttctcctgc ctcagcctcc cgaacagctg ggattacagg tgcccgccac tactctcagc   11280
taatttttttg tattttttagt agagatgggg tttcaccatg ttggccagac tagtctcgaa   11340
ttcctaacct tgtgattcgc ccgcctcggc ctcccaaggt gctgggatta caggcatgag   11400
tagttgacat ttattaagtg tttatatgtg ataagcactg ttagattatc ccatgtaata   11460
catcacttga ttgatttaag agattgtcat ttgaaagatt aaagaatatt tcccagaaag   11520
gatgcttggt caagcctcat catcctggga tggatgggac cttggttttg ggcaagttta   11580
ttacaatttta agactattct aggtcatgga agtgtgtgtt aggacatata agtagttttc   11640
ttgtccagaa tactttgtaa taatatacc taagtttgat cagcttttg gcattcactt   11700
aaattaaatg ttcacaagta ggtacatttt tagaattgtt aagtaatata ctatttgtag   11760
tagcaaaaca ctacaaacaa atacctaata taataagagg gagtggttga ataaactagg   11820
gcatgtcaac taaaaaacat atttgaaatg cagggaaaat gcttactcta ggcaatagtt   11880
acaacttttg tccattatag gtacataaag gaaaagagta cacaaagaat tctattaatg   11940
atgaaattag gaacaatgtt cccatccca atttatacc aaaagaaaat atgttctggc   12000
tgggcgcggt ggctcatgcc tgtaatccta gcagtttggg aggctgagac aggtggatcg   12060
cctgagctca ggagttcaaa accagtctgg gcaacatggc aaaacccgt ctccaccaaa   12120
aatacaaaaa attagccagg cgtgatggca catgcctgta ggtccagcta cttgggaggc   12180
cgaggtggga ggatcgcttg agctcggat gtggaggctg cagtgagcaa agctcacacc   12240
actgcactct agcatgggtg acagagtgag acccgtca aaataaataa ataaataaat   12300
gaaaacttat attctataac atgtattctt atgtctttgg ctaaaacaaa agagaagaaa   12360
aataagtaga gagctaagtg aagtgaagtg tcttgaaaca gataagccat aaagtgagat   12420
atatgagtaa atgagtagtt gctggcctag gaattgtttc tgatgttttc acctattgaa   12480
agaattttttt tctttttgta aatctttttt ttggtttgtt aaactgaaaa ataaaagcaa   12540
tgaagagata atattgctgt agtaatgtcc cttagtgcat ccttggagtt agttgtcttg   12600
aatttggcct gctctgattg tcatttgctg tttgctgcat tgaaaaaatt tcagatttac   12660
aaaaatatgt gtgccagggt ggaggaaatt tttaacttga tgaattctca cctttaggac   12720
actgtctgct cttatatggc acttagcaag atgctgcaac aattgtccct gctcatactg   12780
ttggaggaag agggtatttg cagggagatt gctggagtca agatgatcca aatttaaatt   12840
gcagtggtga gcagtggcca ctagagggct gtgaagtact taattctaaa atttccacat   12900
tttaatctgg agcagaggaa actctgaag gaccactggg actaagggag ctcaatccca   12960
aacatcttta tctgagccct aaatgtcttc tacgttattc tttgacaata ctttgttaca   13020
tctcagaatt tgtagttttg aggtggaggt taagttaga aatagtttaa tatattctat   13080
tccagaatat aattcgcttt tttccaaatg aaactgcac taaaagcttt ttacttgaaa   13140
gcaaatacac ttcatatgct ttatgtattt ttgtccctat atcattgaaa tagtagattc   13200
```

-continued

```
aaggctgttt gtaaaaataa gtgactatac tgcatatagg aatagcccca ccttaaagac  13260
tttgatttta aggacattaa gtgggagggt cttttttgcc ttttttttt tgactatcaa   13320
aatactttca catttcttca attcaaagaa caactgttct aaatttagaa gacagacaag   13380
tgaaagagaa tatgctgcca tttccgatgg ttcttttta ctcttgatcc atcactctcc    13440
tgtctttggc tgactctttc tccaaaaagt accccttact tttcctatgc ctttaacttc   13500
tgttttactt actctattgt agaactttga gaagttgtac accacattca ctgctacctc   13560
acattaactc tgcttactca ttgcagtctg ccttctgctc ctcaatgatt gctcctgtga   13620
aggtcatctt tggtttagca cttgtttgaa atctaatagc ctaaatgcac atcgattact   13680
gtttagaatt caaacgacat ttatttattt actttgagat ggagtttcat tcttgtcgcc   13740
cagctggagt acaatggcat gatcttggct cactgcaacc tccacctccc aggttcaagc   13800
gattctcctg cctcagcctc ctgagtagct gggattacag gcaccctcaa ccacgcctgg   13860
ctaagttttg tatttttttt agtagagatg gggtttcgcc atcttggcca ggctggtctc   13920
gaactcctga cctcaggtga tctgcctgcc tcagccccac aaagtgctgg gattacaagc   13980
gtgagccacc acgcccggcc caaatgacat ttatttttaa aagcaactaa accaggaaag   14040
accttcactc attcaatcaa aaaacatgca ttgaacacgt attcttggct agatccggtg   14100
ctgcaaagat gaaagacgcc actcctagcc tcaaggagct tgcagtttag tggtggcact   14160
ggatgtaaaa taatcataag atgtgaggtg aagactgatg aggtctattt tgttgacaca   14220
ggtaaacatt ctcagagaat atttaattag caacatgaca aaaattagtt gatttatttg   14280
aaggatattt aagtgaattt agagatgaga tttgttttta ctttttttaat ttcagagagt  14340
tatgttggtt gcaaaaatct ttgttttcta gtatctattt tataagccat ctgagaccag   14400
gatgttttct ttttaacatg taaacttgat gcagtctctt tgtaaagtaa tgaatccccc   14460
cgtgaacctc aaggagaaga aagtttagct tgaacactta atttcaagta ccttgagaag   14520
ggaacaggct gtattgctca gagaagaagg ctctattagc taaggtagaa ggacaatgta   14580
aaactcttgt gaagacacct aaatgtcatt ccactcaaag cccattatta ataatttgaa   14640
actgtctgct ctgtgaaggc aacgacctat ctttactcat ttttgactct gctaacattt   14700
cttttatag ttgaactaga ggcaaggcaa ggaacttgac atgcttgttt tcccttttaga   14760
ataaagtggc cagaagcagt ttcttctgtg tgatccaaca cttttcttatc cccagagcaa   14820
ctctgcatag tctagatgta ccagagccca gcagcctgtg aggtgatgtg atgtgatgtg   14880
atgtgaacag aaaggctcca tgttggatga tgcctatgaa tctaatcaga ttctcttct    14940
tggtcatttt gatttccaga gaagtcagta gaagcaggtt ctgtgtgtat aaccagagac   15000
tagagggagg aactgacagg gaagctgggc catgagagtg gtgtgctcag cagagtaggg   15060
agtaagagag agctggctcc agaggagatg acaaaatgcc catgtctcca gcacttcttt   15120
agcattctga gttcccatcc tatcatgaat aggaagagtt ttctagctct ccatgaagcc   15180
gaaataggtt tcagacttc cttctttcc cacacacata ataaataccc atcaggtaac    15240
ctgggcatgg ccttttattt aggcactaac aattctaaaa ggaattaata aatgcttcac   15300
tgccatttca cagtgtaaca gcatgccagt ttaccatacc attaacattt agcctcgtgg   15360
tatttctgtg tttttttcagt cagtaatgat ggcattttg ccaagataat atagtgttaa   15420
actgtattgg ttgaaatcct aggctttta aatgtaaact agcactttac aaagtattac   15480
aaaggaaacg aaccagggaa acttgagaag gaactttctt atccacattg ttataggtta   15540
taaaatagtt cctatttaaa ttaaaatacc tactgttgca cttttatgtg tgttttata    15600
tataaataac atctgggttg gcaaaatatgt gattttcgtc aaataggctt tgattgaaga   15660
tgaaatattt ttgtaaaact agtccttttt taaagtttaaa attttatgtt accacatgaa  15720
ttgatcagca gaaattatt tacattatgt aaattgattt ttaagagtat ccacaaggtt    15780
ttagctatta ttttttgaact tgcttcctag cccacacaat taagtaataa gagtaagaaa   15840
aaagaaagca cacatccaaa tcatctatca aaacccagct tctacccaat gacacatcat    15900
tttatttctt gatcttgtaa tgttgagcac atgccttgga catattccta tatgtgggct   15960
ctattcctcg cagcacgtca ctccctcttt tatccgcccc tcttatgtgc tcccactcct   16020
atcctcttca attaaaaatg cctctttctt ttttttttaa gttaattaat taattaattt   16080
ttttttattg atcattcttg ggtgtttctc gcagagggg atttggcagg gtcataggat    16140
aatagtggag ggaaggtcag cagataaaca agtgaacaaa ggtctctggt tttcctaggc   16200
agaggaccct gcgggcttcc acagtatttg tgtccctggg tacttgagat tagggagtgg   16260
tgatgactct taacgagtct gctgccttca agcatctgtt taacaaagca catcttgcat   16320
ggcccttaat ccatttaacc ctgagtggac acagcacatg tttcagagag cacagggttg   16380
ggggtaaggt catagatcaa cagcatccca aggcacagga attttcctta gtacagaaca   16440
aaatgaagtc tcccatgtct acttctttct acacagacac agcaacaatc tgatttctct   16500
atcctttccc cacctttccc cctttcctat tccacaaaaa ccgccatcgt catcatggcc   16560
cgttctcaat gagctgttgg gtacacctcc cagacgggt ggtggccggg cagaggggct    16620
cctcacttcc cagaaggggc ggcgggcag aggtgccccc cacctccggg atggggcggc    16680
ggctgggtgg aggcggggccc ccacctccct cccagacggg gcggctggcc gggcggggggc  16740
tgaccccccca cctgcctctg ggacggggcg gctggccggg cggggcctga ccccccacct   16800
gcctccggga cagggtggct gctgggcaga ggggctcctc acttctcaga cggggcagct   16860
gccgggcgga ggggctcctc acttctcaga cggggtggcc gggcagagac gctcctcacc   16920
tcccagacgg ggtcgcggct gggcagaggc gctcctcaca tcccagacgg ggcggcgggg   16980
cagaggcgct tcccgcatct cagacgatgg gcggccgggc agagcgctc ctcacttcct    17040
agacgtgatg gtggccggga agaggcgctc ctcacttccc agactgggca gccaggcaga   17100
ggggctcctc acatcccaga cgatgggcgg ccaggcagag acgctcctca cttcccagac   17160
ggggtggcgg ccaggcagag gctgcaatct cggcactttg ggaggccaag gcaggctgct   17220
gggaggtgga ggttgtagct agccgagatc acgccactgc actccagcct gggcaacatt   17280
gagcactgag tgaaccagac tccgtctgca atcccggcac ctcggggagc cgaggctggc   17340
ggatcactcg cggttaggag ctggagacca gccggccaa cacagcgaaa ccctgtctcc     17400
accaaaaaaa tacgaaaacc agtcaggcgt ggcggcgcgc acctgcaatc ccaggcactc   17460
gcaggctga ggcaggagaa tcaggcaggg aggttgcagt gagccgcgat ggcagcagta    17520
cagtccagct ttgctcggc atcagaggga taccgtggaa agagagggag agggagactg    17580
tgggagagg gagagggaga gaaaaatgcc tctttcaata tgtaaggtaa gattgataga    17640
tgattgcctt ccgtagttcc tcccaaaatt cataggttga aatcttagcc ctcgagtgg    17700
tggtattagg aagtatggag cctttgggag ataattagct caggagggtg gagccctccc   17760
gaataaattt aatgccttta taagcaagac cccagagagc cctttcaccc ttttctaccc   17820
tatgaggaca cagcgagaag acagctgtct gtgaaccagg aagcaggccc tcactacata   17880
ccgaatctac aagcaacttg atctcagact tcccagtctc ctgaactgcg agatataaat   17940
```

```
gtttgctgtt taagtcaccc agtctaaggt attttgtta tagcagcctg aatggactca    18000
ggcggtaggc aagaggagga cagtgcacct gagttataca ttgggcaagt catttacctt    18060
cattggagcc tcggtttact tgtgttagat atgggaataa tgatagttac actgcagggt    18120
ggttgtgaag attagagaaa gtgcatatac tctgatcagc acagtgcatg gtacttcagt    18180
acacagtgtt aactgaagac acagtgttaa ctgaagacaa agttgaaaac taaagatagc    18240
tagtgaaaca catgttctct gcacatcata cagtttcttg ggcagttttc aaagtgtgac    18300
tctgcagttc ataccaccat tatcacttag tctctaacaa ataatcatat ttgcacatt     18360
tggctggac ttaataattt tatttgggca gcagctggtt tctggaagtg ttcatgggaa     18420
gaaaatgtat attaataaag ttagcaggta atgttctttg ttgaaatgtt ggatattgtt    18480
ggacacaaaa gagtcagggt aaatgtacat ttacagaatt gagcgtcaga gtgtcatagt    18540
tctctaatga tttacaaaga aagaattcct ggaacaagtg aaatacttaa taattaattc    18600
agcctgtatt tctgcaggta atcaactgca gtgataaaaa aataaaaatg gaactgtctt    18660
ttgctcattg gaaagatatt tgctgcattc aaagtcatca aaaaggcgaa gcaatgaaac    18720
ttaagacttt tgggtttaa taattaaaaa tccatcttaa agagaacctt gggctctggc     18780
acggtggctc attcttgtaa tcctagcact ttcggaggcc caggtgggcg gatcacttga    18840
ggtcaggagt ttgagaccag cctggttaac atggtgaaac cccatctcta ctaaaaatac    18900
aaaaattagc tgggtgtggt ggtgtgcgcc tgtaatccca gctacttggg aggctgaggc    18960
acgagaatca cttgaacctg ggagatggag gttgcagtga gccaagattg tgccactgca    19020
ttccagcctg ggtgacacag tgagactctg tcttgaaaaa aaaaaaaaga gagagagacc    19080
gtttgtgaag gtgtgttaca cagagaattc ctgattccta atctccagaa tagaaaaatt    19140
caaaggctca gaatcatccc aaatcaatta tccagtggca tctgcatttt ccgatttcat    19200
tctcactagc cgtgtgaaca tgggcatgac cccaggagcc aaggaattct ctaatgccta    19260
aggacagcca tgaggtcaat gaataacatg tgtcaggttt ccctggcaca gaggagcttc    19320
ccagtaaatg ttattttcct tagctatttc ccatttaaca tgtcaattat tcttagtgag    19380
tttccattca atatgagagt ttatataatt tgtcatattg aataggaact tgctaaggaa    19440
agctgtgtag cagaggaagc agccccaagt gacaggacat aaactttaaa ttcacaagat    19500
gcttgtatgt gaattatgat ggtatctgaa ttaacagtga tatttacagt ttagtaaatac    19560
atttttcttc ccttgtcttg ggcttttata aaaccctgta agtcatgtat gtcaggaatt    19620
ttatcctcat aattgagaga aaaatactcc atattttatt ggaataaga tcagtagatt     19680
ctctgtatat catacaatgt cttgcctact taaattatca ccccccttcc tatttcaaca    19740
aagactttct ctaagtaccc ctggcctctt gccctgatcc atactgttct ccttggtaat    19800
ggagtgagtt tcctgcctgg tgggtgcagc cattggccac atttctctag tgtatggaac    19860
tcaccggata aaaggcctca gatgtaggtc tctttctgct gtcttcaccc aggtgttgtg    19920
gagtgtgtct gtccttgagc actagcttc ccctgtgtgg gctgcctcaa ggctgcatt     19980
catcaggtag ggactgttag ctggtagacc taagccacca ctccagtact gactgtcagt    20040
aaggaaggtg acatgctgac ctccatctgc tacatcattg tgtatatgtc ttcattagtt    20100
ctgcatattg gtgagaaaat ggatgctctg attcctcttg aacccaaga gaatgaaggt     20160
aaaaaaattg aggtcctaat gcaaatttc ttagtacacc caaatctttg gatagagtcc     20220
tgcactcttt gagatatatc acacaatctg tctcactttc ttttcgcata tgttatatat    20280
tttaaaactt ttgttttgg ggccaccact tactggctct gtgattttag gaaagctttt     20340
cagaccctca gaaccccagt ctcttcatct ctaaagtaat aaaatatatg taagaaacct    20400
atttcagcat gtgaattctg tttccttttt tcctctagat gtatcatatc cagttaaaaa    20460
aaaatctact tgaactttgc aggtatcttc agtgtttatt acttctcatt tttaacattt    20520
attggaaatt agcatattgt cagaattgat ataatacaat atgtaacctc tttcattaag    20580
cttatcatttt ttaaaataca aataactatt ctttacttaa attttatttt ctagacacag    20640
ggtcctgctc tctcgaaccc aggctggagt gcagtggcac aatcatagct cactgcagcc    20700
tcaaactctt gggcttaagt gatcctcctg cctcacactc tggagtagct gggattatag    20760
acctgagcca tggtgtccag catgacttaa attttgaata agttgcactt actaattaca    20820
cttacactgc tgcatctgaa agagtaatac aacaatagaa gccttttata gtaattattt    20880
gtggcaggta gactcctaaa atgactccca aatgacccac acccttgtac aatcaatacc    20940
ctgtccttg agtgacagtg acttgctcta atcagttggc tttcagttaa tcaaaagaga    21000
gattatcttg ggctgaacta aactaatccc agcaagataa cagggacttc agtcttgcaa    21060
acagatatca tataaaggga atcatatctg cacatttgat tcttggaccc tgggtaggaa    21120
tttgttagag agcaaggatg tgaataaagg tgggaaataa aggtgtatct ggtgtctctg    21180
ctcaaaagct cacatgtagc tacaaggcag agatttaggg gagtggtatc cacagtcaag    21240
aagaattaat acatagtgtt tgagtctggc ttcttccaat tagcataatg cttttgaggt    21300
tcatccatat tgttgcatta ccagtagttt ttatttattt attttatcag tagtttctaa    21360
attgttgagt agtatattac attgtgtaga tatatcctgt gtgtttatcc atacacattt    21420
atggatattt gggagttgct agttttttagc tattctatga gcattcacat acatgtcttt    21480
gtgtggaaat aggttttcat atctcttggg taaatatacg ggagtggaat tgctagatca    21540
tatggtaaat actctgtata cttaaaatga agagaaactg tcaaactatt ttccataatg    21600
gctctaccat acttgatgtt ttagaaaaga ggaaaaacac tagcaatttt gatgctgtat    21660
gtctacaacc taagagaatc taataatagc gtcctggtct gtcagtgtag gaattgccta    21720
ggtaatacat ggaaggtgtg gagggagcag tgacacagaa aatgtgcgtc agaaagtttt    21780
gcttttccta tcccacgtca tttctgagtc tgatcctccc tactcctcac aaataaattg    21840
gtagattcat ctgttttttgg acccttttct gctctagtta ctgaactatc agagacttca    21900
ggaagagctt aagctaagct attccaggga agttttggtg ttactctgta cttacggact    21960
cctgcgtgtc tgtctctgtc accccagctg ccaactcaac ttagagttta ttagcctggc    22020
attgaccagc acactgtgat attctctgag gcacactgca tgctgctagt gtgccctggt    22080
tcataaagct gggccttcag cattgatccc actccaagtt ccttgctctg tcttcccaca    22140
gctgtccct tggggatgt gggggtctg acatcatttg cattattagt ctattccaag      22200
aaatgcacct gtgcactaat cagttcactt tttctgtctt agtcggcaga tctagccata    22260
gcccaatccc tcaattccta tactaagcct tttattag taaaactgtt atgttatcta      22320
gaaattcatc agtgggaaaa ctacttcaag ggaggtagtt agaggctgca aggtgctaaa    22380
tatttttctt tctttctttt taaatgtaac ttggatctaa agtaaggacg aatttccttt    22440
tattatttgt tcagaatata ccagctggtc ctgtgggcag aagtttgtta aggggcctgg    22500
atgtgaaata acagtgtatc tcgtgtctct gctcaagagc tcacatgtag ctacaaggca    22560
gagatttagg ggagtggcat atacggccaa ctgagaaata acaatattgt cagggactcc    22620
aaggcacttt ggaagatata aagaatttct taaatttct tgtagaattg ttgcaaaagg     22680
```

```
cagacatgct taaatgttta aataagcttc ttgaaaactc atggaacatt caatcacaac   22740
tccaacagtt ctccaaaatt tgatttattc tggccatatt atgcagcaaa gaaacacttg   22800
gctatttatc taaatctctt ctgtcttgta aatgatccta gaaataatc tagaaataca   22860
ttttattaaa gtaatgcatg aggtacatat cgattaccag ccaatagttg aacttaaaca   22920
taatgcatgg gtgtgagggc tggcattgat gattcacaat gaacacagtt gaatatcact   22980
tccctgctga gactcgggta tcatcgcaaa accacagtga gcatcagtgg ggatctgcat   23040
gctctggtca agacagatct ccatgctgag tgtctgtttg ccatgatgaa gagaacagtc   23100
aacaggagtg tttgccatga tgtagagaac agtccgggag gagtgaatgg aggatggggg   23160
catgaggaaa gatgaggctt tctctagtta tgacccttg tgtagaagtt aggagtaggg    23220
gataaatgtt tctgcctaat atttaacttg gaagagaaga tgtccatgtg aaaaactgct   23280
aaatactgaa acaagagagc atgtgactaa gcaataccat gtgtggcaca gaaaacaagt   23340
gcaatagcag tttagcaaag tgagttcagt gtaggctgaa ctggttagag caggtttccg   23400
ggtgaaggtg aggattggtg aggtttgga ttggtagaaa gagacgggga ggacatctca    23460
catcaagaag ttatgccagt ggatttcagg agaattgagt gtttgtgtct gaaaagcctg   23520
taagaatagg gcatgacagt gtggagaaat gcatgaaagt atgaaggatc gtgatatcca   23580
gtttgaggag tgctaactag aggctctgaa gatttgagaa gaaacataat gaaaggtgtt   23640
ctcagcctga tcttggtatg caggactggt aaaccccaaa caccttacca ttctattacc   23700
tctccctcaa ggaatgggtc ccttgataag aatttagtgt aaaaaagatt gtcaattcag   23760
tgctgctgct gagtgctagt ttcttaaac acacacagtt ttcttttgag aattttttt     23820
ctattagata gacgaactgt tatttaaatg aaaaaggcac atagtcccat aaaacaatta   23880
cacattcggg tgataacttc aaaaggaaaa attaaaatgt tcttatgttt tgagcaagca   23940
tttccacttc cagactttgc tgcataaaca tctgtggtca tctagggaag gcctgacctg   24000
gttcagaggt gtcagagcaa tgtaaagtca cggaagtgc gcagttctat tctgggctct    24060
catcttttg cagcggtcca ttctctaatt ttcaaccaca tattaccaga caatctctta    24120
agtcatacac aacaaactga ttctgtttca atgcttagaa ttagaataaa aaagcctaag   24180
caaaaatagc acaaacattt gaaaaacact cctttttct accactccct tcctagaaca    24240
gaaataaaag ccctgtactt taagaaaatg gatggaagaa ttttctttgt acttcttatt   24300
ctccaagtta catttactac ctgatagtgt taataccttt ttgtagtacc tttctttaaa   24360
atatacaggg aaatgatctg ttccaagaaa ctgtgttttt aaatttaatt atagtgtgct   24420
atgatgattt aaaaaatggc cttttgagta aaggacacga acaagttatt taaaaagtga   24480
gcagtaagtg tggtcagtaa acacatcaaa aagttcct cactaatatt caaagaaatg     24540
caaattagaa taataatacc cttgttgctt gtcaaattaa tactttaaca attattatgt   24600
aaattttatg gataggattg caaatcaaca caccttcct ggccactggt gtacataata    24660
gaaattctaa aaatgttctt aggcttgacc aagcatttcc acttctagac tttgctgcac   24720
aaagatctgt ggtcatctag gagaaggctt gacctggttc agaggtatca gagcaatgca   24780
aagtcatgaa aatgctgcaa ttctatcctg gactgtcatc tttttgtag tggtccattc    24840
tctaattttt caatgacgta gtaccagaca gtctcttaag tcaaatgtat ttgtagggct   24900
ctggatttga aattcaatct ggctttcagc cttgatgtgg ccactcccaa cttgtaaagg   24960
acctgtgaag acttagacac agaatcaaac acagaagata agaaaaccaa cttgaaaga    25020
aaatttattg tcaaaattgt actgggtcaa ttgagcaaaa acttcaaaga gcgttttcat   25080
attaaccaaa gcatccctcc tcaattgaaa catataaaga tattgttcac ccctatcctg   25140
actcagagat ccacaaatct gggcattcat catcaccata ttctgctggc aatagtttta   25200
agcagctaaa ttactgttct ctactcttga gtttcctcca tctcttcaga tacagaaagt   25260
tctagaatat attcaaataa tcaaatcttt aattcattcc atatatctgg ctcaagacag   25320
tgtcccaata accttattct agagaaagtc agatttagac ttgtgctcat catcatactc   25380
atgttcttga catcatttta agctctgagg agacatctca cataactctc attgatacgt   25440
gtatacatct gtcactctgt gttttgtgct tgatggatgg acttggatg agatatgcat    25500
agatgatgaa gcagatagct atatatatgg tattgatgta gattcagtac agctgtataa   25560
ttgcatctgt gttcacata tcttgtgtac tgtatcttga ctgtatctgt gtcaatacct    25620
aattgagtta taaggcataa atatgtggag ctcttagcac aatacctggc acactgcaat   25680
cagtcgatgt atgtgtttgt gtgtgtgcgt gtgtgtgtgt gtgatacaga cagaacctgc   25740
taatatgcat aatagtcagg ttgggttgtt ataacaaaat actatagact gtgtggctta   25800
aacggcagac atttgtttct cacagttctg gagtctggga aatccaaggt caagattagt   25860
ttctggtgag agcagtcttc ctcttttgca gctcccatg gtttgcaaat cacagatttc    25920
tcgctgtatt ctcacatagt gtaggaggaa caggggagg gaagggagga agtgcctaag    25980
gacactaatc ccatgatgag agttctatcc accatgacct aattacctcc taatgccacc   26040
atctccaaat actatcacac tgggaattag gtctttaaca tgtgaatcat ttggggtgga   26100
gaagacaaac attcagctca taacaggtaa ggtagaaaat ctcaagaatt tatattttgt   26160
atatgaaaga tcattaatga gcagaatttt aagtttaatg ccaattttaa tctatttta    26220
tcttttctac gattcttttt tactttttaa ttttttaaact ttcatataca aagggataat  26280
atttggctaa atgttctctt ctttttgagc tctggatcat tgttacgatc accccataat   26340
tgtatgtgtg cagagatagt gctttataca ttttaaaac aatttatat acagtattaa    26400
attttatttt tcaataaaca atccatgaga tagaagaac atatattttg ttttacagat    26460
aagctccagg gagagtctag ggtaccttag attgtatggg taaaacatgg ttatttaaa    26520
tcataaataa acagtcttat ttccctaaat gcacatacag gcatccacat caaatgaaat   26580
cacatcacat gaattgaaca ggcagttact gacttagaac tttgcactca caaagacac    26640
actctcctaa atgtctccat catactatac tttttgtccc caaatgccta atcactgaag   26700
cttcagactt tgttgctttg attcccttag gaaaaattcc tggtgtttca gaaaaaaga    26760
gccatttaac tacattagaa gttaaccctc ctttaaaaat gtg                     26803
```

```
SEQ ID NO: 20        moltype = DNA   length = 26803
FEATURE              Location/Qualifiers
source               1..26803
                     mol_type = other DNA
                     note = cDNA
                     organism = Homo sapiens
SEQUENCE: 20
cagttaaggt ggggcaggaa taaatcacaa tggtggaatg tcatcagtta aggcaggaac    60
tggccatttt cacttctttt gtgattcttc acttgcttca ggccatctgg atgtatatgt   120
```

```
gcaggtcaca gggcatacat tggcttagct tgggctcaga ggcctgacaa ggcacagaag   180
gagctgggat agaggtgcaa agtactcatg ctgacctgac atcccatgcc cacggcagac   240
atgactactt gatcggacaa tactttcttg gaatcaaaga cacaacttca cagtcctcag   300
catcatagtt caggcagcct gtatcagtag atcagagtgg gcacatggcc tggtgctatc   360
actccatcct gtgagggggag atgggattgg aatggagctg gaggagtcac aggtggtcct   420
gatatcacag gcctgggagt ctgaaagaag tgcagtaggt agtattatgg ccctcaaaga   480
catctgtgtc ctactgtcta gagtcaatta aagtgttacc taacatagaa aaaggatt    540
tgcaggtggg attaaactaa ggatctcaag atagaaagac tctcctggag tatccagttg   600
tgtccaatgt aagaacaagc gttctcaaaa tagggacaca ggagattgaa ttgcaaagga   660
gatgtgctga taaacggaga ggttggagtg atgccgccat gaggcaagga atgtgggtag   720
cctctagcag ctagcaatga ttcggaaatg gattctcccc cagagtccag aaagatcaca   780
gcagtgctga caccttgatt tgagcccagt gtcacctctg tcagacttct gcccctataga  840
actgtaagag gataaatttg tgtttttaagg cacaaagttt atggtaattt gttatagcag   900
caatgggaaa ctaatacaag aagggttgtg ttatcaacag aaatacagca atcagaagaa   960
agatggttgg ggagagcaga gggtggggtg ggaaggtgat ggattctgtt tgggacattc  1020
tgggtgtcat atgaatatta ttgggaact gtccatcaaa agctcagact tcaaagaaag  1080
aaaggaagga gcaacaatat tttgaaaggg agaaagtagg taatattcaa tatgtgttga  1140
gtacctacaa ggttttagt tctttccacca agttattta tttaattt atggcatcaa   1200
gggggtgttt tttttttct taaaccaaat tttctcagtt aagcatccca tgtaagtggc  1260
cagggggtaaa gagatgtgac taagactaga cagagtgatt tcatcatta catggtacta  1320
tggttctact gaagcactga ggaaggaagt caagagagtt cctgagaaat gtctggagtc  1380
ttagtaacat gcaaagtgag gcagaggtat tgtcagtgtt agctggtcac tttgaaaggt  1440
tagaggtaaa taaagttcag ggcaatggta cttggagagg agtgaatctt tggtaacctg  1500
gaggagatgc ttctcagagg aaaatttctt cacagcatga agtcaccagc tctaagacta  1560
gtgggtgttc tggggatgt tagcagtgac tcactgactg ttggcccagt gagggaggg   1620
atgaaaggct gggtagtggg tagagaatct gactcctcca gccccccacat gtctattcct  1680
gggccttctc ttggtggggg caaaaggtat gcaaagggat ttccgcagtg tctgagtgct  1740
cccaggagac ggaaagtaa ctgatgactt ggagttggag tcttgttggc tcaggcagct   1800
ggggcgtttt gggatttcaa caccctccctt tagtttctat gtatggtgct gagcaagtag  1860
tcaaagactt tggtcttgct ttaccccagt agcccacaag cctgagtaca tggctaacat  1920
ttattgggca cttagtgtgt gccaaagagc tttatgagac aggttctttt tgagtccccat 1980
tatactgata atgggactga taagaaacag aaggtcagaa aggcccagta acttgggcaa  2040
ggtcatgtag ctagtaagtg gtccagctga aatttaaaac caggttatc caactccaaa   2100
tcccacatct gatttatttt gccatgaatt aaaacatagt tctgatttty agaaactccc  2160
agtcccagtg ggaaaacaga tggaatcaca aattaccata acacagtgta gtgatgtaga  2220
tataaaaaca aagacatggg aaccctgaaa ggaagttgta acaccaatag aggaatgcat  2280
ggaggagatc tttcagagga ggtagcctcg tagctgggct caggggtgga tgagttctg   2340
gctagaagcg cattgtgggt agagggagaa catatataga aaggtcagaa gatggtggac  2400
atgtttggaa agagtgagta ctagactgat gaacacgatg agtcaggagc ttatgacgtc  2460
agggggctact gctagcctag ctaatgactg aagattctgt gaaaagaaaa ccctaacatt  2520
tccagctgag tactagggcc atggtgatta tatatcatct ctcatgacaa cacaaatgtt  2580
tgggcttact tatcatcctg ctcagtaatc attatgtcac tcattaaaga tgtatcaggg  2640
taaattttag gtgagaattg attagaaatg taaactctat atatgtagtt acaggcttca  2700
cagtttgcca ctcaaacaat atggtcatcc aatcatgagg cacaaccttc tgctcagaac  2760
ttttttataa ttgggagaaa gtgacatccg agttccatct cttctgagaa ctgtgcagct  2820
cagaaatctt cttccctttt ttgatccccc agttgggtga atgacatta acagtgtgtt   2880
ataagactt ttcatgttta ctaccccata ttcaaaatta agcatttcaa acaactgtat  2940
aattgtctat aaatgtagca ttattagtta attttccttt taacacattg aggttacctc  3000
taatgttttg ctattttaaa ctatgttgaa ataatcatgt ggtttttatt ctttgaatta  3060
ttttatattg taatgttccc tgaaatgaaa ttagttgatc aaaagatgag taatctttc    3120
atgactttg atacatgtca ctcaatcacc ttctggaaga gttggaacaa gagcctattg  3180
ctggcatccc atttcatagc catctccacca atgttggaaa atgggctttt cctatttct    3240
gctaattcat tagttgttaa tggcttattt taactattaa tcccttgtta ttgatgaaag  3300
ttaagcattt tctgtatttt tatttctgt ctaaattcta cttttggcac aatttccttt   3360
gctcacttct tcactggaat ttagtatttt tctttccaat ttgtatgact ccaaaatcag  3420
tgataaaata agcaaagggt ctttcttaga ggctaaacaa gggaatgaat aaggaacaag  3480
aacagcaaag ggatagtgaa taaagataca aaataataac ttattttat ttttgaagct   3540
ttccccaggc agtaattctt gaccttttta agattataaa ttattttgag atatgcattc   3600
ttatcctcaa aatgaattag tacataaaat ttaaatgggt tgatagatcc cctgaagtgt   3660
atccacaaaa tgctctcagg ttaagcaaca ttgttctata ataactgctt taaccaaaat  3720
gtttaattat tgcttgtgtt tacctgtcct agcaaagagc taattgttaa attttgtgtt   3780
agagggtcaa tattataaat aacttaatgt ggcctctctt tcctttcctt tttttgagag   3840
ttttgaggct atcactaagt gggctttaga gtaccaggtg ggaatctgac ctcactgctc   3900
aaactttcaa cttcaggcat gaagtggtcc cagtgatgg ggaacctcag agtctaaaac  3960
aaaaatagta gactgaggcc ctcagaaacc agacttatca gattcagaat ttaatataac  4020
tatgttgaa agattaaag aaaatacate aaattaaaaa gtgagcaaga agcaagaata    4080
acaaatgaac tggcatattt gagaaagaat tttgagcttt tagaaataat acatacactt  4140
attgaaataa aaactcaagt caataggttt aaacagcaaa atgaaatata ttaaagaaaa  4200
ctattgtgct gaaagattta aaaaactatt acacagaatg caaaatgatg aaatagggta  4260
atttaatata tggcagatat gttaagacac tatgaggata gtatgagaag acctgataga  4320
catctaatca cagcacctta aggtgaaaat agagagagtg caccaatatt gaggagttaa  4380
tgtctgagac tattccagaa ctgataaaata gatgaatcta cagatctcag aaacacagct  4440
tttacaaagg ataaatgaag agaaattcac cagagataca ttgtaatgaa tctgtaaatc  4500
accaaagcta aagatattat ttcacaagtg gaatgacagc tgacttctca acaacaacga  4560
aagcaaggag acagttgaaa gacatcttga aaatggtgag agaaaaacta actgttaata  4620
taaaattgtg tacctatcaa aaatatcttt tggccaggcg tggtggctca cgcctataat  4680
cctagcactt tgggaagcca aggaacgtgg atcacttgag gtcaggagtt tgagaccgag  4740
accgtcctgg ccaacatggt gaaaccccat ctctactaaa aatacaaaaa aaaaaaaaa   4800
atagccatgt gtggtggtgt gcacctgtaa tcccagctac ttgggaggct gaggcaggag  4860
```

```
aatcgcttga acccaggagg tagaggttgc agtgagctga gatcatgctg ctgcactcca  4920
gtctgggtga cagagtgaga ctgcctcaaa accaaaccaa accaaaccaa accaatcttt  4980
caagaagtac accataaaga catttccgga taaacagtga atgagattac ttcctaaacg  5040
aatatgtaag gatgtttctt tttaaaattt tttttgggtg tattcatcac ctcaagcatt  5100
tattcttttg tgttgttaca actgataaga atatctaagg atgtttcaaa aggaagaaaa  5160
atgatcccta aagtctggta tattagtttc ttattagttg ctctaagaaa ttactgcaaa  5220
cttagtggct ttaaaaaaca cgaaattatc tttcagttct gtaggtcaga aatttaacct  5280
cctgatttct ggtcagaagt cttactgggc taaaatcagg gtatcagcag ggctgctgga  5340
ggctctggag atgatgtttc tctaatttct agaggcattt gcattcctta gctagtggct  5400
tcttcccaca tcttcaaagc taacagtggc agtcgagtcc ttctcttatc tttttttttt  5460
gggggggggtt ataaatttt tttattatta ttatacttta agttttaggg tacatgtgca  5520
caacgtgcag gtttgttaca tatgtataca tgtgccacat tggtgtgctg cacccattaa  5580
ctcatcattt agcattaggt atatctccta atgctatccg tccccctcc cccacccac  5640
aacagtcccc agtgtgtgat gttcccttc ccttctctta tcttatcact ctgacctctc  5700
ctgcctcctt tctctacttt taaggaccct tgtgattaga ttgggtccac ctaaataatc  5760
caggataatc tctttatttt aaggttagct gattagcaac ctcaattcca tctgtaacct  5820
taatttcttt tttgccatgt aacctaacat agtcacaggc ccaagggaat aataggatgt  5880
gggaattgcg ggtggtggag taggggcatt attctgctta ccacagggga ccttggatgt  5940
cagtaaaaaa tggtgaggaa gaaaacagga aacgtagaat aatctaaaca aatctttgaa  6000
aaataagttg aaatgtgggg ttagaaaaag ggcagaacta aaatgttaag acaaattaaa  6060
atgttaagcc tataagttga gagggagatg atcaaggtta aaaatactca taaatcatat  6120
ttttttgggt aggggggttag atatttatta atttagacc ctgagaagta aaatagtcat  6180
gacaaaaatt taatagtaac cactaaaaca agagaaacag agtatataac ttctaaatca  6240
atatgggaag gggaatggaa taagaaaaca atagcaacca ccaacaccc acccaaaata  6300
aataataagg tgagagagaa aaagaagcat tgaaaagggg ctaaaataaa ataaaaaatt  6360
aagtcatgcc cgtaatccca gcactttgag aggccaaagat gggtggatca cctgaggtca  6420
ggagttcgag accagcctga ccaacatggg gaaaccccat ctctactaaa aattcaaaat  6480
tagctgggtg tgggggtgca tgcctgtaat cccagctact ctggaggctg aggcaggaga  6540
atcgcttgaa cccaggaggc agaggttgtg gtgagcagag attgtgccat tgcattccag  6600
cctgggcagc aagagcgaaa cgccatctaa aaaaaaaaa aaaaaaatta agatagtaaa  6660
acaaatccaa atacattaaa gattacaaaa aatgaaaatg aactaaactt cctagttgaa  6720
agacatattg tcagattgga ttttaaaatc tggcaatgat atttccagga cacagtccta  6780
aaatattaaa cacagaaaag ttgaaagtaa agggatggaa gaacacagtc aaactaacta  6840
gaagagagct gggttcaccc tttatatca gagcagaatt tcactgagaa aacactaaca  6900
ggaagggga aaggcacaac atagtgatga agcacttaat tctcaacaaa tgtatgacac  6960
ttctaaacta ttatgactgc aaaaaaaaaa aaaacctcag catatataaa atttttggaag  7020
agccatggct atcagctgac atgcacttac catatttgca ttgtcctact acaaacttta  7080
cccatatgac caaggtgctg tcttcatccc cattttacag atggggaaat ttccccatag  7140
agaaaaagat ttgggcatg ccttggtttc ttcttgactc tgcttcctgc tgattgatcc  7200
tcacacctca cctggagacc tacttcacat tatccatcag gatgagaact ggtgtgcctt  7260
taccaaagga ccacagtcac cttcaaaacg tgtttagata gatctggatg gagacttatg  7320
tggttgcaga tgaaaaaaaa gtccccatgg tatatctgac tccatgtcat tcactgcatg  7380
aacactcaca cacatgcaca cgtacacagg caaacacaat cctgttctgg tccggcagta  7440
gtgccaacac tcaaatccca ggtcctactc tgaagccttt gaggaaacca ttgtcattct  7500
gggggtttatg ggaatatttc ttcttggtgc cccttgttcc tcacagaagc ttttttttctg  7560
tgctgtgggc ttgctatcct agctttccaa gctatcctag ttttgcaaat ttctctgatc  7620
aatcacatca ggttcttgga tcatcccaaa attaaagagg tacgttttgc tgcaagagac  7680
aaagacattc acctctcaca cagtttgaat tcctgggtag aaacagattt caatgctggc  7740
cagcctctgt agctcccagt gcccctcaa ttatgactcc cgaggcattg gagcaggatc  7800
ctcaccttgc gcaagataa ttaggtgtgc tgaagaaagc cagacactgc tctttcttag  7860
ctctgcatcc ttaaaaagtt accactactc cttctctttg aatcttttgac ttgtcaatgg  7920
taaagtgcct atgattctta aagggataaa aacgcaacct atataaagca cctggcatag  7980
tgcctggcac aggtgggtgt ttaacaaatg ttaactcctt tctatcccac tgtgggtgtc  8040
catatccctc tgggtaggct gcctctggtt tccattgtgt catcagagcc atactaaatc  8100
gatgtgttgg acatggatcc caagaactaa tttctggagt gagttatgcc taccaacttc  8160
cctgatactt acttctgtct ctccatttat caaatgaaa tgtttgcatt tggcctctgc  8220
cagttggagt aaccaaaagg cttagaggtt ttggagaggt cctacactgc catctgtttg  8280
accacatact gcctttcacg tgtaataagc attgttcttt acatttgtct aggaattagc  8340
agttcacaaa gcacattcgc atataagggc ttgtttttga ttgatcttgg cagcaattct  8400
atgagacaag taaaaggtag gtcaagcatt ataatcctca ttttaaatct ggggaaaactg  8460
aatctcaaaa aggttgaaag acttgtctag gggacagtgt gtgggtaaat gagaagttaa  8520
gatttgctga actggcattt cctgactaca tatctagtgt ttatttatgg agaaggcact  8580
acggtggcca agtggctcag agtcacacag ctctgtgcct cagtttattt gtctgtaaaa  8640
tgaagataat aatatattct gaatactgtt gtgggaattc attgagatag ttcacataat  8700
ggcatggata ctgtagtaca ccgcctagat tcaaccccc acgactatcc atgagaatgt  8760
cccatagctc aagaggtcac attctttccc caggtgaagc ccgcatccaa tgactgctca  8820
gtgtgggtat ataaaggcct ggctcccttg ccagtgccac cctacctcct ggcgaatgga  8880
ctgaggcttg cattatgact gcattgcagc tcaactgctc tttccattca gtctttcctt  8940
tacactccaca caggtgagga cccagccatt aaatgcctca catgatgacc tctattgcat  9000
gctaggcttc gtgtgcacac acaaaaacca tcctctatca gtcaggcccc ttacttgcag  9060
aggcaaagag gccagtctgg gttagatgtg caccctgttt ttacaacaga acgagacaaa  9120
caggtcctcc ttaggtgtaa gttcatggcc ttggccccac cctgaaaact cagccatctg  9180
agacagtttt aggactgagg caaccccaga cttttgggttg ttgtttgctg ggcacagcct  9240
cctttttgcca atgttgcaat ccttttgtaag agaccacagg ttgatcaccc gttcctgtta  9300
ctgagcacag agaggtttgt aggccagtct ctccaggaat tctgacgcac tgcaaaatcc  9360
catggtctga atgcttctac cttccctgtg aaagcccctg gcctcagaaa aggaagctgg  9420
tttaagtgac caacatttgg ggtggagctt ccgggcccc agccaccgtg ttacatgcaa  9480
caatcaacag agatattctt tggctagagt tgtttttctg ggtataggac cctataatta  9540
aaatcagctc tccaacttcc cttcctccaa aaagtataca atgtaaggag gaaatgcaa  9600
```

```
attgaaaagt tgctagccct tcccgccaga atgccacccc aagcctcccc tgcaggaagt   9660
tctggagtcc ccaactctgc cccaagcctg aggcccttga taaggtaaag ggatgtgagt   9720
gtggaggccg gagccccct cgccctgtag gctgctcccc ttgctttcc ctttgaatgt    9780
tacagtttag ttctgtgact tacttataat tgcctgaatt ccccgccac gctttctctt   9840
actttggggc ttctcaccgt tcctcttcct ccatcttcct cctctgaccc cactcccaag  9900
cctgaatggg gtgttcctct tccgtgctcc cacaaaaccc tgtgcctctt tcatcgttgc  9960
atatattatg ctgtaatgta gttttctgga ggtgtgaaga ctatgaatcc tatgaagaca 10020
aatacacacc taccttgctg accgttgtat cctcagaatc taatactgca cttggcacac 10080
agtggttggg agtaaatatt catgaggcaa acacacagga aggactcttt tgttatggtt 10140
gtttgttgtt gttgcaagta acataacccc accttgtgct agctgactga cggctctacc 10200
accttgtctt ttgcagcaca agaggaatag gaactgcacc tcttccttca gtttcagctt 10260
gaataatatc aggaagattc gtatcggtct gagttgggtc acgtacccga cgtgctatag 10320
ctgaggatgg ggtaagctga ttggagtttg caacactgtt cacatagcca agatatggaa 10380
agaacctaaa tgtcaactgg tggatgaatg gataaagaaa ttgtggtata tacatacact 10440
ggaatattat tcaaccttaa aaagaaggaa atcctaacat ttgtgacaac atggatggac 10500
ctggagggaa ttatgctgag tgaaataaga cagacacaaa aagacatttc ttgcaggagc 10560
tcacttatat gtggaatcta aatagtcaa gcttaaagaa gagagtagac tactggttgt 10620
caggagcagg agaaaagtgg aaatgaagag gtgatagtta aagggtacaa agtttcagtt 10680
atacaagata aataagttct ggaggtttac tattaatata tcacatagta cctataagta 10740
acaatactgt attgtatact taaaattgct aagagggtat atcttatatg ttcttaccaa 10800
taataataat aatggtaata attaaggggc aggaggacac ttcaaaaggt gatggatatg 10860
tttatggcct tgatggtggt gatggtttca tgagagtata cttatcccca aactaattga 10920
gatgtaaata ttaaatatgt acagcttttt gtatgtcaat cgtacctcag taaagtagtt 10980
taaaaatggt tggactgaga aaaggaggag ctgctcagca acatgaggct gggtgctggg 11040
cagacaaaac ctcacacatg cattactgaa cccacggact catgtctgtg agctttgtgg 11100
ctgtggatgc accatgccaa tgtagtcaag gattcttcaa tgtgtacctt actgattag  11160
ttccctctgt ttatttgtat tgactcctca gttcccttat gggttgcttg ttggctcttg 11220
tggaattatt taagtaaggc tttggttgca ggagtcagac atgcttaagc tggtttttggc 11280
tgtaatgggg aatttgtgag atgtgacaca gtgacaggaa gtgcagccag acgttgtgag 11340
aggcagtaac tgggaatagg aaagttatga gaagttaaga cagtagtaat tgtttctcta 11400
tcgaaggcca taatgttatc attcctgcct ctatctgttt gcttgttctt ctctctcagc 11460
agaatggtct tctctgcttc tctgtgcacc tgcagaaggt gaccacccta aggcttatgg 11520
attcaggagt cctcagtttg agagcagtta ccaaatgcct cgccctgtg aactctagtc 11580
ccagttttctt attcctggta ctggcttagt ttgaggcagc tgccacgt aagtccagtg 11640
agccatggcc tggggacaag gtcaggtaca tgtgtaatca gctgggtcta tgagttgtgg 11700
tggtggcgat ggaggtagct cccagaaaaa tggattacag gttaagaaga gtctatatat 11760
cttgaccaca tttgatgtga cttggaagtt tcaatgtgtg accacttaca aagttatgat 11820
caggtgtctc atttatttat ggtgatgtat gagtccgtgt gtgagtgtgt gtgtgtctgt 11880
gtttgtgt gtgtgtgaga gagagagaga gaatgagaat atgagtggtg gtttcccatt 11940
tattttctta tgggccaaat cctgggctat gagctggaga tataagagta aacaaaatag 12000
acacggtgct tgctgtgacc tgccctggga gacagatatt cacgaggaa tcacataaat 12060
gcagagtctg agctgaggtc ttaagggtga ggataagtaa ctagtcagtg gagcagggga 12120
gggaagggtg ttccatgcct gtgtcaaggt cctgaggtga gagaaagagg tgaatttgag 12180
gaaccaaaag gagttcaggg aacaagaggg gctgtttcac aagctgagtc tggaagctga 12240
gcaggctgag cagattctta ggaactctgc aaaaacttaa gggcttgtct atgaccgtaa 12300
acaactacgg tcgtagataa acaagttggc aaacaactca aggatttaca gtcatcagaa 12360
ttgtaaaact gatcccatgt attttcaaac ctcaaatcct ttgctctgac cttgtgtgtc 12420
taagctagaa ggaagcagga tgcacctctc ccctggctgg aatgaaggga ttcacccaag 12480
ctctcagtct tctcacggca tccagggccc cctgcttgt gtgtggtcta gatttccatt 12540
cccatagtag gaattccttt gggagccttg gggtctctcc tgctagaggg cttcacctgt 12600
gactgtctca attcaaggga ggggttctaa taacattaaa cctcaatatc ttgctctcca 12660
attcctgatg cctcccttc cttctaccct tcccctacct ccttctttcc tatgccacag 12720
gctgcaggt tagtgccaga gcaagtggcc agtcaccatc attgggggttg tggatcctca 12780
gggttcttca gaagcccctt caccatgatc aagagtctcc agtcactcag aattccacgg 12840
ttcccaaatg ccagctctcc cactactccc agcgttctcc atctctggga tgttgggctc 12900
caggcttctc agatgcactg agtaccctag gctaagccac tgatccatca gaacttcata 12960
gcctgagagg agagggagac aggcttgcaa aggagagttc tgactagaca ctgggggtgct 13020
acagatgccc gtaagttgtc cctttacccct cgatgtcccc agtgttggga ccacctggga 13080
atgccagcc ttgtgtgctg attgacttgt agtccctgg ccctgactgg aagcctagtt  13140
ttctctctca tgaccagcta ggccccctagc tccccaggga agaaatccaa tctatttcct 13200
ctgatagtaa tggctaatac ttaaataatg ccaaccacat gccaagcact ttacagttgt 13260
tagcccagtc ttcacaagca ccttgtgagg tgggcaagag tcttatctta ctctcatttt 13320
atagatgtgg cccaggatcc cacagctata gttcatggtc ctgggatttg aacctctggc 13380
caccagacc caccttgtca tgtcctcctc ctgttgtcat aacagaaaag tacaaccaca 13440
tgatgacaca tcaggctatc ctggcaggtt cccaggctgc cccaatgccc aactttctag 13500
gtttacaaag ttgacattta cgaagtttcc aggtttacaa atctagtttc tgattcttta 13560
gtcagcagga atttctctac aaaagctgct tcgaaaattt ccagccaaac cttacacacc 13620
ttggcattac atcttggtga gccaaggcgg aagagaacga gaagtgaagg ccccatggga 13680
agtccctgcg gtcgggagca ccaggccggg gcgggggggg gggggctttc ctgtggccgg 13740
ctccctgccc ctcccacccc cattcaggcc ctgtgagttg aatgaagaga ccctgggaat 13800
gagtccaggt ctgcagggtt agaggaaatt gaaggccctt accagatccc tgttgagaag 13860
tttatgaatt atgagcccct ctgcaaatga gagggttctt ccctgtcagg agggacagat 13920
tgtaggtggc aagattggtg gcagccagta ggctggtctg ctccttcctc tctatttcat 13980
atgtgatga aggcattacc tgcagcaagg gcctgtgtaa atgcatgtga tttacagagc 14040
attttatgta ctgcgtgtca ttcatgcttc cggtgagccc taagtctaag ataggcagaa 14100
tagcatcagg tccatttgc agctgtcaaa atgaggtctg aagggcagaa gtggtgtgcc 14160
cacacacaca caactggttg gctgcagacc tggggactag acccgggact tcgtcctgcc 14220
cagggggtctc ttgccactgc tccccatcaa cttggatggc tttaagcatt tgtgagttgt 14280
ctgctcccctg atggcagaat gcagagacat gaagctacaa gcaggttcgc tcccaacggc 14340
```

```
aaaaaggagg aggggtgttc agaacatcag gtgcttctag agaaagcagg gagagagtat   14400
ctggccttgt ggacaatgtc acggcagagg ccaggtatag ggcatggggg taactggaag   14460
cgggatggac cctgttattc cctaagacat ggcttccacg tagtgctcaa acaaggcctt   14520
tgcccttgct gttccctcca cctggaatat tcttcccctt ccttgacatt gctcaggtct   14580
ccactcttat ctcaccctct cagagagggc ttccctggca actttcccta aaatagccac   14640
ccactcctag gtccctcaaa agcatatcct gctttggatt ttccctatag caatatgccc   14700
tatgaagtta ttttatttgc taacttgttt cttgtctgtt ttcctttgtt agagcgttgg   14760
ggaccttgtc tggcttgttc ccaatgcctg gaagagtgcc tggcacacag gattaagcca   14820
acacatatgt tttgaatgaa tgtgtgcaca catgcatgag ctggcggcag tcggggttgg   14880
ggtaagcacg aaggcccagc tcagttctct gcatgtgacc tcccatccta cgcagataag   14940
aaccagtttg gtttctgcta gcctgagtca ccctcctgga aactgggcct gcttggcatc   15000
aagtcagcca tcagccggcc catctcctca tgctggccaa ccctctgtga gtgtgtggga   15060
ggggaggctg ggctcctcct tgtactctct gaggtgctct ggaaggaggg gcagctccac   15120
cctgggaggg actgtggccc aggtactgcc cgggtgctac tttatgggca gcagctcagt   15180
tgagttagag tctggaagac ctcagaagac ctcctgtcct atgaggccct ccccatggct   15240
ttaggtaagc tccttccact ctcattttt cacctgagaa atgagagagg aaaatgtcta   15300
caattggtgt ttatcaaatg cttttcaggct ctggtgagca agcgtccagg aaaatgtcaa   15360
gcgcatggag ctccaggcct gtctggggga tctgggcacg ggggagccatc catgggagac   15420
catgcaggca ctctgaggca ggggctgcaa gcctagtgcc tgctgggggca gcaggtgaac   15480
agagaggtgt aactgctgtg acagaagtca tggagtcctt ggagtgtgag ggtcattttc   15540
cactgttgat agaatagga aattggtgaa atagccctgt taaatgagag aaagaacagt   15600
gtgagctcaa tgagaaatac taatagaatg tggcactgag ccacaaggtc tgaggcttga   15660
ttgataagga agggtgggga ctgtggagaa ttaagggctt ggcacaggtc agttccacca   15720
gttgtcacaa gagaatgcag gctcaggtgg ccagaacttc tcgcttttcc agaagagtcc   15780
gatattctga tttcattata tatagtattc tgattaaacc agacaataaa gcaagcagat   15840
aaaatattta aagctataagc tgccagtttg caacctccgg ttaggatttg tgtggggcaa   15900
agaaaaaaac tctcaggatc attggtatgt agactctaat tttaagtttc taatttaaaa   15960
ttggcccctg aggctgggcg tggtggctca cacctgtaat cccagcattt gggaggcca   16020
aggtgggtgg atctcttgag gtcaagagtt caaggcctgc ctggccaaca tggtgaaacc   16080
ctgtctctat taaaaataca aaaattagct gggcatgtg gtgcatgtct gcaatcttag   16140
ctacttgggt agctaaggca ggagaattgc tggaacccgg gaggtagagg ttgcagtgaa   16200
tggagatcac accactgcac tccagtctgg gcaatagaga gagacgctct ctctaaaaaa   16260
aaatatgtaa agataaataa aatgaaataa aataggcctc taatgagcag gccattctcc   16320
tttctgggtc ttactttcct tgcactcctt tctgggtgtt aagaggaggt ctagaggaag   16380
ctggacaact cttagcttgt agtaagcaca gtggaagtat cagctcttaa tgggtcatgg   16440
acacgttaca agctaggcgc cgtgctgagc actttacatg gtttatccca ctgaaccctc   16500
tcaataaccc tatgaggaag ggctattatt gctcacattt tcagaagagg aaatggatat   16560
agagagatta gataatttgc ccatggccag acagctagta taagaggagg aggtggattg   16620
actgcagaca ttctgtcttc aaaccactac actatgctat ggaggcacag agacttaatg   16680
aaatcatgga gaggggaatt gctttgtcaa ccacaagcag ttattccggg ggcagcagat   16740
cctcccctgt cccccagtgg gtacaatggt ccctggtggg ttgtgctaca atgttagccc   16800
atggtcttat gtgttttcca aatgtgtaaa gtaggatgct ggaaccactc ttagaaccag   16860
ataccaatac atttgtgaaga aataaatctc tgtgcttaaa actggttcat cccaaaatat   16920
tttgaactga cacacaatag gtgctaaata aatgtgtgtt aacttgaatt ggattgaatt   16980
cgggaaaaaa gtgcaataag cttagtgaag acaccatgtt ccctgggtag aggaaccaca   17040
ttctccatct aaggccagga gtatgggagg tatcaatgtt tgcccagcac agaacagggt   17100
gccaagaaga gaaagttga cggggtgcat actctgactg gaaactggaa gggtgagaac   17160
agagggtaaa ggatagagat ggaaccatgt gcatacactt tgtgttacct tggacaagtc   17220
attcattct ctggacctct gctttctctc tacacaatgg ggtccacca cttcccttac   17280
agctgacttg tatgaagaag gaggtggagg aggaggagaa ggtgaagaca atgctgactc   17340
aaagggtaaa ttattttag gatccaagtt tgaaaacaat tttaggctac tagatatgaa   17400
caacatcttg attatgtagt tgaaggaaat taaagatgaa tggtttaatt aaaaattaat   17460
cagaatgaaa acgattgatt actaatatat ctgcaatggt ttatttttcct gagtggcaga   17520
ctcactaagg tttttgaata ctcctgtgtg attgctctat gtatgtatgt atgtatgtat   17580
gtatgcatgt atctatctat ctgttgtcta ataaaatgga tcacatctct gctaataaaa   17640
acactacact ggcagggtac aattataatc attaactgtg cctggaattt gcagcagcag   17700
ccaccagagg taccagtgcc ctttaagggt tcataattta gaataatcca attatctgag   17760
tttttcaggg actgaggggt ttggcaaggt gtagaacttt cagtaataaa gtcaagaaag   17820
tcctggacaa accaaggtag ttggtcactc tagtccataa ccaggtaaag agctttccct   17880
gtaacctgtg taaggtttta gaatcatttc tttccttatt accaaaaatc ctccccaaat   17940
tttcaagaaa ttatgaacta aatagttact ctatgagata ggagttcagc ccaaaagaaa   18000
caccataaga acaaatataa ttcttgctta tgttaaccat gcaatgaagc agagagaaaa   18060
agtcagtggc ctctttagga ggactgtagt gtgggaagaa ataactaaac tgggtttcaa   18120
tcctgggctg gccaggatct ggagcaagtg agttaatctt tctaagcctt gagtagttc   18180
ttcttcttct tcttcttctt cctcccctt ctcctcttct tcttcctcct ccttctcctc   18240
ttcttcttct tcttcttctt cctcttcttc ttcttcctcc tcctcctcct cctcttcttc   18300
ttcttcctct tcctcttcct cttcctcttc ttcctcttcc tcttattctt cttcgtcgtc   18360
ttcgtcttct ttttattttc aaagtgaaag caagtttatt aagaaagtaa aggaataaaa   18420
gaatggccac tccatagaca gagtagcctg aaccttgagt tcttctataa agtcactatg   18480
aatttatact cattttgaaa gtgggtgtca atatgtctgt ccactttgca cagctgttat   18540
gtggacaaaa ggagatctgt gtgaaagtgt aacacagagc ctaaactata acaggtaagc   18600
aacacagttg tcccccttccc catggtgtct gttcttctcc atttcctcct gtctgcaggg   18660
ggattataaa actaatcatc aaagccaaga aggcaagagc aagcatgtac cgctgaaaac   18720
acaagtaac tgcataagta atgactttca gtgcagattc atagctaacc cataaactgc   18780
tgggcaaaaa atcatcttgg aaggctctga acctcagaaa ggattcacag taagttaacc   18840
atgtagatct gagaggagag tagcttcttg tagataacag ttggattata taccatgtcc   18900
tgatcccctt catcatccag gagagcagag gtggtcaccc tgatagcagc aagcctgggg   18960
gctgcagctt ggtgggtaga ggtactcagg ggtacagatg tctccaaacc tgtcctgctg   19020
ccttagggag cttctaataa gttgatggat ttggttaaaa ttaacttggc tacttggcag   19080
```

```
gactgggtca gtgaggacca acaaaaagaa gacatcagat tatacctgg ggtttgtat    19140
ttcttgtgtt tctttctctt ctttgtacta aaatatttac ccatgactgg gaaagagcaa   19200
ctggagtctt tgtagcatta tcttagcaaa aatttacaaa gtttggaaaa caatattgcc   19260
catattgtgt ggtgtgtcct gtgacactca ggattcaagt gttggccgaa gccactaaat   19320
gtgagatgaa gccattacaa ggcagtgtgc acatctgtcc acccaagctg gatgccaaca   19380
tttcacaaat agtgcttgcg tgacacaaat gcagttccag gaggcccaaa tgaaaatgtt   19440
tgtactgaaa tttgttaaag cttcccgaca aactagattt atcagtaagg attgttttct   19500
gcaagggga tgaaacttgt ggggtgagcc atttgggctg aggaggaggg aggttggagc   19560
tgagaaatgt ggagacaatt tccctttaga aggactgaat ctccctgcct ctctggggtg   19620
cggcagccag caggatccaa tggtgtatat gtctccccag ctcccccattc agtgatatca   19680
tgtcagtagc ttgaaattat ccgtggtggg agtattatgt catgccaaatt ggcaaatgga   19740
aactttatt ggagattcaa ttgttaaact tttaccagca caacactgcc ctgccttcag   19800
agtcaatgac cctatccaag tttaatccat ctgtccactg tctccaacac gatctttata   19860
aaacacacct gacaacatta cccttttatt cagtttttta aaagataagt ttccagctca   19920
tcggggtggc tttaaaggcc atttctcctc tggacctcac ccaactttc aaatcacttt    19980
tcctacccct acctctaaat gctactaaaa ctccagccat cctgaataat aagacttttg   20040
aaaagtagat tatgggctgg gcacagtggc tcacacctgt aatcccagca ctttgggagg   20100
ccaagatggg tggatcacct gaggtcggga gttcgagacc agcctgacta acatagtgaa   20160
accctgtctc tactaaaaat acaaaattag ttggggtgg tggcacaagc ctgtaatccc    20220
agctactcag gaggttgagg caggggaatt gcttgaacct gggaggcgga ggttgcggtg   20280
agcctagatt gctccactgc actccagcct gggcaacaag agcgaaactc catctcaaaa   20340
aaataaataa ataaaataaa tagattacat cagataccct tggcctaggt tgtttatgac   20400
caactctcct gctgagaata actagaaaag ctagacaaaa catatttcca aaagatctct   20460
ttggaggcat cagagaatgg ccaaggctgt aaggaactgc ctgagcccag agaggtggag   20520
cccagcactg gtgcccttta ctcctgggga catgtgctgg tttcaaaaac ttcagctgag   20580
cttttgagca ttcatggaac ttggtggggg agatgaaatt tgtaccttaa atcctgccta   20640
cagggagggt ccctgataat ccccacccaa tttggaaatc tgggtcagcc ttcacaggta   20700
ctgaagccct cctctgaatg atctcaagtc ctgctagggt agaggttacc tgcttttgaa    20760
aggctcctgg cctacctgtg cagcaggagc aaaagtgaac catctcaggg tacagataac   20820
aatcatccag agccttgaat gacctctact gtgcttaata tatagtattc agcagtcagt   20880
aaaaaggatt taggcacatg caagatgacc tgtgtatcag ggagaaatag gcaataaatt   20940
gagatccagc agggatttga atcatggatt tgaatcaggg gcagccttcg aaagaactat   21000
ggagaatata ctcagattta aaacataaga ttggaatttt tggcagagaa ctaacaactg   21060
tacaaaaaag gaaccaaatg gaaatcctag aactgaaaga tgcaattaac cgatcgttgag   21120
aaatagccaa catcattga acacttccca tgtgacagc tgtgctaaac actttcagg    21180
catcaacata agatgtgtcc ccttacagca gtgcagtgtc cctcctaaga catggacagc   21240
ctggtttccc tatctctctg cttcatcaaa acccctttac gtgggcctta gacactcctg   21300
ttgtctctag tgtctagtag cacagggctc agcacatgga agccactaga tacaatttga   21360
tgaccaggac ctccgatgaa agccatgggt gctgattggg aaggcattgt cttttatgtg   21420
ctatggtctt aaagcttcat ccaggaagca gaactcgggg ggtgctgagg acccagaacc   21480
gagaataaga ttagtcagag atttcctgtg ggcagaaatc ataaggacgc caactgtttg   21540
ggtgagataa gacgaaacca agagtggact tgtggccaga agcgtgagga agaggagag   21600
agcttccctt gtccccttc ttcctctccc taagccacag tgattgacag ccccccccct    21660
ttggagtcag agcaggcttg agactggact gggaaaggag ggtgggtcag gatacagagc   21720
aggaaggctg ggagtgcagg gcaggagcaa ggggctgggg cattcattgt gcctgatctc   21780
tcccactttta cctgggggtaa agaagcatat gcaaagcca cggtgtgagt atttcccaag    21840
tgccaggtca agggcatgat tcatcacgtg cagcatttca ttcaatcctt atagtaaccg   21900
atgatgtggc ttctattatt agctctatca gataatgaaa ctgagaccaa gacaggctct   21960
gcacattgtg tggggtaatg acacagggg attcagacct agactccata actcctgccc    22020
cagggaccac ccccacccctc accctgtgca tgtcgacaaa ggacagactg ggccacttct   22080
caggacacag cggggaaatg acacagaca gggaggttcc aggagcccg agcgtcttt     22140
ctccaggaga atactctctg aattcagact ggggtcagag aaacatttac ccaggagccg   22200
cagtgtgggt gggctttt acttgaaacg ctgtctgaag gcagtggcca ggatggaact    22260
ctccacccta ccttggcaag ccacttctct tctgcaatct gtaaggacat tgttgagaga   22320
attatggtct ttccaattcg gagggttgaa gaaagacaaa taggagagaa cctatcatag   22380
tcaggtgcta gctgccttct ctttcagaga gtgtgaaat aaagtgatac acttgattat    22440
tagcaaatac tttggaaatt ttaaacgcta atattcaaca cactctggaa gaggcaaata   22500
agtagacagg ttcatataca tcatctcctt cagctagtcc tcacaaaaac aaacaaatga   22560
ataaacaaaa ttcttcttttg gccctcatag gaagacactg ttctttgaac gtgtttcaaa   22620
aaggatgggt gactcactca aggtcacact gtttatgagg acagtacagg aatacagaca   22680
tgccatttg cctgaaaaaa tccatcaccc agggaggtga cacaattttg cagaaatgtt    22740
ctatttcctc tgaaggatac attctttaaa cctttgggaa attcattcat agtcttcctc   22800
ctttgaagga ttaactctct ggacacaaag tgtttgattc tgatttgttg gttggaagat   22860
gtgttggttg agagaaagat tctgatttgt tggttgaaaa tagactcatc aagatcaact   22920
gctgtagtag taaatatttt gacattttgt ctgtattcct gtgctgccct cacaagctgc   22980
atcaccttga gtgagtcatt catacttttt tgtttgtttt tgtttggag atggagtctt   23040
actctgttgc ctaggctgga gtgcggtggc gtgatcttgg ctcactgcga cctccatctc   23100
ctgggttcaa gtgatcctcc tgcctcagcc tcccgagtg ctggattac aggcacatgc     23160
caccatccct gctaattttt gcattttcag tagagacgga gtttcaccat gttggtcagg   23220
ttggtcttga actcctgacc tcaggtgatc cgcccacctc agcctccca agtgctggga   23280
ttacaggtgt gagccaccgt gcccagccca gccatcattt ttgaaacacg tttgagaaac   23340
agtgtcttcc tttgagggcc aaggagacat ttttttttgtt tatttgtttg ttttttgtgag   23400
gactagctga aggggtgat gtatattaac ctgcctactt atttgcctct tcccagagtg     23460
tgataatat taggggttaa agtttctgaa gcatttgtta ataaagcccg gggctggagg   23520
tcagaagacc tggatttctc tgcatacttt tgccatcagc aagctgtgtg accttggaca   23580
gatcccttt ttgtctaaat cttttctgagt cttcttgaaa acaatgccag gttgggacag    23640
gatgattgcc aagctcccgt ccagctctaa aacactgcaa cgtatgcttc tgcaccagca   23700
ctgtccatcc tgtagatcat gcagaaattc tcttcaactt tttcctaccc ataaaatagg   23760
agcatgctta cctttttcct aatgttccag gccccggtc tagaatattg taagtaagga   23820
```

```
agttaatgtg tatcagagcc cattatgggc cagaagttct cctcttcctt cctacacctg  23880
cttcctccct ccctccctcc ctctttccct tccttccttc catccatttg tgaagaagac  23940
atgatcaccc tcattctgag agtgaagaga cagaggctca actaatgaaa tgatttgttc  24000
aaggtcacac gggtggcaca aggcaagtgg cagaggttga atttagaccc attcctgtcc  24060
aaatgctgag tttatgtcat cgtcccgaga ccataacttc aaagatgtaa gatagtggga  24120
aaagagttga tttcaaagca cctctcagaa ggactcactt tacatcaggg gtcagcagac  24180
tcaggccaaa tccggtccat tccccgcttt tgcaaagaaa gttgtagtgg aacacagcta  24240
ggcttattga tttatggatt gccaacgtcc ttttgtgaaa cagacagctg agctgagtaa  24300
tcgtggcgca caaaacctaa aatatttact atctcgtcct ttacagaatg tttgccaatc  24360
tatggtccgg agtccaaggc tgtccatttt tcaaagaaca caaagtgaca tgagactgtc  24420
ccatgtgcag ggagccctat catttttatta tgaaaaaacg gcctttctgc tcaaatctgt  24480
tttttaaaaa gtcaacaaac agactctggg tacctgtcag gaacagtagg gagtttggtt  24540
tccattgtgc tcttcttccc aggaactcaa tgaaggggaa atagaaatct taattttggg  24600
gaaattgcac aggggaaaaa ggggagggaa tcagttacaa cactccattg cgacacttag  24660
tggggttgaa agtgacaaca gcaagggttt ctcttttttgg aaatgcgagg agggtatttc  24720
cgcttctcgc agtggggcag ggtggcagac gcctagcttg ggtgagtgac tatttctttta  24780
taaaccacaa ctctgggccc gcaatggcag tccactgcct tgctgcagtc acagaatgga  24840
aatctgcaga ggcctccgca gtcacctaat cactctcctc ctcttcctgt tccattcaga  24900
gacgatctgc cgaccctctg ggagaaaatc agcaagatg caagccttca ggtaaggcta  24960
ccccaaggag gagaaggtga gggtggatca gctggagact ggaaacatat cacagctgcc  25020
agggggctgcc aggccccaga gggcctgaga actgggtttg gctggagag gatgtccatt  25080
attcaagaaa gaggctgtta catgcatggg cttcaggact tgtgtttcaa aatatcccag  25140
atgtggatag tgcgaccgga gggctgtctt actttcccag agactcagga acccagtgag  25200
taatagatgc atgccaagga gtgggactgc gattcaggcc tagttgaatg tgctgacaga  25260
gaagcagaga ggggcaccag gggcacagcc cgaaggccca gactgatatg ggcaaggcct  25320
gtctgtgctg acatgtcgga gggtcccact ctccagggac cttggtttcc ccgtctgtga  25380
catctgtgac atgagagtca cgataactcc ttgtgtgcct tacaggggttg ttgtgaaaat  25440
taaatgcaca gataatagcg taacagtatt ccgtgcattg taaagagcct gaaaccatt  25500
atgatttgaa aatggaatcg gctttgtgag accatcacta ttgtaaagat gtgatgctga  25560
tagaaatgac aggactgctt gtgcatgccc tctgcagtgt cagattccag cagtgaaatc  25620
atgttgggt gacttctccc ccactctgac ctttatgttt gtctgggccg aggctgcaag  25680
tcgggctctg tgggtgtatg agtgacaagt ctctcccttc cagatatggg gactgtctgc  25740
ttccctaggt tgcctctccc tgctctgatc agctagaagc tccaggagat cctcctggag  25800
gccccagcag gtgatgttta tccctccaga ctgaggctaa atctagaaac taggataatc  25860
acaaacaggc caatgctgcc atatgcaaag cactttggtt tgcctggcca ccctcgtcg  25920
agcatgtggg ctcttcagag ccacctgatg aggtgggtac agttagccac acttcacagg  25980
tgaagaggtg aggcacaggt cccaggtcag gctggccgga gctctgttta ttacgtctca  26040
cagctttgag tcctgctctc aaccagagag gcccttacc aagaagaaag gattgggacc  26100
cagaatcagg tcactggctg aggtagagag gaagccgggt tgttcccaag ggtagctgct  26160
cctgcaggac tctgagcagg tcaccagcta atggaggaaa ggctctaggg aaagaccctt  26220
ctggtctcag actcagagcg agttagctgc aaggtgttcc gtctcttgaa acttctacct  26280
aggtgctatg gtagccacta gtctcaggtg gctatttaaa tttatactta aatgaatgaa  26340
aatagaagaa aatttaaaat ccagaccctt ggtcacacta tccacattta aagaggtcaa  26400
tagccacatg tggttagtgg ccaccctatt gggcagtgca gctacagaac attttttgcat  26460
cccagaaagt tcttttggat gttgctgctc tacagcatgc tttgctgaaa cagaagtgcc  26520
ttccctggga atctcagatg ggaagcaagt aaggagggga gtcaaatgtg ggctcactgc  26580
tcaccagctg tgaggggttgg gcctgcctct taaccattgt caggcctcagt cttctcatcc  26640
atgcatgccg tgggtatact aaaatactat ccccctggaa gagctggatg caaatttgac  26700
aagttctggg ggacacagga aggtgccaag cacaaggctg ggcacatggt ggctgtgcac  26760
tacagctgag tccttttcct tttcagaatc tgggatgtta acc                     26803

SEQ ID NO: 21        moltype = AA   length = 177
FEATURE              Location/Qualifiers
source               1..177
                     mol_type = protein
                     organism = Homo sapiens
SEQUENCE: 21
MEICRGLRSH LITLLLFLFH SETICRPSGR KSSKMQAFRI WDVNQKTFYL RNNQLVAGYL   60
QGPNVNLEEK IDVVPIEPHA LFLGIHGGKM CLSCVKSGDE TRLQLEAVNI TDLSENRKQD  120
KRFAFIRSDS GPTTSFESAA CPGWFLCTAM EADQPVSLTN MPDEGVMVTK FYFQEDE     177

SEQ ID NO: 22        moltype = AA   length = 159
FEATURE              Location/Qualifiers
source               1..159
                     mol_type = protein
                     organism = Homo sapiens
SEQUENCE: 22
MALETICRPS GRKSSKMQAF RIWDVNQKTF YLRNNQLVAG YLQGPNVNLE EKIDVVPIEP   60
HALFLGIHGG KMCLSCVKSG DETRLQLEAV NITDLSENRK QDKRFAFIRS DSGPTTSFES  120
AACPGWFLCT AMEADQPVSL TNMPDEGVMV TKFYFQEDE                         159

SEQ ID NO: 23        moltype = AA   length = 180
FEATURE              Location/Qualifiers
source               1..180
                     mol_type = protein
                     organism = Homo sapiens
SEQUENCE: 23
MALADLYEEG GGGGEGEDN ADSKETICRP SGRKSSKMQA FRIWDVNQKT FYLRNNQLVA    60
GYLQGPNVNL EEKIDVVPIE PHALFLGIHG GKMCLSCVKS GDETRLQLEA VNITDLSENR  120
```

```
KQDKRFAFIR SDSGPTTSFE SAACPGWFLC TAMEADQPVS LTNMPDEGVM VTKFYFQEDE    180

SEQ ID NO: 24            moltype = AA  length = 143
FEATURE                  Location/Qualifiers
source                   1..143
                         mol_type = protein
                         organism = Homo sapiens
SEQUENCE: 24
MQAFRIWDVN QKTFYLRNNQ LVAGYLQGPN VNLEEKIDVV PIEPHALFLG IHGGKMCLSC     60
VKSGDETRLQ LEAVNITDLS ENRKQDKRFA FIRSDSGPTT SFESAACPGW FLCTAMEADQ    120
PVSLTNMPDE GVMVTKFYFQ EDE                                            143

SEQ ID NO: 25            moltype = DNA  length = 3804
FEATURE                  Location/Qualifiers
source                   1..3804
                         mol_type = other DNA
                         note = cDNA
                         organism = Homo sapiens
SEQUENCE: 25
taatttcagt gaaattatat aacttggtta catttaggtt acttattaca aatgaaaata     60
aatatactaa cagaagctgc ctcatatgca aatgagtaac atgttagaga ctaaaataca    120
caaaaaaatg catgtgcttt agctcatata aacaatatac aggacaactt accgggtagc    180
ataaacaacc aacaacggac tatcaaaagg aacctcgtca tctagtaact ttaaccttgt    240
tggtagatct cctttttcca tctccatata cacaggattg gaacttgcca tttctgaaat    300
ataaagcata tccttttcca aacttatctc cttaggcgga aatattcaat ttatgaacat    360
gttcattcag caatcattag tcacgtacct actgtgtgga cctattatgt gcaaggccca    420
atattaagca ttacaagaga aacaaataaa agtacaagag atgtaatttc tactttttaag   480
aaccttaaaa tctaattggg aggcaaagca tattaaaagt tttaaataag acgaaggaac    540
atataattaa tacatcagtg actattactc ttaaaataat gagtatctag cctatatat    600
agcaactgtc catataagca cacatcaaaa accaatatac atagctatca tcaatgccaa    660
gttgctcagt tttttctaga actagtattc ctactccatc ttttagaatt aaattcaatg    720
aaattaattt taaatatttt gaccttttt taaagttacc agtatagcaa atactcattc    780
tctgaagaac agaagatttg acttttgga atagccaaaa gtcacttaaa atcaagtctg    840
gtgaaaggag tgatgatcta aaactatttg tggtttaaaa aaaaaaagta tgaatctaaa    900
gtaaagtggg tttttttcca agtagttttc ttttttagtt tttagaaac agggtctcat    960
tctgttgccc aggctggagt gcagtggtga tcactgcaac cttgaactcc tggctgtgtg   1020
tgtgtgtgtg tgtgtgtgca gcgacggggt cttcctacgt tgcctagctg cagtgcctgt   1080
gtgcacacat gcgcacatgc gtgtgtggag agacagggtc ttgctacgtt gcctagctgc   1140
aatacctggt tgtgtgcatg tgtgtgtgtg tagagacaag gtcttgaaac gttgtctagg   1200
ctggcatgtg tgtgtgtgtt tatatgtatg tgtgtgtaga cagggtcttg ctacattgca    1260
taggctggtg tgtgtgtttt tgtgtgtgta gagacgggt cttgctacgt tgcctaagct    1320
gggcaagtat tttcaactg cctctgaaga caaatcccca ataacagttc caaaagctgt    1380
ttcccataat tatcacatca ttagaagggt gaggcctact caccaggttc taagagccaa    1440
cattcatttt ctgatacatg ctttttttaaa aaagtcattt tttcccccagt ctcattgttt    1500
cccatttgac tgtgtcaggc aataagtact ttaaaggaat tcagaggagg aggccattca    1560
gaggtttggg gaagcctgat gactgcgcgg gagctaaacc agacatatcc acctaaattc    1620
aagtaagcag ccatatcact caaattgccc accatgcttc ctctagccag cactggtagt    1680
aacaactatc actctggctg atggagactc ttttctgctc ttctgtgact gggtatgatc    1740
acataataga gacagataca gtaaatttcc aatgagtaat aatgtcacac atttgaactt    1800
acctgaggag aaatagcttg tttcttattt cacacaaaag acaatctacc tcaactcaga    1860
aaaaaaaaaa ttattatgct tttaactgct atatttgaat taaagcagat ctgtaactat    1920
agatccatgt ttctagaaag ctaaaatatc tttaagtaag atgacataaa aatgtatctc    1980
tattcactt  tggtaatgaa tgaaaagttg cttaaagtct aaagtattag aaatatggca    2040
tctgttattc aagtaggatt tggaattaag aaaattcact tcttcaaaaa catgggacta    2100
tggctgcaga aagggcaatg catatagttt ttagggtagg atagctggtt tctattatat    2160
gtcaggatga catatgcgac cttccgccaa ggtagatact gcgggctatg caccaaagtc    2220
tctgaggcag acatgtaagc gagctcttca cctatattca ttctttttcct cctggacagg    2280
ttacatttcc cagtttcctt tgcagttagt tgtggctata tgacagaatt ctcatcaatg    2340
gaaatgtaca cagaagagag gtaagccact accaggccag gcctataaga cagcactttc    2400
tacatgcttt ccccagacat agcaaccaaa acatgaccac atcccttaag ggaagatgga    2460
gctgaaaata atggaaggaa cttggaatgc tagaatgctg aattaccacc tgggagacag    2520
ctacccactg acctggaata cctgtcctgg actgttacat gagcaagaaa tacacttcta    2580
tttatgtatg agttacttca ttatcagata tttattacag cagtttagct acctaagatc    2640
tctctctgcc tcagactgct tatctataaa atggaataac actctact ccaaacatta    2700
ttgtaaggat gaaatgagac aatgctgaaa agtgtttacc ataatatctg ccacacaata    2760
agtaccccat atagtatttc tgtattagta agttacatga gagattttct tcttttaata    2820
catctgcatt tataaacatt ttactttaac ctcaacttcc ccagcactgc tctaccttt    2880
tctgaatgtc attatgagag aaataaaact aattctagg gccaggcatg gtggctcaca    2940
cctataatcc cagcattttg ggaggccaag gtgggaagac tgctttgagg tcaggatttc    3000
aagaccaacc tggcaacac agtaagaccc catctctata aaaaaatgaa gaaatcagag    3060
ggtacagtgg cacatgcctg taatcccacg actcagaaaa ctgaggcagg aggatcgctt    3120
gaacccaagg gatcaaggct acagtgagcc atgatcacac cactgcattc cagcctgggc    3180
acagagtgag accctgtctc taaaaataaa aaatagggcc aggcacagtg gttgatgcct    3240
gtgatcccaa cactttggga ggcaaggca ggtagatcac ttgaggtcag gcgtttgaga    3300
ccagcttggc cgacatggca aaaccctgtc tctactaaaa tacaaaaatt agctgggcgt    3360
ggtggtgcac gcctgcagtc ccagctactt gggaggctga ggcaagacaa tcacttgaac    3420
ccaggaggcg gaggttgcag tgagccaaga tggcgccact gcactcaaac agaatgaaac    3480
tctgtctcaa aaaaataaa ataaataaaa atttaaaaac taatttctta taatccagtt    3540
gtgaatttaa ccaatgtctg aaagaactat taaaagttaa aatgaatgga aaacagaata    3600
```

```
aagggttgac cagaacagat gtgattttct acttaaatct ttttttaaa ccccaaaatt    3660
caaaactgct aatgttttt aatacgaatt tctatctttg ataaggcaat ctgagtatta    3720
cctttcaatc cttcaataaa agtatcccaa acagaagggc tattactgta actaagcttg   3780
atactctcct tcgctctttt caag                                          3804

SEQ ID NO: 26           moltype = DNA  length = 3804
FEATURE                 Location/Qualifiers
misc_feature            2122..2131
                        note = n is a, c, g, or t
source                  1..3804
                        mol_type = other DNA
                        note = cDNA
                        organism = Homo sapiens
SEQUENCE: 26
ggcttctggc tctgagtgag gtcctgctgc aaggtttcct agatgagcca ctgagactct    60
aataagatcc agtggaaata accaggctct cgtcggaata taagtcccaa gggaagctgt    120
gccagtcttg tgggcgactg cctgacttct cctttcattt cagcaccatg aagcttctca    180
cgggcctggt tttctgctcc ttggtcctgg gtgtcagcag ccgaagcttc ttttcgttcc    240
ttggcgaggc ttttgatggt aaggcttcag aaggtttgca ggattctga agagaaacat     300
caccctggac ctgataaaact ggggaaaatg atgctttcgg aaggctgctt ttgaaccaca   360
gagttgctag tgtctgcgtt gctgaggcct gccaggaact agggtttgct gggttgcctg    420
tctcgagtct ttcagagctg ctgggaatat cccctttccc agctagtcag cttctcagga    480
tgtgttaagt ggatggatca catttcagaa gccgctgcaa ggtatatcaa aaacacatct    540
cctgagccgt aagggacggg gcatccagta acaacgcaca cggggtattt ttgggcttcc    600
ttaagatttg agccgctgcc ttaggttgtg ctgcccaatg tgcctgggga gctgctaaac    660
agattagaga gtcgaggatt gttgtcagtt actcagagaa agaacaatca tccttttccag   720
gagcacctga gctgtttgtt ttgcgtagaa gatgcaaaat aaggcctgca atgggtataa    780
aatgtccctc agcataaatc gcataggagt atgactaagg ctgttgactc ttctgtcttc    840
tttctccttc ctccttcgat ttcctagttg gataatgtac agggctcttt agcctcgctc    900
tgtcagggga tccccttcctg gtttgttctg tttccattct tccttctcca gccttctga    960
caagagctgg gaactaacgt gcctcaagcc cccacaagga ccacagcatt ttctcattta    1020
gtttcagaat gactctgtga cgcaatcttc ctctcttgga aggtgagaaa gctgatcttg    1080
gaaggtgaga agctgagac ttagagcagc tgaagccaat gcccagggac ttactgccag     1140
tcagcaggtg gcagggcaga ggtttgagcc ggctgtgct tgaggtcagg gctcttgcca     1200
ggtagacgca tcactgacca cctcctagag gttgatggtt atgaatctca ggcacacctt    1260
ggcatcacct gaaataccca tgccttcaac tccccagcag agtctgcaga aactggcctg    1320
gggtgtggcc tgggcactgg gactttcagt ttctctctgg gtgattagaa agtgcagcca    1380
aggctcacgc ctgtaattcc agcactttgg gaggccaagg tggatgaatc acttgaggtc    1440
atgagttccg gagcagcctg gccaacatgg tgaaacccg tctctactaa aaatactaaa     1500
atgtagccag gcgtggtggc aggcacctgt aatcccagct actcaggagg ctgaagcacg    1560
agaatcactt gaacccgaga agcagaggtt gcagtgacta gagatcgcac cagtgtcctc   1620
caacctgggt gacagagcga gactccatct aaaaaaaatg aaaagaaag tgcagccaag     1680
gcagagcacc actgccctat tgcttcctca agcaaccac agcatcagta cagcctacta    1740
agaaagtatt tagggacttt tatgctccta acagtcactg gaactcacgt cacaatgacg   1800
tgtattccat ttgcaagaat atatacttta ggtcggggtg cggtggctca cgcctgtaat   1860
cccagcactt tgggaggcca aggcagggg atcacgaggt caggagttcg agaccagcct    1920
gaccaacatg gtgaaatccc cgtctctact aaaaaataca aaattagcca ggcgtgatgg    1980
cgcatgcctg taatctcagc tactcaggag gctgaggcag aagaatctct tgaacctggg   2040
aggtggaggt tgcgatgagc tgagatagca ccactgcact ccagcctggg cgacagagca    2100
agactctgtc taaaaaaaaa annnnnnnnn naaaaaaaaa aaaaaaaaaa aaaaaaaaa     2160
aaagaaatata aactttagta gtcagggcag aagtactctg tgtctgccac cttttctcagg  2220
atcagtattc catgtcacta cctcattcat acacactcc ggatcttatc ataggcagct     2280
tcattctata gcagtggctc ttcaccaggg cacttgaaga agccaactag gataaaggaa   2340
tgtgcttctc aacccatggt atccaaggct gctatgatca caggctgaaa gcttgaagtc   2400
agtggaagat ttgtccttcc tcattcccct ctaaggtgtt gttggagtct ttatgttctc    2460
ctgatgtccc ttctgccttt ccttccttt ccaggggctc gggacatgtg gagagcctac     2520
tctgacatga gagaagccaa ttacatcggc tcagacaaat acttccatgc tcggggggaac    2580
tatgatgctg ccaaaagggg aactgggggt gcctgggctg cagaagtgat caggtaactg    2640
gagctcctgg gacgttaggg ctgggtgagc agagcttgcc tgccttggac agtcaggagg   2700
gagacgagct ccttgtggag aagttagagg ctgcggcccc tcctcctctt gccctctctc    2760
tgcctctgtg ctcagtgtga ggtctgagtg gatggtagga gtgagtgatt cctcatcctc    2820
cctctctggg tgctgttcat ccagcctagg ggtgcccagc ctggctgaat ggggtggtgc    2880
ccagtgtttt catccctcct tccttggcct ttctgggctc ctctctgagc cctccttgg     2940
aacagggaga atgggagggt gggctattgc tcactggctc gattattaat ctccttcttg   3000
cctgccttga ttacacggat gccagagaga atatccagag attctttggc catggtgcgg   3060
aggactcgct ggctgatcag gctgccaatg aatggggcag gagttggcaaa gaccccaatc   3120
acttccgacc tgctggcctg cctgagaaat actgagcttc ctcttcactc tgctctcagg   3180
agatctggct gtgaggccct cagggcaggg atacaaagcg gggagagggt acacaatggg    3240
tatctaataa atacttaaga ggtgaatt tggaaactg gggtttatac tttgtggtat        3300
agactgcctg tttagtatga agggggcgatc catgcacatc taagtgaacg tggaggctgg    3360
gtgggtggga gacgactcct gggcacacag ggcatcctgg gcatccctga ggcaaggaca    3420
tgatgagttc agtggccacc cccacaggat cccaggggct tcagcagatc ccacccctta    3480
ccccatgtga gcagctgccc agtgagtctg taggaacccg agccacattc ccagtgagtt    3540
caactgcacc ccggcacgtt ttgctagcac ctcaatggag agctccttgc ttgcagcttt   3600
ggcttgtggc acccagcaaa agcttcctgc cacccagtgg ctacagccac acactctcca   3660
gcaagattta atctcagcct tgtgaggagc ccttccccaa atttattctt ttctgtgttt   3720
tttatccctt agtagctaat ctcatgttag ccattaataa ctctctatgt taaaccctc    3780
cttttgtatc tgcggctaca ttga                                          3804
```

```
SEQ ID NO: 27         moltype = DNA  length = 3804
FEATURE               Location/Qualifiers
source                1..3804
                      mol_type = other DNA
                      note = cDNA
                      organism = Homo sapiens
SEQUENCE: 27
gtataaatgc agaggtgcag taactgggct tttcaggata ccagatgga  gttgtggtgt   60
tgttttgctt gtggtttta  acgttaactt tttttttccc tttatttaa  gagaagcaca  120
aaatgaacaa actagtgagc ccagcaacat ggatggaaat tccggagatg cagactgctt  180
tcagccagca gtcaaaaggg tatgggcaaa aaaatatgaa ccatttgggg ctcaagtttc  240
tccaaatact ttatgtgact gcaagtactg tatacgctta tttcctgtga ctcagttctt  300
ctaactaaga tgttaagcat ttggcttaaa gtgtatagca ttacaaagag tatttcccca  360
gctttggctt gccagccaac tttccattga ctctagcctg ttagccattt ttattgtttt  420
ttgtttgttt gtttgtttgt tttcctcaca tgtacacata catacagatt gttcttatat  480
gtgattttgt tctctgggaa taaaatcttc attcaacaga ggcaatatga cagaaaaacc  540
gaagtttcat gtatatgatt tttcaaagaa agtgaattgg ccctcatgtt aaacctagca  600
tttcagagct gaaagtgtct tctcattaaa tattgaagaa atcatttgag ggtgtggaga  660
aggatggaca gaattagctg cttgtgtatt tattcttctc ctgcaacttt gccacgtctat  720
tttgtacctc ccttcctaat tatgataaag cttctcttaga gagcagtcag gcaatgtgta  780
ttaaatgttt aaagctttac acccttagtt ctacttgtgg acatttattt cttaagaaag  840
atgtatacta agatttagat agaaatattc attacagtat cataataaag acagtagcaa  900
ggattctgtt atctgtgttg cattaataca atagagattg atgcaactgt tcattatttt  960
gaaagcatta atgataatat tgcatcaaag agttcactga acagattgta cagtacagtt 1020
ttacacacaa aaaaatagt  ttgtgagctt taaaaggggcc ttcaaatgaa tatgctaaac 1080
ggttatcttt caataaagag agtatgggta agtcttaatt tctttcattt atttcagtaa 1140
tttaatgttt ttgttgttgt tattgtttgt ttttttgaga cagagtcttg ctctgtcacc 1200
caggctggag tgcagtggtg caatctcagc tcactgcaat ctcggctcac tgcaacgtct 1260
gcctcctgga ttcaagcaat tcttctgcct cagcctccgg agtagctggg attacaggcg 1320
tgcaccacca tacctagcta attttttgtat ttttagtaga dacggagttt tgccatattg 1380
gccaggctgg tgttgaactc ctggcctcat gtgatccgcc catctcagcc tccaaagtg  1440
ctggggttac aggcatgagc cactgtgcca gcctatttca gtaacttaat gttttacag  1500
gcatgtatta cctataaaat taataaagcc agtgaggtat ttcttttttg aactaaagca 1560
aagctaataa taagttatag agaagttaga gaagaaatct attaagtgat actttctttg 1620
tatactgttg ggctgagtac ccttgattct tggtggtgaa caagttatca gaaatttctt 1680
ggccaggagc cgtggctcac acctgtagtc ccagcacttt gggagtccaa ggtgggtgga 1740
tcacttgagg tcagaatttc tagatcagcc tggccagcat ggtgaaaccc tgtctctatt 1800
aaaaatacag aaattagcca ggcatggtga cgtgcgcctg taattccagc tacctgggag 1860
gctgaggcag caaatcact  tgaacctggc aggcggagtt cgcagtggc  tgggatcgcg 1920
tcgctgcact ccagcctgga tgacagagca agactccatc tcaaagaaaa aataaaaaag 1980
aaatttatt  acttgtgtga attttacaa  tacagatgct tctcgactta aatgggggcta 2040
catcccaata aactcataag ttgcaaatac tgtaaatcaa aaatgcattg aatacaccta 2100
atgtatggaa caccatagtt tagcctatcc tactttaaat gtgttccgaa cacttagatt 2160
agcctgtagt tgggcagcat tacctactat aaagtgtatt ttctaataaa atgttgaata 2220
tctcatgtaa ctcattgaat actgaaagtg aaaaacaatg tatgggtact caaaatatgg 2280
tttctctact gaatgtgaat cactttgaca ccatcataaa gttgaaaaat tccaagtcaa 2340
accattgtaa gtcaggggcc atcagttattc agtggtaaat gctggctcta actattcttc 2400
caagtcagtg gttgactgct gtttattcta taaagggtta caattatag  attctctcac 2460
ttgtagaatg agagattcag aattaatagc agacagagtc cctaccttga tggagctttc 2520
atttaagtgt gaaagtcagg tgacctaaca aggccttggc ataagtttag gatttggatt 2580
gttatgggag cttgggtagg gacatgtcat aggtaaggca acagcagggg tagagataag 2640
cttgacatat gtcaaaaatc atgaagacat cagtaatcct tgaagttggc tgaaaggtat 2700
agagttgaga aagtagttaa aaaaaaaaaa gtcaggctga gtctaggtaa ggatgtgttt 2760
ctctgaggtc agatttgttc ctgtaccata aagggactat ttagaatctt aaagctggag 2820
caatttaaaa cgttaagttt tcagattgag gtcagatttg tgacttcatg tgaggtcaga 2880
tttgttcctg taccataaag ggactattta gaatcttaaa gctggagcaa tttaaaacgt 2940
taagttttca gattgacgtt ttttgaggta tagttaataa cctgaatgtt ctgattctag 3000
tcttggtagt caataagagt tgaccagatg aatttcatag ctttgtagag gatgaaatat 3060
ttcaaggctg atttgcacaa atgtttacat agatcatgta tctttcataa gtaatatatt 3120
tgtattatta caaggctgta aaaatttaag caggttgtta atagcacagg gggtaacaga 3180
ttaataaaat taatgaataa aattactaaa agagtccaga agtaaaccca aatacgtgga 3240
ggaattaagc atatgtatga tacacatgac attttaaaaa tcagtgggaa aaggtaaatt 3300
attttacaaa tggtgttaga agcactgatt gataattttg ttaaagaaa  cttagattcc 3360
ctattttact cctaatccaa aataaattct gagtggatct aagattaagc acactagttaag 3420
ccggaagctc agcatggtag catgtgtctg taatctccgc aatttaggag actgagtttg 3480
gctgggggagg tggtgatatg cgcctagaaa aaaaaattt  ttaagccac  agatgtataa 3540
gcaaaaagcg ggcaaagagg cggaattttt ttttttttt  ttgatgaagt ctcacttgtc 3600
gcccaggctg gaacgcagtg gcgtgatctc agctcactgc aacctctgcc tcccgggttc 3660
aagcgattct cctgcctcag cctcccaagt agctgggatt acaggcacct gccgaggaga 3720
ggattttttt ataattaaaa caaaacaaaa caaaaaaaca ccaaactgga agataaagta 3780
tttacaacat gtaaagagct gttt                                        3804

SEQ ID NO: 28         moltype = AA  length = 122
FEATURE               Location/Qualifiers
source                1..122
                      mol_type = protein
                      organism = Homo sapiens
SEQUENCE: 28
MKLLTGLVFC SLVLGVSSRS FFSFLGEAFD GARDMWRAYS DMREANYIGS DKYFHARGNY  60
```

```
DAAKRGPGGA WAAEVISDAR ENIQRFFGHG AEDSLADQAA NEWGRSGKDP NHFRPAGLPE    120
KY                                                                  122

SEQ ID NO: 29           moltype = AA   length = 122
FEATURE                 Location/Qualifiers
source                  1..122
                        mol_type = protein
                        organism = Homo sapiens
SEQUENCE: 29
MKLLTGLVFC SLVLGVSSRS FFSFLGEAFD GARDMWRAYS DMREANYIGS DKYFHARGNY    60
DAAKRGPGGA WAAEVISDAR ENIQRFFGHG AEDSLADQAA NEWGRSGKDP NHFRPAGLPE    120
KY                                                                  122

SEQ ID NO: 30           moltype = AA   length = 122
FEATURE                 Location/Qualifiers
source                  1..122
                        mol_type = protein
                        organism = Homo sapiens
SEQUENCE: 30
MKLLTGLVFC SLVLGVSSRS FFSFLGEAFD GARDMWRAYS DMREANYIGS DKYFHARGNY    60
DAAKRGPGGA WAAEVISDAR ENIQRFFGHG AEDSLADQAA NEWGRSGKDP NHFRPAGLPE    120
KY                                                                  122

SEQ ID NO: 31           moltype = DNA   length = 5687
FEATURE                 Location/Qualifiers
source                  1..5687
                        mol_type = other DNA
                        note = cDNA
                        organism = Homo sapiens
SEQUENCE: 31
ctctctggtt gcccttaaca ttttttcctt catttcaact ttggtgggtc tgatgattat    60
gtgtcttggg gttgctcttc tcgaggagta tcttagtagt attctctgta tttcctgaat    120
ttgaatgttg gcctgtcttt ctaggttggg gaagttctcc tggataatat cctgaagagt    180
attttcaac ttggttctat tctccttgtt actttcaggt accaatca aacgtagatt       240
tggtcttgtc acatagtccc atatttcttg gaggttttat tcgttccttt ttattctttt    300
ttctctagtt ttgtcttctc gctttatttc actaagttga tcttcaatct ctgatatcct    360
tgcttctgct tgattgattc agctatcccc cgctcgatat tacaaaccat gtcacgaggc    420
gtggacaccc ccatgatat ggggagtatt atcacccccc tcttccccca ctggatatta     480
caaaccatgt catagggagg tggacatccc ccacaatg aggagtaata tcacacccct      540
ttccccgcag tggatattat gaaccatgtc acaggcggtt aaacacccc aacgatatgg     600
ggagtaatat cacactcctc tccccctgg atattacgaa ccatgtcatg gggggtggac     660
acccttgca atatggggag taaaatcacc cccctctccc ccaactggat attatgaacc     720
atgtcacagt gggggaaaaa tcctctgtga tatgcagagt aatatcaccc cactctcacc    780
acctggatat tacgaaccat gtcacagggg ggtggacacc cccaagatg ggggagtaat     840
atcacctcac tctctgccac cagatattac aaactgtgtc acagggggt gaacaacccc     900
cacaatatgg ggagcactat caccccccctc cccagggta ttatgatcca tgtcacaggg    960
gggtggatac caccccactat atggggagta atatcaccctt tctctcccgc cctggttttt   1020
atgaaccgtg tcacaggggg gtggacaccc cttgcgatat ggggagtaat atcaccccc    1080
tctccaccat ctggatatta cgaaccatgt cacaggggg tggacacccc tgcgatatgg    1140
ggaggaatat gcccctctcc ccacctggat attacaaatc atgtcacggg ggacggacat   1200
cccccacaat atgggagta atatcaccac actctcccct gctggatatt acgaaccata    1260
tcacaggcgg ctggagacac aaggcattaa caatatttcg agtaatatta tctttccctt   1320
tgaacattat gaacaatatg acagagggg gtacacctcc tgcgatattg ggagtaatgt    1380
catccccctcc cccactggat attaggaacc atattactgg gggatgtatt cccccttcta   1440
gattgggagg aagatcatac ttgccctccc tgaatatttg aaacaatatc ataggggtt   1500
gtacactttt acgatattgg gagtaatatc atcctttctc ccctggaaa ttaggaacaa   1560
tatcacaggg gtggtgtaca ccctgcaat atttagggta atattattgt cttctccccct  1620
cgatattagg aacaatatta caaggacggt gtaaagtacc tgccaaattg ggaaaaatac   1680
tatcctctcc ctcttgtata ttagaaacaa taacacaggg ggaatgtaca cccactgcca   1740
tattgggagt aatatcatac tcgccccatc cccagatat taggaacaat atcacagcag   1800
gggtgtacac ttttacgata ttgggagtaa tcatactc tctcccccctg gaaattagga   1860
ataatatcac agagatggtg tagaccctct gcaatactta ggataatatt atcatctccc   1920
ccctcgatat taggaacaat attacgggga gtgtaaatta cctgccaaat tggaggtaat   1980
cctctcctct ctctccctgt attttagaaa ataacaca caggaaatgt aacacactgc     2040
gatattcgga gtaatatctt cttcccccca cctggatatt aggaacaata acacgacgg    2100
ggcgtacacc cctcgcgata ttgaatgtaa tgtcatcctc tccctccctt tatattcga    2160
acaatatcac aggggggtgt acaaccctg caatattgga agtagtatca tccattctcc   2220
catgaatat aggaacaata tcacagggg agagtacacc ctctgcaatt tcgggagtaa    2280
catcatcctc tcgttccctg gatattataa acaacaccac ggggggtgg ggtgtacac    2340
acccttcgat attgggagta atataatcct ttccctccct atatattaga agcaatatca   2400
caggggttgg tgtaaacttc ttgcgatatg gggattaata tcacccccct ctcctgccct   2460
ggatattatg aaccatatca cagggaggtg acacactttt gcgatatggg gagtaatatc   2520
acgcccctc ccccccgat attcgaacc atatcacaag ggagtggacc cccccacga      2580
tatgggagt aatatcaccc ccctctcccg cctggatat tacgaaccat atcacaggga     2640
gatgacacc cccgcgatg cggggagtaa tgtcacccc ttctgccccc taggatatta     2700
cgaaccatat catggacacc ctccacgata ttggaaataa tatcatcctc tccccttgg    2760
atattaggaa caatatcaca ggggttgta cacctcctat gatattggaa gtaatatcat    2820
cctctcccctc ctgatatta gcaacaatat cacagggagt gtgtacaacc ccagcgatat   2880
ttggagtaat atcaccctct caccccatgg atatgagaaa caatatcaca ggggaggtgt   2940
```

-continued

```
acatcccacg tgatattgtg tgtaatatca ttcttcccca acccctgcaa tattgtggtg 3000
taatataatt ctctcccttc ctggacatta tgaacaatat cactactagg tgatacatta 3060
ggagtaatgt atccatagga tattatgagg aatatcacag ggtgtacacc cactgtgata 3120
ttagaggtaa tatctcccta aaatattaag aagaatatct tacacccact gtgactttag 3180
aagtaatatc tccctaaaac gttacaaata acatcgcagg gtgtacactc acagtgatat 3240
taggagtaat atctccctag aatattacaa atacacatgg tgtaaaccca ctgtgacttt 3300
agaagaacta tctccctaaa ataatacaaa aatatcgcag tgtataccat aatatcccct 3360
agaatatcat aaataatatc acagggtgta cacccactgt gataatagga ataataccac 3420
cccaggatat tatgaataat gtcacaggct gtacacccac tatgacatta ggagtaaatat 3480
ctccctagga cactatgaat aacatcacag atttttacacc catggtgtgc acccactatg 3540
atattaggag taatatctgc acaggatata acaaataata gtacagggtg tacacatatg 3600
atatacaccc actgtgatat taggagaaat atatccctag gatattatga ataacctctc 3660
agagtacaca cacatggtat acaccctctg tggcattagg aacaataact ttctaaaaca 3720
ttacgaataa catcacgaaa tgtacacaca tggtttacac ccactgtgac aggtgcaata 3780
tctcccttgg atattatgaa taacaacaaa ctatcactgt catattagga gtaatttctc 3840
cctagaatat tacaaataac atcacagggt gttcatttat ggtgcacacc cactgtgata 3900
ttaggagtaa tatctcccta ggatattact tttcatataa aagtgtgtac atccactgtg 3960
atattgggaa aaatatttct ctaggatatt atgaataata tcacagagcg tacacccact 4020
gtgatattag gagtaataat tccctgggtt attatgaata atatcacagg atgtacaacc 4080
actgtgatat taggagcaat atcttcctag gatattacaa ataatatcac agggtgtaca 4140
cccactgtga tattaaagta attttttaggt tattgtgaat aatatcacca agtgtacaaa 4200
catggtgtac actcactgta ataatcaggag taatatctca gtaaaatatt atgaataata 4260
tcacagggta tacacccact gtgatattag cagtagtatc tttgtaggat attacaaata 4320
atatcacagg gtgtatgccc actatgacat tagaagcaat atctccctag gatatcaaaa 4380
ataatatcac agggtgtaca acttctacat cccaggttct aagggattct cctgcttcag 4440
cctcctgagt ggctgggatt acagatgccc accaccacac ctggctaatt tcgtatttc 4500
agtagagatg gggtatcacc atgctggtca ggctggtctg gaacttctga cctcaggtga 4560
tccaccagcc tcggccttcc aaagtgctgg gaatacaggt gtgagccaac gtgcttggca 4620
gagagttata tattaaataa atctggaaac atagctccca tgtttgagtg tgcatttact 4680
tttatgaaga aattatgtca gaaaacctaa ggatgataat aaatatgaaa agtaactggc 4740
atgtaaaaag gtcttttgat taagaactat aaggttcgat ttcattttta gataacgtga 4800
tcctagctct tgtatagtgc ttataaatat tctacatcaa aggaatttgt tgcacagtgt 4860
cagaataaaa taaagtgtat ttcactgctt cttaattttt aaattagact gagtttgttt 4920
tcctagagag agaagaacat ttttttattt ttctgaaaag agtaggccat atttttactga 4980
gatcttagat ttgttatata ttaggttttg gtcttctaac attctccagt ggattttctc 5040
taaagtaggt atgcacagaa agagttgaat agcaaaaaag taaatcatgt aataattctg 5100
agattttttgg gtttgtcaca actgagaaat attgctgagg gtgtatggtc ctcaagtgtg 5160
aaaatgttcc ttgtgaattg cttgtatccg aaatatacac acaacattaa gtcctggttt 5220
ttatctttta tttttttccaa tcctttttttc ttctcaaggt gtccaagtca cacagagcca 5280
cagaatctca caggtgtctc agaattcctc ctcctgggac tctcagagga tccagaactg 5340
cagccactcc ttgctgggct gttcctatcc atgtgcctgg tcacgatgct ggggaactg 5400
ctcatcatcc tggccgtcag ccctgactcc cacctccaca tccccatgta cttcttcctc 5460
tccaacctgt ccttgcctga cattgtgttc accttgccca cggtccccaa gatgattgta 5520
gacatgcaat cacatagcag agtcatctcc catgcaggct gtctgacaca gatacctttc 5580
tttgtccttt ttgtatgtat agatgacatg ctcctgactg tgatggccta tgactgattt 5640
gtggccatct gtcacccccct gcactaccca gtcatcatga atcctca     5687
```

SEQ ID NO: 32        moltype = DNA   length = 5687
FEATURE             Location/Qualifiers
source              1..5687
                     mol_type = other DNA
                     note = cDNA
                     organism = Homo sapiens
SEQUENCE: 32

```
attgaatttt atctcagagc ccacatgaag caggatcaaa gtcagtacac atgaaaacta 60
gagcccaaag actataaagc atgaaataag gatttaagct aaccctatct tgtaaggggt 120
ttgtaaagcc cagcttgcat ctgagctaca ctagcaccag acagccact cagtaatggg 180
gtttctcaag gttattgctt ttcattcagt tgaaatgaga gtcatttctt acccttatgc 240
cctgtgagat ttcactggag gttgttcact gaaacatttt catatcattg catcaaccct 300
cttgaactca ctgtgcctgc cccagttca gtctgtgact cacaagtacc ctgcagcaaa 360
agaaatccaa tagagggcaa atccctcacc ttaccttcct ttctaagacc tttgatgttc 420
tcatgtgtca tttcataatt gggattgtca attagtcgcc tcatctctgg tcctcacttt 480
cctctctccc agccaaactc aaccttcagc ccacacaatg gaattcaaca aaatgaggta 540
acagtttttct gtgtgagtca ctctgggcaa ctctgttcac agagcactgt gaggtgagca 600
gccagaaccc aggcaagtgt ttcagccatc caagaactgg caggcagccc aagagacact 660
ctcacctgat gacagactag caggatgagt cctggaggaa atggttccca acagctgcag 720
aaggagtctc ttggctcatg cacagcaatg ctcttctcaa ttaaaaacgt tgtcattatt 780
gacactgcag tgtaaaatcc ttttacactg tgctcacatt tctacaggcc ttcacctgct 840
ctgccatta aagacaagc ccttcatga gatgatgaca tctctaagtt actgttccac 900
ccaaacagtc ctatataatg aagagaaaaa ttttgctcggc cctcaaaagg caaacacaag 960
gagaaagatt tccacaagct gttttctcttt gctgagcact tagaggaaaa ctgtaagtgg 1020
ttggaagaag gctttgtttt ctacaagact tttagttatt cctcagaaat tttcctgctt 1080
attcccagag gaggtcatct cttagatgct gtcagtcaga tagggattgg cagccaagca 1140
gaggtgtca gagggttttc caactaatgt ggccagcgga aaactgccaa agaagcaggg 1200
atccttagga caaataaact ggaagatatt ttggggataa aaataaatcc ttttgaaaat 1260
gaaagatgga gagtgctgt atatacaaat tgccctgttc tgaacaatgt tgtcactagg 1320
actgccctg gagaccaatg atacaaacca aatgttctc agcatgcttt tgatggtctt 1380
tttctccaaa gttatctatt ctgtttccat ttcattctca caggcttgc catgggggttc 1440
tcataagatt tcacattggt cataatccag gtggccctgg actgcaacct ctgagttggc 1500
```

-continued

```
aacatcagaa taggaattac gaaaaaccaa tttaaagtta aatacagaca caggcaaaag   1560
agagatgggt tgtcgaagct agtgcctagg tggacactgc ctcacatttt taattccaga   1620
agccatcagt actgagtgtc agatctcatt agtcaaacac agtgatcagg aatcctgttt   1680
tcctggagga tttccttgag ggagggacca ctcaagagtc tgaaatattt cacgtcatag   1740
agtatggatc tcaccccaac acccaatcag aaaatgggaa gaactggaaa ccaaaattcc   1800
ccctcccgct gtggaaggat gaaaaccaga gtgttggagt tctgtcctga taatggagca   1860
gacagctagg cagcaatcaa tgagggccag tacaggaatt cagtgctaag tattgggtca   1920
taacagaagt agggaaggta ttaatccagt gctatatgag gatcctggga cactggctcc   1980
tagtaatcta gttataacta ttagcaaaaa agaaaaaaaa aatcagtgat gtgaagagat   2040
ggcctaaagg agctccagca atatagctaa gcagctggca agtggtctga ggagcattgc   2100
aattccaggc ctcctaaggt ggcagtacgg gcactggtaa gacattctgc tgtggtgaaa   2160
ctagtttacc atagaggatt cacaattaaa ataggcaaac aggaaatgca agacagaggc   2220
taacaaaggg tttttttttt ggtgggggggg agttgtttgt ttgtttgttt gttttctgag   2280
acggagtctt cctctgttgc ccaggctgga atgcagtggc acgatctcag ctcactacaa   2340
cctctgcctc ccaggttcaa gcagttcttc tgcctcagcc tcccaggttc aagcagttct   2400
tctgcctcag cctcccaagt acctgggact atagctgtgt gccaccacat tgactaattt   2460
ttgtactttt agtacagact gggtttcacc atgttggcca ggctggtgtc gaactcctga   2520
cctcaagtaa tcccccgcc ttggcctccc aaagtgctgg aattacaggc atgagccacc   2580
acacctggcc agttttttggt aattcttaaa gaactcaatg agcaactc aaacaaccat   2640
aaagactata gagctcatgg ttgaatttta gatagctaaa cagacaggag tttttgtaag   2700
ttttgtaagt cttgctcatc cttccctctt ccatcctcta tctcaactat tctgtctacc   2760
attaaagcac cttagacctt gagtttggca atgcaacaag tgtgtgctca acacgaaata   2820
ggtaattcaa tagcaaagcc ctaaacagc ctggcttgat tatttctcag ggcatgcagt   2880
tcctttgaag caggatcatt ttaataataa taataataga aataataata gaaattgaag   2940
acaattattt cacaatttcc atacacctaa gagctataca tatgaatgat aatgcataat   3000
tgtaaagcat gcatattaca ggtaataaat atgttagcta attataaaca atgcccattt   3060
tcatatagtt tatccttgcc aaataaaact gtaaaaaaaa gacacctttc aaatgctgct   3120
aaggagtaat acctgaatga ggttgattta atggagtctt agttcctgca tgtgttctaa   3180
ttgaatagac tatgtagtaa ttcccttaca tacccatcca tgtccaagaa cagtgaagat   3240
cttatttaa tatgaattat tgcagatgat tagcacagtc tagccaaacc attccagtaa   3300
ttgttttttac ttgttatatt aatatataaa ttctcaaagg atataacagt gatgttgggt   3360
gaatttcact gaatgatagc tcaaacacct gaaatattga ctaagaaaac taatttatca   3420
atactgataa tcaattttaa tatgttaatt gattgtaata caggattctg tggttcaaaa   3480
aaaaagaaca agcaaaaaaa cttttcttcca tttccaaata ccaattaata gatctctact   3540
tccccttgga tttcttctta ccacctacca cctccaatct tcattctttc ctcacaaact   3600
aaacataaaa gttacctaca aagcatagaa tctgtgttaa aggatattct tgcttgtttt   3660
aagtccaaaa ttaaacagct ctgaattatt aaaaagcaca tgaattcaaa tgtcctattc   3720
taataagaaa atggtttaca tttctctatg ttcaaggaaa aaaatagtca agggtgtaca   3780
agtggggtaa aaattttc cagtaggtta tgtgatttaa gttatagaaa cgaaccaggc   3840
aattcaatta aatgtcatgg aaagtaggtt ttttctttc ctctttttt ctaatatgta   3900
cactttgtga gaagataaat ccatagtgtg ataatttgtc cactgggtcc atcagacact   3960
ggagacagct tcctaagaat tataaggctt ctaaaggctt ctaaagccta aattgcctag   4020
agcattttgt gtgccaggca ctttgctagg tgccctaggg atgcaagaag tataaatgtt   4080
ttatgagaat acaggctgga aatgtattct tgattattcc tgtggaattt ctaggcagaa   4140
aagagtctaa tggggtatag gtatattttc tcaacacaat tttctgagcc tttaccagat   4200
gcagttctat ggtttgaatg tgtccctcag agtttgtgtg ttggaaactt aatccccaat   4260
gcaataatgt tggtgaggcc taatgaaagc ctaataatgt aggtgaggc taatgagagc   4320
tgtttagacc atgaaggctc ttccctcatg gatggattaa tgctgttatg gtgggaatgc   4380
gttcattatt actggggtgg gttcataata aaaagatgag tttggcctgc tattctctct   4440
ctttctcatc ctctcttcca ccatgggatg acacagcaag aaggccctg caagatgccc   4500
tccccctcagt attggacttc acagcctcca ggaccataag ccaataaatt tttgttcatt   4560
ataaatttcc cagtctgtgg tattctgtta tagcaacact caatttatgc attacttcca   4620
gattcttatg gctataccta cttctcacag tttgtattca cccctcctc aaccaagtac   4680
ccttaacaca gttcccatag tcacaaagcc aggtcactga agctgccctc tctccaacca   4740
cacacatata gatcaaatga ccccagacat agagctgatt gagaaggagg gaccagtacg   4800
agctctgctt ccccagcagc ttcctgaaaa gaagaggcaa tacaacccaa cccaaaagtg   4860
caagagaagt aacacctcat gggatgagct taattaatca atgggagagg acactagaag   4920
acactagagg atctcccttc ctcccttct ttcccacttc accccctcca gtctctgaac   4980
catgactat ttcaaaggtg cagtaatgct atattggct tctctgaaga tatcctatga   5040
ggccaagtca tcagctttgt tcattatcta agagtggtag ccagctcacc agcacttccc   5100
atcatgtttg ccctccctct ttcccttgtg ttacttccca ttttcccta cttctgcttt   5160
cttggcatta aattctactc tgcaatgtta ggatataagt ttttgcctca gattctgttt   5220
tctaggaaac ccatgctaag acaacactgg cagtggccct ggaaaagtaa acctcatgat   5280
ggatttggag ttggattgtt cactgatctg aaggacagag gactccactt aagtggtaag   5340
cagtgtagct atgaactctg ccacgcaggc ctcacaatta ctgaggcttc ttttacctgt   5400
ggttaactgg gacacagaac agcaggaaat tgagtgtaga ggttatcaag tagctgcttc   5460
acttaattgg tataatttta tggagttaac ctggtttaga gtccagagaa cattccacat   5520
agcctagaaa gggtagttat ttgtccttac cataatcaag tcatactttg aatatgagtt   5580
ttccttccct gttcagcacc acttctctta gacttaagaa tgcctgatct gttgatatta   5640
tgtcccatgt aacattgcct gagacaaaga tatccatgta ccttaaa              5687
```

| | | |
|---|---|---|
| SEQ ID NO: 33 | moltype = AA  length = 140 | |
| FEATURE | Location/Qualifiers | |
| source | 1..140 | |
| | mol_type = protein | |
| | organism = Homo sapiens | |

SEQUENCE: 33

```
MGFQKFSPFL ALSILVLLQA GSLHAAPFRS ALESSPADPA TLSEDEARLL LAALVQDYVQ   60
MKASELEQEQ EREGSSLDSP RSKRCGNLST CMLGTYTQDF NKFHTFPQTA IGVGAPGKKR  120
```

```
DMSSDLERDH RPHVSMPQNA                                                 140

SEQ ID NO: 34           moltype = AA  length = 128
FEATURE                 Location/Qualifiers
source                  1..128
                        mol_type = protein
                        organism = Homo sapiens
SEQUENCE: 34
MGFQKFSPFL ALSILVLLQA GSLHAAPFRS ALESSPADPA TLSEDEARLL LAALVQDYVQ     60
MKASELEQEQ EREGSRIIAQ KRACDTATCV THRLAGLLSR SGGVVKNNFV PTNVGSKAFG    120
RRRRDLQA                                                             128

SEQ ID NO: 35           moltype = AA  length = 141
FEATURE                 Location/Qualifiers
source                  1..141
                        mol_type = protein
                        organism = Homo sapiens
SEQUENCE: 35
MGFQKFSPFL ALSILVLLQA GSLHAAPFRS ALESSPADPA TLSEDEARLL LAALVQDYVQ     60
MKASELEQEQ EREGSSLDSP RSKRCGNLST CMLGTYTQDF NKFHTFPQTA IGVGAPGKKR    120
DMSSDLERDH RPHVSMPQNA N                                              141

SEQ ID NO: 36           moltype = AA  length = 116
FEATURE                 Location/Qualifiers
source                  1..116
                        mol_type = protein
                        organism = Homo sapiens
SEQUENCE: 36
APFRSALESS PADPATLSED EARLLLAALV QDYVQMKASE LEQEQEREGS SLDSPRSKRC     60
GNLSTCMLGT YTQDFNKFHT FPQTAIGVGA PGKKRDMSSD LERDHRPHVS MPQNAN        116

SEQ ID NO: 37           moltype = AA  length = 187
FEATURE                 Location/Qualifiers
source                  1..187
                        mol_type = protein
                        organism = Homo sapiens
SEQUENCE: 37
TSEETISTVQ EKQQNISPLV RERGPQRVAA HITGTRGRSN TLSSPNSKNE KALGRKINSW     60
ESSRSGHSFL SNLHLRNGEL VIHEKGFYYI YSQTYFRFQE EIKENTKNDK QMVQYIYKYT    120
SYPDPILLMK SARNSCWSKD AEYGLYSIYQ GGIFELKEND RIFVSVTNEH LIDMDHEASF    180
FGAFLVG                                                              187

SEQ ID NO: 38           moltype = AA  length = 168
FEATURE                 Location/Qualifiers
source                  1..168
                        mol_type = protein
                        organism = Homo sapiens
SEQUENCE: 38
VRERGPQRVA AHITGTRGRS NTLSSPNSKN EKALGRKINS WESSRSGHSF LSNLHLRNGE     60
LVIHEKGFYY IYSQTYFRFQ EEIKENTKND KQMVQYIYKY TSYPDPILLM KSARNSCWSK    120
DAEYGLYSIY QGGIFELKEN DRIFVSVTNE HLIDMDHEAS FFGAFLVG                 168
```